US009771358B2

(12) United States Patent
Zhang et al.

(10) Patent No.: US 9,771,358 B2
(45) **Date of Patent: *Sep. 26, 2017**

(54) DIHYDROPYRIMIDINE COMPOUNDS AND THEIR APPLICATION IN PHARMACEUTICALS

(71) Applicant: SUNSHINE LAKE PHARMA CO., LTD., Dongguan, Guangdong (CN)

(72) Inventors: Yingjun Zhang, Dongguan (CN); Qingyun Ren, Dongguan (CN); Xinchang Liu, Dongguan (CN); Siegfried Goldmann, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,226

(22) PCT Filed: Mar. 27, 2015

(86) PCT No.: PCT/CN2015/075299

§ 371 (c)(1),
(2) Date: Aug. 3, 2016

(87) PCT Pub. No.: WO2015/144093

PCT Pub. Date: Oct. 1, 2015

(65) Prior Publication Data

US 2016/0347746 A1 Dec. 1, 2016

(30) Foreign Application Priority Data

Mar. 28, 2014 (CN) .......................... 2014 1 0126202
Oct. 29, 2014 (CN) .......................... 2014 1 0596489

(51) Int. Cl.

| | |
|---|---|
| ***C07D 417/14*** | (2006.01) |
| ***A61K 31/506*** | (2006.01) |
| ***A61K 31/5377*** | (2006.01) |
| ***A61K 45/06*** | (2006.01) |
| ***A61K 31/541*** | (2006.01) |
| ***C07D 417/04*** | (2006.01) |

(52) U.S. Cl.

CPC .......... *C07D 417/14* (2013.01); *A61K 31/506* (2013.01); *A61K 31/5377* (2013.01);
(Continued)

(58) Field of Classification Search

CPC ............................ C07D 417/14; A61K 31/506
See application file for complete search history.

(56) References Cited

U.S. PATENT DOCUMENTS 5,250,531 A 10/1993 Cooper
6,057,332 A 5/2000 Michne et al.
(Continued)

FOREIGN PATENT DOCUMENTS

CN 101744823 B 6/2010
CN 103664897 A 3/2014
(Continued)

OTHER PUBLICATIONS

Gentil et al, 2014, International Journal of Women's Health, vol. 6, p. 605-611.*
(Continued)

*Primary Examiner* — Rebecca Anderson
*Assistant Examiner* — Karen Cheng
(74) *Attorney, Agent, or Firm* — Kam W. Law; Squire Patton Boggs (US) LLP

(57) ABSTRACT

Provided herein are dihydropyrimidine compounds and their pharmaceutical applications, especially for use in treating and preventing HBV diseases. Specifically, provided herein are compounds having Formula (I) or (Ia), or an enantiomer, a diastereoisomer, a tautomer, a hydrate, a solvate, or a pharmaceutically acceptable salt thereof, wherein the variables of the formulas are as defined in the specification. Also provided herein is the use of the compounds having Formula (I) or (Ia), or an enantiomer, a diastereoisomer, a tautomer, a hydrate, a solvate, or a pharmaceutically acceptable salt thereof for treating and preventing HBV diseases.

(I)

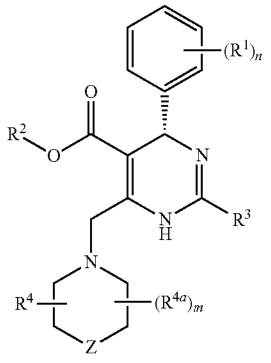

(Ia)

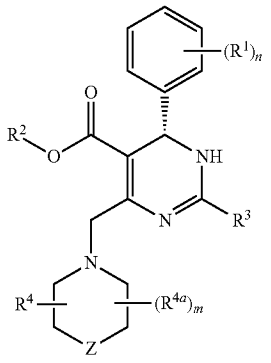

18 Claims, No Drawings

(52) U.S. Cl.
CPC ............ *A61K 31/541* (2013.01); *A61K 45/06* (2013.01); *C07D 417/04* (2013.01)

(56) References Cited

U.S. PATENT DOCUMENTS

| | | | |
|---|---|---|---|
| 6,218,538 | B1 | 4/2001 | Downs et al. |
| 6,436,943 | B1 | 8/2002 | Stoltefuss et al. |
| 6,503,913 | B1 | 1/2003 | Goldmann et al. |
| 6,696,451 | B1 | 2/2004 | Stoltefuss et al. |
| 7,074,784 | B2 | 7/2006 | Goldmann et al. |
| 7,157,461 | B2 | 1/2007 | Murugesan et al. |
| 8,106,196 | B2 | 1/2012 | Li et al. |
| 8,168,642 | B2 | 5/2012 | Li et al. |
| 8,329,902 | B2 | 12/2012 | Li et al. |
| RE44,987 | E | 7/2014 | Goldmann et al. |
| 8,802,669 | B2 | 8/2014 | Li et al. |
| 9,233,933 | B2 | 1/2016 | Vandyck et al. |
| 9,233,978 | B2 | 1/2016 | Guo et al. |
| 9,266,904 | B2 | 2/2016 | Guo et al. |
| 2013/0267517 | A1 | 10/2013 | Guo et al. |
| 2015/0031687 | A1 | 1/2015 | Guo et al. |
| 2015/0152096 | A1 | 6/2015 | Zhang et al. |
| 2015/0218182 | A1 | 8/2015 | Zlotnick et al. |
| 2015/0292045 | A1 | 10/2015 | Levrero et al. |

FOREIGN PATENT DOCUMENTS

| | | | |
|---|---|---|---|
| CN | 103664899 | A | 3/2014 |
| CN | 103664925 | A | 3/2014 |
| CN | 104650069 | A2 | 5/2015 |
| CN | 104650070 | A | 5/2015 |
| EP | 0202654 | A2 | 11/1986 |
| WO | WO0058302 | A1 | 10/2000 |
| WO | WO0168639 | A1 | 9/2001 |
| WO | WO0168641 | A1 | 9/2001 |
| WO | WO0168642 | A1 | 9/2001 |
| WO | WO0168647 | A1 | 9/2001 |
| WO | WO2008154818 | A1 | 12/2008 |
| WO | WO2008154819 | A1 | 12/2008 |
| WO | WO2008154820 | A1 | 12/2008 |
| WO | WO2010069147 | A1 | 6/2010 |
| WO | WO 2014153459 | A2 | 9/2014 |
| WO | WO2015074546 | A1 | 5/2015 |
| WO | WO2015/078391 | * | 6/2015 |
| WO | WO2015180631 | A1 | 12/2015 |

OTHER PUBLICATIONS

International Search Report of PCT/CN2015/075299.
Written Opinion of PCT/2015/075299.

* cited by examiner

DIHYDROPYRIMIDINE COMPOUNDS AND THEIR APPLICATION IN PHARMACEUTICALS

CROSS-REFERENCE TO RELATED APPLICATIONS

This is a U.S. national stage application of the International Patent Application No. PCT/CN2015/075299, filed Mar. 27, 2015, which claims priorities to Chinese Patent Application No. 201410126202.0, filed Mar. 28, 2014, and No. 201410596489.3, filed Oct. 29, 2014, all of which are incorporated herein by reference in their entirety.

FIELD

The invention relates to dihydropyrimidine compounds and pharmaceutical compositions thereof, and further relates to uses of the compounds or the pharmaceutical compositions in the manufacture of a medicament, especially for use in preventing, managing, treating or lessening a viral disease or an HBV disease.

BACKGROUND

The hepatitis B virus belongs to the family of hepadnaviridae. It can cause acutely and/or persistently or progressively chronic diseases. Many other clinical manifestations in the pathological morphology are also caused by HBV—in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has good activity, its resistance develops rapidly during the treatment and relapse effects often appear after the treatment has stopped. The $IC_{50}$ value of lamivudine (3-TC) is 300 nM (*Science,* 2003, 299, 893-896).

Deres, et al, have reported heteroaryl-substituted dihydropyrimidine (HAP) compounds which were represented by Bay41-4109 and Bay39-5493, and these compounds play a role in blocking HBV replication by preventing the proper formation of viral core particles (nucleocapsids). Bay41-4109 has demonstrated better drug metabolic parameters in clinical study (*Science,* 2003, 299, 893-896). The study of these compounds' mechanism of action indicated that through reacting with 113-143 amino acid residues of a core protein, heteroaryl-substituted dihydropyrimidine compounds have changed the angle between dimers which can form nucleocapsids, and led to forming unstably expanded nucleocapsids, which accelerate the degradation of the core protein (*Biochem. Pharmacol.,* 2003, 66, 2273-2279).

WO 2014029193 and CN 103626752 disclose dihydropyrimidine compounds and their application in pharmaceuticals, especially their uses in medicament for treating and preventing hepatitis B. CN 103626752 describes dihydropyrimidine racemic compounds substituted by carboxylic acid, which can inhibit the growth of the HBV in cell culture, wherein, the $EC_{50}$ of the compound of formular (II) is 360 nm.

formular (II)

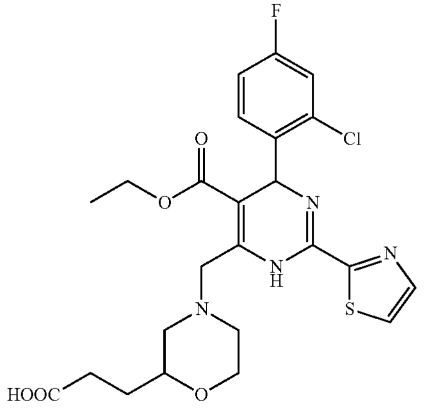

SUMMARY

The invention disclosed herein provides a series of dihydropyrimidine compounds substituted by carboxylic acid, and all of the compounds of the invention are isomer forms which were split to gain by a large number of repeating experiments. For example, the compound of formular (II) is split to give the four isomer compounds of formular (III), M1, M2, M3 and M4. Wherein, the $EC_{50}$ of M1, M2, M3 and M4 is 48 nm, 110 nm, >16.4 μM and >16.4 μM respectively. The $EC_{50}$ of M1, M2 are lower than the one of the compound of formular (II), the $EC_{50}$ of M1 is lower than the one of M3 and M2, the $EC_{50}$ of M2 is lower than M4, besides, the big differences of pharmacokinetic parameters and liver microsome stability between isomers are impossible to be predicted when reading CN 103626752.

formular (III)

M1

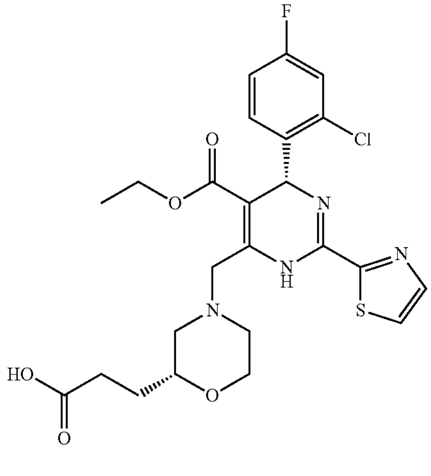

-continued

M2

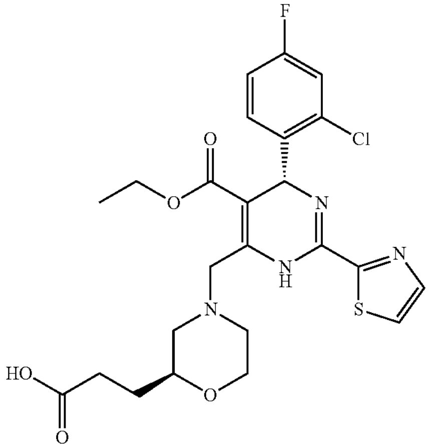

M3

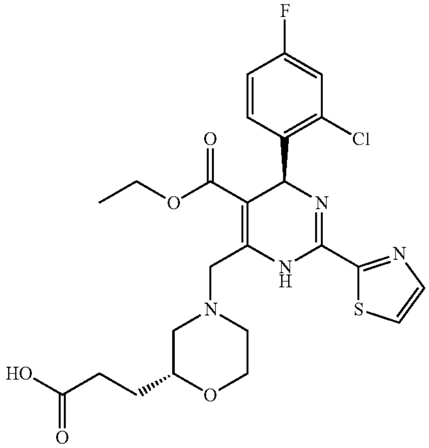

M4

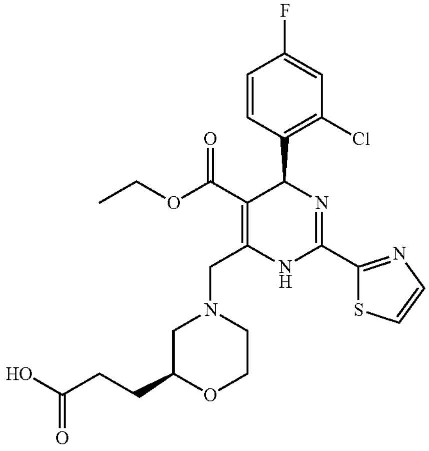

The inventors had researched the synthesis, antiviral activity, drug metabolism parameters and liver microsome stability of dihydropyrimidine compound isomers substituted by carboxylic acid and found the compound of the invention has an unexpected antiviral activity against HBV and a good character of drug metabolism. The compound of the invention can be effectively used as antiviral drugs, especially the drugs used for treating and/or preventing hepatitis B.

The invention relates to novel dihydropyrimidine compounds and pharmaceutical compositions, and their uses in the manufacture of a medicament for preventing, managing, treating or lessening a viral disease, especially hepatitis B (HBV) infection or a disease caused by hepatitis B infection. The inventors had researched the synthesis, antiviral activity, drug metabolism parameters and liver microsome stability of dihydropyrimidine compound isomers substituted by carboxylic acid. All of the compounds of the invention are isomer forms, the antiviral activity, drug metabolism parameters and liver microsome stability are very different among different isomers. An isomer compound having unexpectedly superior anti-HBV activity and drug metabolism was obtained.

In one aspect, provided herein are compounds having Formula (I) or (Ia), or an enantiomer, a diastereoisomer, a tautomer, a hydrate, a solvate, a prodrug, a stereoisomer, an N-oxide, or a pharmaceutically acceptable salt thereof, (I)

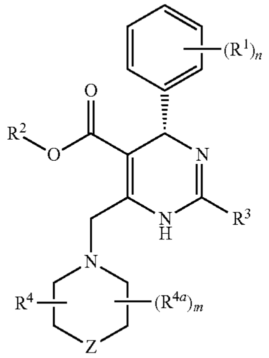

, or (Ia)

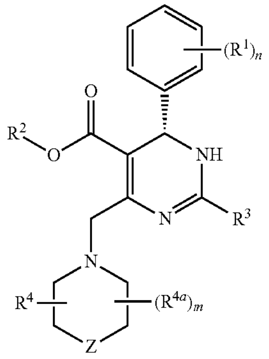

wherein each $R^1$ is independently H, F, Cl, Br, I, nitro, trifluoromethyl or cyano;

each $R^2$ is independently methyl or ethyl;

each $R^3$ is independently thiazolyl, oxazolyl or imidazolyl; optionally each of thiazolyl, oxazolyl and imidazolyl is independently substituted with methyl or cyclopropyl;

each Z is independently O or S;

each $R^4$ is independently $-(CR^5R^{5a})_t-C(=O)-OH$;

each $R^{4a}$ is independently H, methyl or isopropyl;

each $R^5$ and $R^{5a}$ is independently H, F or methyl, or $R^5$ and $R^{5a}$, together with the carbon atom to which they are attached, form cyclopropyl or $-C(=O)$, namely $CR^5R^{5a}$ is cyclopropyl or $-C(=O)$;

wherein, each n is independently 1, 2 or 3;

each m is independently 0, 1 or 2; and t is 1, 2, 3 or 4.

In certain embodiments, $R^3$ is

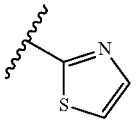,
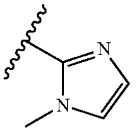,
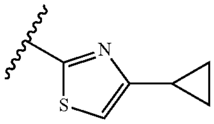 or 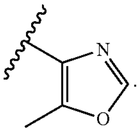.

In one aspect, provided herein is a pharmaceutical composition comprising the compound disclosed herein.

In some embodiments, the pharmaceutical composition further comprises a pharmaceutically acceptable carrier, excipient, diluent, adjuvant, vehicle or a combination thereof.

In some embodiments, the pharmaceutical composition further comprises one or more anti-HBV agents.

In other embodiments, the anti-HBV agent is an HBV polymerase inhibitor, immunomodulator or interferon.

In still other embodiments, the anti-HBV agent comprises at least one selected from the group consisting of lamivudine, telbivudine, tenofovir, entecavir, adefovir, alfaferone, alloferon, celmoleukin, clevudine, emtricitabine, famciclovir, interferon, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, ampligen, phosphazid, heplisav, interferon α-2b, levamisole, and propagermanium.

In another aspect, provided herein is use of the compound or the pharmaceutical composition in the manufacture of a medicament for preventing, managing, treating or lessening a viral disease.

In some embodiments, the viral disease is hepatitis B infection or a disease caused by hepatitis B infection.

In other embodiments, the disease caused by hepatitis B infection is cirrhosis or hepatocellular carcinoma.

In another aspect, provided herein is the compound or the pharmaceutical composition for use in preventing, managing, treating or lessening a viral disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is a method for preventing, managing, treating or lessening a viral disease in a patient comprising administering to the patient a therapeutically effective amount of the compound or the pharmaceutical composition.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein are methods for preventing, managing, treating or lessening a viral disease or an HBV disease, which comprises administering a pharmaceutically effective amount of the compound or the pharmaceutical composition disclosed herein to a patient.

In another aspect, provided herein is use of the pharmaceutical composition or the compound disclosed herein in the manufacture of a medicament for preventing, managing or treating a viral disease or an HBV disease and lessening the severity of a viral disease or an HBV disease in a organism.

In some embodiments, the organism is a mammal; in other embodiments, the organism is a human. In still other embodiments, the method further comprises contacting a kinase with an anti-HBV agent.

In another aspect, provided herein is a method of inhibiting HBV infection, comprising contacting the cell with an effective HBV inhibiting amount of a compound disclosed herein or a pharmaceutical composition thereof. In other embodiments, the method further comprises contacting the cell with an anti-HBV agent.

In another aspect, provided herein is a method of treating HBV disease, the method comprises administering to a patient in need of such treatment an effective therapeutic amount of a compound disclosed herein or a pharmaceutical composition thereof. In other embodiments, the method further comprises administering an anti-HBV agent.

In another aspect, provided herein is a method of inhibiting HBV infection, the method comprises administering to a patient in need of an effective therapeutic amount of a compound disclosed herein or a pharmaceutical composition thereof. In other embodiments, the method further comprises administering an anti-HBV agent.

In another aspect, provided herein include methods of preparing, separating, purifying compounds of Formula (I) or (Ia) and the specific compounds of the invention.

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provide in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the *Handbook of Chemistry and Physics,* $75^{th}$Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, "patient" refers to a human (including adults and children) or other animal. In one embodiment, "patient" refers to a human.

The term "comprising" is meant to be open ended, including the indicated component but not excluding other elements.

The term "Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "Chiral" refers to molecules which have the property of non-superimposability of the mirror image partner, while the term "achiral" refers to molecules which are superimposable on their mirror image partner.

The term "Enantiomers" refer to two stereoisomers of a compound which are non-superimposable mirror images of one another.

The term "Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

As described herein, compounds may optionally be substituted with one or more substituents, such as those illustrated above, or compounds as exemplified by particular classes, subclasses, and species disclosed herein. The term "optionally substituted" can exchanged with the one "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents include, but are not limited to, H, F, Cl, Br, I, nitro, trifluoromethyl, cyano, oxo (═O), methylene (═$CH_2$), alkoxy, hydroxy, mercapto, alkylamino, alkyl, cycloalkyl, amino, aryl, arylalkyl, heteroaryl, heteroarylalkyl, heterocyclyl, heterocyclylalkyl, trifluoromethoxy, trifluoromethyl sulfonyl or —$(CR^5R^{5a})_t$—C(═O)—OH and the like. Wherein $R^5$, $R^{5a}$ and t are as defined herein.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl group" refers to, respectively, discloses a methyl, ethyl, $C_3$ alkyl, $C_4$ alkyl, $C_5$ alkyl, $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched chain monovalent hydrocarbon radical of 1-20 carbon atoms, wherein the alkyl radical may be optionally substituted independently with one or more substituents described herein. Unless otherwise specified, alkyl groups contain 1-20 carbon atoms. In some embodiments, alkyl groups contain 1-10 carbon atoms. In other embodiments, alkyl groups contain 1-8 carbon atoms. In still other embodiments, alkyl groups contain 1-6 carbon atoms, and in yet other embodiments, alkyl groups contain 1-4 carbon atoms. In other embodiments, alkyl groups contain 1-3 carbon atoms.

Some non-limiting examples of alkyl group include, but are not limited to, methyl (Me, —$CH_3$), ethyl (Et, —$CH_2CH_3$), 1-propyl (n-Pr, —$CH_2CH_2CH_3$), 2-propyl (i-Pr, —$CH(CH_3)_2$), 1-butyl (n-Bu, —$CH_2CH_2CH_2CH_3$), 2-methyl-1-propyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), 1-pentyl (—$CH_2CH_2CH_2CH_2CH_3$), and the like.

The term "haloalkyl" or "haloalkoxy" refers to an alkyl or alkoxy radical substituted with one or more halogen atoms (i.e., F, Cl, Br or I), which may be either the same or different. Wherein the alkyl and alkoxy groups are as defined herein. Some non-limiting examples of such radicals include but are not limited to trifluoromethyl, trifluoroethyl, trifluoromethoxy, and the like.

The term "alkenyl" refers to a linear or branched-chain monovalent hydrocarbon radical of 2-12 carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. In some embodiments, alkenyl groups contain 2-8 carbon atoms. In other embodiments, alkenyl groups contain 2-6 carbon atoms. In still other embodiments, alkenyl groups contain 2-4 carbon atoms. Examples include, but are not limited to, ethenyl or vinyl (—CH═$CH_2$), allyl (—$CH_2$CH═$CH_2$), and the like.

The term "cycloalkyl" refers to a monovalent or multivalent, non-aromatic, saturated or partially unsaturated ring having 3 to 12 carbon atoms as a monocyclic, bicyclic, or tricyclic ring system, wherein the cycloalkyl radical may be optionally substituted with one or more substituents described herein. In some embodiments, a cycloalkyl contains 3 to 12 carbon atoms. In other embodiments, a cycloalkyl contains 3 to 8 carbon atoms, and in still other embodiments, a cycloalkyl contains 3 to 6 carbon atoms.

Examples include, but are not limited to, cyclopropyl, cyclobutyl, cyclopentyl, cyclohexyl, suberyl, and the like.

The term "heterocyclyl" refers to a saturated or partially unsaturated, non-aromatic, monocyclic, bicyclic or tricyclic ring containing 3-12 ring atoms of which at least one ring atom is selected from nitrogen, sulfur and oxygen. Wherein the heterocyclyl radical may be optionally substituted with one or more substituents described herein. Unless otherwise specified, heterocyclyl maybe carbon or nitrogen linked, and of which a —$CH_2$— group can optionally be replaced by a —C(═O)— group. Ring sulfur atoms may be optionally oxidized to form S-oxides. Ring nitrogen atoms maybe optionally oxidized to form N-oxides. In some embodiments, heterocyclyl may be $C_{2-10}$ heterocyclyl, which contains 2-10 carbon atoms and at least one heteroatom selected from nitrogen, sulfur and oxygen; In other embodiments, heterocyclyl may be $C_{2-9}$ heterocyclyl, which contains 2-9 carbon atoms and at least one heteroatom selected from nitrogen, sulfur and oxygen; In still other embodiments, heterocyclyl may be $C_{2-7}$ heterocyclyl, which contains 2-7 carbon atoms and at least one heteroatom selected from nitrogen, sulfur and oxygen; In yet other embodiment, heterocyclyl may be $C_{2-5}$ heterocyclyl, which contains 2-5 carbon atoms and at least one heteroatom selected from nitrogen, sulfur and oxygen. Some non-limiting examples of heterocyclyl include pyrrolidinyl, tetrahydrofuranyl, tetrahydrothienyl, tetrahydropyrimidinyl, tetrahydropyranyl, piperidyl, morpholinyl, thiomorpholinyl, piperazinyl, homopiperazinyl, and the like. Some non-limited examples of heterocyclyl wherein —$CH_2$— group is replaced by —C(═O)— moiety are 2-oxypyrrolidinyl, 2-piperidinonyl, 3-morphlinonyl, 3-thiomorpholinonyl and the like.

The term "halogen" refers to F, Cl, Br or I.

The term "alkoxy" refers to an alkyl group, as previously defined, attached to the rest of the molecule through an oxygen atom. Some non-limiting examples include methoxy (MeO, —$OCH_3$), ethyoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), and the like.

The term "aryl" refers to a monocyclic, bicyclic or tricyclic carbocyclic ring system having a total of six to fourteen ring members, or six to twelve ring members, or six to ten ring members. Wherein at least one ring in the system is aromatic, wherein each ring in the system contains 3 to 7 ring members and that has one or more points of attachment to the rest of the molecule. The aryl is optionally substituted with one or more substituents described herein.

The term "heteroaryl" refers to a monocyclic, bicyclic, or tricyclic ring system having a total of 5 to 14 ring members, or 5 to 12 ring members, or 5 to 10 ring members or 5 to 6 ring members, wherein at least one ring in the system is aromatic, and at least one ring in the system contains one or more heteroatoms selected from nitrogen, sulfur and oxygen, wherein each ring in the system contains 5 to 7 ring members and that has one or more points of attachment to the rest of the molecule. The term "heteroaryl" may be used interchangeably with the term "heteroaryl ring" or "heteroaromatic compound". In some embodiments, heteroaryl may be $C_{1-9}$ heteroaryl, which contains 1-9 carbon atoms and at least one heteroatom selected from nitrogen, sulfur and oxygen; In other embodiments, heteroaryl may be $C_{1-7}$ heteroaryl, which contains 1-7 carbon atoms and at least one heteroatom selected from nitrogen, sulfur and oxygen; In other embodiments, heteroaryl may be $C_{1-6}$ heteroaryl, which contains 1-6 carbon atoms and at least one heteroatom selected from nitrogen, sulfur and oxygen; In still other embodiment, heteroaryl may be $C_{1-5}$ heteroaryl, which contains 1-5 carbon atoms and at least one heteroatom selected from nitrogen, sulfur and oxygen; In yet other embodiment, heteroaryl may be $C_{1-4}$ heteroaryl, which contains 1-4 carbon atoms and at least one heteroatom selected from nitrogen, sulfur and oxygen; In other embodiment, heteroaryl may be $C_{1-3}$ heteroaryl, which contains 1-3 carbon atoms and at least one heteroatom selected from nitrogen, sulfur and oxygen. Some non-limiting examples of suitable heteroaryl rings include the following monocycles: furanyl (e.g., 2-furanyl, 3-furanyl), imidazolyl (e.g., N-imidazolyl, 1-methyl-1H-imidazolyl, 2-imidazolyl, 4-imidazolyl, 5-imidazolyl), 3-isoxazolyl, 4-isoxazolyl, 5-isoxazolyl, 2-oxazolyl, 4-oxazolyl, 5-oxazolyl, thiazolyl (e.g., 2-thiazolyl, 4-thiazolyl, 5-thiazolyl); and some following bicycles examples include, but are not limited to, benzothiazolyl, benzimidazolyl, and the like.

As described herein, a bond drawn from a substituent to the center of one ring within a ring system (as shown Figure a) represents substitution of the substituent at any substitutable position on the rings. For example, as shown in Figure b, c, d, e, f, g and h.

Figure a

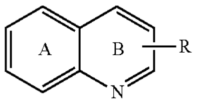

Figure b

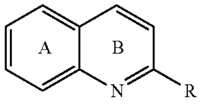

Figure c

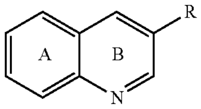

Figure d

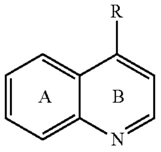

Figure e

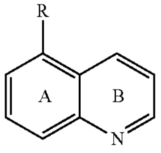

Figure f

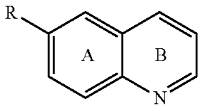

Figure g

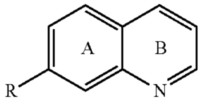

-continued

Figure h

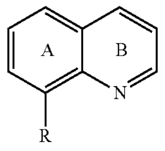

Furthermore, what need to be explained is that the phrases "each . . . and . . . is independently", "each of . . . and . . . is independently" are used interchangeably. It should be broadly understood that the specific options expressed by the same symbol are variable independently of each other in different groups; or the specific options expressed by the same symbol are variable independently of each other in same groups. For example, figure p, specific options of multiple m are variable independently of each other, and specific options of multiple $R^{4a}$ are independently of each other.

Figure p

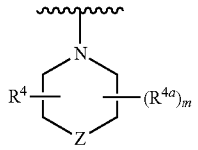

As described herein, there are two attaching points within a system attaching to the rest of the molecule, for example, either E or E', as shown in Formula q, can attach to the rest of the molecule and be used interchangeably with each other.

Figure q

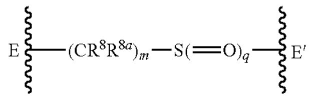

As described herein, a double bond attached to the rest of the molecule by a wave bond (as shown Figure k) refers to (Z) double bond isomers or (E) double bond isomers, or a mixture of (Z) double bond isomers and (E) double bond isomers.

Figure k

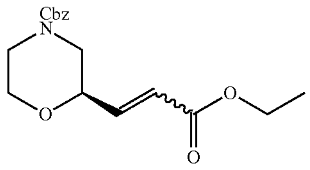

(Z) or (E)

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula (I) or (Ia). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14 of the A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Review Drug Discovery,* 2008, 7, 255-270, and Hecker et al., Prodrugs of Phosphates and Phosphonates, *J Med. Chem.,* 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker, et al., McGraw-Hill Dictionary of Chemical Terms (1984) McGraw-Hill Book Company, New York and Eliel, et al., "*Stereochemistry of Organic Compounds*", John Wiley & Sons, Inc., New York, 1994.

Any asymmetric atom (e.g., carbon or the like) of the compound(s) disclosed herein can be present in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci,* 1977, 66, 1-19, which is incorporated herein by reference. Some non-limiting examples of pharmaceutically acceptable salts include inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid salt, 2-hydracrylic acid salt, alginate, ascorbate, aspartate, benzenesulfonate, benzoate, bisulfate, borate, butyrate, camphanic acid salt, camphorsulfonate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine.

The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include $-CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$ (deuterium, D), $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$.

In another aspect, the compounds of the invention include isotopically enriched compounds as defined herein, for example those into which radioactive isotopes, such as $^{3}H$, $^{14}C$ and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) or (Ia) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I) or (Ia). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

DESCRIPTION OF COMPOUNDS OF THE INVENTION

The invention relates to novel dihydropyrimidine compounds and pharmaceutical compositions, and their uses in the manufacture of a medicament for preventing, managing, treating or lessening a viral disease, especially hepatitis B (HBV) infection or a disease caused by hepatitis B infection.

In one aspect, provided herein are compounds having Formula (I) or (Ia) or an enantiomer, a diastereoisomer, a tautomer, a hydrate, a solvate, a prodrug, a stereoisomer, an N-oxide, or a pharmaceutically acceptable salt thereof, (I)

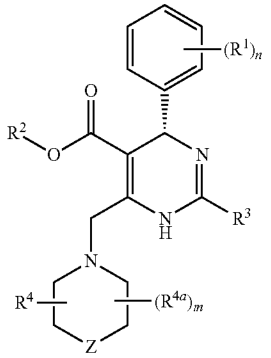

, or (Ia)

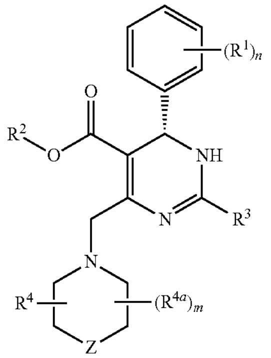

wherein each $R^1$ is independently H, F, Cl, Br, I, nitro, trifluoromethyl or cyano;

each $R^2$ is independently methyl or ethyl;

each $R^3$ is independently thiazolyl, oxazolyl or imidazolyl; wherein optionally each of thiazolyl, oxazolyl and imidazolyl is independently unsubstituted or substituted with methyl or cyclopropyl;

each Z is independently O or S;

each $R^4$ is independently $-(CR^5R^{5a})_t-C(=O)-OH$;

each $R^{4a}$ is independently H, methyl or isopropyl;

each $R^5$ and $R^{5a}$ is independently H, F or methyl, or $R^5$ and $R^{5a}$ together with the carbon atom to which they are attached, for cyclopropyl or $-C(=O)$, namely $CR^5R^{5a}$ is cyclopropyl or $-C(=O)$;

wherein, each n is independently 1, 2 or 3;

each m is independently 0, 1 or 2; and t is independently 1, 2, 3 or 4;

In certain embodiments, $R^3$ is

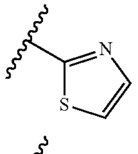
,
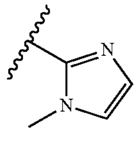
,

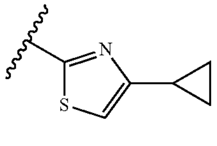
or
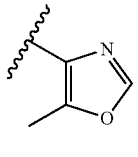
.

In other embodiments, provided herein is one of the compounds as follows, or an enantiomer, a diastereoisomer, a tautomer, a hydrate, a solvate, or a pharmaceutically acceptable salt thereof, and not limited to:

-continued
(1)
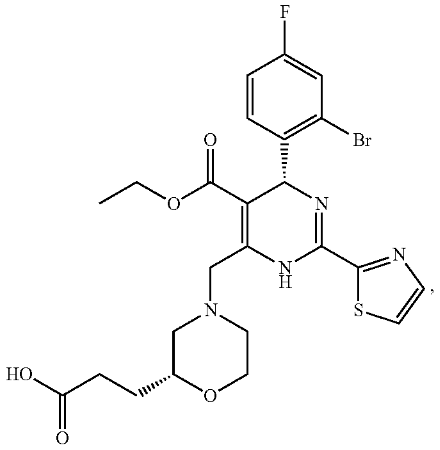
(2)
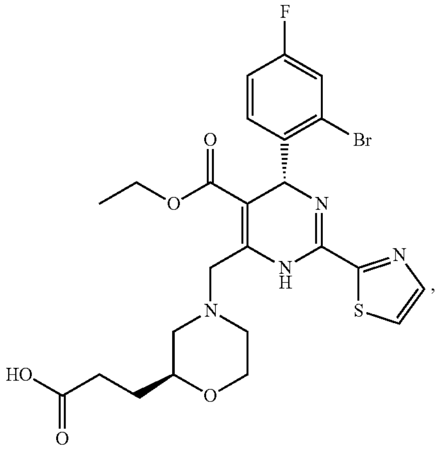
(3)
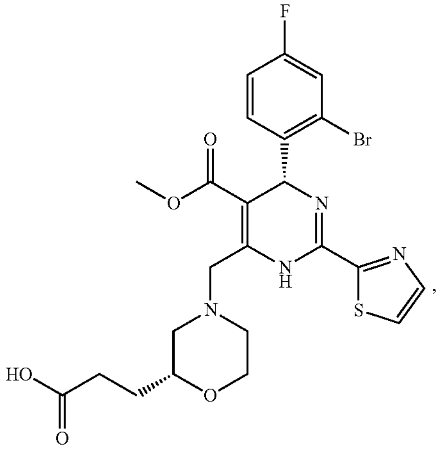
(4)
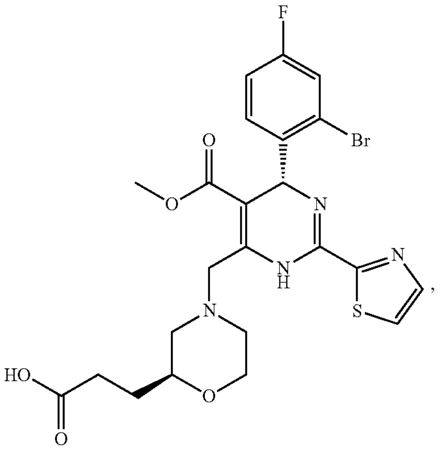
(5)
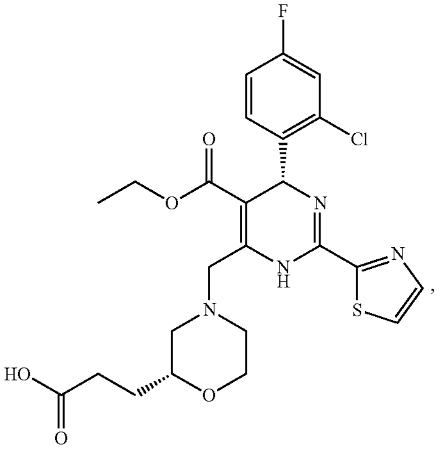
(6)
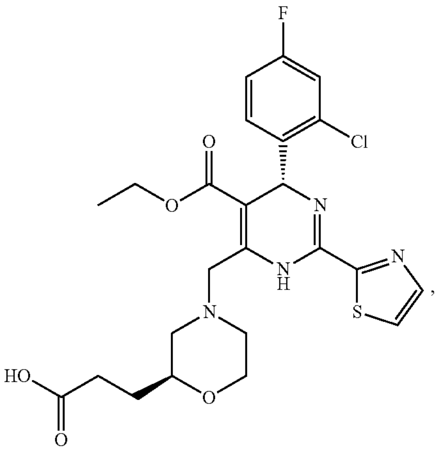

-continued
(7)
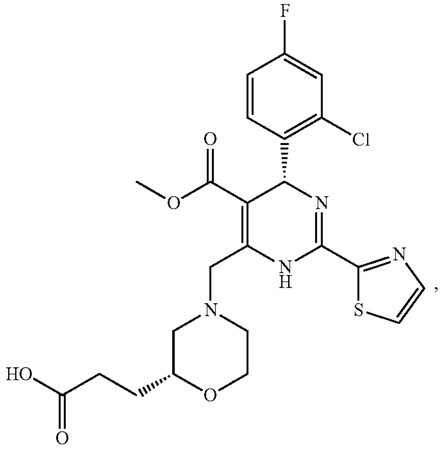
(8)
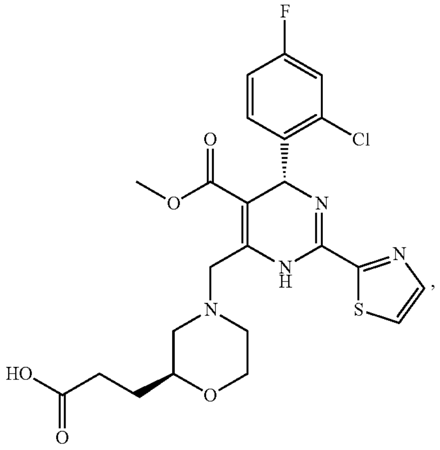
(9)
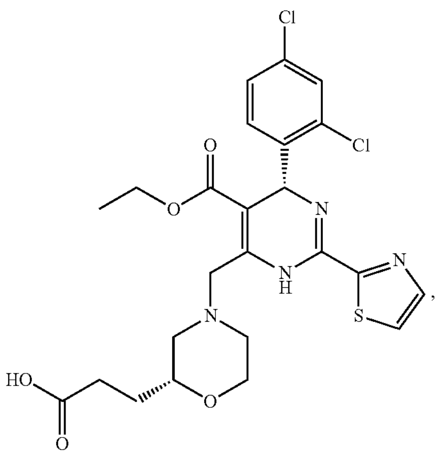
-continued
(10)
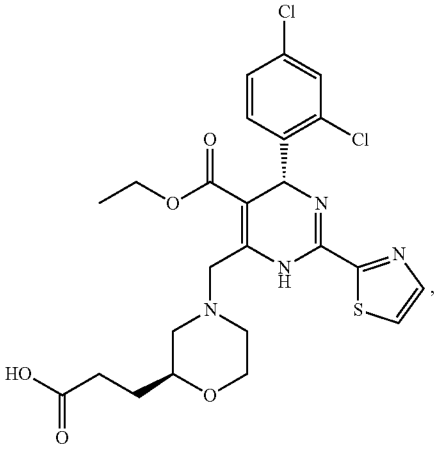
(11)
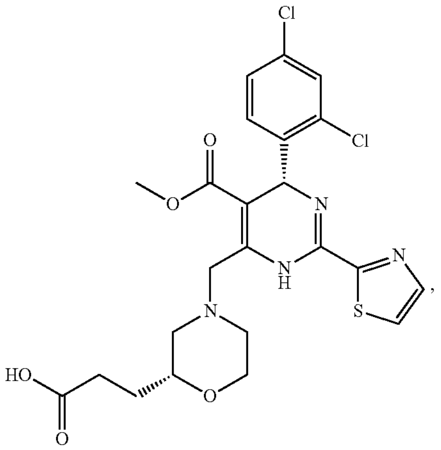
(12)
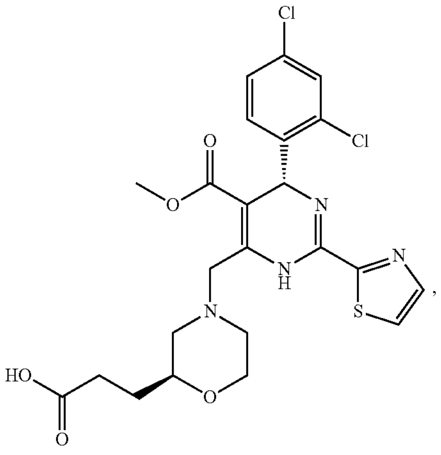

-continued
(13)
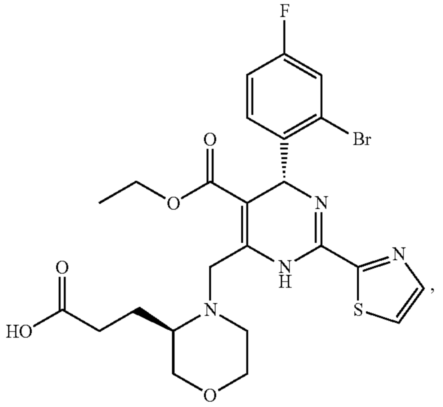
(14)
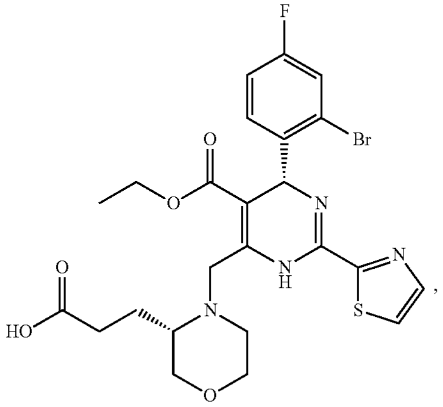
(15)
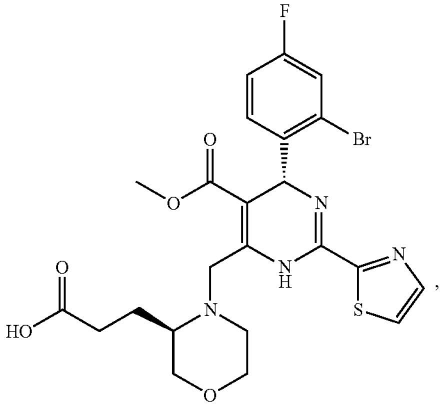
(16)
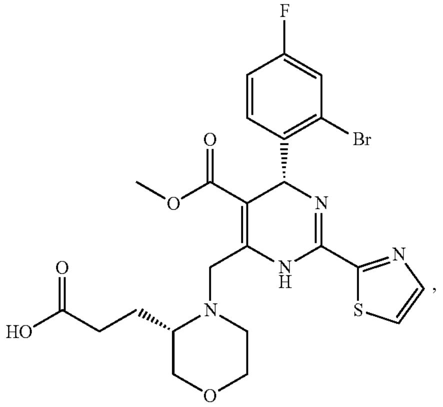
-continued
(17)
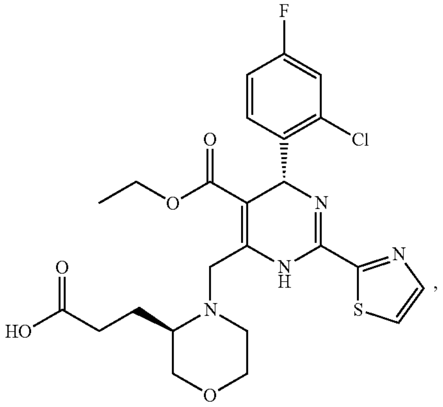
(18)
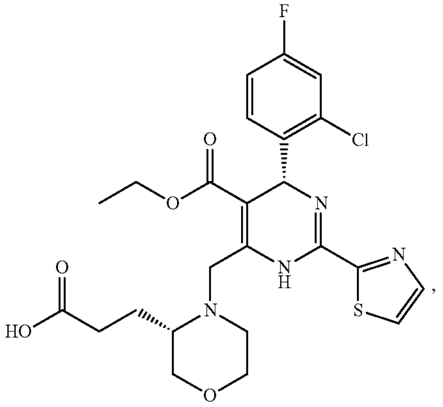
(19)
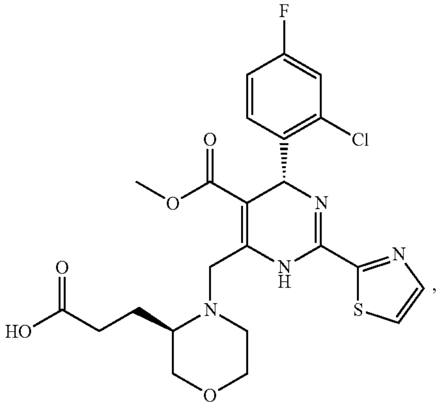
(20)
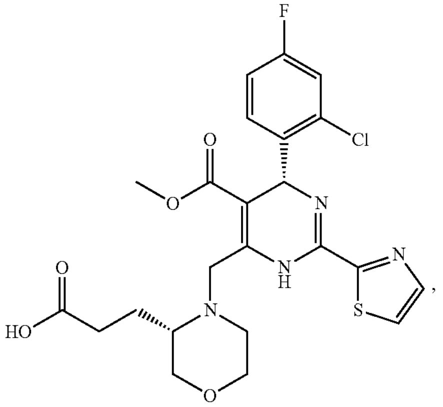

-continued
(21)
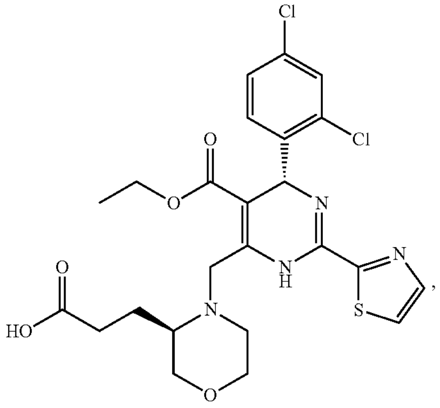
(22)
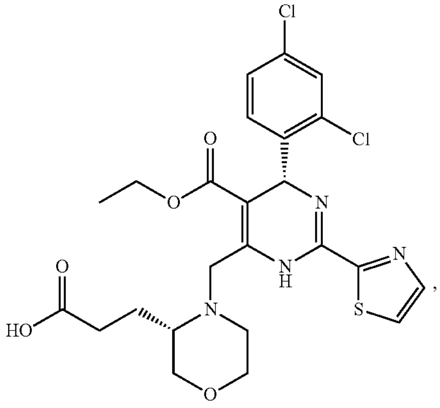
(23)
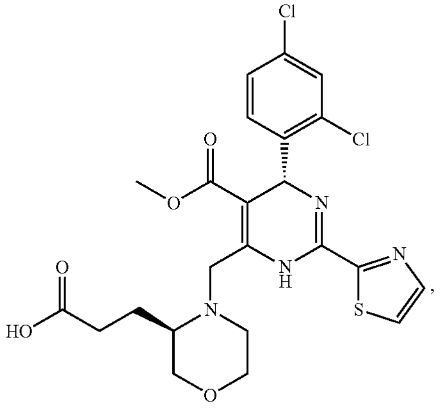
(24)
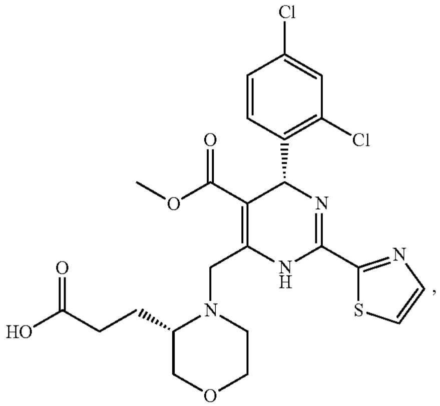
-continued
(25)
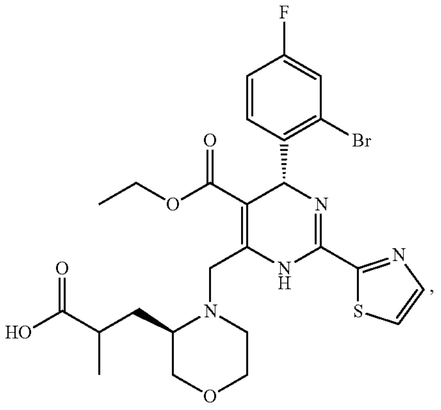
(26)
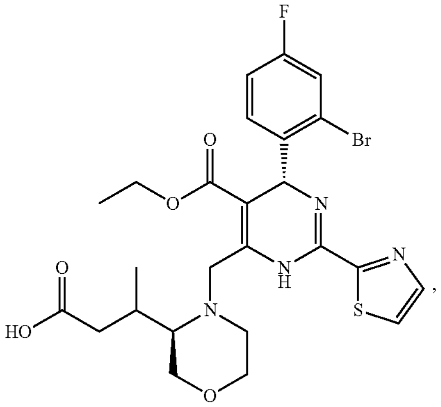
(27)
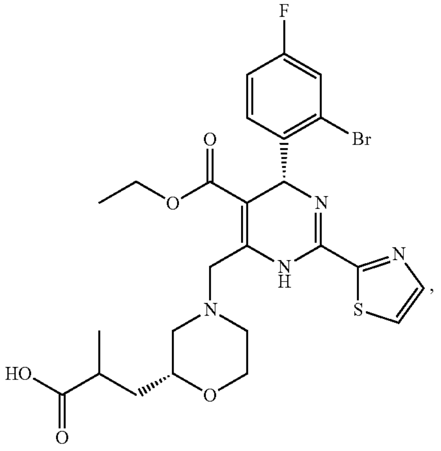

-continued
(28)
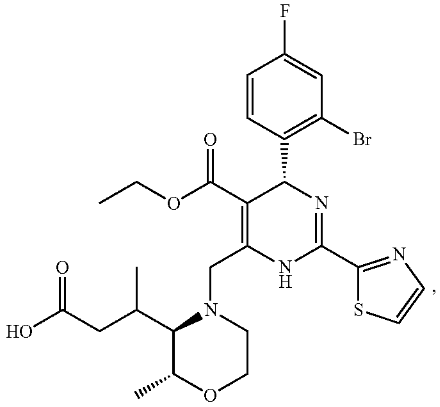,
(29)
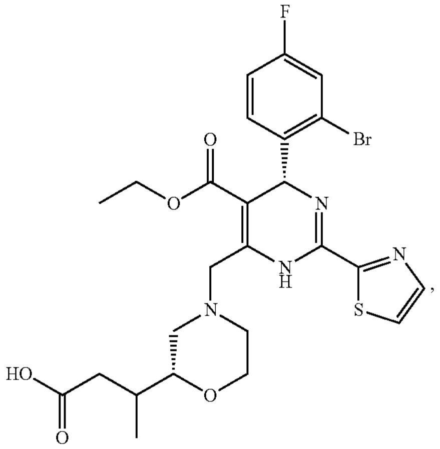,
(30)
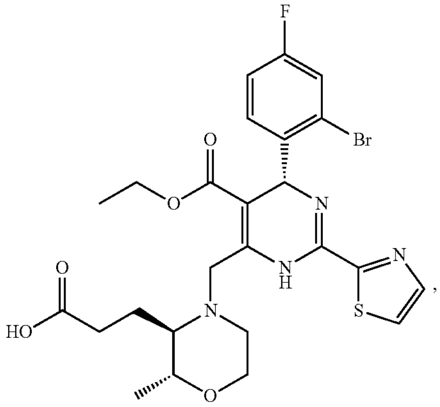,
(31)
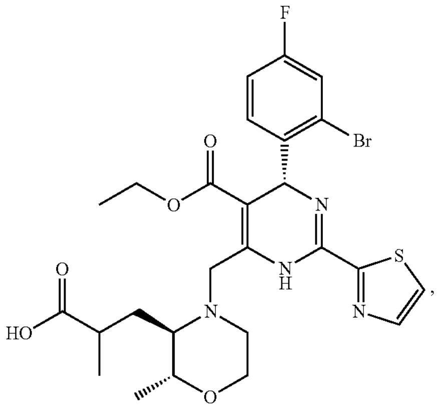,
-continued
(32)
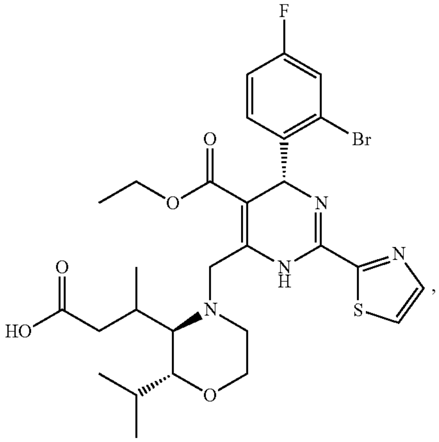,
(33)
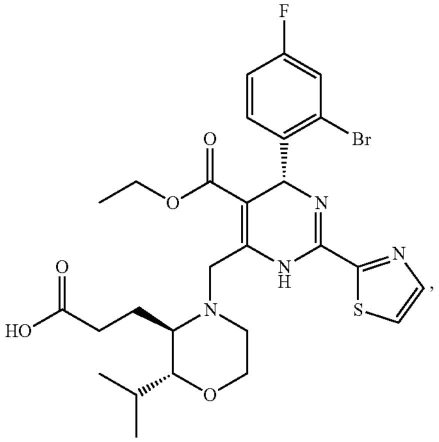,
(34)
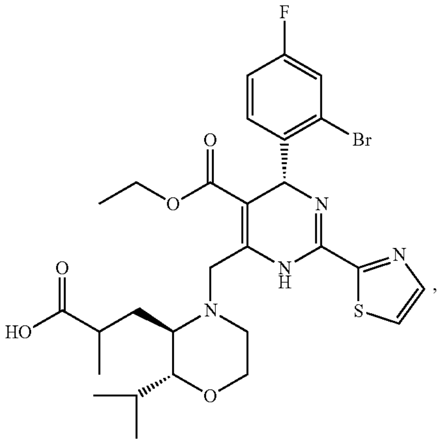, -continued
(35)
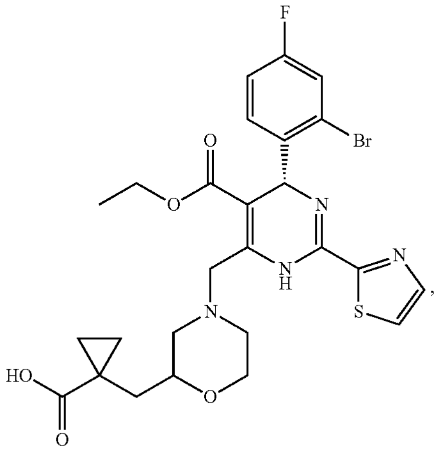
(36)
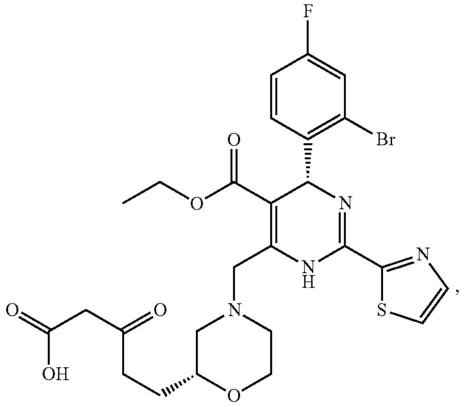
(37)
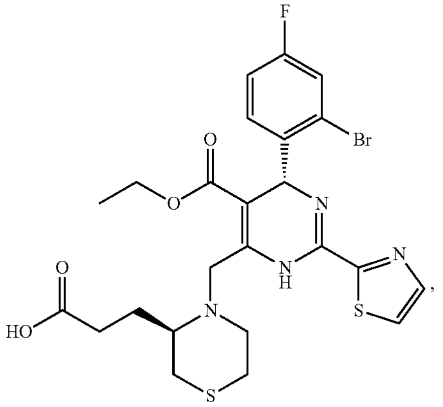
-continued
(38)
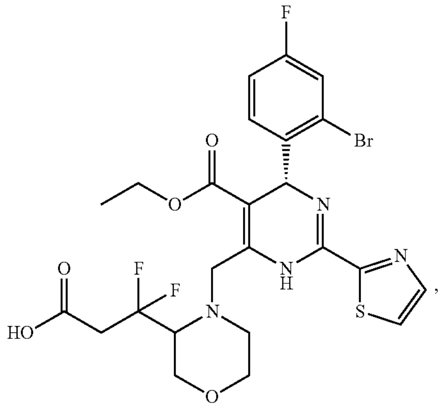
(39)
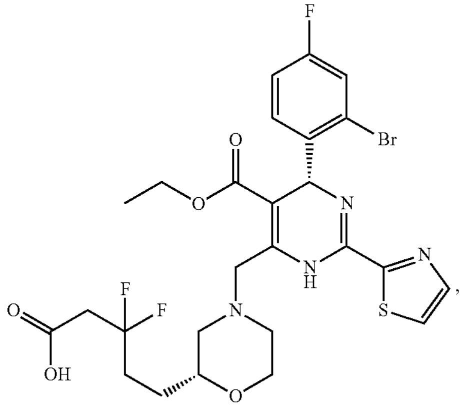
(40)
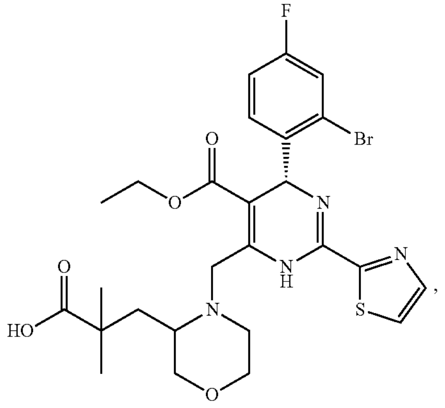
(41)
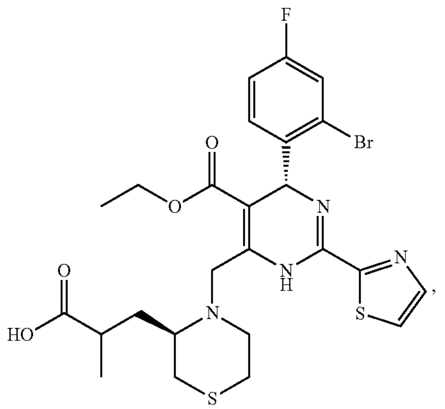

-continued
(42)
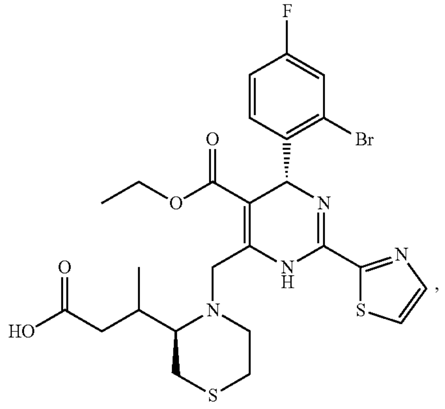
(43)
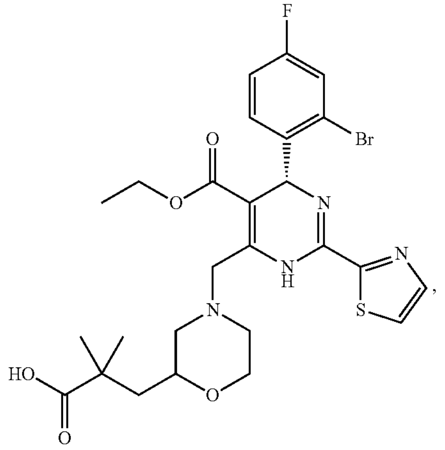
(44)
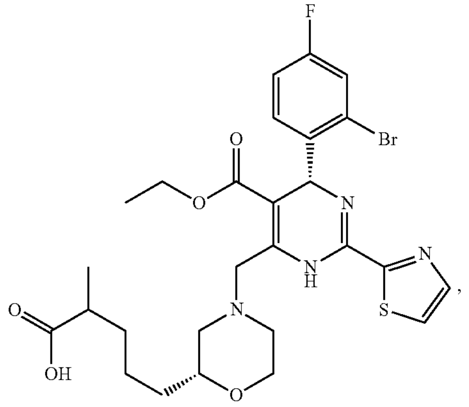
-continued
(45)
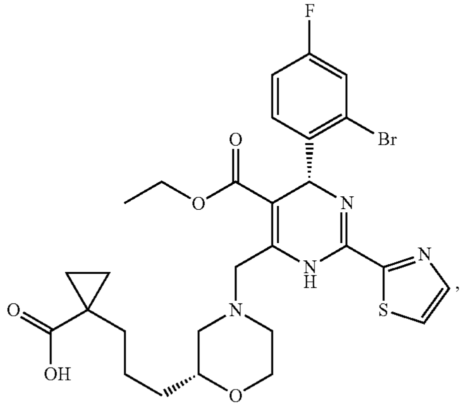
(46)
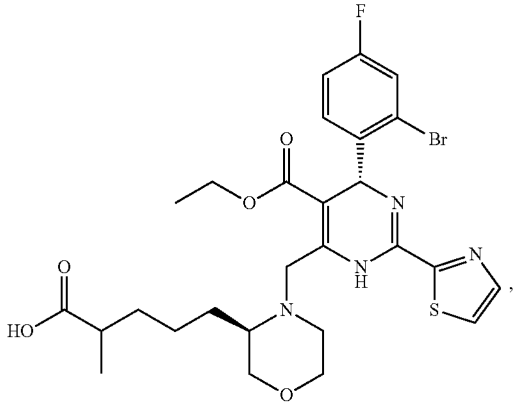
(47)
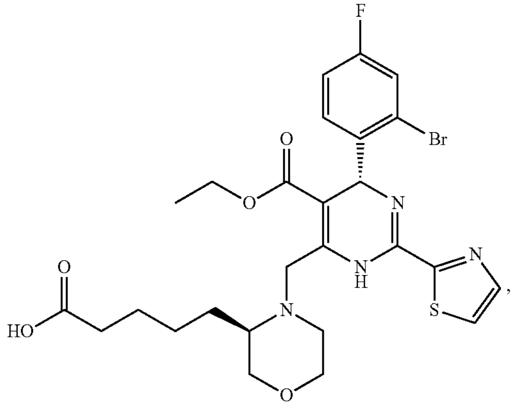

-continued
(48)
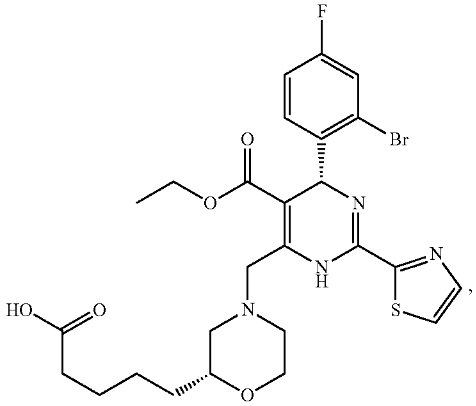,
(49)
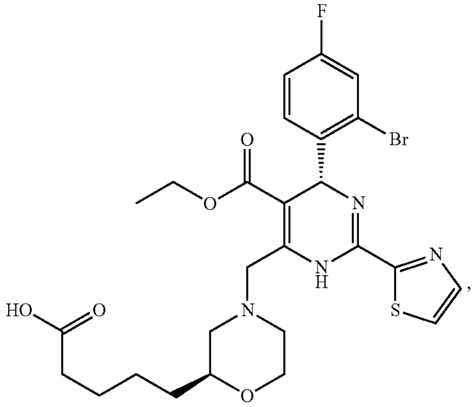,
(50)
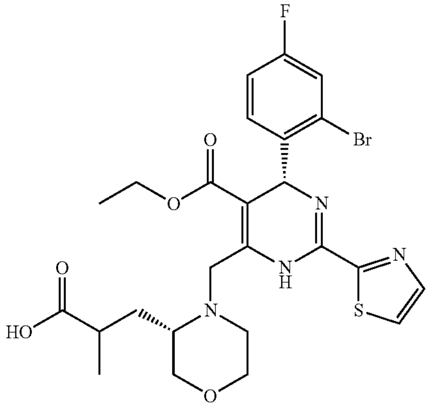,
(51)
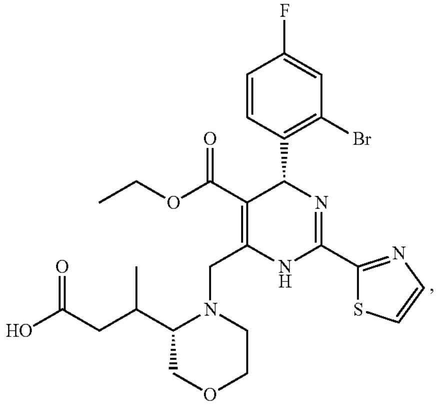,
-continued
(52)
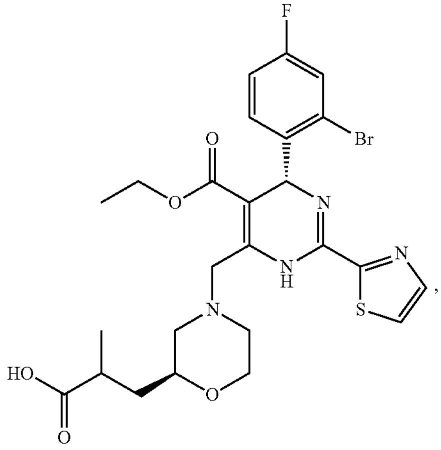,
(53)
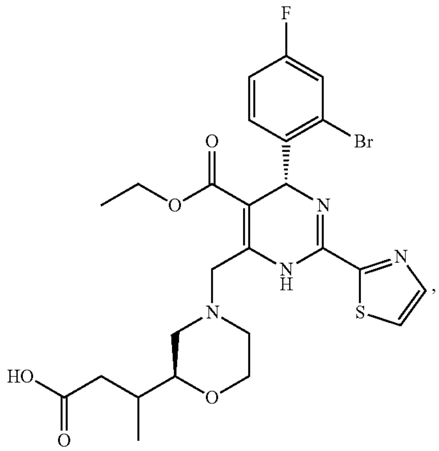,
(54)
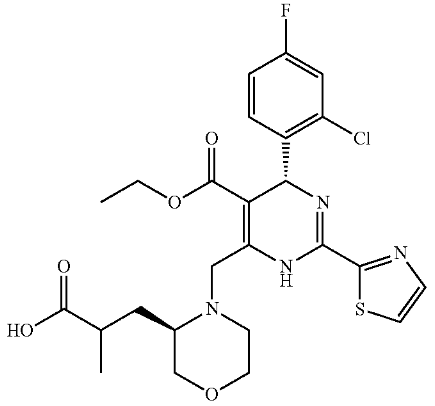, -continued
(55)
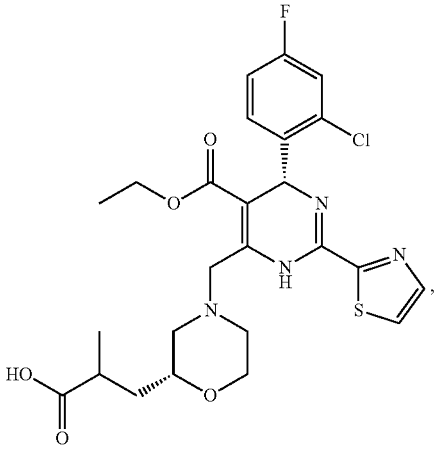
(56)
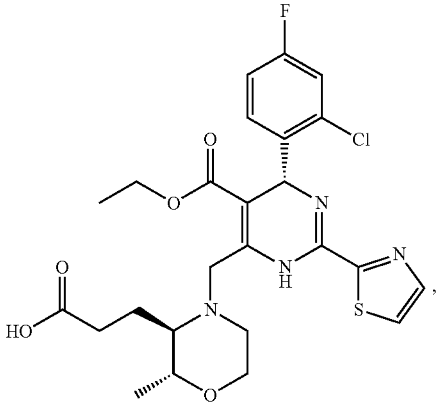
(57)
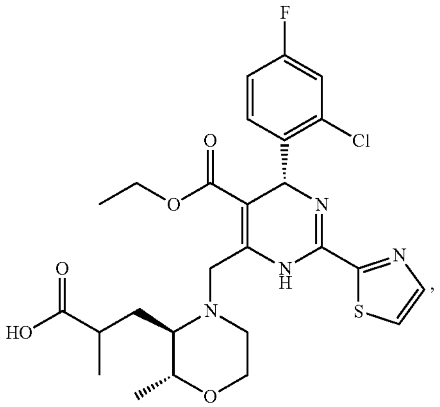
-continued
(58)
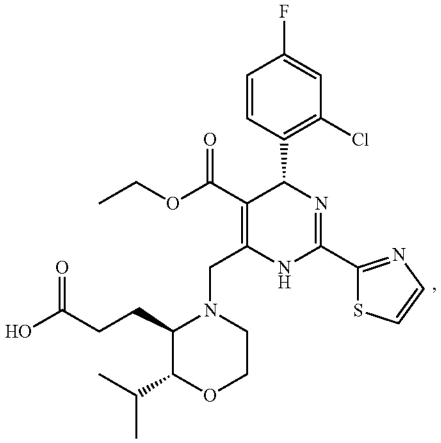
(59)
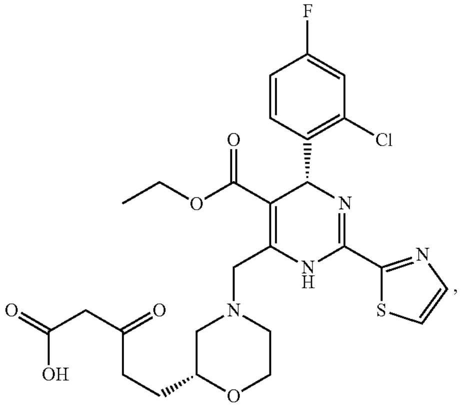
(60)
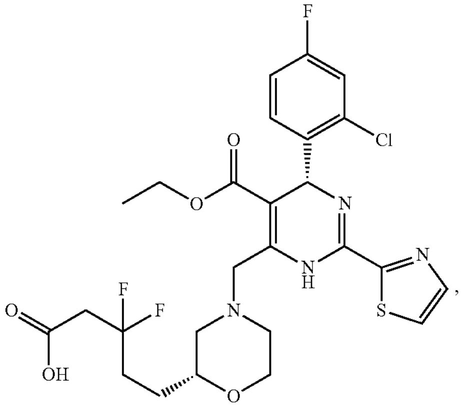

-continued
(61)
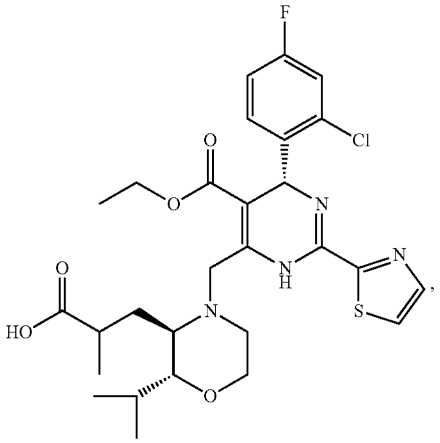
(62)
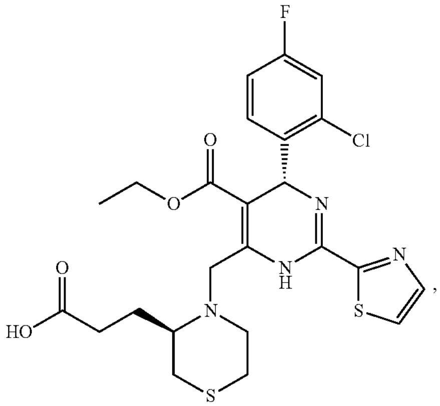
(63)
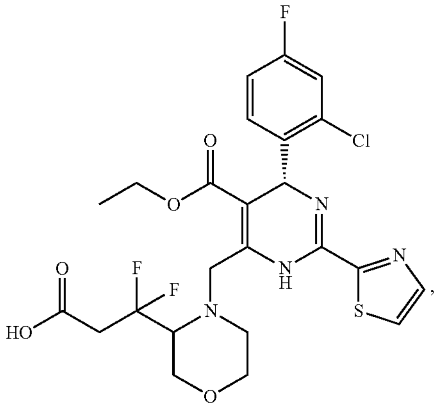
-continued
(64)
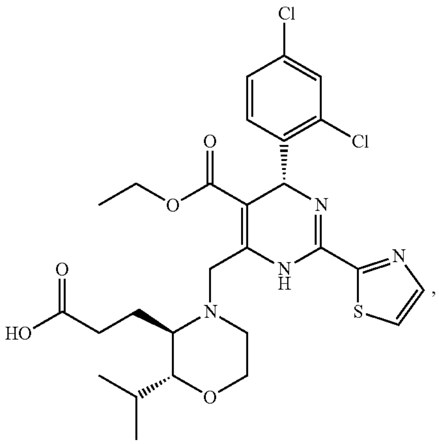
(65)
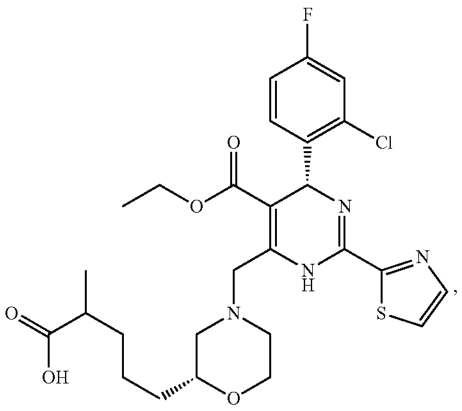
(66)
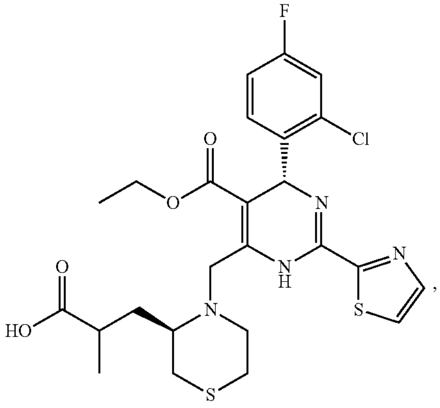

-continued
(67)
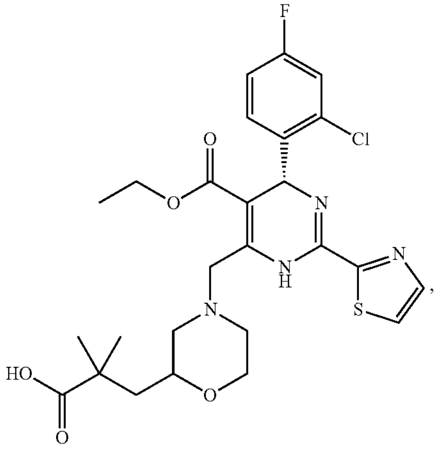
(68)
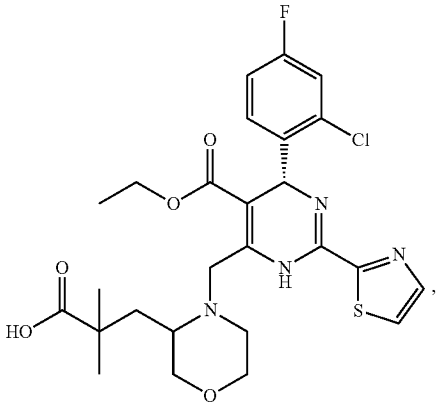
(69)
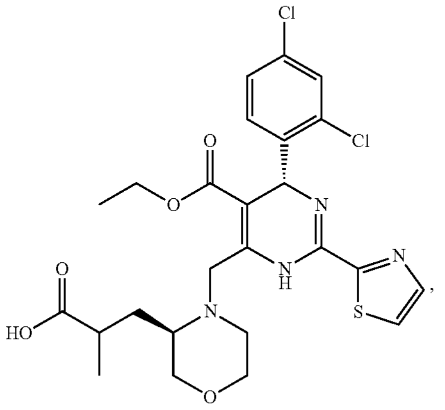
-continued
(70)
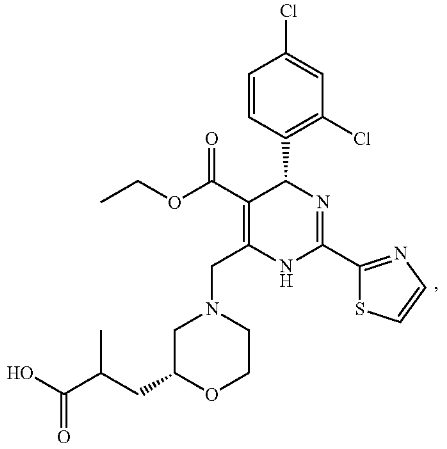
(71)
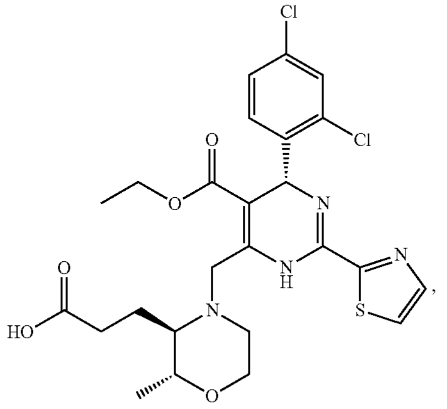
(72)
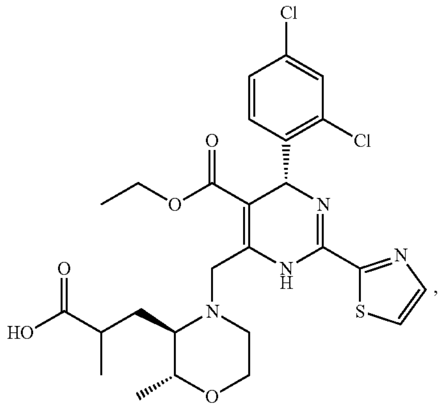

-continued
(73)
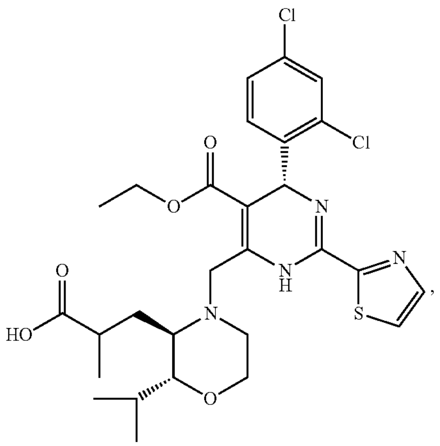
(74)
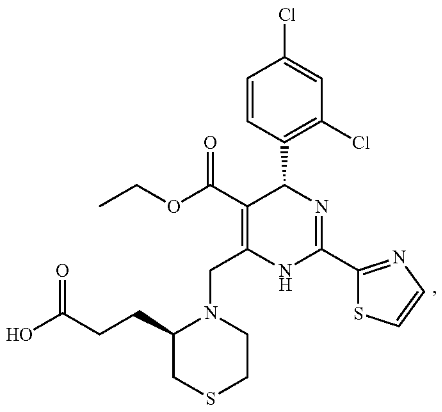
(75)
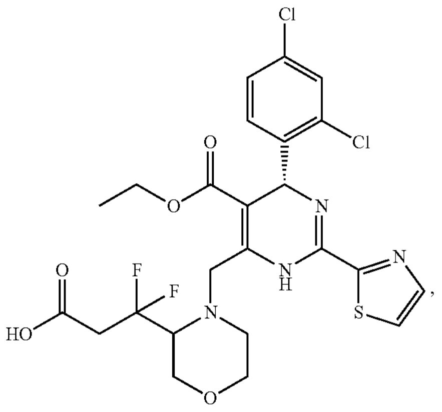
-continued
(76)
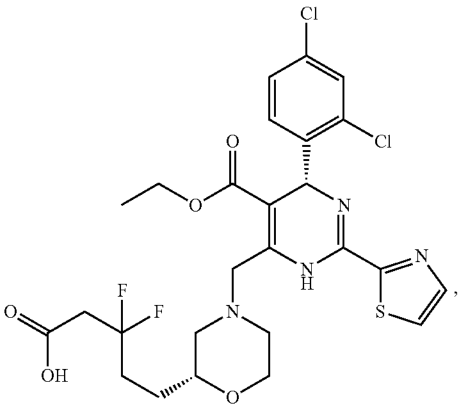
(77)
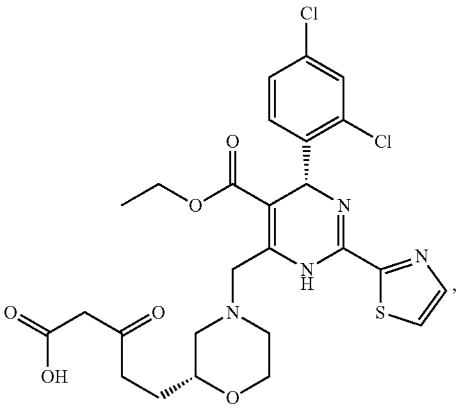
(78)
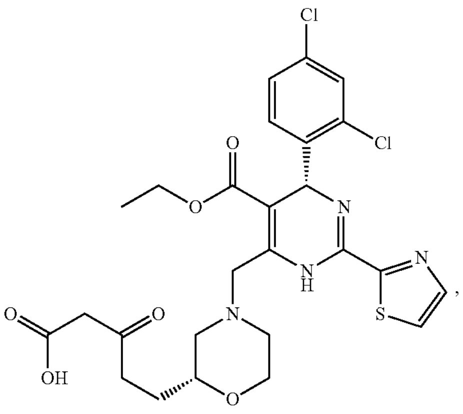

-continued
(79)
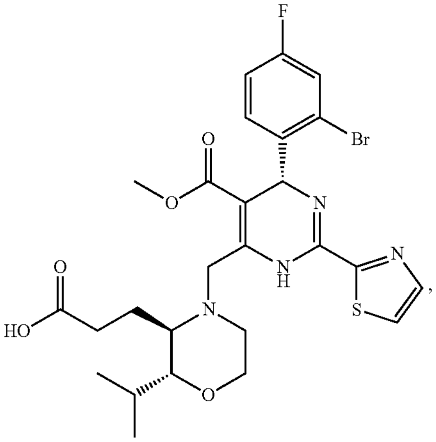
(80)
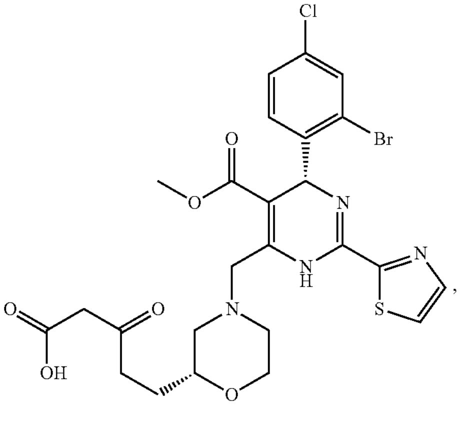
(81)
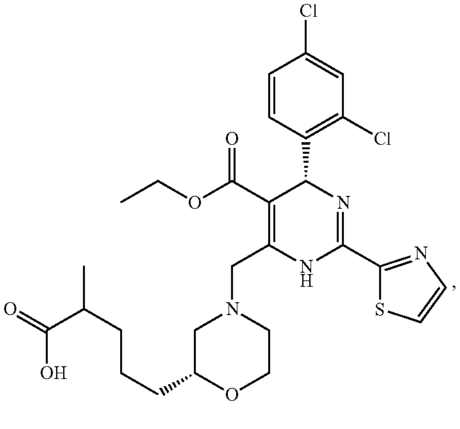
-continued
(82)
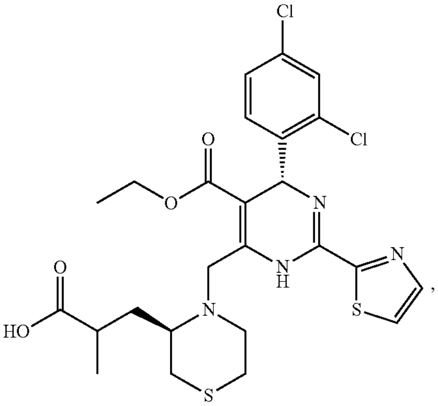
(83)
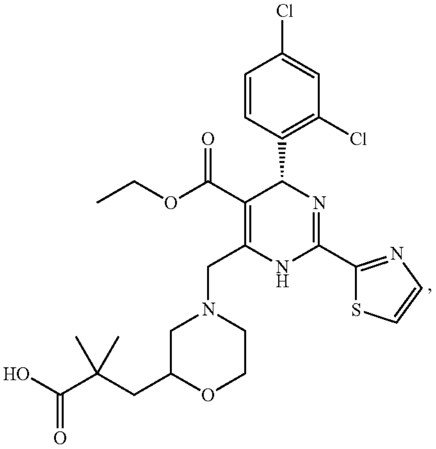
(84)
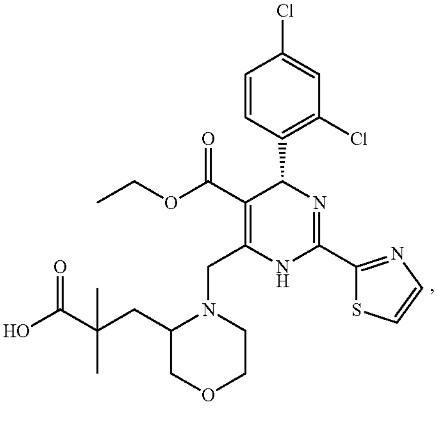

(85)
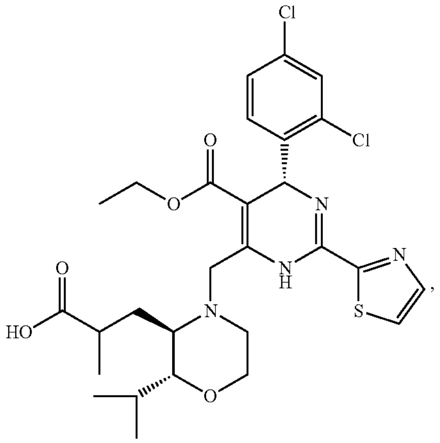
(86)
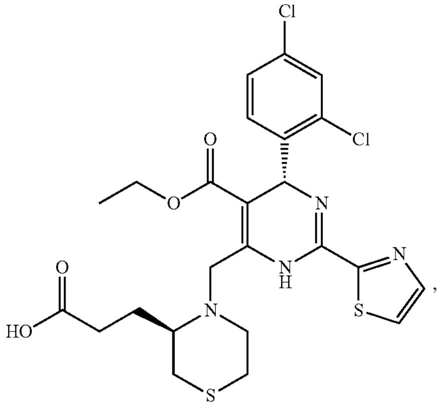
(87)
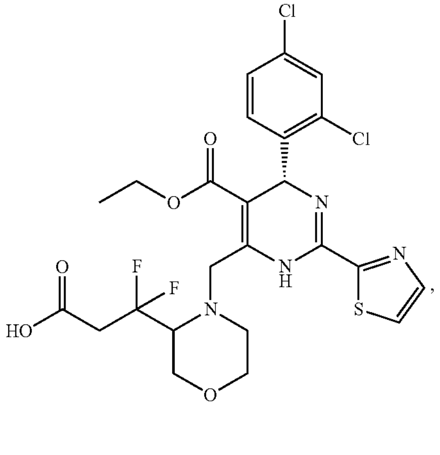
(88)
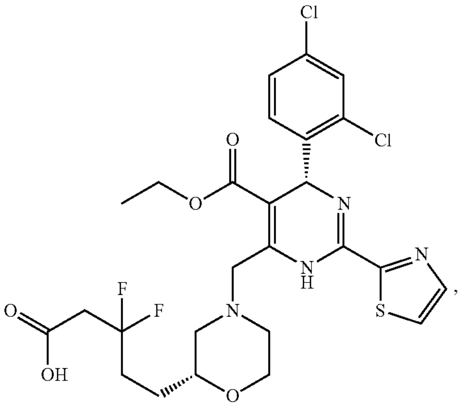
(89)
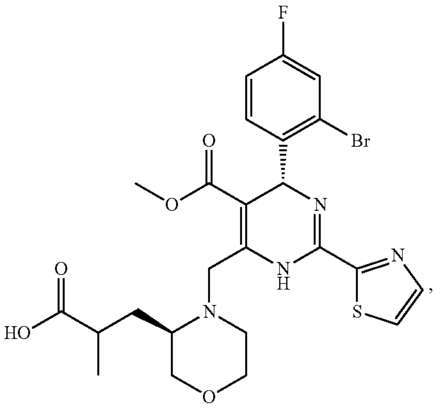
(90)
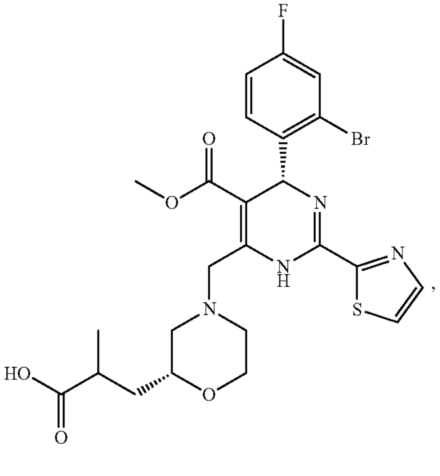

-continued
(91)
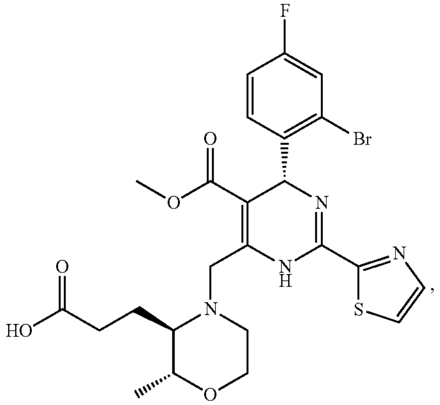
(92)
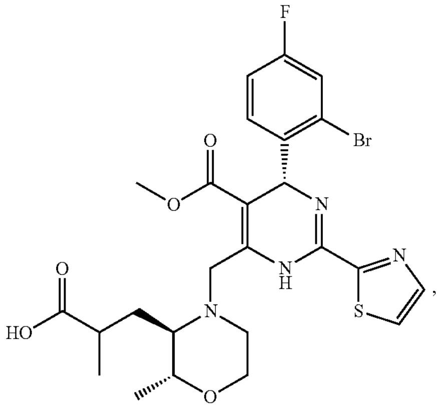
(93)
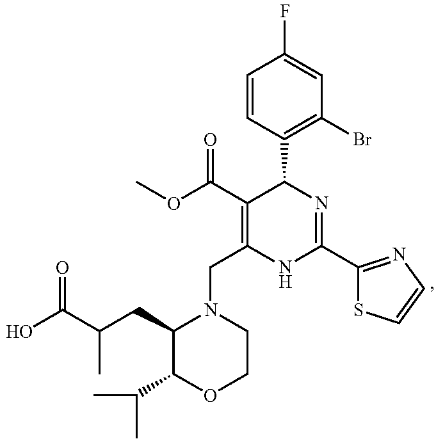
-continued
(94)
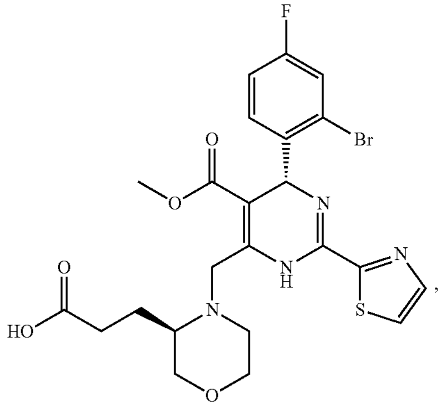
(95)
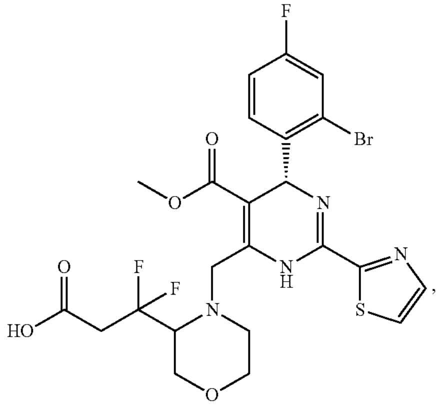
(96)
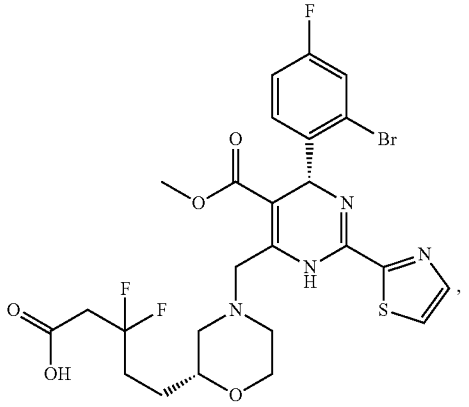
(97)
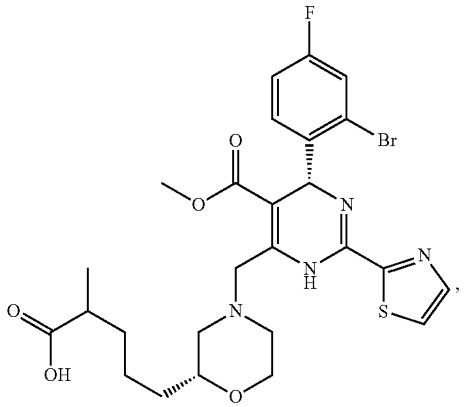

-continued
(98)
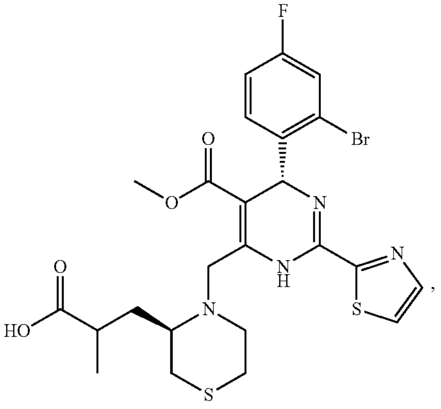
(99)
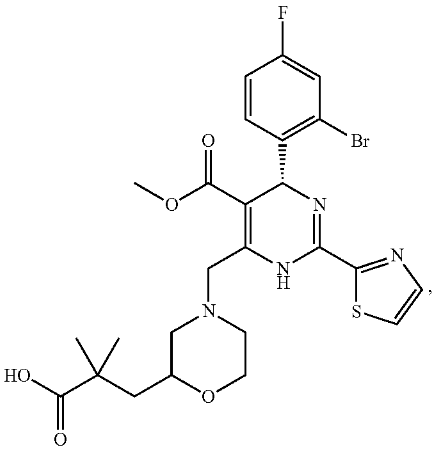
(100)
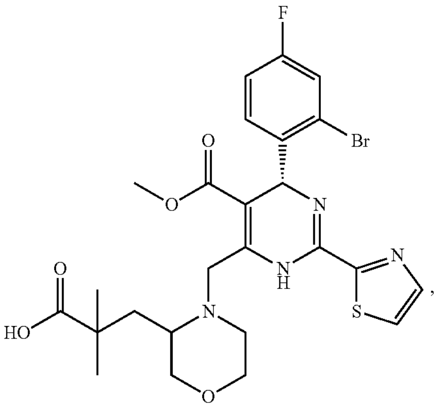
-continued
(101)
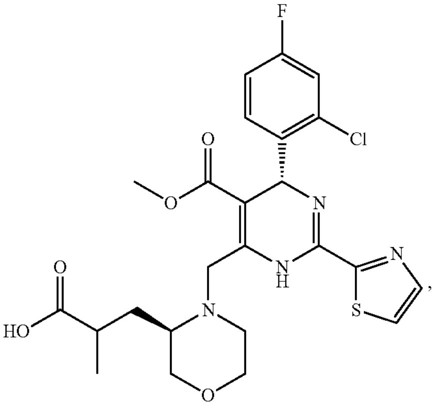
(102)
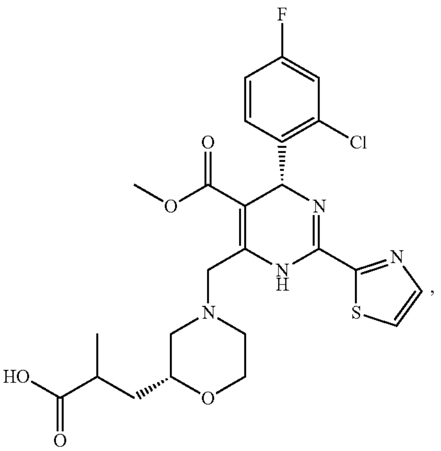
(103)
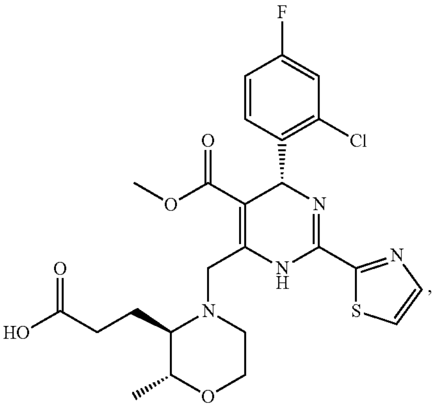

-continued
(104)
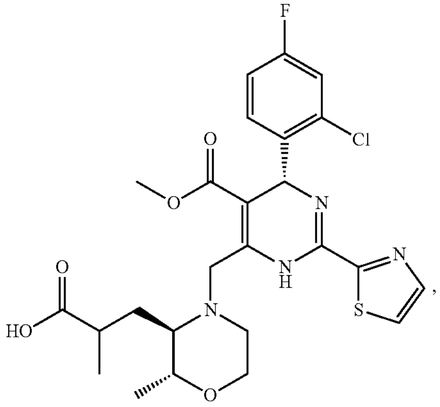
(105)
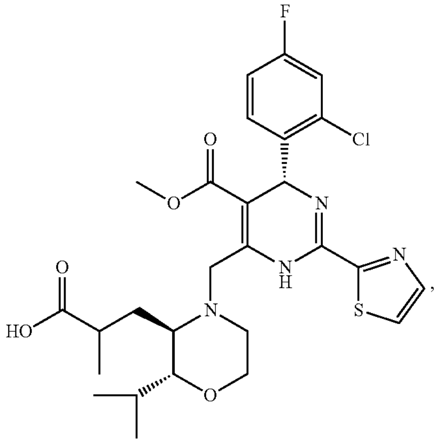
(106)
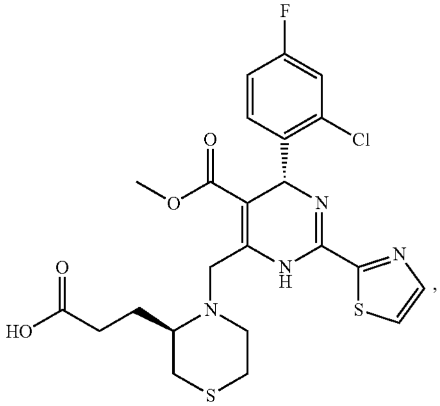
-continued
(107)
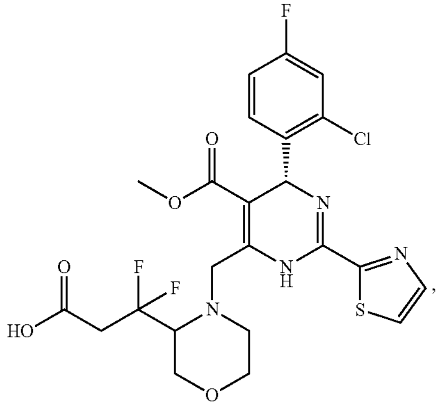
(108)
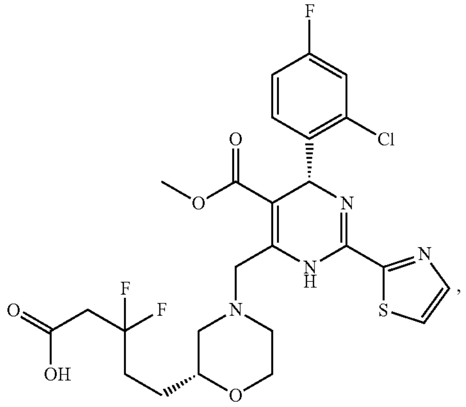
(109)
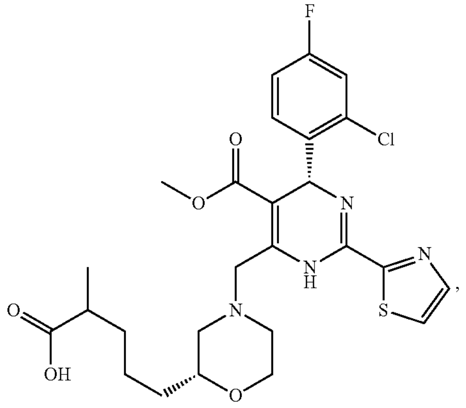
(110)
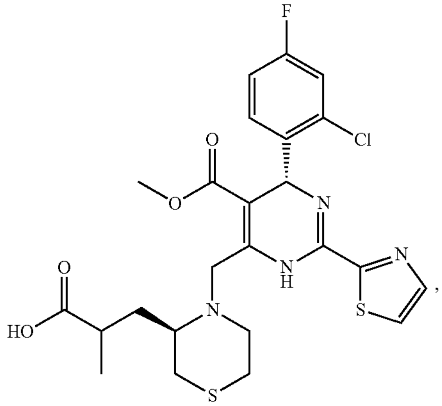

-continued
(111)
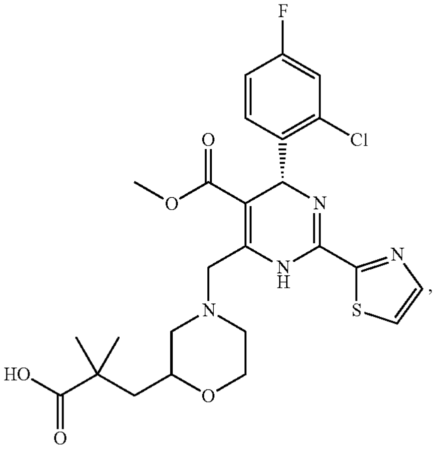
(112)
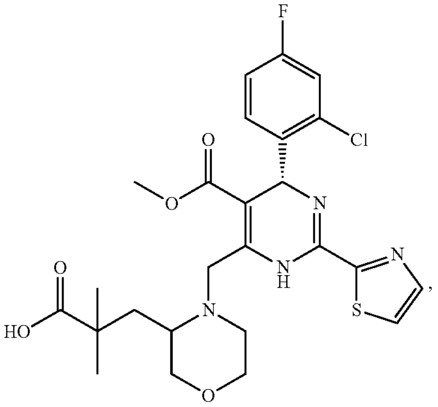
(113)
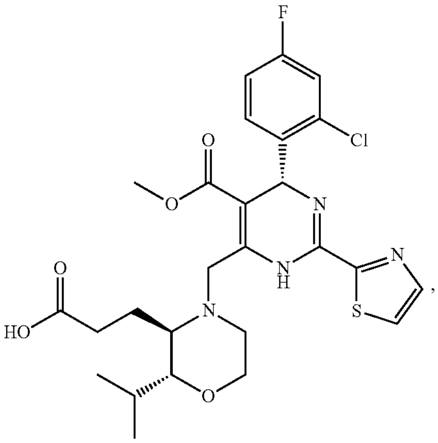
-continued
(114)
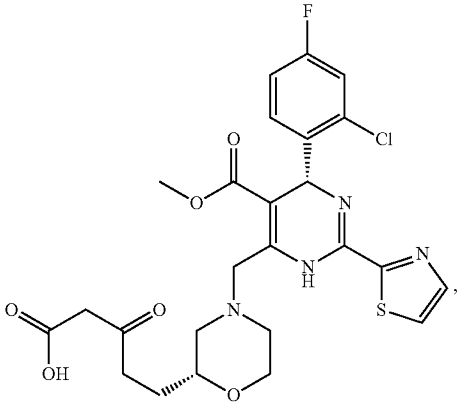
(115)
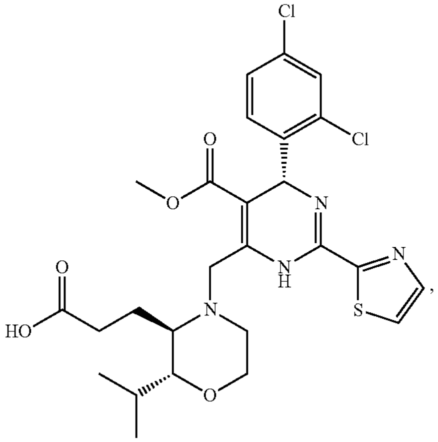
(116)
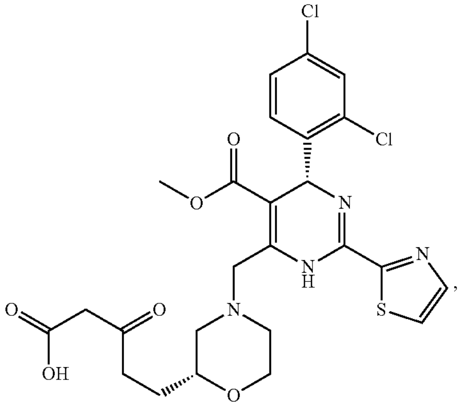

-continued
(117)
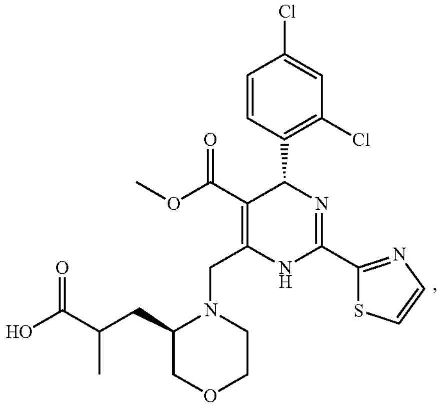
(118)
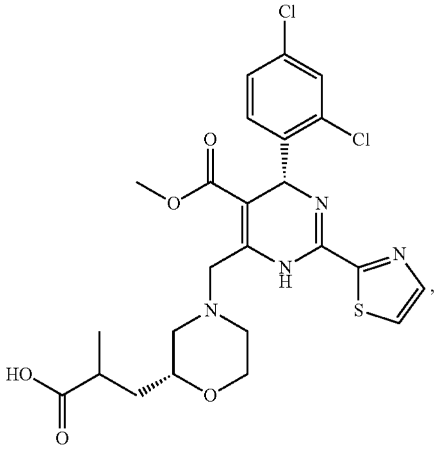
(119)
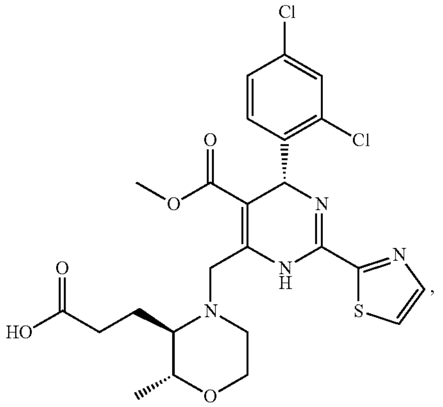
-continued
(120)
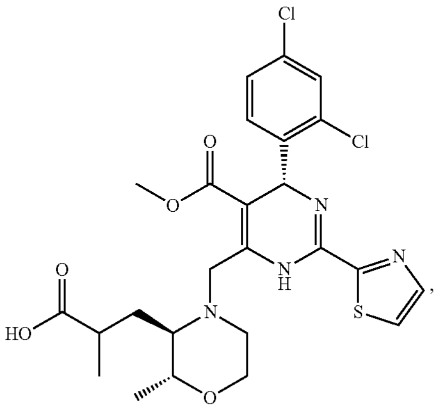
(121)
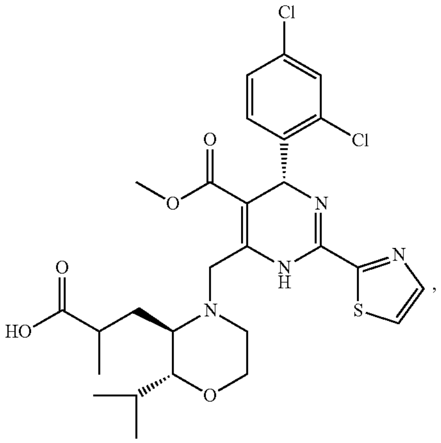
(122)
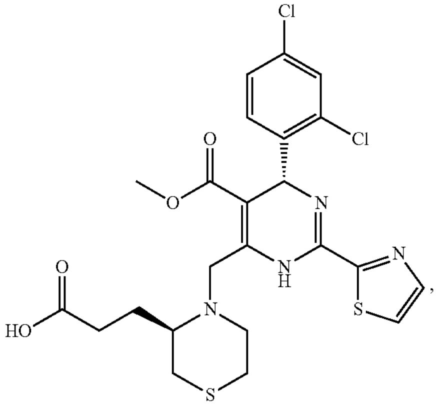

-continued
(123)
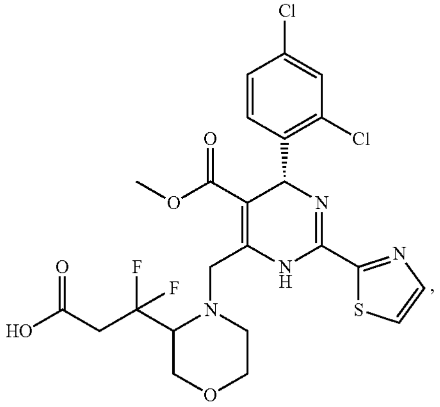
(124)
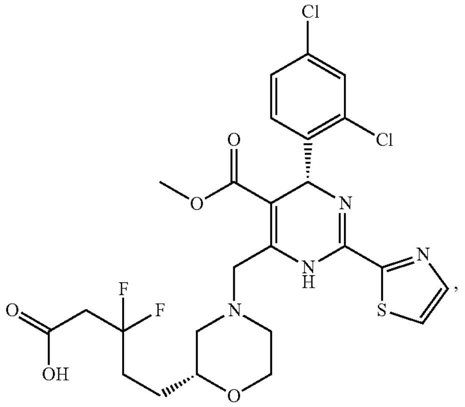
(125)
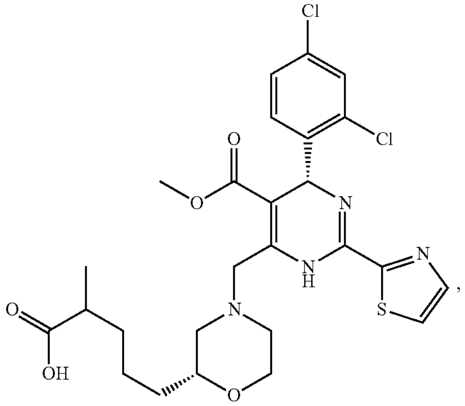
(126)
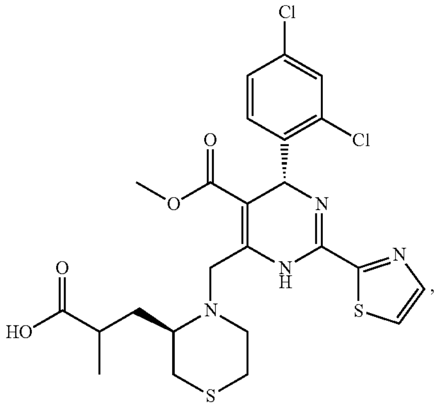
-continued
(127)
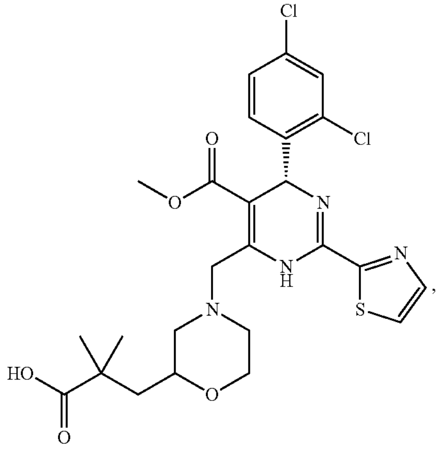
(128)
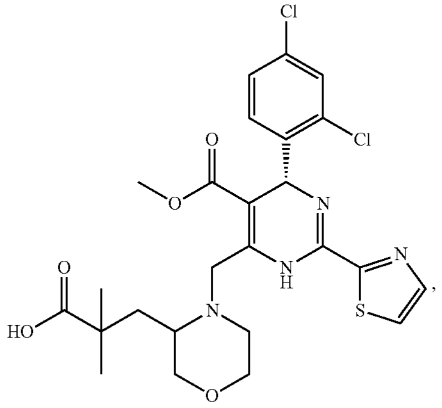
(129)
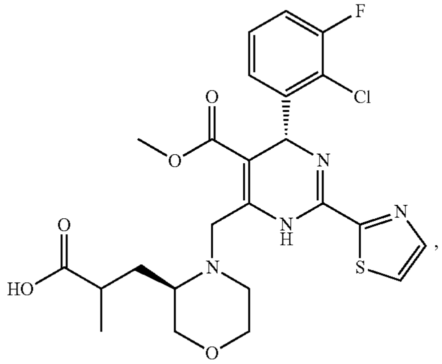
(130)
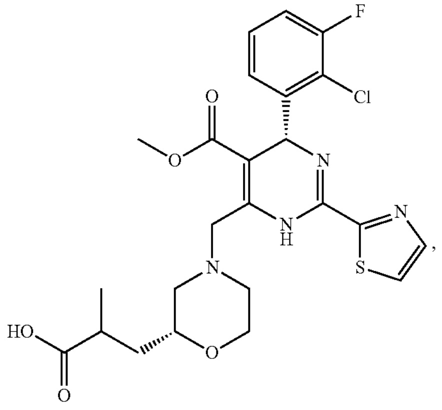

-continued
(131)
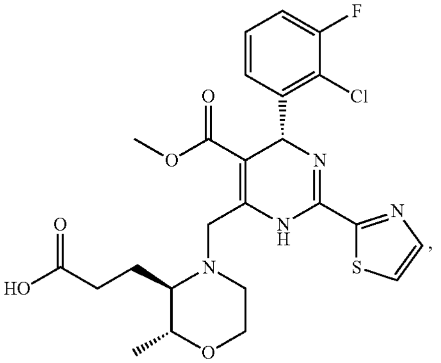
(132)
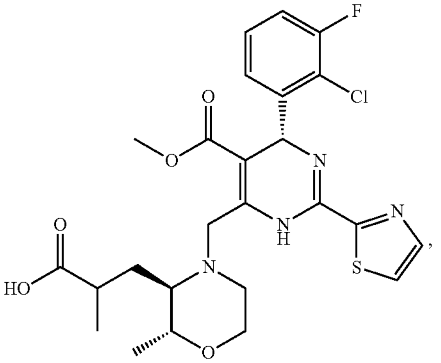
(133)
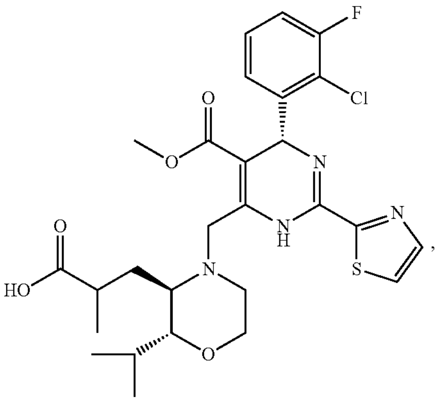
(134)
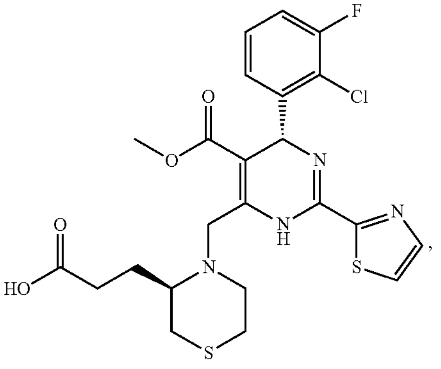
-continued
(135)
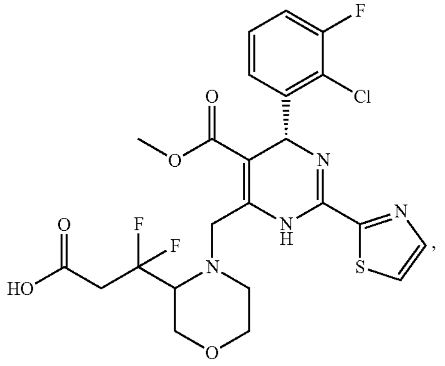
(136)
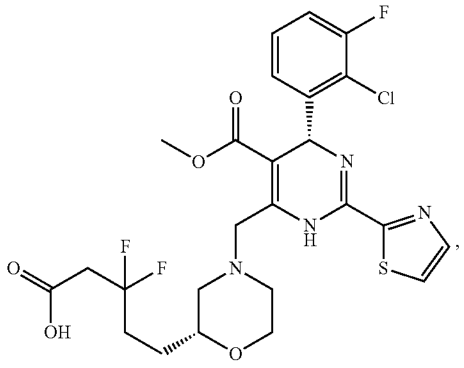
(137)
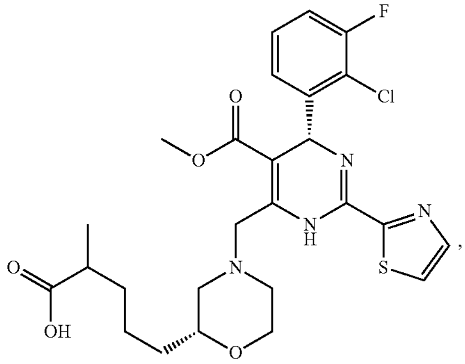
(138)
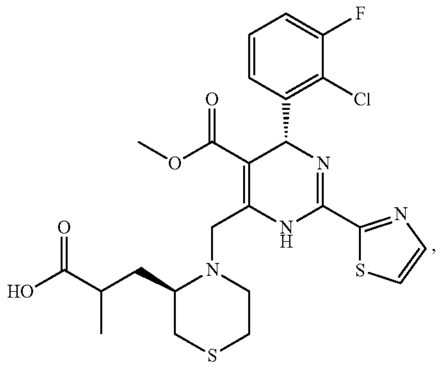

-continued
(139)
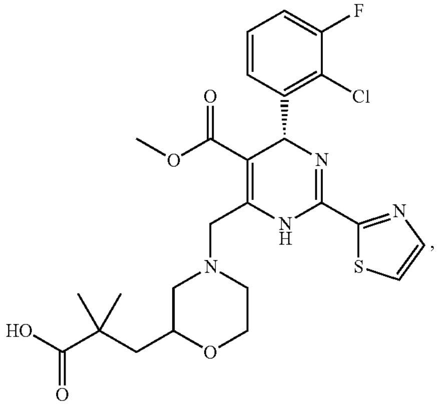
(140)
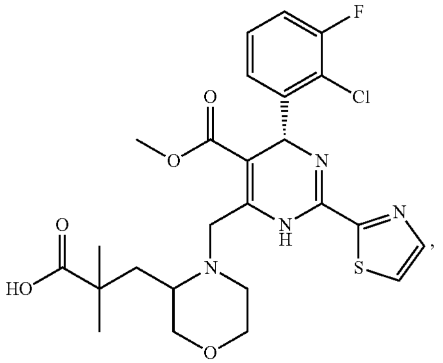
(141)
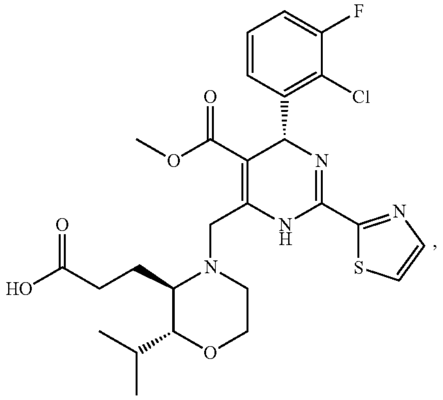
(142)
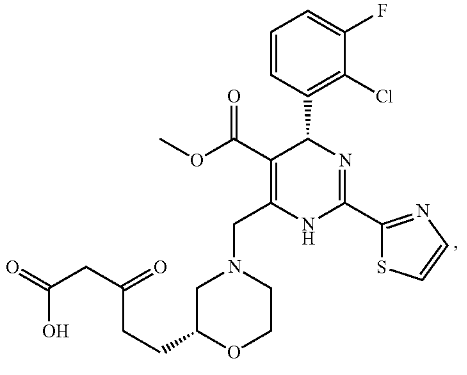
-continued
(143)
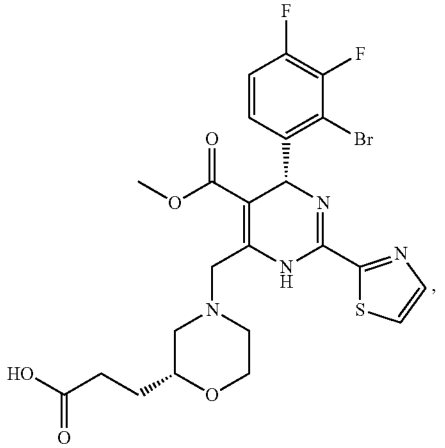
(144)
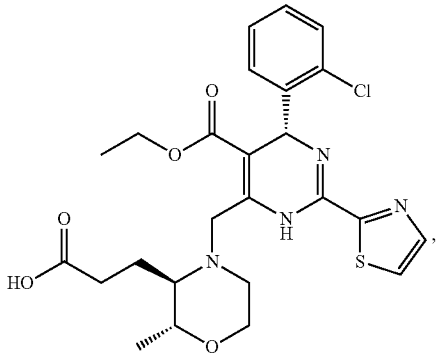
(145)
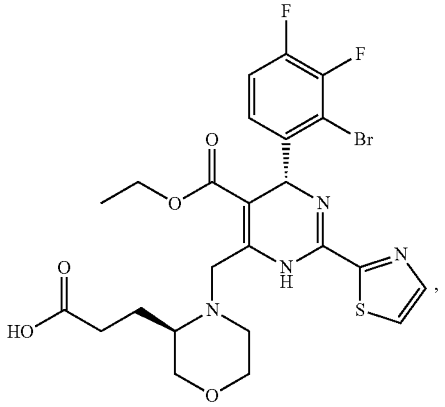
(146)
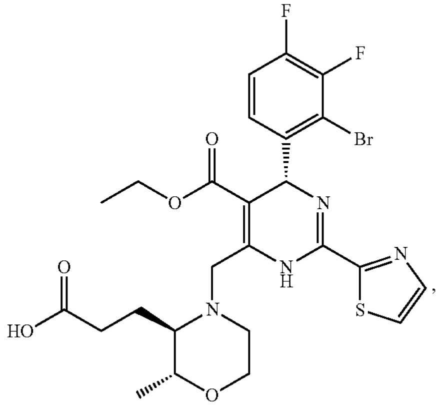

-continued
(147)
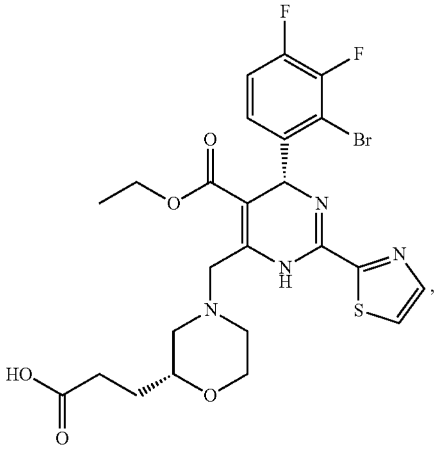
(148)
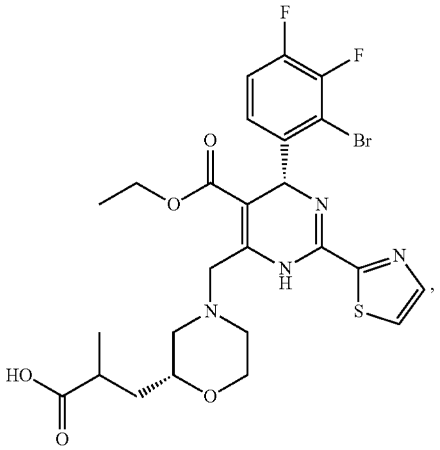
(149)
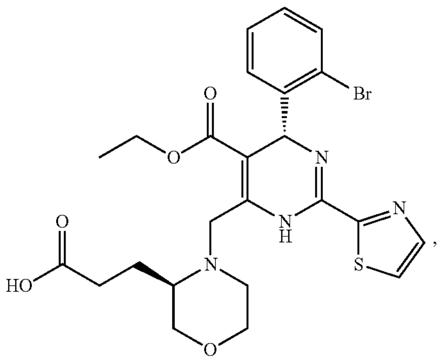
(150)
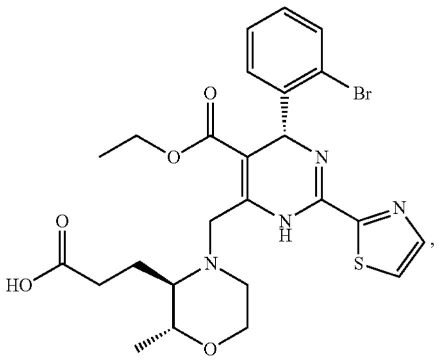
-continued
(151)
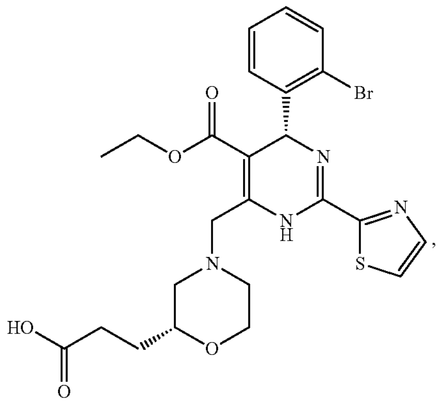
(152)
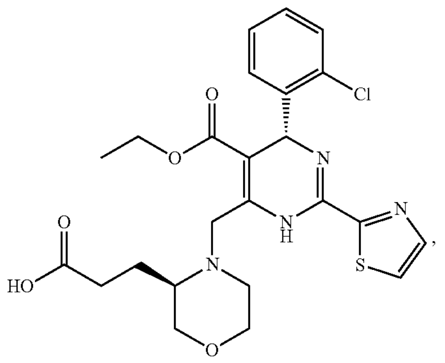
(153)
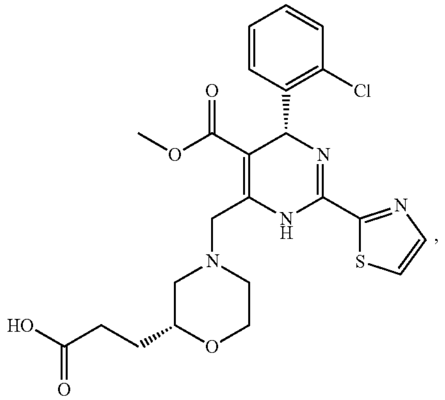
(154)
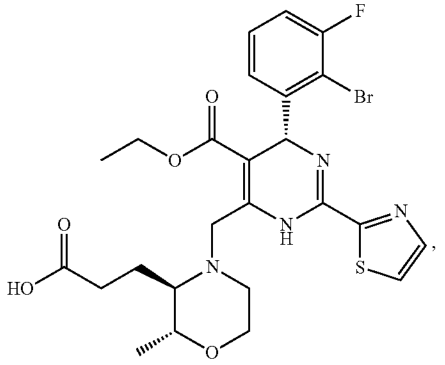

-continued
(155)
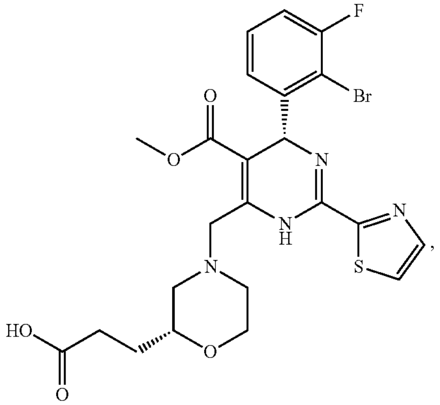
(156)
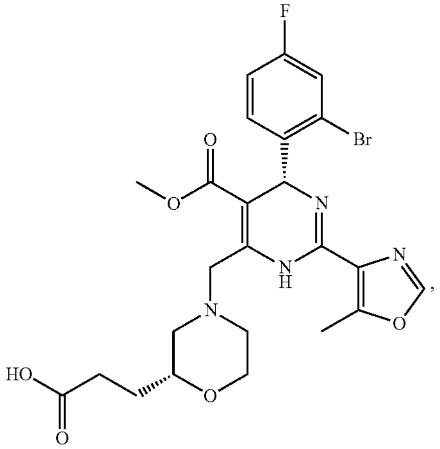
(157)
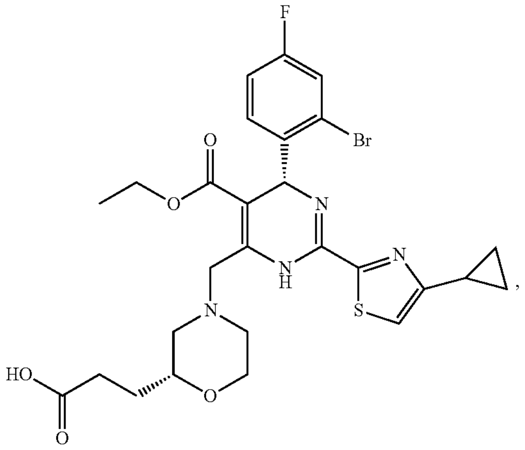
-continued
(158)
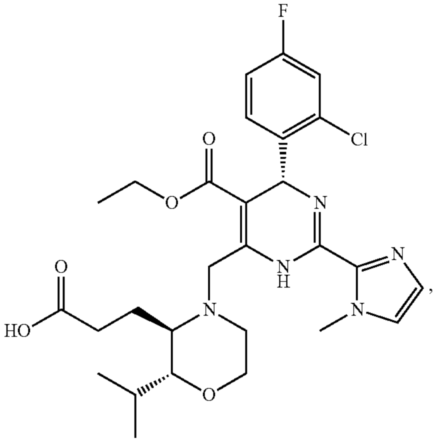
(159)
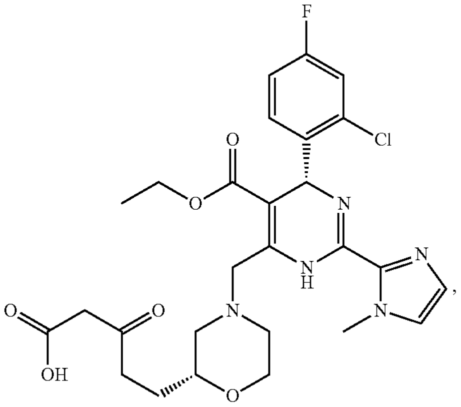
(160)
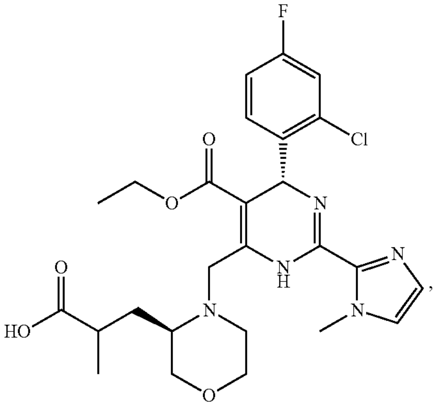

-continued
(161)
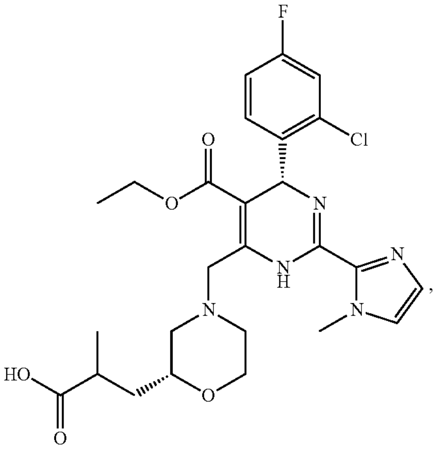
(162)
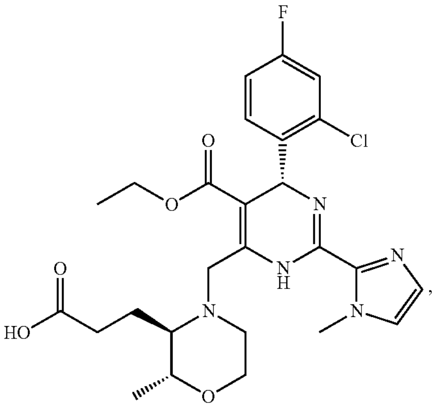
(163)
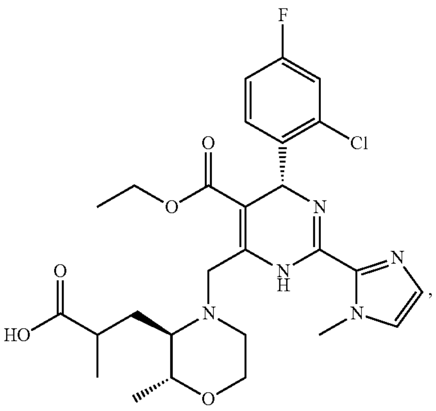
-continued
(164)
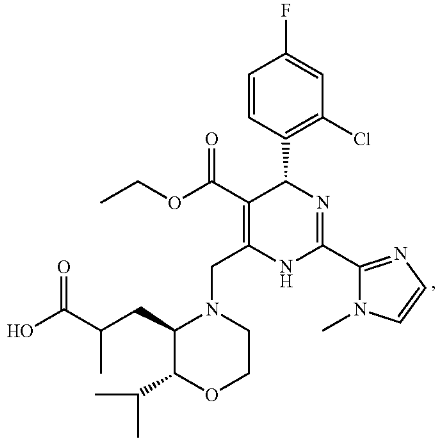
(165)
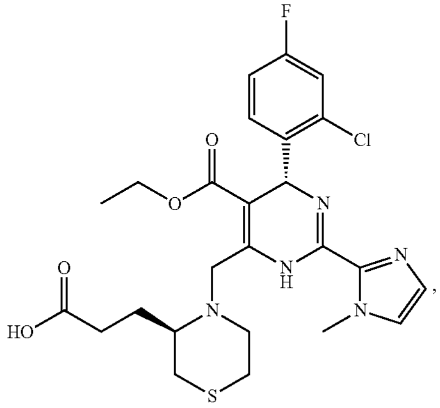
(166)
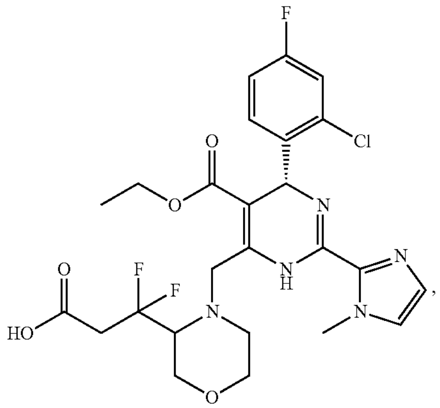

-continued
(167)
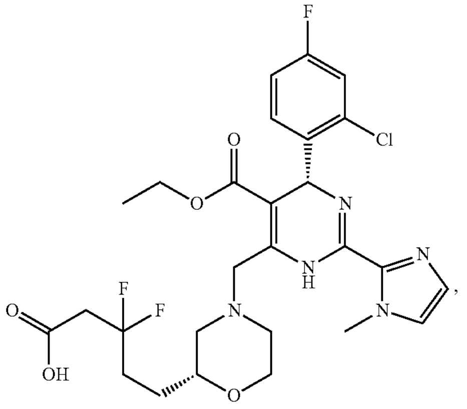
(168)
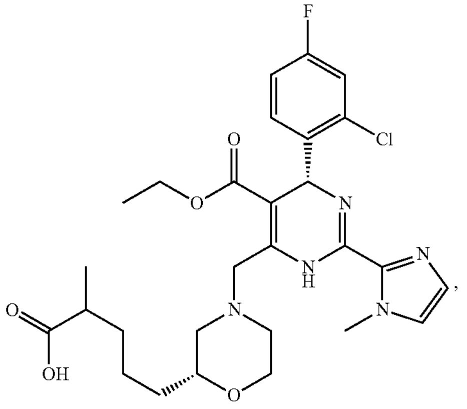
(169)
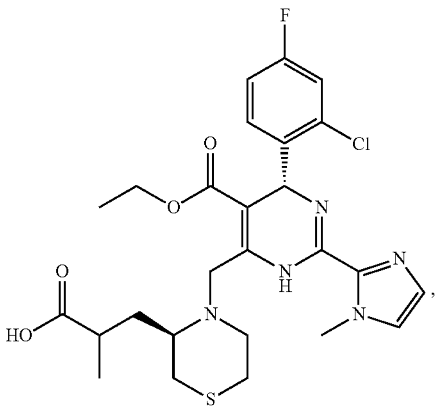
-continued
(170)
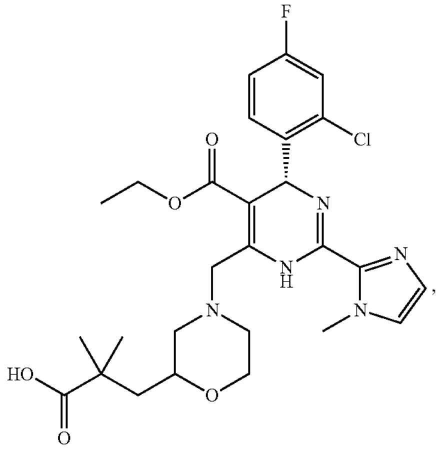
(171)
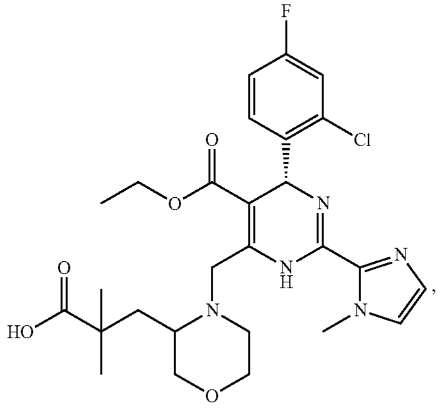
(172)
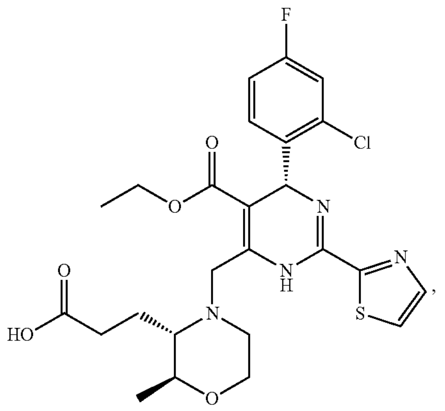

-continued
(173)
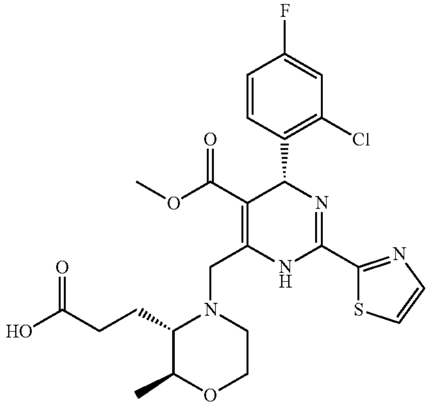
,
(174)
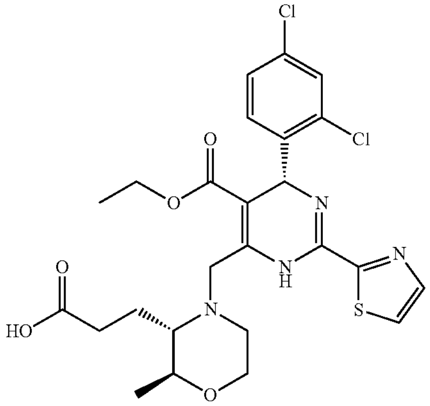
,
(175)
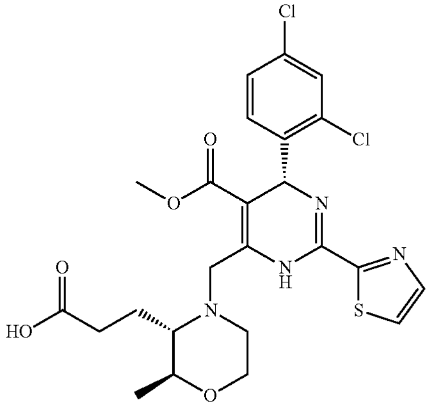
,
(176)
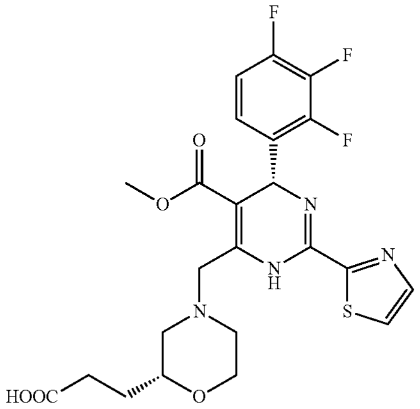
,
-continued
(177)
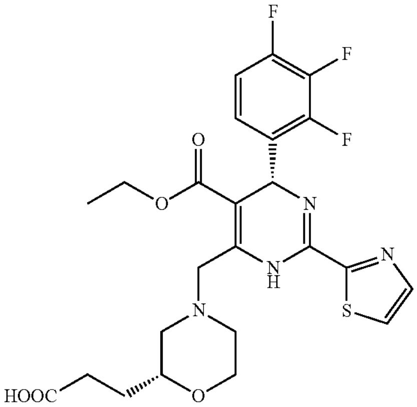
,
(178)
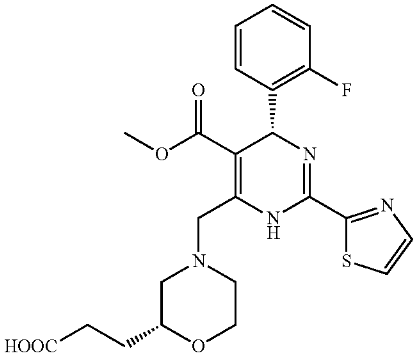
,
(179)
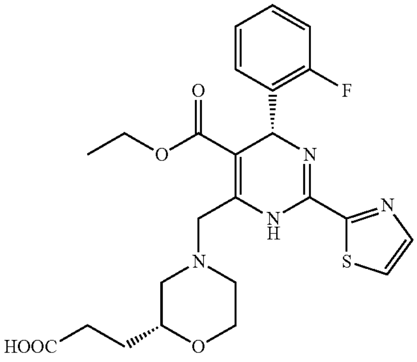
,
(180)
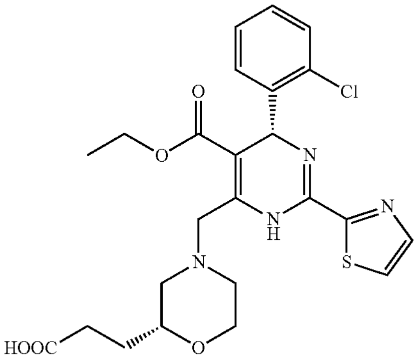
, -continued (180)

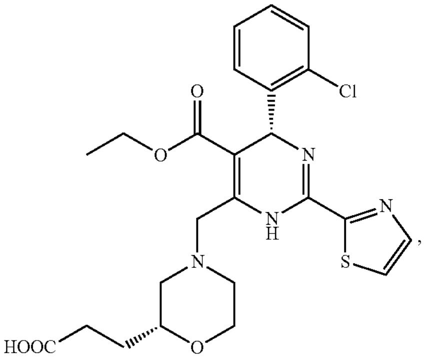

(181)

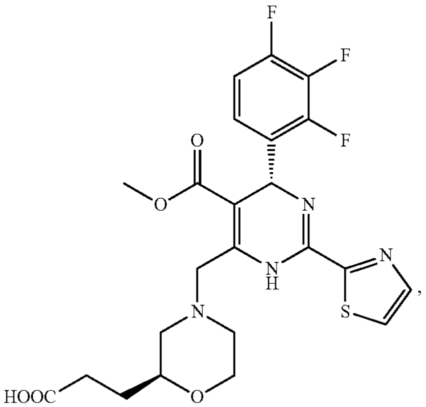

(182)

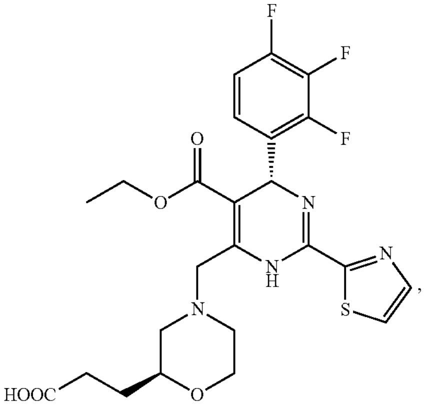

(183)

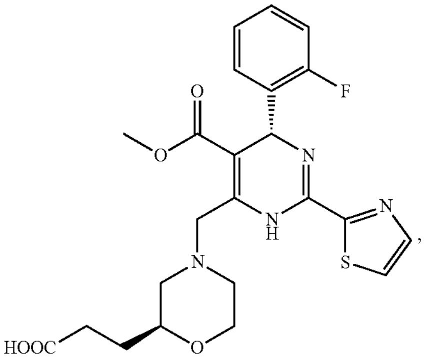

-continued (184)

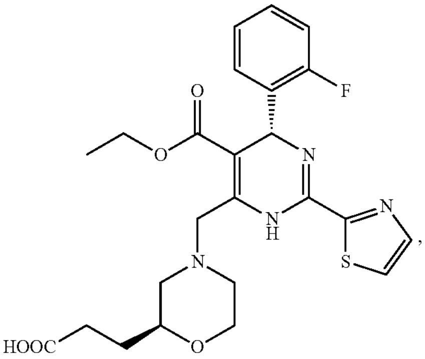

or (185)

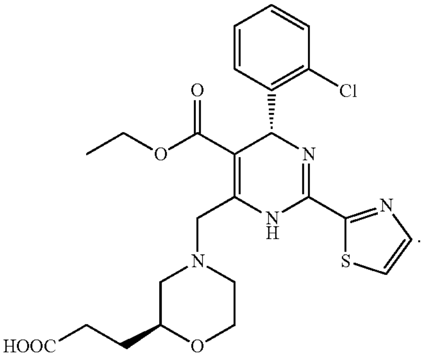

In one aspect, provided herein is a pharmaceutical composition comprising the compound disclosed herein.

In certain embodiments, the pharmaceutical composition further comprises a pharmaceutically acceptable carrier, excipient, diluent, adjuvant, vehicle or a combination thereof.

In certain embodiments, the pharmaceutical composition further comprises an anti-HBV agent.

In certain embodiments, the anti-HBV agent is an HBV polymerase inhibitor, immunomodulator or interferon.

In certain embodiments, the anti-HBV agent comprises at least one selected from the group consisting of lamivudine, telbivudine, tenofovir, entecavir, adefovir dipivoxil, alfaferone, alloferon, celmoleukin, clevudine, emtricitabine, famciclovir, feron, fepatect CP, intefen, interferon α-1b, interferon α, interferon α-2, interferon α-2a, interferon α-2b, interferon β-1a, interleukin-2, mivotilate, nitazoxanide, peginterferon alfa-2a, ribavirin, roferon-A, sizofiran, euforavac, rintatolimod, phosphazid, heplisav, levamisole, and propagermanium.

In another aspect, provided herein is use of the compound or the pharmaceutical composition in the manufacture of a medicament for preventing, managing, treating or lessening a viral disease or an HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is the compound or the pharmaceutical composition for use in preventing, managing, treating or lessening a viral disease or an HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is to a method for preventing, managing, treating or lessening a viral disease or an HBV disease comprising administering to a patient a therapeutically effective amount of the compound or the pharmaceutical composition.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein are methods for preventing, managing, treating or lessening a viral disease or an HBV disease, which comprises administering a pharmaceutically effective amount of the compound disclosed herein or the pharmaceutical composition disclosed herein to a patient.

In another aspect, provided herein are methods for preventing, managing, treating or lessening a viral disease or an HBV disease in a patient, which comprises administering a pharmaceutically effective amount of the compound disclosed herein to a patient.

In another aspect, provided herein are methods for preventing, managing, treating or lessening a viral disease or an HBV disease in a patient, which comprises administering a pharmaceutically effective amount of the pharmaceutical compositions disclosed herein to a patient.

In another aspect, provided herein is use of the compound disclosed herein in the manufacture of a medicament for preventing, managing, or treating a viral disease or an HBV disease, and lessening the severity of a viral disease or an HBV disease.

In another aspect, provided herein is use of the pharmaceutical composition disclosed herein in the manufacture of a medicament for preventing, managing, or treating a viral disease or an HBV disease, and lessening the severity of a viral disease or an HBV disease in a organism.

In some embodiments, the organism or patient is a mammal; in other embodiments, the organism or patient is a human. In still other embodiments, the method further comprises contacting the kinase or organism with an anti-HBV agent.

In another aspect, provided herein is a method of inhibiting HBV infection, comprising contacting a cell or a plurality of cells with an effective HBV inhibiting amount of a pharmaceutically compound disclosed herein or a composition thereof. In other embodiments, the method further comprises contacting the cells with an anti-HBV agent.

In another aspect, provided herein is a method of treating HBV disease, the method comprises administering to a patient in need of such treatment an effective therapeutic amount of a pharmaceutically compound disclosed herein or a composition thereof. In other embodiments, the method further comprises administering to the patient an anti-HBV agent.

In another aspect, provided herein is a method of inhibiting an HBV infection, the method comprises administering to a patient in need of an effective therapeutic amount of a pharmaceutically compound disclosed herein or a composition disclosed herein. In other embodiments, the method further comprises administering to the patient an anti-HBV agent.

In another aspect, provided herein include methods of preparing, methods of separating, and methods of purifying the compounds of Formula (I) or (Ia) and a specific compound.

Provided herein includes the use of a compound disclosed herein, or a pharmaceutically acceptable salt thereof, in the manufacture of a medicament for inhibiting HBV infection effectively, including those described herein. The compounds disclosed herein are useful in the manufacture of a medicament for inhibiting HBV infection. The compounds disclosed herein are also useful in the manufacture of a medicament to attenuate, prevent, manage or treat disorders through inhibition of HBV. Also provided herein is a pharmaceutical composition comprising a therapeutically effective amount of a compound of Formula (I) or (Ia) and a specific compound in association with at least one pharmaceutically acceptable carrier, adjuvant or diluent.

Also provided herein is a method of inhibiting HBV disorders in a subject having or susceptible to such disorder, the method comprising treating the subject with a therapeutically effective amount of a compound of Formula (I) or (Ia) and a specific compound.

Unless otherwise stated, all stereoisomers, geometric isomers, tautomers, N-oxides, hydrates, solvates, metabolites, and pharmaceutically acceptable salts and prodrugs of the compounds disclosed herein are within the scope of the invention.

The term "pharmaceutically acceptable" refers to a substance that is acceptable for use in pharmaceutical applications from a toxicological perspective and does not adversely interact with the active ingredient.

The compounds disclosed herein also include salts of such compounds which are not necessarily pharmaceutically acceptable salts, and which may be useful as intermediates for preparing and/or purifying compounds of Formula (I) or (Ia) and/or for separating enantiomers of compounds of Formula (I) or (Ia) or and specific compounds.

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, malic acid, 2-hydroxy acrylic acid, lactic acid, citric acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, benzenesulfonic acid, methanesulfonic acid, ethanesulfonic acid or trifluoromethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium, a salt of $N^+(R^{14})_4$ or an alkaline earth metal hydroxide, and the like. Some non-limiting examples of suitable salts include organic salts derived from amino acids, such as glycine and arginine, ammonia (primary, secondary, and tertiary amines), salts of $N^+(R^{14})_4$ such as $R^{14}$ is H, $C_{1-4}$ alkyl, $C_{6-10}$ aryl or $C_{6-10}$ aryl-$C_{1-4}$-alkyl, and cyclic amines, such as piperidine, morpholine and piperazine, and inorganic salts derived from sodium, calcium, potassium, magnesium, manganese, iron, copper, zinc, aluminum, lithium, and the like. Further salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

Pharmaceutical Composition, Formulations, Uses and Administration of Compounds and Pharmaceutical Compositions The invention features pharmaceutical compositions that include a compound of Formula (I) or (Ia), a compound listed herein, or a compound named in Examples 1 to 32, and a pharmaceutically acceptable carrier, adjuvant, or excipient. The amount of the compound disclosed herein can inhibit HBV effectively, and is suitable for use in treating or lessening the disease induced by viruses, especially acute and chronic persistent HBV infections. Chronic viral diseases induced by HBV can worsen the morbidity and the chronic HBV infection can cause liver cirrhosis and/or henatocellular carcinoma in many cases.

The compounds disclosed herein are suitable for the treatment of acute and chronic viral infections, particularly suitable for inhibiting HBV effectively. The compounds disclosed herein are suitable for use in treating or lessening the diseases induced by viruses in a patient, especially acute and chronic persistent HBV infections. Chronic viral diseases induced by HBV can worsen the morbidity and the chronic HBV infection can cause liver cirrhosis and/or henatocellular carcinoma in many cases.

The present invention includes pharmaceutical preparations which, besides nontoxic, inert pharmaceutically suitable carriers, comprise one or more compounds disclosed herein or a combination thereof or which consist of one or more active ingredients disclosed herein or a combination thereof.

The pharmaceutical preparations mentioned above may also comprise other active pharmaceutical ingredients apart from the compounds disclosed herein.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or excipient, which, as used herein, includes any and all solvents, diluents, or other liquid excipient, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy,* 21st ed., 2005, Lippincott Williams & Wilkins, Philadelphia, and Swarbrick et al., *Encyclopedia of Pharmaceutical Technology*, eds. 1988-1999, Marcel Dekker, New York, all of which are herein incorporated by reference in their entireties, are disclosed various carriers used in formulating pharmaceutically acceptable compositions and known techniques for the preparation thereof. Except in so far as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, aluminium, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants. As a matter of convenience, local anesthetics, preservatives, buffering agents and so on, can be dissolved in carriers directly.

The pharmaceutical composition comprising the compound disclosed herein may be administered in any of the following routes: orally, inhaled by spray, locally, rectally, nasally, vaginally, parenterally such as subcutaneous, intravenous, intramuscular, intraperitoneal, intrathecal, intraventricular, intrasternal, or intracranial injection or infusion, or administered with the aid of an explanted reservoir, wherein the administration routes by orally, intramuscular, intraperitoneal or intravenous injection are preferred.

The compound or the acceptable pharmaceutical composition comprising the compound disclosed herein may be administered in a unit dosage form. The dosage form may be in a liquid form, or a solid form. The liquid form includes true solution, colloids, particulates, emulsions, suspensions. Other dosage forms include tablets, capsules, dropping pills, aerosols, pills, powder, solutions, suspensions, emulsions, granules, suppositories, lyophilized powder for injection, clathrates, implants, patches, liniments, and the like.

Oral tablets and capsules may comprise excipients, e.g., binders such as syrup, Arabic gum, sorbitol, tragacanth, or polyvinylpyrrolidone; fillers such as lactose, sucrose, corn starch, calcium phosphate, sorbitol, aminoacetic acid; lubricants such as magnesium stearate, saponite, polyethylene glycol, silica, disintegrating agents such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other medium is added before use. This liquid preparation may comprise conventional additives, e.g., suspending agents such sorbitol, cellulose methyl ether, glucose syrup, gelatin, hydroxyethyl cellulose, carboxymethyl cellulose, aluminum stearate gel, hydrogenated edible grease; emulsifying agents such as lecithin, sorbitan monooleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppository may comprise a conventional suppository substrate, such as cocoa butter or other glyceride.

For non-gastric administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an enclosed bottle or ampoule.

For topical application on skin, the compound disclosed herein may be made into a suitable form of ointment, lotion or cream, wherein the active ingredient is suspended or dissolved in one or more carrier(s). Some non-limiting examples of the carriers used for an ointment include mineral oil, liquid vaseline, albolene, propylene glycol, polyoxyethylene, polyoxypropylene, emulsified wax, water, and the like; Some non-limiting examples of the carriers used for a lotion and a cream include mineral oil, sorbitan monostearic ester, tween 60, cetyl esters wax, hexadecylene aromatic alcohol, 2-octyl dodecanol, benzyl alcohol, water, and the like.

In general, it has been proved that, advantageously, whether in human medicine or in veterinary medicine, the total dose of the active compound disclosed herein is about 0.5 to 500 mg every 24 hours, preferably 1 to 100 mg per kg body weight. If appropriate, the drug is administrated by single dose for multiple times, to thereby achieve the desired effect. The amount of the active compound in a single dose is preferably about 1 to 80 mg, more preferably 1 to 50 mg per kg weight body. Nevertheless, the dose may also be varied according to the type and body weight of the object to be treated, the kind and extent of severity of diseases, the type of the preparation and the administration manner of the drug, and the administration period or the time interval.

Provided herein is the pharmaceutical composition further comprising an anti-HBV agent. And the anti-HBV agent is an HBV polymerase inhibitor, immunomodulator or interferon.

The anti-HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole or propagermanium and so on.

In another aspect, provided herein is use of a compound and the pharmaceutical composition in the manufacture of a medicament for preventing, managing, treating or lessening the HBV disease in a patient, comprising administering a pharmaceutically effective amount to a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or may be the same as acute hepatitis. A patient with chronic virus infection may develop active disease, which can progress to cirrhosis and liver cancer.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiment, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

The compound disclosed herein exhibits a relatively strong antiviral effect. This kind of compound has unexpected antiviral activity to HBV, and thus is adapted to be used for treating various virus-caused diseases, in particular acute and chronic viral diseases caused by HBV may lead to various syndromes having different extents of severity. As well known, chronic HBV infection may lead to hepatic cirrhosis and/or liver cell carcinoma.

Examples of indications capable of being treated by the compound disclosed herein include: acute and chronic viral infections capable of leading to infectious hepatitis, such as HBV infection, and particularly preferred chronic HBV infection and acute HBV infection.

The invention further relates to the use of the compounds and compositions defined above for producing a medicament for the treatment and prophylaxis of the diseases described above, preferably of viral diseases, in particular of hepatitis B.

General Synthetic Procedures

If any differences between the chemical name and chemical structure in the specification, the chemical structure is dominant.

Generally, the compounds disclosed herein may be prepared by methods described herein, wherein the substituents are as defined for Formulas (I) or (Ia), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (200-300 mesh) was purchased from Qingdao Ocean Chemical Factory. $^1H$ NMR spectra were recorded with a Bruker 400 MHz or 600 MHz spectrometer using $CDCl_3$, $d_6$-DMSO, $CD_3OD$ or $d_6$-acetone as solutions (reported in ppm), and using TMS (0 ppm) or chloroform (7.25 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), br.s (broadened singlet), ddt (doublet of doublet of triplets), dddd (doublet of doublet of doublet of doublets), td (triplet of doublets) and brs (broadened singlet). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pumps and a G1316A TCC (Temperature Control of Column, maintained at 30° C.). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 μm). Injection volume was decided by the sample concentration. The flow rate was 0.6 mL/min; the peak of HPLC was recorded with UV-Vis detection at 210/254 nm. The mobile phases consisted of a combination of A (0.1% formic acid in $CH_3CN$) and B (0.1% formic acid in $H_2O$). The conditions of gradient elution are described in Table 1:

TABLE 1

| Conditions of gradient elution | | |
|---|---|---|
| t (min) | A ($CH_3CN$, 0.1% HCOOH) | B ($H_2O$, 0.1% HCOOH) |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron), 10 min, 0.6 mL/min flow rate, a combination of A (0.1% formic acid in $CH_3CN$) and B (0.1% formic acid in $H_2O$) in gradient mode (5% to 95%). Column was operated at 40° C.

Purification of compound by preparative chromatography was implemented on Agilent 1260 Series high performance liquid chromatography (HPLC) with UV detection at 278 nm (Daicel CHIRALPAK IC, 10.0×250 mm, 5 micron), 40 min, 2.0 mL/min flow rate, n-hexane-ethanol (97:3, v/v). Column was operated at 30° C.

The following abbreviations are used throughout the specification:

MeCN, $CH_3CN$ acetonitrile
DCM, $CH_2Cl_2$ methylene chloride
$CHCl_3$ chloroform
$CDCl_3$ chloroform-d
DMSO-$d_6$ dimethyl-$d_6$ sulfoxide
Acetone-$d_6$ $CD_3COCD_3$
$D_2O$ oxide
$CCl_4$ carbon tetrachloride
Boc tert-butyloxycarbonyl
$(Boc)_2O$ Di-tert-butyl dicarbonatePE petroleum ether (60-90° C.)
v:v, v/v volume ratio
EtOAc, EA ethyl acetate
HCl hydrochloric acid
$K_2CO_3$ potassium carbonate
$NaHCO_3$ sodium bicarbonate
NaOH sodium hydroxide
NaCl sodium chloride
$Na_2SO_4$ sodium sulfate
$Et_3N$, TEA triethylamine
NBS N-bromosuccinimide
$H_2O$ water
mL milliliter
RT, rt room temperature
Rt retention time
$H_2$ hydrogen
EDC.HCl 1-(3-dimethylaminopropyl)-3-ethylcarbodiimide hydrochloride
HOAT 1-hydroxy-7-azabenzotriazole
DIPEA N,N-diisopropylethylamine
DCC N,N'-dicyclohexylcarbodiimide
DMF N,N-dimethylformamide
CbzCl N-(Benzyloxycarbonyloxy)succinimide
$LiAlH_4$ lithium aluminum hydride
THF tetrahydrofuran
DMSO dimethylsulfoxide
Pd/C, Pd—C palladium on carbon
CuCN copper (I) cyanide
$CH_3OH$ methanol
$N_2$ nitrogen
$NH_4Cl$ ammonium chloride
$Ac_2O$ Acetic anhydride $[a]_D^{25}$ specific rotation, measuring temperature is 25° C., using d sodium light.
$t_{1/2}$ half-life period
AUC area under the curve
Vss apparent volume of distribution
CL clearance
F absolute bioavailability
Dose dosage
$T_{max}$ time to peak
$C_{max}$ peak concentration
hr*ng/mL blood concentration*time
Synthesis of Intermediates Compounds having Formula (I) or (Ia) may be prepared by methods described herein.

Scheme 1

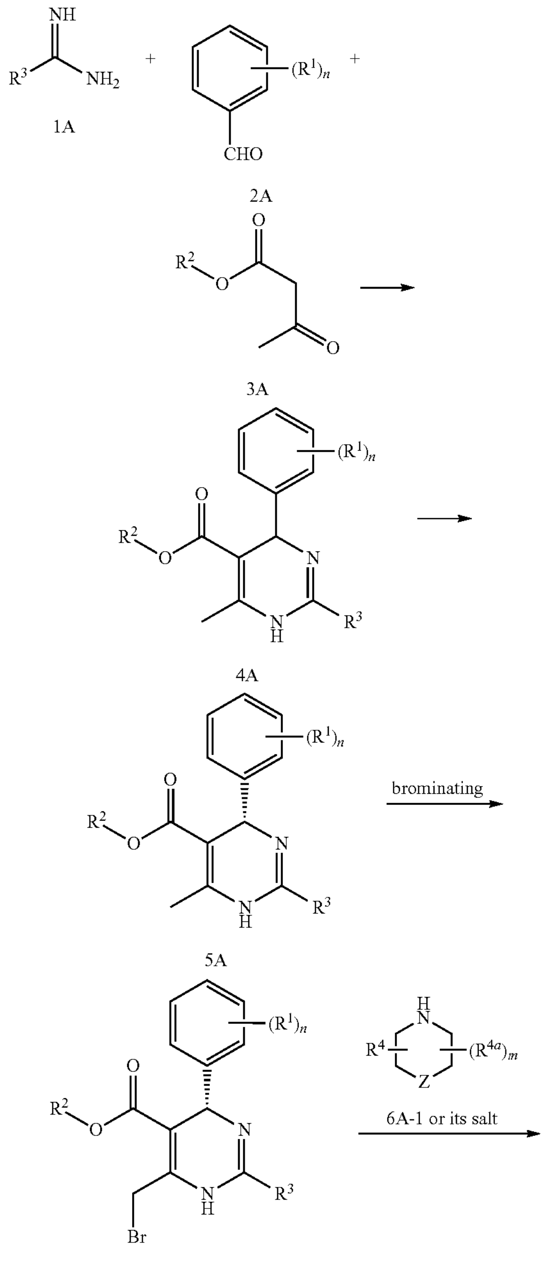

1A, 2A, 3A, 4A, 5A, 6A

-continued

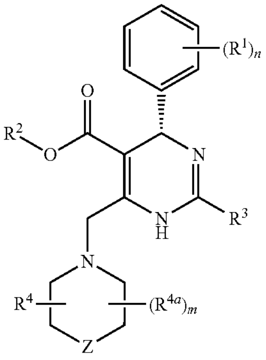

7A

Pyrimidine compound 7A can be prepared by a general synthetic procedure illustrated in Scheme 1, wherein each $R^1$, $R^2$, $R^3$, $R^4$, $R^{4a}$, m and n is as defined herein. By one-pot reaction, compound 1A, compound 2A and compound 3A can react to obtain compound 4A in the presence of a base. Purification of compound 4A by preparative chromatography can give compound 5A, and then compound 5A can react with brominating agent to give compound 6A. The compound 6A can react with compound 6A-1 or its salt to give target compound 7A.

Scheme 2

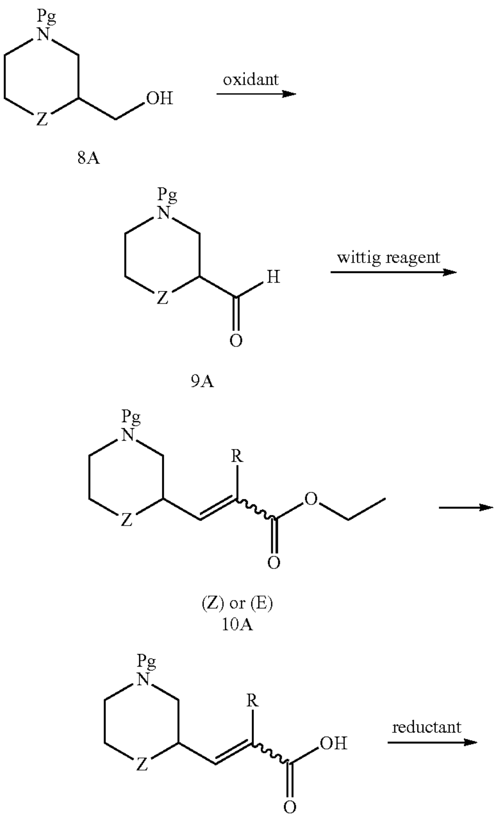

8A, 9A, (Z) or (E) 10A, (Z) or (E) 11A

-continued

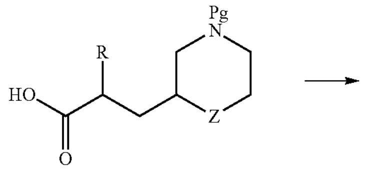

12A

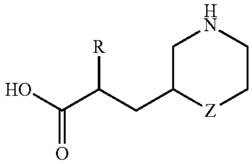

13A

The target compound 13A can be prepared by the process illustrated in Scheme 2, wherein Z is as defined herein. R is hydrogen or methyl. Pg is an amino protecting group, such as Boc, Fmoc, Cbz, and the like. Compound 8A can be converted to compound 9A in the presence of an oxidant (eg. Dess-Martin periodinane). Wittig reaction of compound 9A with Wittig reagent can give compound 10A. Compound 10A can be converted to compound 11A by hydrolysis, and then compound 11A can be reduced to afford compound 12A in the presence of a reductant. Subsequently, the protecting group Pg of compound 12A can be removed to afford compound 13A.

Scheme 3

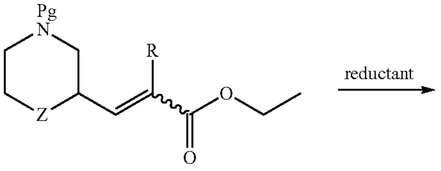

10A
(Z) or (E)

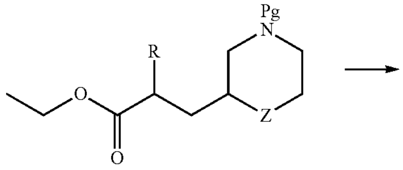

14A

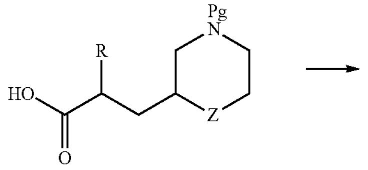

12A

-continued

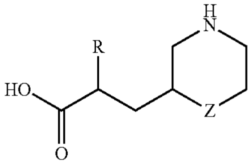

13A

The target compound 13A can be prepared by the process illustrated in Scheme 3, wherein Z is as defined herein. R is hydrogen or methyl. Pg is an amino protecting group, such as Boc, Fmoc, Cbz, and the like. Compound 10A can be reduced to afford compound 14A in the presence of a reductant, and then compound 14A can be converted to compound 12A by hydrolysis. Subsequently, the protecting group Pg of compound 12A can be removed to afford compound 13A.

Scheme 4

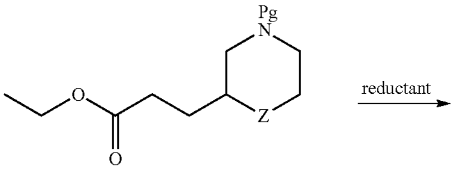

15A

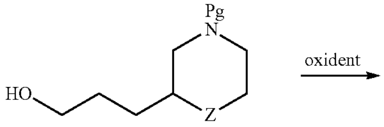

16A

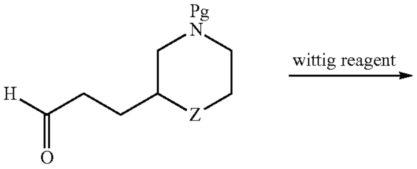

17A

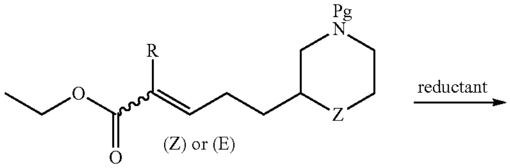

18A

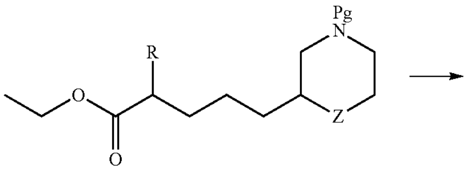

19A

-continued

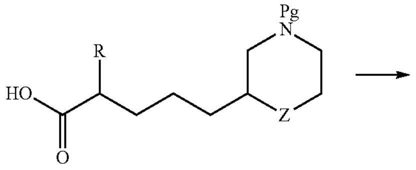

20A

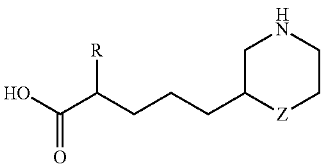

21A

The target compound 21A can be prepared by the process illustrated in Scheme 4, wherein Z is as defined herein. R is hydrogen or methyl. Pg is an amino protecting group, such as Boc, Fmoc, Cbz, and the like. Compound 15A can be converted to compound 16A in the presence of a reductant. Compound 16A can be converted to compound 17A in the presence of an oxidant (eg. Dess-Martin periodinane). Wittig reaction of compound 17A with Wittig reagent to give compound 18A. Compound 18A can be reduced to afford compound 19A, and then compound 19A can be converted to compound 20A by hydrolysis. Subsequently, the protecting group Pg of compound 20A can be removed to afford compound 21A.

Scheme 5

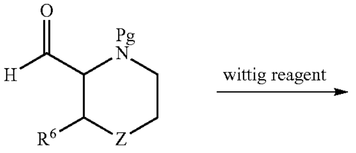

22A

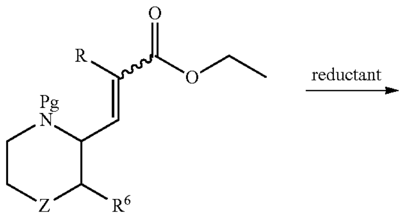

23A
(Z) or (E)

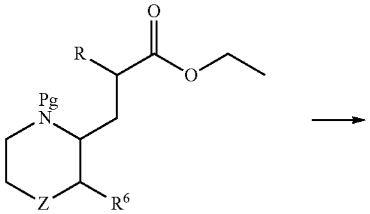

24A

-continued

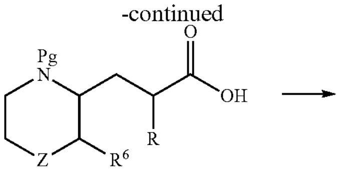

25A

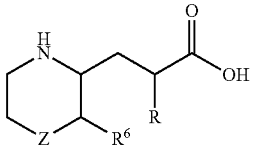

26A

The target compound 26A can be prepared by the process illustrated in Scheme 5, wherein Z is as defined herein. R is hydrogen or methyl. $R^6$ is hydrogen, methyl ethyl, propyl or isopropyl. Pg is an amino protecting group, such as Boc, Fmoc, Cbz, and the like. Wittig reaction of compound 22A with Wittig reagent to give compound 23A. Compound 23A can be reduced to afford compound 24A, and then compound 24A can be converted to compound 24A by hydrolysis. Subsequently, the protecting group Pg of compound 25A can be removed to afford compound 26A.

Scheme 6

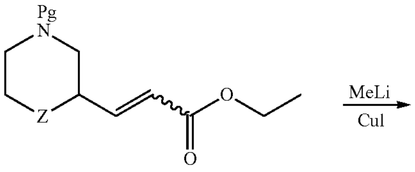

27A
(Z) or (E)

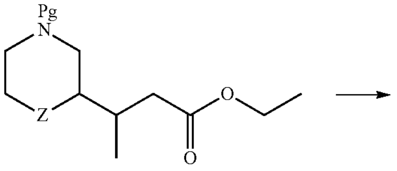

28A

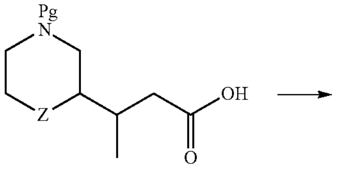

29A

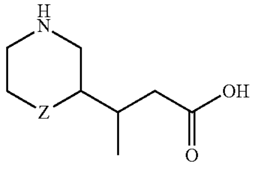

30A

The target compound 30A can be prepared by the process illustrated in Scheme 6, wherein Z is as defined herein. Pg is an amino protecting group, such as Boc, Fmoc, Cbz, and the like. Compound 27A can be converted to compound 28A in the presence of CuI and MeLi, and then compound 28A can be converted to compound 29A by hydrolysis. Subsequently, the protecting group Pg of compound 29A can be removed to afford compound 30A.

Scheme 7

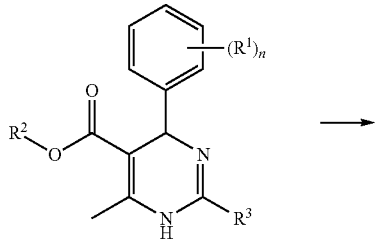

4A

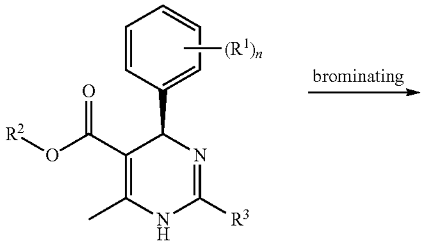

31A

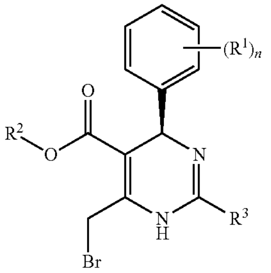

32A

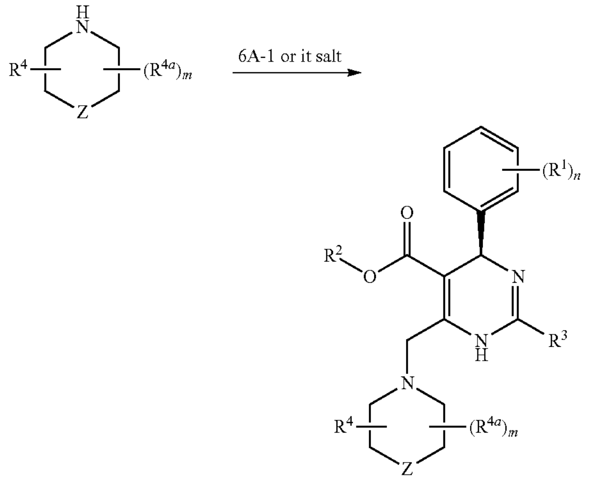

33A

The target compound 33A can be prepared by the process illustrated in Scheme 7, wherein $R^1$, $R^2$, $R^3$, $R^4$, $R^{4a}$, m and n are as defined herein. Compound 4A can give compound 31A by preparative chromatography, and compound 31A can react with brominating agent to give compound 32A, and then compound 32A can react with compound 6A-1 or its salt to give target compound 33A.

EXAMPLES

The invention is illustrated further by the following examples, which are not be construed as limiting the invention in scope.

Example 1

(R)-Ethyl 4-(2-bromo-4-fluorophenyl)-6-(bromomethyl)-2-(thiazol-2-yl)-1,4-dihydropyrimidine-5-carboxylate

Step 1) (R)-ethyl 4-(2-bromo-4-fluorophenyl)-6-methyl-2-(thiazol-2-yl)-1,4-dihydropyrimidine-5-carboxylate

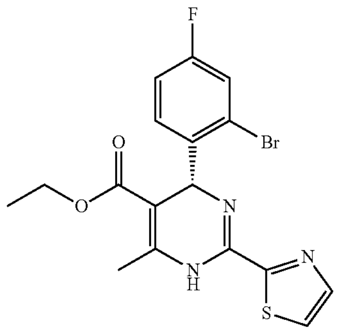 [SMILES: CCOC(=O)C1=C(C)NC(c2nccs2)=N[C@H]1c1ccc(F)cc1Br]

A solution of ethyl 4-(2-bromo-4-fluorophenyl)-6-(bromomethyl)-2-(thiazol-2-yl)-1,4-dihydropyrimidine-5-carboxylate (5 g, 11.8 mmol, synthetic procedures disclosed in WO2010069147A) in a mixture of MeOH and DCM (v/v=1/1, 20 mL) was separated by Preparative chromatography to give the title compound as a yellow solid (2 g, 40%). The compound was characterized by the following spectroscopic data:

$[a]_D^{25}$=−80.71 (c=0.3023 g/100 mL, MeOH);

MS (ESI, pos.ion) m/z: 424.0 $[M+H]^+$; and $^1H$ NMR (400 MHz, DMSO-$d_6$): δ 9.88 (s, 1H), 7.97 (d, 1H), 7.89 (d, 1H), 7.54 (dd, 1H), 7.35 (dd, 1H), 7.23 (td, 1H), 5.96 (s, 1H), 3.93 (q, 2H), 2.46 (s, 3H), 1.03 (t, 3H).

Step 2) (R)-ethyl 4-(2-bromo-4-fluorophenyl)-6-(bromomethyl)-2-(thiazol-2-yl)-1,4-dihydropyrimidine-5-carboxylate

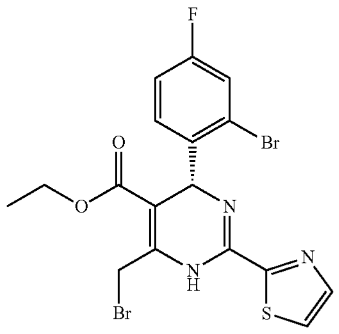 [SMILES: CCOC(=O)C1=C(CBr)NC(c2nccs2)=N[C@H]1c1ccc(F)cc1Br]

To a warmed 76° C. solution of (R)-ethyl 4-(2-bromo-4-fluorophenyl)-6-methyl-2-(thiazol-2-yl)-1,4-dihydropyrimidine-5-carboxylate (1 g, 2.4 mmol) in $CCl_4$ (20 mL) was added NBS (0.47 g, 2.64 mmol). After the addition, the reaction was stirred at 76° C. for another 30 minutes. Then the mixture was cooled to rt, and the solvent was removed in vacuo. The residue was purified by silica gel column chromatography (PE/EtOAc (v/v)=5/1) to give the title compound as a yellow solid (0.85 g, 70%). The compound was characterized by the following spectroscopic data:

MS (ESI, pos.ion) m/z: 503.9$[M+H]^+$; and $^1H$ NMR (600 MHz, DMSO-$d_6$): δ 10.23 (s, 1H), 8.01 (d, 1H), 7.98 (d, 1H), 7.62 (dd, 1H), 7.42 (dd, 1H), 7.29 (td, 1H), 6.01 (s, 1H), 4.79 (br, 2H), 4.01 (q, 2H), 1.08 (t, 3H).

Example 2

3-((R)-4-(((R)-6-(2-Bromo-4-fluorophenyl)-5-(ethoxycarbonyl)-2-(thiazol-2-yl)-3,6-dihydropyrimidin-4-yl)methyl)morpholin-2-yl)propanoic acid Step 1) (S)-benzyl 2-(hydroxymethyl)morpholine-4-carboxylate

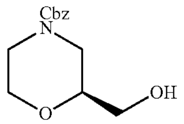 [SMILES: O=C(OCc1ccccc1)N1CCO[C@H](CO)C1]

A mixture of (S)-morpholin-2-ylmethanol hydrochloride (15 g, 97.6 mmol), THF (150 mL), $H_2O$ (150 mL) and $NaHCO_3$ (16.4 g, 195.2 mmol) was stirred at 25° C. for 10 minutes, then to the mixture was added Cbz-C1 (13.8 mL, 97.6 mmol). The reaction mixture was stirred at 25° C. for 6 hours. After the reaction was completed, the organic phase was separated, to the organic phase was added EtOAc (300 mL), and the resulting organic mixture was washed with brine (200 mL×4), dried over anhydrous $Na_2SO_4$ and concentrated in vacuo. The residue was purified by silica gel column chromatography (PE/EtOAc (v/v)=3/1) to give the title compound as a colorless oil (25.9 g, 100%). The compound was characterized by the following spectroscopic data:

MS (ESI, pos.ion) m/z: 252.1$[M+H]^+$; and $^1H$ NMR (400 MHz, $CDCl_3$): δ 7.39-7.28 (m, 5H), 5.18-5.11 (m, 2H), 3.92 (br, 3H), 3.67-3.52 (m, 4H), 3.01 (br.s, 1H), 2.83 (br.s, 1H), 2.58 (s, 1H).

Step 2) (S)-benzyl 2-formylmorpholine-4-carboxylate

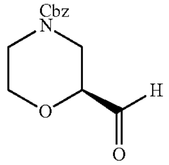 [SMILES: O=C[C@@H]1CN(C(=O)OCc2ccccc2)CCO1]

To a solution of (S)-benzyl 2-(hydroxymethyl)morpholine-4-carboxylate (10 g, 40 mmol) in DCM (200 mL) was added Dess-Martin periodinane (20.4 g, 48 mmol) at 0° C., and the mixture was stirred at 0° C. for 1 hour. The reaction mixture was quenched with saturated aqueous $NaHCO_3$ (200 mL), and the resulting mixture was stirred for 20 minutes at 0° C. The organic phase was washed with saturated aqueous $NaHCO_3$ (200 mL) and saturated brine (200 mL) in turn, dried over anhydrous $Na_2SO_4$ and filtered. The filtrate was used directly in the next step.

Step 3) (R)-benzyl 2-(3-ethoxy-3-oxoprop-1-en-1-yl)morpholine-4-carboxylate

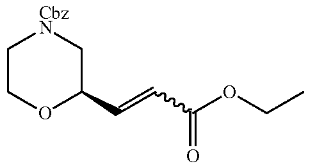

(Z) or (E)

To a mixture of (S)-benzyl 2-formylmorpholine-4-carboxylate (9.96 g, 40 mmol) and DCM (200 mL) was added ethyl (triphenylphoranyliranylidene)acetate (14 g, 40 mmol) at 25° C. The mixture was stirred at 25° C. for 3 hours, and then concentrated in vacuo to remove the solvent. The residue was purified by silica gel column chromatography ($DCM/CH_3OH$ (v/v)=12/1) to give the title compound as a colorless oil (7 g, 55%). The compound was characterized by the following spectroscopic data:

MS (ESI, pos.ion) m/z: 320.2$[M+H]^+$; and $^1H$ NMR (400 MHz, $CDCl_3$): δ 7.41-7.32 (m, 5H), 6.86-5.87 (m, 2H), 5.20-5.15 (m, 2H), 4.25-4.13 (m, 3H), 4.10-4.04 (m, 1H), 4.03-3.93 (m, 2H), 3.63 (q, 1H), 3.05 (br.s, 1H), 2.76 (br.s, 1H), 1.30 (t, 3H).

Step 4) (R)-3-(4-((benzyloxy)carbonyl)morpholin-2-yl)acrylic acid

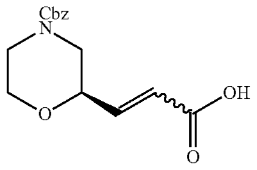

(Z) or (E)

To a mixture of (R)-benzyl 2-(3-ethoxy-3-oxoprop-1-en-1-yl)morpholine-4-carboxylate (3.2 g, 10 mmol) and ethanol (64 mL) was added solution of LiOH.H2O (4.2 g, 100 mmol) in $H_2O$ (64 mL) at 25° C. The mixture was stirred at 25° C. for 1 hour, and then concentrated in vacuo. The residue was diluted in EtOAc (250 mL), and the resulting mixture was adjusted to pH 4-5 with concentrated hydrochloric acid. The separated organic phase was washed with brine (100 mL), dried over anhydrous $Na_2SO_4$ and concentrated in vacuo to give the title compound as colourless oil (2.9 g, 100%). The compound was characterized by the following spectroscopic data:

MS (ESI, neg.ion) m/z: 290.2$[M-H]^-$; and $^1H$ NMR (600 MHz, DMSO-$d_6$): δ 12.34 (s, 1H), 7.38-7.32 (m, 5H), 6.79-5.86 (m, 2H), 5.14-5.09 (m, 2H), 4.12-4.01 (m, 2H), 3.89-3.78 (m, 2H), 3.57-3.45 (m, 1H), 3.01 (br, 1H), 2.77 (br, 1H).

Step 5) (R)-3-(morpholin-2-yl)propanoic acid hydrochloride

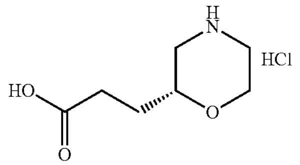 [SMILES: O=C(O)CC[C@@H]1CNCCO1 ; Cl]

A mixture of (R)-3-(4-((benzyloxy)carbonyl)morpholin-2-yl)acrylic acid (2.7 g, 9.3 mmol), Pd/C (10%, 270 mg) and ethanol (60 mL) was stirred at 25° C. under $H_2$ for 12 hours, and filtered. The filtrate was concentrated in vacuo to give the title compound as colourless oil. Then the oil was diluted with EtOAc (40 mL), and then to the resulting mixture was added hydrogen chloride in ethyl acetate (4 mol/L, 10 mL). The mixture was stirred at 25° C. for 12 hours, and then filtered. The filter cake was washed with EtOAc (40 mL) to give the title compound as a white solid (1.62 g, 89%). The compound was characterized by the following spectroscopic data:

MS (ESI, neg.ion) m/z: 158.2[M−H]$^-$; and $^1$H NMR (400 MHz, $D_2O$): δ 4.03 (dd, 1H), 3.78-3.67 (m, 2H), 3.25 (t, 2H), 3.08 (td, 1H), 2.85 (dd, 1H), 2.27-2.23 (m, 2H), 1.73-1.67 (m, 2H).

Step 6) 3-((R)-4-(((R)-6-(2-bromo-4-fluorophenyl)-5-(ethoxycarbonyl)-2-(thiazol-2-yl)-3,6-dihydropyrimidin-4-yl)methyl)morpholin-2-yl)propanoic acid

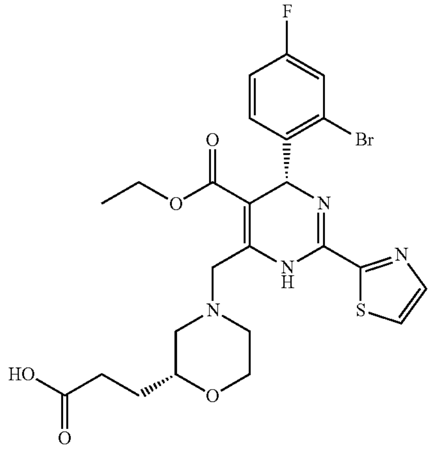 [SMILES: CCOC(=O)C1=C(CN2CCO[C@H](CCC(=O)O)C2)NC(c2nccs2)=N[C@H]1c1ccc(F)cc1Br]

A mixture of (R)-ethyl 4-(2-bromo-4-fluorophenyl)-6-(bromomethyl)-2-(thiazol-2-yl)-1,4-dihydropyrimidine-5-carboxylate (4.74 g, 9.42 mmol), (R)-3-(morpholin-2-yl) propanoic acid hydrochloric (1.5 g, 9.42 mmol), potassium carbonate (2.6 g, 18.84 mmol) and anhydrous ethyl alcohol (90 mL) was stirred at 30° C. under $N_2$ for 12 hours, then filtered, and the filtrate was concentrated in vacuo. The residue was purified by silica gel column chromatography ($DCM/CH_3OH$ (v/v)=25/1) to give the title compound as a yellow solid (2.3 g, 42%). The compound was characterized by the following spectroscopic data:

MS (ESI, pos.ion) m/z: 581.2[M+H]$^+$; and $^1$H NMR (400 MHz, DMSO-$d_6$): δ 12.06 (s, 1H), 9.65 (s, 1H), 8.02 (d, 1H), 7.94 (d, 1H), 7.57 (dd, 1H), 7.39 (dd, 1H), 7.22 (td, 1H), 6.03 (s, 1H), 3.96 (q, 2H), 3.89-3.85 (m, 3H), 3.61-3.47 (m, 2H), 2.81-2.75 (m, 2H), 2.38-2.21 (m, 3H), 2.04-2.02 (m, 1H), 1.65-1.60 (m, 2H), 1.06 (t, 3H).

Example 3

3-((R)-4-(((R)-6-(2-Bromo-4-fluorophenyl)-5-(ethoxycarbonyl)-2-(thiazol-2-yl)-3,6-dihydropyrimidin-4-yl)methyl)morpholin-2-yl)-2-methylpropanoic acid Step 1) (R)-benzyl 2-(3-ethoxy-2-methyl-3-oxoprop-1-en-1-yl)morpholine-4-carboxylate

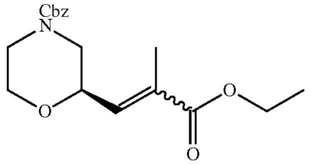

(Z) or (E)

To a mixture of (S)-benzyl 2-formylmorpholine-4-carboxylate (4.99 g, 20 mmol) and DCM (180 mL) was added ethyl 2-(triphenylphosphoranylidene)propionate (7.25 g, 20 mmol) at 25° C. The mixture was stirred at 25° C. for 12 hours, and then filtered. The filtrate was concentrated in vacuo. The residue was purified by silica gel column chromatography (PE/EtOAc (v/v)=15/1) to give the title compound as colourless oil (3 g, 45%). The compound was characterized by the following spectroscopic data:

MS (ESI, pos.ion) m/z: 334.3[M+H]$^+$; and $^1$H NMR (400 MHz, DMSO-$d_6$): δ 7.38-7.30 (m, 5H), 6.48 (d, 1H), 5.12 (s, 2H), 4.31-4.23 (m, 1H), 4.13 (q, 2H), 3.84-3.79 (m, 3H), 3.52 (td, 1H), 3.02 (br, 1H), 2.83 (br, 1H), 1.83 (s, 3H), 1.22 (t, 3H).

Step 2) (R)-3-(4-((benzyloxy)carbonyl)morpholin-2-yl)-2-methylacrylic acid

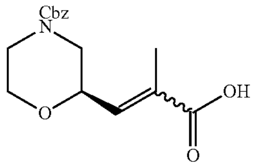

(Z) or (E)

To a mixture of (R)-benzyl 2-(3-ethoxy-2-methyl-3-oxoprop-1-en-1-yl)morpholine-4-carboxylate (2.3 g, 6.9 mmol) and ethanol (46 mL) was added a solution of Lithium hydroxide monohydrate (2.89 g, 69 mmol) in $H_2O$ (23 mL) at 25° C. The mixture was stirred at 25° C. for 1 hour, and then concentrated in vacuo. The residue was diluted in EtOAc (250 mL), and the resulting mixture was adjusted to pH 4-5 with concentrated hydrochloric acid. The organic phase was separated. The separated organic phase was washed with brine (100 mL), dried over anhydrous $Na_2SO_4$ and concentrated in vacuo to give the title compound as colourless oil (2 g, 95%). The compound was characterized by the following spectroscopic data:

MS (ESI, pos.ion) m/z: 306.2[M+H]$^+$; and $^1$H NMR (400 MHz, $CDCl_3$): δ 8.82 (br, 1H), 7.41-7.33 (m, 5H), 6.74 (d, 1H), 5.19 (s, 2H), 4.33-4.20 (m, 1H), 4.05-3.85 (m, 3H), 3.64-3.58 (m, 1H), 3.20-3.05 (m, 1H), 2.88 (br, 1H), 1.93 (s, 3H).

Step 3) 3-((R)-4-((benzyloxy)carbonyl)morpholin-2-yl)-2-methylpropanoic acid

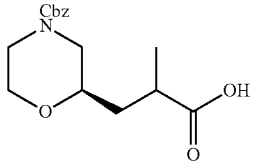 [SMILES: CC(C[C@@H]1CN(C(=O)OCc2ccccc2)CCO1)C(=O)O]

A mixture of (R)-3-(4-((benzyloxy)carbonyl)morpholin-2-yl)-2-methylacrylic acid (2 g, 6.6 mmol), Pd/C (10%, 200 mg) and ethanol (40 mL) was stirred at 25° C. under 10.1 MPa $H_2$ for 12 hours, and then filtered through. The filtrate was concentrated in vacuo to give the title compound as colourless oil (1.9 g, 94%). The compound was characterized by the following spectroscopic data:

MS (ESI, pos.ion) m/z: 308.1[M+H]$^+$; and $^1$H NMR (400 MHz, $CDCl_3$): δ 8.70 (br, 1H), 7.41-7.33 (m, 5H), 5.17 (s, 2H), 4.07-3.85 (m, 3H), 3.59-3.42 (m, 2H), 3.02 (br, 1H), 2.84-2.67 (m, 2H), 2.03-1.78 (m, 1H), 1.65-1.45 (m, 1H), 1.31-1.22 (m, 3H).

Step 4) 2-methyl-3-((R)-morpholin-2-yl)propanoic acid

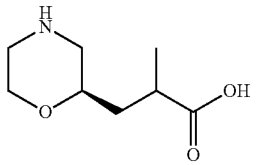

To a mixture of 3-((R)-4-((benzyloxy)carbonyl)morpholin-2-yl)-2-methylpropanoic acid (0.7 g, 2.3 mmol) and benzaldehyde (14 mL) was added aluminum trichloride (1.84 g, 13.8 mmol) at 0° C. under $N_2$. After the addition, the mixture was heated to 25° C. and stirred for 12 hours. The mixture was cooled and to the mixture was added $H_2O$ (20 mL) with stirring, and then added EtOAc (40 mL). The separated organic phase was discarded and the separated water phase was extracted with EtOAc (40 mL×4). The separated water phase was adjusted to pH 7 with aqueous NaOH (3 mol/L), and then centrifuged. The supernatant liquid was concentrated in vacuo to give the title compound as a white solid (0.4 g, 100%). The compound was characterized by the following spectroscopic data:

MS (ESI, pos.ion) m/z: 174.3[M+H]$^+$.

Step 5) 3-((R)-4-(((R)-6-(2-bromo-4-fluorophenyl)-5-(ethoxycarbonyl)-2-(thiazol-2-yl)-3,6-dihydropyrimidin-4-yl)methyl)morpholin-2-yl)-2-methylpropanoic acid

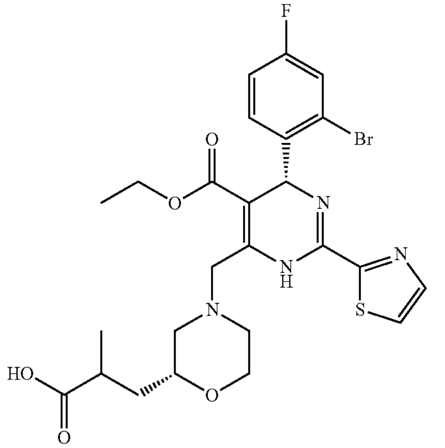 [SMILES: CCOC(=O)C1=C(CN2CCO[C@H](CC(C)C(=O)O)C2)NC(c2nccs2)=N[C@H]1c1ccc(F)cc1Br]

A mixture of (R)-ethyl 4-(2-bromo-4-fluorophenyl)-6-(bromomethyl)-2-(thiazol-2-yl)-1,4-dihydropyrimidine-5-carboxylate (0.87 g, 1.73 mmol), 2-methyl-3-((R)-morpholin-2-yl) propanoic acid (0.3 g, 1.73 mmol), potassium carbonate (0.48 g, 3.46 mmol) and anhydrous ethyl alcohol (20 mL) was stirred at 30° C. under $N_2$ for 12 hours, then filtered, and filtrate was concentrated in vacuo. The residue was purified by silica gel column chromatography (DCM/$CH_3OH$ (v/v)=25/1) to give the title compound as a yellow solid (0.55 g, 53%). The compound was characterized by the following spectroscopic data:

MS (ESI, pos.ion) m/z: 595.2[M+H]$^+$; and $^1$H NMR (400 MHz, DMSO-$d_6$): δ 12.06 (s, 1H), 9.67 (s, 1H), 8.01-7.98 (m, 1H), 7.94 (d, 1H), 7.56 (dd, 1H), 7.38 (dd, 1H), 7.22 (td, 1H), 6.03 (s, 1H), 3.96 (q, 2H), 3.90-3.86 (m, 2H), 3.61-3.53 (m, 2H), 2.76 (dd, 2H), 2.48-2.33 (m, 1H), 2.06-1.78 (m, 2H), 1.68-1.58 (m, 1H), 1.47-1.28 (m, 2H), 1.09-1.04 (m, 6H).

Example 4

3-((R)-4-(((R)-6-(2-Bromo-4-fluorophenyl)-5-(ethoxycarbonyl)-2-(thiazol-2-yl)-3,6-dihydropyrimidin-4-yl)methyl)morpholin-2-yl)butanoic acid Step 1) (2R)-benzyl 2-(4-ethoxy-4-oxobutan-2-yl) morpholine-4-carboxylate

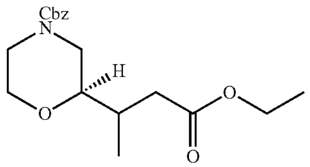 [SMILES: CCOC(=O)CC(C)[C@@H]1CN(C(=O)OCc2ccccc2)CCO1]

To a cooled 0° C. mixture of CuI (1.64 g, 8.6 mmol) and anhydrous THF (100 mL) was added a solution of lithium methide in ether (1.6 mol/L, 10.75 mL, 17.2 mmol) dropwise. The mixture was stirred at 0° C. for 1 hour and then cooled to −78° C., and then to the mixture was added a solution of (R)-benzyl 2-(3-ethoxy-3-oxoprop-1-en-1-yl) morpholine-4-carboxylate (1.1 g, 3.44 mmol) in anhydrous THF (10 mL), and the resulting mixture was stirred at −78° C. for 1 hour. Then the mixture was quenched with saturated aqueous $NH_4Cl$ solution (50 mL), and the resulting mixture was extracted with EtOAc (50 mL×3). The separated organic phase was washed with brine (50 mL), dried over anhydrous $Na_2SO_4$ and concentrated in vacuo. The residue was purified by silica gel column chromatography (EtOAc/PE (v/v)=1/10) to give the title compound as colourless oil (1.1 g, 94.8%). The compound was characterized by the following spectroscopic data:

MS (ESI, pos.ion) m/z: 336.1[M+H]$^+$; and $^1$H NMR (400 MHz, $CDCl_3$): δ 7.43-7.27 (m, 5H), 5.17 (s, 2H), 4.18-4.11 (m, 2H), 3.89 (s, 2H), 3.50 (d, 1H), 3.15 (t, 1H), 3.01 (s, 1H), 2.86-2.54 (m, 2H), 2.23-2.06 (m, 2H), 1.27 (dd, 3H), 0.99 (d, 3H).

Step 2) 3-((R)-4-((benzyloxy)carbonyl)morpholin-2-yl)butanoic acid

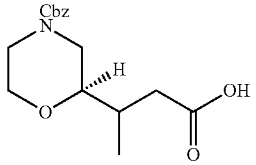 [SMILES: CC(CC(=O)O)[C@@H]1CN(C(=O)OCc2ccccc2)CCO1]

To a mixture of (2R)-benzyl 2-(4-ethoxy-4-oxobutan-2-yl)morpholine-4-carboxylate (1.1 g, 3.28 mmol) and ethanol (15 mL) was added a solution of NaOH (1.31 g, 32.8 mmol) in $H_2O$ (15 mL), and the reaction mixture was stirred at 25° C. for 1.5 hours. The mixture was concentrated in vacuo, and the residue was diluted with EtOAc (40 mL). The resulting mixture was adjusted to pH 2 with concentrated hydrochloric acid, and the separated organic phase was washed with brine (20 mL), dried over anhydrous $Na_2SO_4$ and concentrated in vacuo to give the title compound as colourless oil (1.1 g, 100%). The compound was characterized by the following spectroscopic data:

MS (ESI, neg.ion) m/z: 306.2[M−H]$^-$.

Step 3) 3-((R)-morpholin-2-yl)butanoic acid

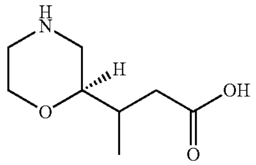

To a mixture of 3-((R)-4-((benzyloxy)carbonyl)morpholin-2-yl)butanoic acid (1.5 g, 4.88 mmol) and benzaldehyde (40 mL) was added aluminum trichloride (3.91 g, 2.93 mmol) at 0° C. under $N_2$, then the mixture was heated to 25° C. and stirred for 6 hours. The mixture was cooled and quenched with $H_2O$ (40 mL) with stirring, and then to the mixture was added EtOAc (40 mL). The separated organic phase was discarded. The separated water phase was extracted with EtOAc (40 mL), and then the separated water phase was adjusted to pH 7 with aqueous NaOH (3 mol/L), then centrifuged. The supernatant liquid was concentrated in vacuo to give the title compound as a white solid (0.85 g, 100%). The compound was characterized by the following spectroscopic data:

MS (ESI, pos.ion) m/z: 174.2[M+H]$^+$.

Step 4) 3-((R)-4-(((R)-6-(2-bromo-4-fluorophenyl)-5-(ethoxycarbonyl)-2-(thiazol-2-yl)-3,6-dihydropyrimidin-4-yl)methyl)morpholin-2-yl)butanoic acid

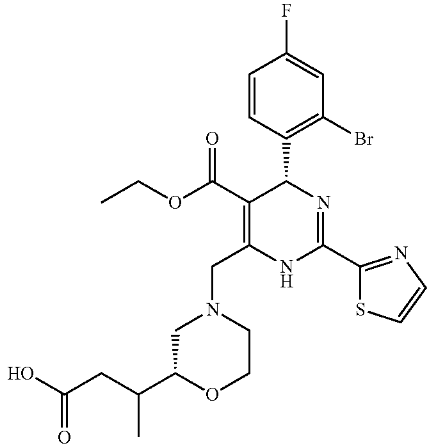 [SMILES: CCOC(=O)C1=C(CN2CCO[C@H](C(C)CC(=O)O)C2)NC(c2nccs2)=N[C@H]1c1ccc(F)cc1Br]

A mixture of (R)-ethyl 4-(2-bromo-4-fluorophenyl)-6-(bromomethyl)-2-(thiazol-2-yl)-1,4-dihydropyrimidine-5-carboxylate (0.5 g, 1 mmol), 3-((R)-morpholin-2-yl)butanoic acid (0.17 g, 1 mmol), potassium carbonate (0.27 g, 2 mmol) and anhydrous ethyl alcohol (30 mL) was stirred at 30° C. under $N_2$ for 24 hours, then filtered, and filtrate was concentrated in vacuo. The residue was purified by silica gel column chromatography (DCM/$CH_3OH$ (v/v)=25/1) to give the title compound as a yellow solid (0.06 g, 10%). The compound was characterized by the following spectroscopic data:

MS (ESI, pos.ion) m/z: 595.20[M+H]$^+$; and $^1$H NMR (400 MHz, DMSO-$d_6$): δ 12.08 (s, 1H), 9.68 (s, 1H), 8.01 (d, 1H), 7.92 (d, 1H), 7.59-7.24 (m, 3H), 6.03 (s, 1H), 4.65 (br, 1H), 4.15-3.85 (m, 5H), 3.75-3.55 (m, 3H), 2.80-2.75 (m, 1H), 2.39-2.35 (m, 1H), 2.06-1.95 (m, 3H), 1.22 (d, 3H), 1.08 (t, 3H).

Example 5

3-((2R,3R)-4-(((R)-6-(2-Bromo-4-fluorophenyl)-5-(ethoxycarbonyl)-2-(thiazol-2-yl)-3,6-dihydropyrimidin-4-yl)methyl)-2-methylmorpholin-3-yl)propanoic acid Step 1) (2S,3R)-2-(benzylamino)-3-hydroxybutanoic acid

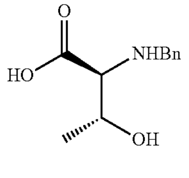

A mixture of (2S,3R)-2-amino-3-hydroxybutanoic acid (16.7 g, 140 mmol), aqueous NaOH solution (2 mol/L, 70 mL, 140 mmol) and benzaldehyde (14.56 g, 137 mmol) was stirred at 25° C. for 1 hour. The mixture was cooled to 0° C., and then to the mixture was added sodium borohydride (3 g, 80 mmol) in portions. After the addition, the mixture was warmed to 25° C. for 12 hours. After the reaction was finished, the mixture was extracted with DCM (30 mL×3). The separated organic phase was discarded. The separated water phase was cooled to 10° C. and adjusted to 2 with concentrated hydrochloric acid, then the resulting water phase was stirred at 5° C. for 4 hours to precipitate out solid, the resulting mixture was filter to give the title compound as a white solid (19.5 g, 68%). The compound was characterized by the following spectroscopic data:

MS (ESI, pos.ion) m/z: 210.1[M+H]$^+$.

Step 2) (2R,3S)-4-benzyl-2-methyl-5-oxomorpholine-3-carboxylic acid

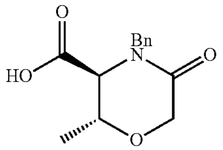 [SMILES: C[C@H]1OCC(=O)N(Cc2ccccc2)[C@@H]1C(=O)O]

To a mixture of (2S,3R)-2-(benzylamino)-3-hydroxybutanoic acid (21.4 g, 102.4 mmol), THF (110 mL) and a solution of $K_2CO_3$ (42.5 g, 307.2 mmol) in water (70 mL) was added 2-chloroacetyl chloride (17.8 g, 157.7 mmol) slowly at 0° C. After the addition, the mixture was stirred at 0° C. for 3 hours, then to the mixture was added a solution of sodium hydroxide (16.4 g, 409.6 mmol) in water (40 mL). After the addition, the mixture was stirred at 5° C. for 4 hours, the mixture was warmed to 25° C. The resulting mixture was extracted with PE (50 mL×2). The separated water phase was cooled to 15° C., and to the water phase was added concentrated hydrochloric acid until a lot of solid precipitate was formed. The mixture was stirred at 10° C. for 12 hours, then filtered. The filter cake was washed with water to give the title compound as a white solid (18.1 g, 71%). The compound was characterized by the following spectroscopic data:

MS (ESI, pos.ion) m/z: 250.1[M+H]$^+$.

Step 3) ((2R,3R)-4-benzyl-2-methylmorpholin-3-yl) methanol

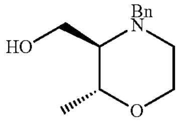 [SMILES: C[C@H]1OCCN(Cc2ccccc2)[C@@H]1CO]

To a solution of (2R,3S)-4-benzyl-2-methyl-5-oxomorpholine-3-carboxylic acid (26.5 g, 106 mmol) in toluene (237 mL) was added 70% sodium bis(2-methoxyethoxy) aluminumhydride (153 mL, 549 mmol) slowly at 0° C. under $N_2$. After the addition, the mixture was stirred at 25° C. for 12 hours, then cooled to 10° C. To the mixture was added EtOH (43 mL) dropwise. The mixture was washed with 2 mol/L aqueous NaOH solution (50 mL×3), the separated water phase was discarded, and the organic phase was extracted with 2 mol/L hydrochloric acid (100 mL×2). The separated organic phase was discarded. To the water phase was added EtOAc (300 mL), adjusted to pH 7-8 with 2 mol/L aqueous NaOH solution, and the organic phase was dried over anhydrous $Na_2SO_4$, and concentrated in vacuo to give the title compound as a light yellow solid (12.2 g, 52%). The compound was characterized by the following spectroscopic data:

MS (ESI, pos.ion) m/z: 222.1 [M+H]$^+$.

Step 4) (2R,3R)-tert-butyl 3-(hydroxymethyl)-2-methylmorpholine-4-carboxylate

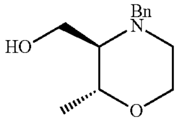 [SMILES: C[C@H]1OCCN(Cc2ccccc2)[C@@H]1CO]

A mixture of ((2R,3R)-4-benzyl-2-methylmorpholin-3-yl)methanol (9.5 g, 43 mmol), MeOH (100 mL), Pd/C (0.95 g, 10%) and $(Boc)_2O$ (10 g, 46 mmol) was stirred at 25° C. under $N_2$ for 24 hours, then filtered. The filtrate was concentrated in vacuo. The residue was purified by silica column chromatography (PE/EtOAc (v/v)=2/1) to give the title compound as light yellow oil (8.5 g, 85%). The compound was characterized by the following spectroscopic data:

MS (ESI, pos.ion) m/z: 132.2 [M+H−100]$^+$.

Step 5) (2R,3S)-tert-butyl 3-formyl-2-methylmorpholine-4-carboxylate

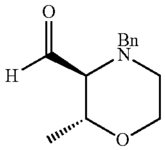 [SMILES: C[C@H]1OCCN(Cc2ccccc2)[C@@H]1C=O]

To a mixture of (2R,3R)-tert-butyl 3-(hydroxymethyl)-2-methylmorpholine-4-carboxylate (8.5 g, 36.7 mmol) in DCM (170 mL) was added Dess-Martin periodinane (18.7 g, 44 mmol) at 0° C. The reaction mixture was stirred at 0° C. for 3 hours, saturated aqueous $NaHCO_3$ solution (170 mL) was added. The resulting mixture was stirred for 30 minutes and separated. The separated organic phase was washed with saturated aqueous $NaHCO_3$ solution (85 mL×2) and saturated brine (85 mL×2) in turn, dried over anhydrous $Na_2SO_4$, filtered, and concentrated in vacuo to give the title compound as colourless oil (5.8 g, 69%).

Step 6) (2R,3R)-tert-butyl 3-(3-ethoxy-3-oxoprop-1-en-1-yl)-2-methylmorpholine-4-carboxylate

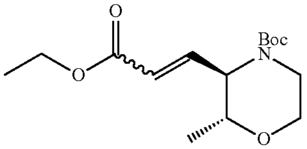

(Z) or (E)

To a mixture of (2R,3S)-tert-butyl 3-formyl-2-methylmorpholine-4-carboxylate (1.3 g, 5.6 mmol) and DCM (40 mL) was added ethyl 2-(triphenylphosphoranylidene)acetate (1.95 g, 5.6 mmol) at 0° C. The reaction mixture was stirred at 25° C. for 12 hours, and concentrated in vacuo. The residue was purified by silica column chromatography (EtOAc/PE (v/v)=1/16) to give the title compound as colourless oil (0.73 g, 41%). The compound was characterized by the following spectroscopic data:

MS (ESI, Pos.ion) m/z: 200.2[M+H−100]$^+$; and $^1$H NMR (600 MHz, $CDCl_3$): δ 6.96 (dd, 1H), 5.89 (dd, 1H), 4.21-4.04 (m, 2H), 4.04-3.90 (m, 1H), 3.90-3.79 (m, 1H), 3.79-3.22 (m, 4H), 1.44 (s, 9H), 1.40 (s, 3H), 1.26 (m, 3H).

Step 7) (2R,3R)-tert-butyl 3-(3-ethoxy-3-oxopropyl)-2-methylmorpholine-4-carboxylate

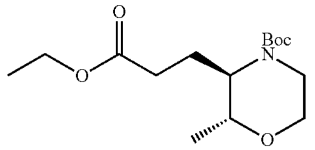 [SMILES: CCOC(=O)CC[C@@H]1[C@@H](C)OCCN1C(=O)OC(C)(C)C]

A mixture of (2R,3R)-tert-butyl 3-(3-ethoxy-3-oxoprop-1-en-1-yl)-2-methylmorpholine-4-carboxylate (0.73 g, 2.4 mmol), EtOAc (35 mL) and Pd/C (10%, 0.73 g, 6.86 mmol) was stirred at 25° C. for 12 hours under $H_2$, and then filtered. The filtrate was concentrated in vacuo to give the title compound as colourless oil (0.7 g, 95%). The compound was characterized by the following spectroscopic data:

MS (ESI, pos.ion) m/z: 202.2 [M+H−100]$^+$.

Step 8) 3-((2R,3R)-4-(tert-butoxycarbonyl)-2-methylmorpholin-3-yl)propanoic acid

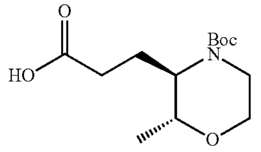 [SMILES: C[C@H]1OCCN(C(=O)OC(C)(C)C)[C@@H]1CCC(=O)O]

A mixture of (2R,3R)-tert-butyl 3-(3-ethoxy-3-oxopropyl)-2-methylmorpholine-4-carboxylate (0.84 g, 2.8 mmol), EtOH (10 mL) and a solution of $LiOH.H_2O$ (1.2 g, 28 mmol) in water (10 mL) was stirred at 25° C. for 30 minutes, then to the reaction mixture were added EtOAc (15 mL) and water (10 mL). The resulting mixture was adjusted to pH 5-6 with concentrated hydrochloric acid. The separated organic phase was washed with saturated brine (50 mL×2), dried over anhydrous $Na_2SO_4$, and concentrated in vacuo to give the title compound as colourless oil (0.62 g, 86%). The compound was characterized by the following spectroscopic data:

MS (ESI, pos.ion) m/z: 174.2 [M+H−100]$^+$; and

MS (ESI, Neg.ion) m/z: 272.2 [M−H]$^-$.

Step 9) 3-((2R,3R)-2-methylmorpholin-3-yl)propanoic acid hydrochloride

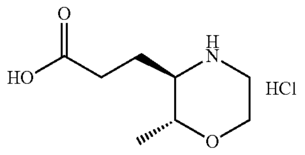

A mixture of 3-((2R,3R)-4-(tert-butoxycarbonyl)-2-methylmorpholin-3-yl)propanoic acid (0.62 g, 2.3 mmol) and a solution of HCl in EtOAc (4 mol/L, 40 mL) was stirred at 25° C. for 4 hours, and then filtered. The filter cake was washed with EtOAc (40 mL) to give the title compound as a hoary solid (0.36 g, 92%). The compound was characterized by the following spectroscopic data:

MS (ESI, pos.ion) m/z: 174.1 [M+H]$^+$.

Step 10) 3-((2R,3R)-4-(((R)-6-(2-bromo-4-fluorophenyl)-5-(ethoxycarbonyl)-2-(thiazol-2-yl)-3,6-dihydropyrimidin-4-yl)methyl)-2-methylmorpholin-3-yl)propanoic acid

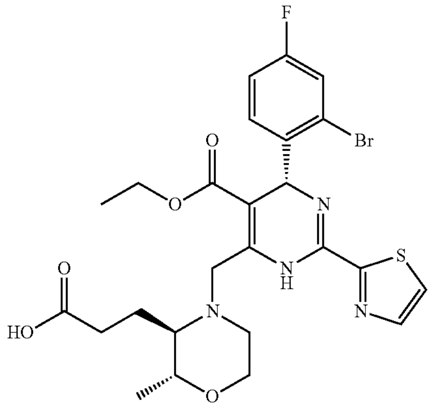 [SMILES: CCOC(=O)C1=C(CN2CCO[C@H](C)[C@H]2CCC(=O)O)NC(c2nccs2)=N[C@H]1c1ccc(F)cc1Br]

A mixture of 3-((2R,3R)-2-methylmorpholin-3-yl)propanoic acid hydrochloride (0.44 g, 2.1 mmol), EtOH (40 mL), $K_2CO_3$ (0.58 g, 4.2 mmol) and (R)-ethyl4-(2-bromo-4-fluorophenyl)-6-(bromomethyl)-2-(thiazol-2-yl)-1,4-dihydropyrimidine-5-carboxylate (1.16 g, 2.3 mmol) was stirred at 25° C. for 24 hours, and then filtered. The filtrate was concentrated in vacuo. The residue was purified by silica column chromatography ($DCM/CH_3OH$ (v/v)=50/1) to give the title compound as a yellow solid (0.63 g, 50%). The compound was characterized by the following spectroscopic data:

MS (ESI, Pos.ion) m/z: 595.2 [M+H]$^+$; and $^1$H NMR (400 MHz, DMSO-$d_6$): δ 12.04 (s, 1H), 9.73 (s, 1H), 8.02 (d, 1H), 7.94 (d, 1H), 7.56 (dd, 1H), 7.38 (dd, 1H), 7.21 (td, 1H), 6.02 (s, 1H), 4.22 (d, 1H), 3.96 (q, 2H), 3.89-3.73 (m, 2H), 3.57 (t, 1H), 3.52-3.44 (m, 1H), 2.82 (d, 1H), 2.51-2.48 (m, 1H), 2.34-2.12 (m, 3H), 1.95-1.79 (m, 1H), 1.77-1.57 (m, 1H), 1.22 (d, 4H), 1.06 (t, 3H).

Example 6

3-((2R,3R)-4-(((R)-6-(2-Bromo-4-fluorophenyl)-5-(ethoxycarbonyl)-2-(thiazol-2-yl)-3,6-dihydropyrimidin-4-yl)methyl)-2-methylmorpholin-3-yl)-2-methylpropanoic acid Step 1) (2R,3R)-tert-butyl 3-(3-methoxy-2-methyl-3-oxoprop-1-en-1-yl)-2-methylmorpholine-4-carboxylate

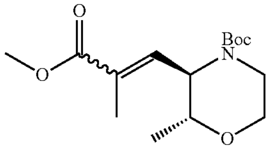

(Z) or (E)

To a mixture of (2R,3S)-tert-butyl 3-formyl-2-methylmorpholine-4-carboxylate (2.29 g, 10 mmol) and DCM (100 mL) was added methyl 2-(triphenylphoranylidene)propanoate (3.48 g, 10 mmol) at 0° C. The mixture was stirred at 25° C. for 12 hours, and then concentrated in vacuo. The residue was purified by silica gel column chromatography (EtOAc/PE (v/v)=1/16)) to give the title compound as colourless oil (1.59 g, 53%). The compound was characterized by the following spectroscopic data:

MS (ESI, Pos.ion) m/z: 200.1[M+H−100]$^+$.

Step 2) (2R,3R)-tert-butyl 3-(3-methoxy-2-methyl-3-oxopropyl)-2-methylmorpholine-4-carboxylate

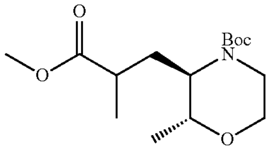 [SMILES: COC(=O)C(C)C[C@@H]1[C@@H](C)OCCN1C(=O)OC(C)(C)C]

To a mixture of (2R,3R)-tert-butyl 3-(3-methoxy-2-methyl-3-oxoprop-1-en-1-yl)-2-methylmorpholine-4-carboxylate (1.59 g, 5.3 mmol) and methanol (50 mL) was Pd/C (1.59 g, 1.5 mmol). The mixture was stirred at 25° C. under $H_2$ for 12 hours, and filtered. The filtrate was concentrated in vacuo to give the title compound as colourless oil (1.15 g, 72%). The compound was characterized by the following spectroscopic data:

MS (ESI, pos.ion) m/z: 202.2 [M+H−100]$^+$.

Step 3) 3-((2R,3R)-4-(tert-butoxycarbonyl)-2-methylmorpholin-3-yl)-2-methylpropanoic acid

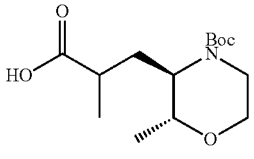 [SMILES: CC(C[C@@H]1[C@@H](C)OCCN1C(=O)OC(C)(C)C)C(=O)O]

To a dried flask was added (2R,3R)-tert-butyl 3-(3-methoxy-2-methyl-3-oxopropyl)-2-methylmorpholine-4-carboxylate (1.0 g, 3.3 mmol) and ethanol (35 mL). After the dissolution, to the mixture was added solution of LiOH $H_2O$ (1.38 g, 33 mmol) in $H_2O$ (35 mL). The resulting mixture was stirred at 25° C. for 30 minutes, and then diluted with EtOAc (60 mL) and $H_2O$ (30 mL), and the resulting mixture was cooled to 0° C. and adjusted to pH 5-6 with concentrated hydrochloric acid. The separated organic phase was washed with brine (100 mL×2), dried over anhydrous $Na_2SO_4$ and concentrated in vacuo to give the title compound as colourless oil (0.9 g, 90%). The compound was characterized by the following spectroscopic data:

MS (ESI, pos.ion) m/z: 188.1 [M+H−100]$^+$.

Step 4) 2-methyl-3-((2R,3R)-2-methylmorpholin-3-yl)propanoic acid hydrochloride

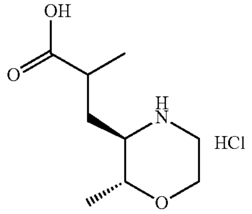

To a dried flask was added 3-((2R,3R)-4-(tert-butoxycarbonyl)-2-methylmorpholin-3-yl)-2-methylpropanoic acid (0.9 g, 3 mmol) and a solution of HCl in EtOAc (4 mol/L, 60 mL), and the resulting mixture was stirred at 25° C. for 4 hours. The mixture was concentrated in vacuo to give the title compound as light brown oil (0.51 g, 76%). The compound was characterized by the following spectroscopic data:

MS (ESI, Pos.ion) m/z: 188.3 [M+H]$^+$.

Step 5) 3-((2R,3R)-4-(((R)-6-(2-bromo-4-fluorophenyl)-5-(ethoxycarbonyl)-2-(thiazol-2-yl)-3,6-dihydropyrimidin-4-yl)methyl)-2-methylmorpholin-3-yl)-2-methylpropanoic acid

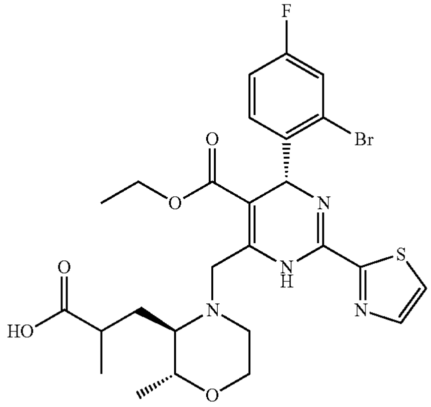 [SMILES: CCOC(=O)C1=C(CN2CCO[C@H](C)[C@H]2CC(C)C(=O)O)NC(c2nccs2)=N[C@H]1c1ccc(F)cc1Br]

To a dried flask was added 2-methyl-3-((2R,3R)-2-methylmorpholin-3-yl)propanoic acid hydrochloride (0.67 g, 3 mmol), ethanol (50 mL), potassium carbonate (0.83 g, 6 mmol) and (R)-ethyl 4-(2-bromo-4-fluorophenyl)-6-(bromomethyl)-2-(thiazol-2-yl)-1,4-dihydropyrimidine-5-carboxylate (1.7 g, 3.3 mmol). The reaction mixture was stirred at 25° C. under $N_2$ for 24 hours, then filtered, and filtrate was concentrated in vacuo. The residue was purified by silica gel column chromatography (DCM/$CH_3OH$ (v/v)=50/1) to give the title compound as a yellow solid (0.23 g, 13%). The compound was characterized by the following spectroscopic data:

MS (ESI, Pos.ion) m/z: 609.3 $[M+H]^+$; and $^1H$ NMR (400 MHz, DMSO-$d_6$): δ 10.33 (s, 1H), 8.07 (d, 1H), 7.94 (d, 1H), 7.58 (dd, 1H), 7.45 (dd, 1H), 7.26 (td, 1H), 6.02 (s, 1H), 4.88 (d, 1H), 4.33 (d, 1H), 4.05-3.85 (m, 5H), 3.65-3.35 (m, 3H), 2.68-2.61 (m, 1H), 1.97-1.85 (m, 2H), 1.26-1.06 (m, 9H).

Example 7

5-((R)-4-(((R)-6-(2-Bromo-4-fluorophenyl)-5-(ethoxycarbonyl)-2-(thiazol-2-yl)-3,6-dihydropyrimidin-4-yl)methyl)morpholin-2-yl)pentanoic acid

Step 1) (R)-ethyl 3-(morpholin-2-yl)propanoate

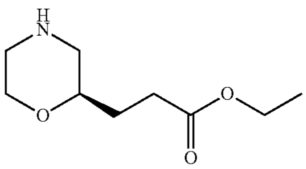

A mixture of (R)-benzyl 2-(3-ethoxy-3-oxoprop-1-en-1-yl)morpholine-4-carboxylate (3.4 g, 10.65 mmol), Pd/C (10%, 340 mg) and EtOH (60 mL) was stirred at 25° C. for 12 hours, then filtered, and filtrate was concentrated in vacuo to give the title compound as colourless oil (1.9 g, 95.5%). The compound was characterized by the following spectroscopic data:

MS (ESI, pos.ion) m/z: 188.2$[M+H]^+$; and $^1H$ NMR (600 MHz, DMSO-$d_6$): δ 4.05 (q, 2H), 3.70-3.67 (m, 2H), 3.38 (td, 1H), 3.75 (d, 1H), 2.66-2.57 (m, 2H), 2.37-2.27 (m, 3H), 1.63-1.52 (m, 2H), 1.18 (t, 3H).

Step 2) (R)-tert-butyl 2-(3-ethoxy-3-oxopropyl)morpholine-4-carboxylate

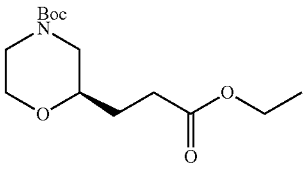 [SMILES: CCOC(=O)CC[C@@H]1CN(C(=O)OC(C)(C)C)CCO1]

To a mixture of (R)-ethyl 3-(morpholin-2-yl)propanoate (1.83 g, 9.77 mmol), $(Boc)_2O$ (2.56 g, 11.73 mmol) and EtOH (40 mL) was added triethylamine (1.48 g, 14.66 mmol). The reaction mixture was stirred at 25° C. for 12 hours, and concentrated in vacuo. The residue was diluted with EtOAc (200 mL). The separated organic phase was washed with 1% hydrochloric acid (100 mL×2) and saturated brine (100 mL) in turn, dried over anhydrous $Na_2SO_4$, filtered, and concentrated in vacuo to give the title compound as light yellow oil (2.8 g, 100%). The compound was characterized by the following spectroscopic data:

MS (ESI, pos.ion) m/z: 232.3$[M+H-56]^+$; and $^1H$ NMR (400 MHz, DMSO-$d_6$): δ 4.05 (q, 2H), 3.80-3.67 (m, 3H), 3.36-3.23 (m, 2H), 2.83 (br, 1H), 2.53 (br, 1H), 2.43-2.30 (m, 2H), 1.73-1.56 (m, 2H), 1.40 (s, 9H), 1.18 (t, 3H).

Step 3) (R)-tert-butyl 2-(3-hydroxypropyl)morpholine-4-carboxylate

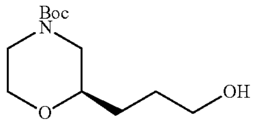 [SMILES: CC(C)(C)OC(=O)N1CCO[C@H](CCCO)C1]

To Lithium aluminium hydride (0.43 g, 11.34 mmol) was added THF (40 mL) at 0° C., and then a solution of (R)-tert-butyl 2-(3-ethoxy-3-oxopropyl) morpholine-4-carboxylate (2.7 g, 9.45 mmol) in THF (20 mL) was added dropwise. After the addition, the reaction mixture was stirred at 0° C. for 1 hour. To the mixture was added water (0.5 mL), aqueous sodium hydroxide solution (10%, 1 mL) and water (1.5 mL) in turn. The resulting mixture was stirred for 30 minutes, then to the mixture was added EtOAc (300 mL). The separated organic phase was washed with (150 mL×3) dried over anhydrous $Na_2SO_4$, filtered, and concentrated in vacuo. The residue was purified by silica gel column chromatography (PE/EtOAc (v/v)=2/1) to give the title compound as colourless oil (1.34 g, 58%). The compound was characterized by the following spectroscopic data:

MS (ESI, pos.ion) m/z: 190.2$[M+H-56]^+$; and $^1H$ NMR (400 MHz, $CDCl_3$): δ 3.93-3.82 (m, 3H), 3.71-3.62 (m, 2H), 3.53 (td, 1H), 3.41-3.35 (m, 1H), 2.93 (td, 1H), 2.65 (dd, 1H), 2.12 (s, 1H), 1.75-1.68 (m, 2H), 1.64-1.52 (m, 2H), 1.48 (s, 9H).

Step 4) (R)-tert-butyl 2-(3-oxopropyl)morpholine-4-carboxylate

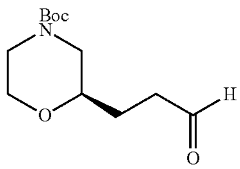 [SMILES: CC(C)(C)OC(=O)N1CCO[C@H](CCC=O)C1]

To a solution of (R)-tert-butyl 2-(3-hydroxypropyl)morpholine-4-carboxylate (1.34 g, 5.5 mmol) in DCM (50 mL) was added Dess-Martin periodinane (2.8 g, 6.6 mmol) at 0° C. The resulting mixture was stirred at 0° C. for 1 hour. To the reaction mixture was added saturated aqueous $NaHCO_3$ (50 mL), and stirred for 20 minutes. The separated organic phase was washed with saturated aqueous $NaHCO_3$ (50 mL×2) and saturated brine (50 mL), dried over anhydrous $Na_2SO_4$ and filtered. The filtrate was used directly in the next step.

Step 5) (R)-tert-butyl 2-(5-ethoxy-5-oxopent-3-en-1-yl)morpholine-4-carboxylate

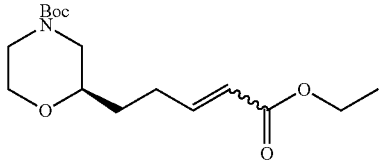

(Z) or (E)

To a dried flask was added (R)-tert-butyl 2-(3-oxopropyl) morpholine-4-carboxylate (0.93 g, 3.83 mmol) and DCM (50 mL). After the raw material was dissolve, to the solution was added ethyl (triphenylphsphoranylidene)acetate (1.33 g, 3.83 mmol) at 25° C., then the mixture was stirred at 25° C. for 12 hours. The mixture was filtered, and the filtrate was concentrated in vacuo. The residue was purified by silica gel column chromatography (PE/EtOAc (v/v)=6/1) to give the title compound as colourless oil (0.86 g, 72%). The compound was characterized by the following spectroscopic data:

MS (ESI, pos.ion) m/z: 214.3$[M+H-100]^+$; and $^1H$ NMR (400 MHz, $CDCl_3$): δ 6.99-6.91 (m, 1H), 5.87-5.81 (m, 1H), 4.19 (q, 2H), 3.90-3.80 (m, 3H), 3.48 (td, 1H), 3.37-3.31 (m, 1H), 2.95-2.75 (m, 1H), 2.59 (t, 1H), 2.42-2.22 (m, 2H), 1.69-1.58 (m, 2H), 1.46 (s, 9H), 1.29 (t, 3H).

Step 6) (R)-tert-butyl 2-(5-ethoxy-5-oxopentyl)morpholine-4-carboxylate

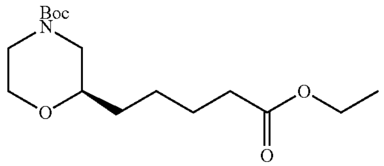 [SMILES: CCOC(=O)CCCC[C@@H]1CN(C(=O)OC(C)(C)C)CCO1]

To a dried flask was added (R)-tert-butyl 2-(5-ethoxy-5-oxopent-3-en-1-yl) morpholine-4-carboxylate (0.86 g, 2.74 mmol), Pd/C (10%, 172 mg) and ethanol (30 mL). The reaction mixture was stirred at 25° C. under $H_2$ for 12 hours, and filtered. The filtrate was concentrated in vacuo to give the title compound as colourless oil (0.75 g, 100%). The compound was characterized by the following spectroscopic data:

MS (ESI, pos.ion) m/z: 216.3$[M+H-100]^+$; and $^1H$ NMR (400 MHz, $CDCl_3$): δ 4.12 (q, 2H), 3.88-3.78 (m, 3H), 3.48 (td, 1H), 3.35-3.27 (m, 1H), 2.90 (td, 1H), 2.56 (t, 1H), 2.29 (t, 2H), 1.69-1.59 (m, 2H), 1.54-1.48 (m, 2H), 1.46 (s, 9H), 1.43-1.31 (m, 2H), 1.25 (t, 3H).

Step 7) (R)-5-(4-(tert-butoxycarbonyl)morpholin-2-yl)pentanoic acid

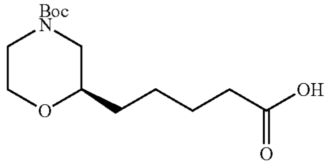 [SMILES: CC(C)(C)OC(=O)N1CCO[C@H](CCCCC(=O)O)C1]

To a dried flask were added (R)-tert-butyl 2-(5-ethoxy-5-oxopentyl) morpholine-4-carboxylate (0.75 g, 2.38 mmol) and ethanol (7.5 mL). After the dissolution, to the mixture was added a solution of $LiOH.H_2O$ (1 g, 23.8 mmol) in $H_2O$ (7.5 mL). The resulting mixture was stirred at 25° C. for 1 hour, diluted in EtOAc (180 mL) and water (50 mL), and the resulting mixture was adjusted to pH 6-7 with concentrated hydrochloric acid. The separated organic phase was washed with brine (100 mL×2), dried over anhydrous $Na_2SO_4$ and concentrated in vacuo to give the title compound as colourless oil (0.5 g, 74%). The compound was characterized by the following spectroscopic data:

MS (ESI, neg.ion) m/z: 286.2$[M-H]^-$; and $^1H$ NMR (400 MHz, $CDCl_3$): δ 9.04 (br, 1H), 3.95-3.75 (m, 3H), 3.50 (td, 1H), 3.38-3.30 (m, 1H), 2.93 (td, 1H), 2.58 (t, 1H), 2.36 (t, 2H), 1.73-1.63 (m, 2H), 1.58-1.49 (m, 2H), 1.47 (s, 9H), 1.44-1.34 (m, 2H).

Step 8) (R)-5-(morpholin-2-yl)pentanoic acid hydrochloride

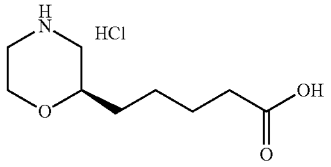 [SMILES: O=C(O)CCCC[C@@H]1CNCCO1 ; Cl]

To a dried flask were added (R)-5-(4-(tert-butoxycarbonyl)morpholin-2-yl)pentanoic acid (0.5 g, 1.74 mmol) and EtOAc (1 mL). After the dissolution, to the mixture was added a solution of HCl in EtOAc (4 mol/L, 8 mL), and the resulting mixture was stirred at 25° C. for 3 hours. Then the mixture was filtered, the filter cake was washed with EtOAc (1 mL) and dried under vacuum for 6 hours to give the title compound as a white solid (0.31 g, 80%). The compound was characterized by the following spectroscopic data:

MS (ESI, pos.ion) m/z: 188.2$[M+H]^+$; and $^1H$ NMR (400 MHz, $D_2O$): δ 4.03 (dd, 1H), 3.81-3.71 (m, 2H), 3.27 (t, 2H), 3.10 (td, 1H), 2.85 (t, 1H), 2.32 (t, 2H), 1.59-1.45 (m, 4H), 1.44-1.27 (m, 2H).

Step 9) 5-((R)-4-(((R)-6-(2-bromo-4-fluorophenyl)-5-(ethoxycarbonyl)-2-(thiazol-2-yl)-3,6-dihydropyrimidin-4-yl)methyl)morpholin-2-yl)pentanoic acid

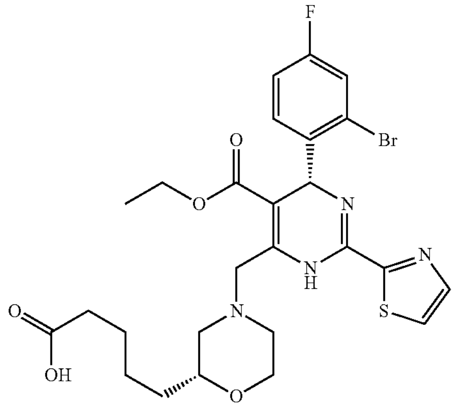 [SMILES: CCOC(=O)C1=C(CN2CCO[C@H](CCCCC(=O)O)C2)NC(c2nccs2)=N[C@H]1c1ccc(F)cc1Br]

To a dried flask were added (R)-ethyl 4-(2-bromo-4-fluorophenyl)-6-(bromomethyl)-2-(thiazol-2-yl)-1,4-dihydropyrimidine-5-carboxylate (0.34 g, 0.67 mmol), (R)-5-(morpholin-2-yl)pentanoic acid hydrochloride (0.15 g, 0.67 mmol), potassium carbonate (0.19 g, 1.34 mmol) and anhydrous ethyl alcohol (20 mL). The reaction mixture was stirred at 30° C. under $N_2$ for 12 hours, and then filtered, and the filtrate was concentrated in vacuo to remove the solvent. The residue was purified by silica gel column chromatography (DCM/$CH_3OH$ (v/v)=25/1) to give the title compound as a yellow solid (0.3 g, 73%). The compound was characterized by the following spectroscopic data:

MS (ESI, pos.ion) m/z: 609.1[M+H]$^+$; and $^1$H NMR (400 MHz, DMSO-$d_6$): δ 11.98 (s, 1H), 9.69 (s, 1H), 8.01 (d, 1H), 7.92 (d, 1H), 7.55 (dd, 1H), 7.39 (dd, 1H), 7.21 (td, 1H), 6.04 (s, 1H), 3.96 (q, 2H), 3.90-3.86 (m, 3H), 3.59 (t, 1H), 3.47 (br, 1H), 2.82 (d, 1H), 2.72 (d, 1H), 2.37-2.30 (m, 1H), 2.16 (t, 2H), 1.99 (t, 1H), 1.47-1.22 (m, 6H), 1.06 (t, 3H).

Example 8

3-((R)-4-(((R)-6-(2-Bromo-4-fluorophenyl)-5-(ethoxycarbonyl)-2-(thiazol-2-yl)-3,6-dihydropyrimidin-4-yl)methy)morpholin-3-yl)propanoic acid Step 1) (S)-tert-butyl 3-formylmorpholine-4-carboxylate

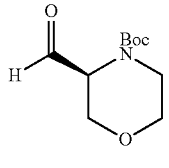 [SMILES: CC(C)(C)OC(=O)N1CCOC[C@H]1C=O]

To a solution of (R)-tert-butyl 3-(hydroxymethyl)morpholine-4-carboxylate (1.47 g, 6.77 mmol) in DCM (30 mL) was added Dess-Martin periodinane (3.44 g, 8.12 mmol) at 0° C. The resulting mixture was stirred at 0° C. for 1 hour. The reaction mixture was quenched with saturated aqueous $NaHCO_3$ (30 mL), and stirred for 30 minutes. The separated organic phase was washed with saturated aqueous $NaHCO_3$ (30 mL×3) and brine (30 mL), dried over anhydrous $Na_2SO_4$ and filtered. The filtrate was concentrated in vacuo. The residue was used directly in the next step.

Step 2) (R)-tert-butyl 3-(3-ethoxy-3-oxoprop-1-en-1-yl)morpholine-4-carboxylate

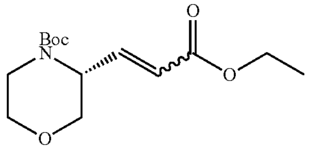

(Z) or (E)

To a dried flask were added (S)-tert-butyl 3-formylmorpholine-4-carboxylate (1.46 g, 6.77 mmol) and DCM (40 mL). After the raw material was dissolved, to the mixture was added ethyl 2-(triphenylphosphoranylidene)acetate (2.36 g, 6.77 mmol) at 25° C. The resulting mixture was stirred at 25° C. for 12 hours, and then filtered. The filtrate was concentrated in vacuo to remove the solvent. The residue was purified by silica gel column chromatography (PE/EtOAc (v/v)=10/1) to give the title compound as colourless oil (1.05 g, 54%). The compound was characterized by the following spectroscopic data:

MS-ESI: (ESI, pos.ion) m/z: 186.1[M+1-100]$^+$; and $^1$H NMR (400 MHz, $CDCl_3$): δ 6.69 (dd, 1H), 5.89 (dd, 1H), 4.56 (s, 1H), 4.20-4.12 (m, 2H), 3.94-3.82 (m, 2H), 3.77-3.65 (m, 2H), 353-3.43 (m, 1H), 3.27-3.10 (m, 1H), 1.41 (s, 9H), 1.29-1.23 (m, 3H) ppm.

Step 3) (R)-tert-butyl 3-(3-ethoxy-3-oxopropyl)morpholine-4-carboxylate

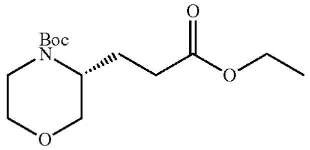 [SMILES: CCOC(=O)CC[C@@H]1COCCN1C(=O)OC(C)(C)C]

To a dried flask were added (R)-tert-butyl 3-(3-ethoxy-3-oxoprop-1-en-1-yl) morpholine-4-carboxylate (1.05 g, 3.68 mmol), Pd/C (10%, 200 mg) and ethanol (20 mL). The mixture was stirred at 30° C. under $H_2$ overnight, and filtered. The filtrate was concentrated in vacuo to give the title compound as colourless oil (0.96 g, 91%). The compound was characterized by the following spectroscopic data:

MS-ESI: (ESI, pos.ion) m/z: 188.1[M+1-100]$^+$; and $^1$H NMR (400 MHz, $CDCl_3$): δ 4.12 (q, 2H), 3.98 (s, 1H), 3.84-3.69 (m, 3H), 3.56 (dd, 1H), 3.42 (td, 1H), 3.12 (t, 1H), 2.37-2.27 (m, 2H), 2.25-2.15 (m, 1H), 1.92-1.83 (m, 1H), 1.45 (s, 9H), 1.25 (t, 3H) ppm.

Step 4) (R)-3-(4-(tert-butoxycarbonyl)morpholin-3-yl)propanoic acid

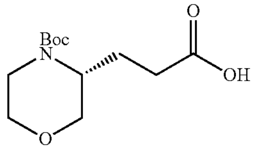 [SMILES: CC(C)(C)OC(=O)N1CCOC[C@H]1CCC(=O)O]

To a dried flask were added (R)-tert-butyl 3-(3-ethoxy-3-oxopropyl) morpholine-4-carboxylate (0.96 g, 3.34 mmol) and ethanol (10 mL). After the dissolution, to the mixture was added a solution of $LiOH.H_2O$ (1.4 g, 33.4 mmol) in $H_2O$ (10 mL). The resulting mixture was stirred at 25° C. for 0.5 hour, and then to the mixture was added EtOAc (150 mL) and water (50 mL). The resulting mixture was adjusted to pH 5-6 with concentrated hydrochloric acid at 0° C. The separated organic phase was washed with brine (100 mL), dried over anhydrous $Na_2SO_4$, filtered and concentrated in vacuo to give the title compound as colourless oil (0.85 g, 98%). The compound was characterized by the following spectroscopic data:

MS-ESI: (ESI, pos.ion) m/z: 160.1[M+1-100]$^+$; and $^1$H NMR (400 MHz, $CDCl_3$): δ 8.08 (br, 1H), 4.03 (br.s, 1H), 3.88-3.72 (m, 3H), 3.58 (dd, 1H), 3.44 (td, 1H), 3.13 (t, 1H), 2.43-2.29 (m, 2H), 2.27-2.20 (m, 1H), 1.94-1.83 (m, 1H), 1.46 (s, 9H) ppm.

Step 5) (R)-3-(morpholin-3-yl)propanoic acid hydrochloride

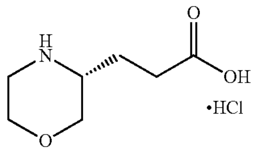 [SMILES: O=C(O)CC[C@@H]1COCCN1 ; Cl]

To a dried flask were added (R)-3-(4-(tert-butoxycarbonyl)morpholin-3-yl)propanoic acid (0.9 g, 3.47 mmol) and a solution of HCl in EtOAc (4 mol/L, 15 mL), and the resulting mixture was stirred at 25° C. for 4 hours. Then the mixture was filtered to give the title compound as a white solid (0.53 g, 78%). The compound was characterized by the following spectroscopic data:

MS-ESI: (ESI, pos.ion) m/z: 160.1[M+1]$^+$; and $^1$H NMR (400 MHz, $D_2O$): δ 4.04-3.96 (m, 2H), 3.75-3.68 (m, 1H), 3.52 (dd, 1H), 3.40-3.35 (m, 1H), 3.34-3.29 (m, 1H), 3.22-3.15 (m, 1H), 2.47 (t, 2H), 1.83 (ddd, 2H) ppm.

Step 6) 3-((R)-4-(((R)-6-(2-bromo-4-fluorophenyl)-5-(ethoxycarbonyl)-2-(thiazol-2-yl)-3,6-dihydropyrimidin-4-yl)methy)morpholin-3-yl)propanoic acid

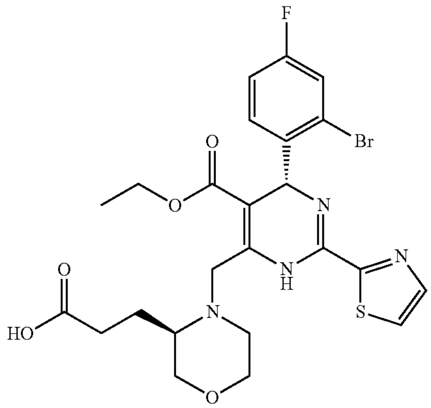 [SMILES: CCOC(=O)C1=C(CN2CCOC[C@H]2CCC(=O)O)NC(c2nccs2)=N[C@H]1c1ccc(F)cc1Br]

To a dried flask were added (R)-ethyl 4-(2-bromo-4-fluorophenyl)-6-(bromomethyl)-2-(thiazol-2-yl)-1,4-dihydropyrimidine-5-carboxylate (6.5 g, 13 mmol), (R)-3-(morpholin-3-yl)propanoic acid hydrochloride (2.5 g, 13 mmol), potassium carbonate (3.4 g, 26 mmol) and anhydrous ethyl alcohol (200 mL). The reaction mixture was stirred at 30° C. under $N_2$ for 12 hours, then filtered, and the filtrate was concentrated in vacuo. The filtered was concentrated in vacuo. The residue was purified by silica gel column chromatography ($DCM/CH_3OH$ (v/v)=25/1) to give the title compound as a yellow solid (4.1 g, 54%). The compound was characterized by the following spectroscopic data:

MS (ESI, pos.ion) m/z: 581.2[M+H]$^+$; and $^1$H NMR (400 MHz, DMSO-$d_6$): δ 12.09 (s, 1H), 9.83 (s, 1H), 8.03 (d, 1H), 7.94 (d, 1H), 7.56 (dd, 1H), 7.40 (dd, 1H), 7.21 (td, 1H), 6.03 (s, 1H), 4.22 (d, 1H), 3.97 (q, 2H), 3.89 (d, 1H), 3.79-3.71 (m, 2H), 3.64-3.60 (m, 1H), 3.41 (dd, 1H), 2.88-2.83 (m, 1H), 2.57-2.52 (m, 1H), 2.47-2.44 (m, 1H), 2.38-2.18 (m, 2H), 1.80-1.73 (m, 1H), 1.64-1.54 (m, 1H), 1.06 (t, 3H).

Example 9

3-((R)-4-(((R)-6-(2-Chloro-4-fluorophenyl)-5-(ethoxycarbonyl)-2-(thiazol-2-yl)-3,6-dihydropyrimidin-4-yl)methyl)morpholin-2-yl)propanoic acid Step 1) (R)-ethyl 4-(2-chloro-4-fluorophenyl)-6-methyl-2-(thiazol-2-yl)-1,4-dihydropyrimidine-5-carboxylate

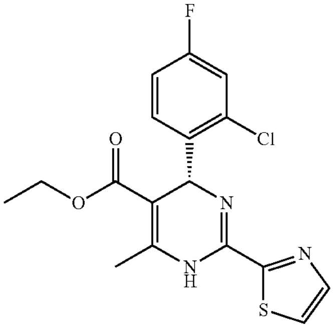 [SMILES: CCOC(=O)C1=C(C)NC(c2nccs2)=N[C@H]1c1ccc(F)cc1Cl]

The title compound was prepared by the procedure described in step 1 of Example 1 using ethyl 4-(2-chloro-4-fluorophenyl)-6-methyl-2-(thiazol-2-yl)-1,4-dihydropyrimidine-5-carboxylate (5 g, 13.2 mmol, synthetic procedures disclosed in WO2010069147A) to give the title compound as a yellow solid (2.1 g, 42%). The compound was characterized by the following spectroscopic data:

$[a]_D^{25}$=−59.6 (c=0.3020 g/100 mL, MeOH);

MS (ESI, pos.ion) m/z: 380.2 $[M+H]^+$; and $^1$H NMR (600 MHz, DMSO-$d_6$): δ 9.92 (s, 1H), 7.97 (d, 1H), 7.90 (d, 1H), 7.41 (dd, 1H), 7.37 (dd, 1H), 7.19 (td, 1H), 6.00 (s, 1H), 3.93 (q, 2H), 2.46 (s, 3H), 1.03 (t, 3H).

Step 2) (R)-ethyl 6-(bromomethyl)-4-(2-chloro-4-fluorophenyl)-2-(thiazol-2-yl)-1,4-dihydropyrimidine-5-carboxylate

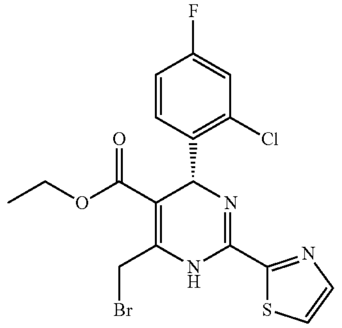 [SMILES: CCOC(=O)C1=C(CBr)NC(c2nccs2)=N[C@H]1c1ccc(F)cc1Cl]

The title compound was prepared by the procedure described in step 2 of Example 1 using (R)-ethyl 4-(2-chloro-4-fluorophenyl)-6-methyl-2-(thiazol-2-yl)-1,4-dihydropyrimidine-5-carboxylate (0.91 g, 2.4 mmol), $CCl_4$ (20 mL) and NBS (0.47 g, 2.64 mmol) to give the title compound as a yellow solid (0.8 g, 73%). The compound was characterized by the following spectroscopic data:

MS (ESI, pos.ion) m/z: 457.9 $[M+H]^+$; and $^1$H NMR (400 MHz, DMSO-$d_6$): δ 9.67 (s, 1H), 8.01 (d, 1H), 7.97 (br, 1H), 7.44-7.41 (m, 2H), 7.22 (td, 1H), 5.99 (s, 1H), 4.83 (br, 2H), 4.02 (q, 2H), 1.07 (t, 3H).

Step 3) 3-((R)-4-(((R)-6-(2-chloro-4-fluorophenyl)-5-(ethoxycarbonyl)-2-(thiazol-2-yl)-3,6-dihydropyrimidin-4-yl)methyl)morpholin-2-yl)propanoic acid

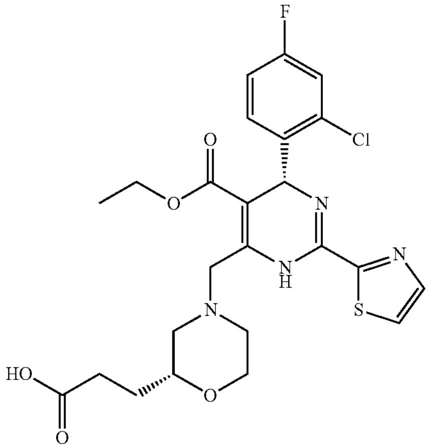 [SMILES: CCOC(=O)C1=C(CN2CCO[C@H](CCC(=O)O)C2)NC(c2nccs2)=N[C@H]1c1ccc(F)cc1Cl]

The title compound was prepared by the procedure described in step 6 of Example 2 using (R)-ethyl 6-(bromomethyl)-4-(2-chloro-4-fluorophenyl)-2-(thiazol-2-yl)-1,4-dihydropyrimidine-5-carboxylate (0.46 g, 1 mmol), (R)-3-(morpholin-2-yl)propanoic acid hydrochloric (0.2 g, 1 mmol), potassium carbonate (0.28 g, 2 mmol) and anhydrous ethyl alcohol (10 mL) to give the title compound as a yellow solid (0.25 g, 47%). The compound was characterized by the following spectroscopic data:

MS (ESI, pos.ion) m/z: 537.3 $[M+H]^+$; and $^1$H NMR (400 MHz, DMSO-$d_6$): δ 9.65 (s, 1H), 8.02 (d, 1H), 7.94 (d, 1H), 7.44-7.38 (m, 2H), 7.18 (td, 1H), 6.05 (s, 1H), 3.96 (q, 2H), 3.89-3.85 (m, 3H), 3.59-3.46 (m, 2H), 2.80-2.74 (m, 2H), 2.36-2.21 (m, 3H), 2.03-1.98 (m, 1H), 1.64-1.59 (m, 2H), 1.06 (t, 3H).

Example 10

3-((R)-4-(((R)-6-(2-Chloro-4-fluorophenyl)-5-(methoxycarbonyl)-2-(thiazol-2-yl)-3,6-dihydropyrimidin-4-yl)methyl)morpholin-2-yl)propanoic acid Step 1) (R)-methyl 4-(2-chloro-4-fluorophenyl)-6-methyl-2-(thiazol-2-yl)-1,4-dihydropyrimidine-5-carboxylate

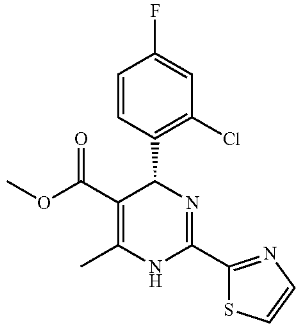 [SMILES: COC(=O)C1=C(C)NC(c2nccs2)=N[C@H]1c1ccc(F)cc1Cl]

The title compound was prepared by the procedure described in step 1 of Example 1 using methyl 4-(2-chloro-4-fluorophenyl)-6-methyl-2-(thiazol-2-yl)-1,4-dihydropyrimidine-5-carboxylate (5 g, 13.7 mmol, synthetic procedures disclosed in WO2010069147A) to give the title compound as a yellow solid (2.1 g, 42%). The compound was characterized by the following spectroscopic data:

$[a]_D^{25}$=−81.49 (c=0.5031 g/100 mL, MeOH);

MS (ESI, pos.ion) m/z: 366.1 $[M+H]^+$; and $^1$H NMR (400 MHz, DMSO-$d_6$): δ 7.81 (d, 1H), 7.68 (d, 1H), 7.36 (dd, 1H), 7.29 (dd, 1H), 7.11 (td, 1H), 5.90 (s, 1H), 3.41 (s, 3H), 2.34 (s, 3H).

Step 2) (R)-methyl 6-(bromomethyl)-4-(2-chloro-4-fluorophenyl)-2-(thiazol-2-yl)-1,4-dihydropyrimidine-5-carboxylate

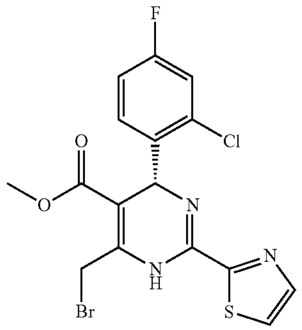 [SMILES: COC(=O)C1=C(CBr)NC(c2nccs2)=N[C@H]1c1ccc(F)cc1Cl]

The title compound was prepared by the procedure described in step 2 of Example 1 using (R)-methyl 4-(2-chloro-4-fluorophenyl)-6-methyl-2-(thiazol-2-yl)-1,4-dihydropyrimidine-5-carboxylate (0.88 g, 2.4 mmol), $CCl_4$ (20 mL) and NBS (0.47 g, 2.64 mmol) to give the title compound as a yellow solid (0.78 g, 73%). The compound was characterized by the following spectroscopic data:

MS (ESI, pos.ion) m/z: 445.6 $[M+H]^+$; and $^1H$ NMR (600 MHz, DMSO-$d_6$): δ 8.02 (d, 1H), 7.96 (br, 1H), 7.46-7.40 (m, 2H), 7.22 (td, 1H), 5.98 (s, 1H), 4.83 (br, 2H), 3.57 (s, 3H).

Step 3) 3-((R)-4-(((R)-6-(2-chloro-4-fluorophenyl)-5-(methoxycarbonyl)-2-(thiazol-2-yl)-3,6-dihydropyrimidin-4-yl)methyl)morpholin-2-yl)propanoic acid

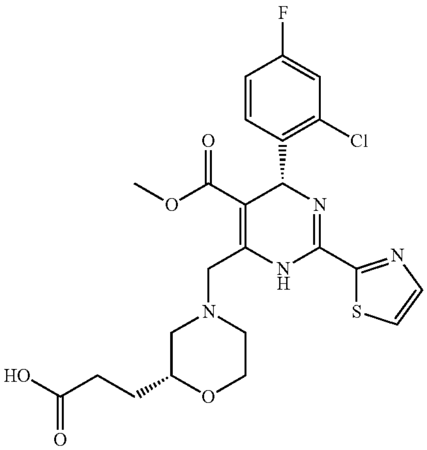 [SMILES: COC(=O)C1=C(CN2CCO[C@H](CCC(=O)O)C2)NC(c2nccs2)=N[C@H]1c1ccc(F)cc1Cl]

The title compound was prepared by the procedure described in step 6 of Example 2 using (R)-methyl 6-(bromomethyl)-4-(2-chloro-4-fluorophenyl)-2-(thiazol-2-yl)-1,4-dihydropyrimidine-5-carboxylate (1 g, 2.25 mmol), (R)-3-(morpholin-2-yl)propanoic acid hydrochloric (0.44 g, 2.25 mmol), potassium carbonate (0.16 g, 1.1 mmol) and anhydrous ethyl alcohol (20 mL) to give the title compound as a yellow solid (0.45 g, 38%). The compound was characterized by the following spectroscopic data:

MS (ESI, pos.ion) m/z: 522.9 $[M+H]^+$; and $^1H$ NMR (400 MHz, DMSO-$d_6$): δ 12.12 (s, 1H), 9.71 (s, 1H), 8.03 (d, 1H), 7.96 (d, 1H), 7.44-7.38 (m, 2H), 7.18 (td, 1H), 6.02 (s, 1H), 3.94-3.82 (m, 3H), 3.62-3.54 (m, 2H), 3.53 (s, 3H), 2.78 (dd, 2H), 2.38-2.26 (m, 3H), 2.06-1.99 (m, 1H), 1.66-1.59 (m, 2H).

Example 11

3-((R)-4-(((R)-6-(2-Bromo-4-fluorophenyl)-5-(methoxycarbonyl)-2-(thiazol-2-yl)-3,6-dihydropyrimidin-4-yl)methyl)morpholin-2-yl)propanoic acid Step 1) (R)-methyl 4-(2-bromo-4-fluorophenyl)-6-methyl-2-(thiazol-2-yl)-1,4-dihydropyrimidine-5-carboxylate

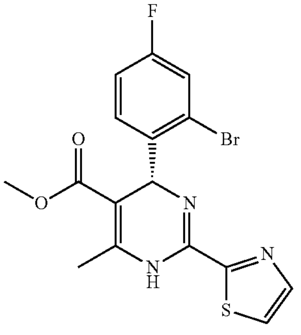 [SMILES: COC(=O)C1=C(C)NC(c2nccs2)=N[C@H]1c1ccc(F)cc1Br]

The title compound was prepared by the procedure described in step 1 of Example 1 using methyl 4-(2-bromo-4-fluorophenyl)-6-methyl-2-(thiazol-2-yl)-1,4-dihydropyrimidine-5-carboxylate (5 g, 12.2 mmol, synthetic procedures disclosed in WO2010069147A) to give the title compound as a yellow solid (2 g, 40%). The compound was characterized by the following spectroscopic data:

$[a]_D^{25}$=−86.04 (c=0.3022 g/100 mL, MeOH);

MS (ESI, pos.ion) m/z: 410.0 $[M+H]^+$; and $^1H$ NMR (400 MHz, DMSO-$d_6$): δ 7.79 (d, 1H), 7.67 (d, 1H), 7.42 (dd, 1H), 7.36 (dd, 1H), 7.15 (td, 1H), 5.85 (s, 1H), 3.40 (s, 3H), 2.33 (s, 3H).

Step 2) (R)-methyl 4-(2-bromo-4-fluorophenyl)-6-(bromomethyl)-2-(thiazol-2-yl)-1,4-dihydropyrimidine-5-carboxylate

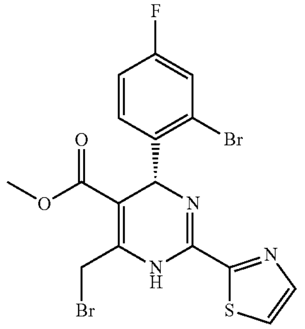 [SMILES: COC(=O)C1=C(CBr)NC(c2nccs2)=N[C@H]1c1ccc(F)cc1Br]

The title compound was prepared by the procedure described in step 2 of Example 1 using (R)-methyl 4-(2-bromo-4-fluorophenyl)-6-methyl-2-(thiazol-2-yl)-1,4-dihydropyrimidine-5-carboxylate (0.98 g, 2.4 mmol), $CCl_4$ (20 mL) and NBS (0.47 g, 2.64 mmol) to give the title compound as a yellow solid (0.8 g, 68%). The compound was characterized by the following spectroscopic data:

MS (ESI, pos.ion) m/z: 489.9$[M+H]^+$; and $^1H$ NMR (400 MHz, $CDCl_3$): δ 7.87 (d, 1H), 7.54 (d, 1H), 7.40 (dd, 1H), 7.35 (dd, 1H), 7.03 (td, 1H), 6.11 (s, 1H), 4.97 (d, 1H), 4.64 (d, 1H), 3.69 (s, 3H).

Step 3) 3-((R)-4-(((R)-6-(2-bromo-4-fluorophenyl)-5-(methoxycarbonyl)-2-(thiazol-2-yl)-3,6-dihydropyrimidin-4-yl)methyl)morpholin-2-yl)propanoic acid

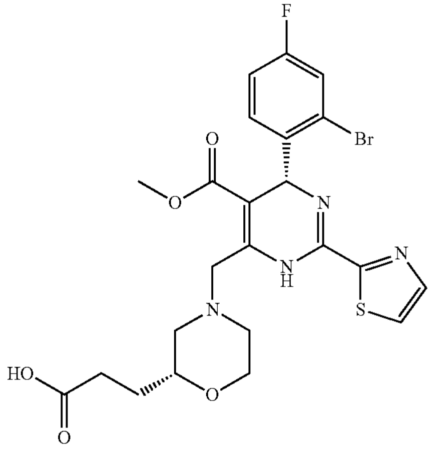 [SMILES: COC(=O)C1=C(CN2CCO[C@H](CCC(=O)O)C2)NC(c2nccs2)=N[C@H]1c1ccc(F)cc1Br]

The title compound was prepared by the procedure described in step 6 of Example 2 using (R)-methyl 4-(2-bromo-4-fluorophenyl)-6-(bromomethyl)-2-(thiazol-2-yl)-1,4-dihydropyrimidine-5-carboxylate (0.49 g, 1 mmol), (R)-3-(morpholin-2-yl)propanoic acid hydrochloric (0.2 g, 1 mmol), potassium carbonate (0.14 g, 1 mmol) and anhydrous ethyl alcohol (10 mL) to give the title compound as a yellow solid (0.26 g, 45%). The compound was characterized by the following spectroscopic data:

MS (ESI, pos.ion) m/z: 567.2[M+H]$^+$; and $^1$H NMR (400 MHz, DMSO-d$_6$): δ 12.03 (s, 1H), 9.69 (s, 1H), 8.01 (d, 1H), 7.93 (d, 1H), 7.56 (dd, 1H), 7.38 (dd, 1H), 7.23 (td, 1H), 6.01 (s, 1H), 3.93-3.83 (m, 3H), 3.60-3.53 (m, 2H), 3.52 (s, 3H), 2.77 (dd, 2H), 2.38-2.25 (m, 3H), 2.05-1.99 (m, 1H), 1.65-1.59 (m, 2H).

Example 12

3-((R)-4-(((R)-6-(2,4-dichlorophenyl)-5-(ethoxycarbonyl)-2-(thiazol-2-yl)-3,6-dihydropyrimidin-4-yl)methyl)morpholin-2-yl)propanoic acid Step 1) (R)-ethyl 4-(2,4-dichlorophenyl)-6-methyl-2-(thiazol-2-yl)-1,4-dihydropyrimidine-5-carboxylate

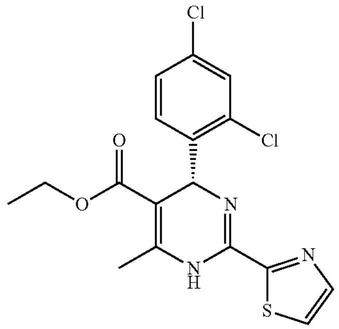 [SMILES: CCOC(=O)C1=C(C)NC(c2nccs2)=N[C@H]1c1ccc(Cl)cc1Cl]

The title compound was prepared by the procedure described in step 1 of Example 1 using ethyl 4-(2,4-dichlorophenyl)-6-methyl-2-(thiazol-2-yl)-1,4-dihydropyrimidine-5-carboxylate (5 g, 12.6 mmol, synthetic procedures disclosed in WO2010069147A) to give the title compound as a yellow solid (1.9 g, 38%). The compound was characterized by the following spectroscopic data:

$[a]_D^{25}$=−39.07 (c=0.3032 g/100 mL, MeOH);

MS (ESI, pos.ion) m/z: 396.1 [M+H]$^+$; and $^1$H NMR (400 MHz, DMSO-d$_6$): δ 9.93 (s, 1H), 7.97 (d, 1H), 7.90 (d, 1H), 7.58 (d, 1H), 7.41 (dd, 1H), 7.35 (d, 1H), 6.00 (s, 1H), 3.93 (q, 2H), 2.46 (s, 3H), 1.03 (t, 3H).

Step 2) (R)-ethyl 6-(bromomethyl)-4-(2,4-dichlorophenyl)-2-(thiazol-2-yl)-1,4-dihydropyrimidine-5-carboxylate

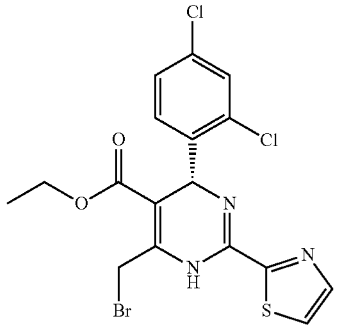 [SMILES: CCOC(=O)C1=C(CBr)NC(c2nccs2)=N[C@H]1c1ccc(Cl)cc1Cl]

The title compound was prepared by the procedure described in step 2 of Example 1 using ((R)-ethyl 4-(2,4-dichlorophenyl)-6-methyl-2-(thiazol-2-yl)-1,4-dihydropyrimidine-5-carboxylate (0.95 g, 2.4 mmol), $CCl_4$ (20 mL) and NBS (0.47 g, 2.64 mmol) to give the title compound as a yellow solid (0.74 g, 65%). The compound was characterized by the following spectroscopic data:

MS (ESI, pos.ion) m/z: 475.6 [M+H]$^+$; and $^1$H NMR (600 MHz, DMSO-d$_6$): δ 8.03 (d, 1H), 7.98 (d, 1H), 7.66-7.62 (m, 1H), 7.47-7.35 (m, 2H), 5.99 (s, 1H), 4.82 (br, 2H), 4.02 (q, 2H), 1.09 (t, 3H).

Step 3) 3-((R)-4-(((R)-6-(2,4-dichlorophenyl)-5-(ethoxycarbonyl)-2-(thiazol-2-yl)-3,6-dihydropyrimidin-4-yl)methyl)morpholin-2-yl)propanoic acid

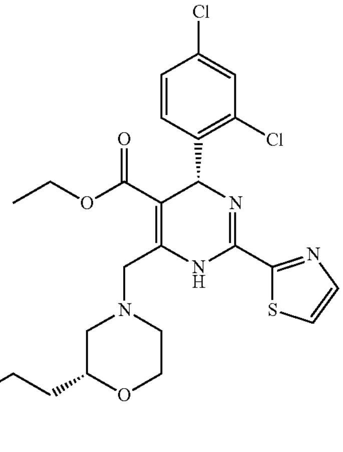

The title compound was prepared by the procedure described in step 6 of Example 2 using (R)-ethyl 6-(bromomethyl)-4-(2,4-dichlorophenyl)-2-(thiazol-2-yl)-1,4-dihydropyrimidine-5-carboxylate (0.98 g, 2.1 mmol), (R)-3-(morpholin-2-yl)propanoic acid hydrochloric (0.4 g, 2.1 mmol), potassium carbonate (0.58 g, 4.2 mmol) and anhydrous ethyl alcohol (20 mL) to give the title compound as a yellow solid (0.71 g, 61%). The compound was characterized by the following spectroscopic data:

MS (ESI, pos.ion) m/z: 553.2[M+H]$^+$; and $^1H$ NMR (400 MHz, DMSO-$d_6$): δ 12.04 (s, 1H), 9.66 (s, 1H), 8.02 (d, 1H), 7.95 (d, 1H), 7.61 (br, 1H), 7.38 (br, 2H), 6.05 (s, 1H), 3.96 (q, 2H), 3.89-3.86 (m, 3H), 3.61-3.46 (m, 2H), 2.77 (t, 2H), 2.36-2.23 (m, 3H), 2.02 (t, 1H), 1.63 (dd, 2H), 1.05 (t, 3H).

Example 13

3-((R)-4-(((R)-6-(2,4-dichlorophenyl)-5-(methoxy-carbonyl)-2-(thiazol-2-yl)-3,6-dihydropyrimidin-4-yl)methyl)morpholin-2-yl)propanoic acid Step 1) (R)-methyl 4-(2,4-dichlorophenyl)-6-methyl-2-(thiazol-2-yl)-1,4-dihydropyrimidine-5-carboxylate

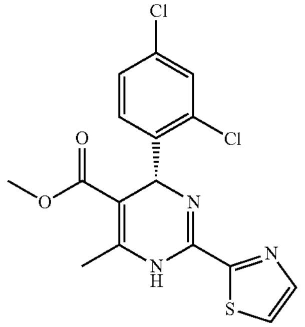 [SMILES: COC(=O)C1=C(C)NC(c2nccs2)=N[C@H]1c1ccc(Cl)cc1Cl]

The title compound was prepared by the procedure described in step 1 of Example 1 using methyl 4-(2,4-dichlorophenyl)-6-methyl-2-(thiazol-2-yl)-1,4-dihydropyrimidine-5-carboxylate (5 g, 13.1 mmol, synthetic procedures disclosed in WO2008154820A) to give the title compound as a yellow solid (1.9 g, 38%). The compound was characterized by the following spectroscopic data:

$[a]_D^{25}$=−46.08 (c=0.3038 g/100 mL, MeOH);

MS (ESI, pos.ion) m/z: 382.1 $[M+H]^+$; and $^1H$ NMR (400 MHz, DMSO-$d_6$): δ 9.99 (s, 1H), 7.98 (d, 1H), 7.90 (d, 1H), 7.59 (d, 1H), 7.40 (dd, 1H), 7.33 (d, 1H), 5.98 (s, 1H), 3.49 (s, 3H), 2.47 (s, 3H).

Step 2) (R)-methyl 6-(bromomethyl)-4-(2,4-dichlorophenyl)-2-(thiazol-2-yl)-1,4-dihydropyrimidine-5-carboxylate

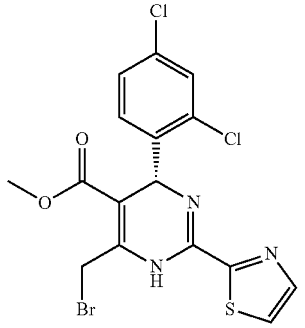 [SMILES: COC(=O)C1=C(CBr)NC(c2nccs2)=N[C@H]1c1ccc(Cl)cc1Cl]

The title compound was prepared by the procedure described in step 2 of Example 1 using (R)-methyl 4-(2,4-dichlorophenyl)-6-methyl-2-(thiazol-2-yl)-1,4-dihydropyrimidine-5-carboxylate (0.92 g, 2.4 mmol), $CCl_4$ (20 mL) and NBS (0.47 g, 2.64 mmol) to give the title compound as a yellow solid (0.72 g, 65%). The compound was characterized by the following spectroscopic data:

MS (ESI, pos.ion) m/z: 459.9 $[M+H]^+$; and $^1H$ NMR (600 MHz, DMSO-$d_6$): δ 9.91 (s, 1H), 8.01 (d, 1H), 7.96 (d, 1H), 7.62 (br, 1H), 7.40 (br, 2H), 6.01 (s, 1H), 4.86 (br, 2H), 3.56 (s, 3H).

Step 3) 3-((R)-4-(((R)-6-(2,4-dichlorophenyl)-5-(methoxycarbonyl)-2-(thiazol-2-yl)-3,6-dihydropyrimidin-4-yl)methyl)morpholin-2-yl)propanoic acid

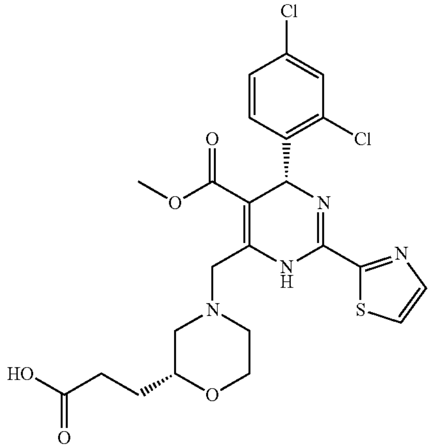 [SMILES: COC(=O)C1=C(CN2CCO[C@H](CCC(=O)O)C2)NC(c2nccs2)=N[C@H]1c1ccc(Cl)cc1Cl]

The title compound was prepared by the procedure described in step 6 of Example 2 using (R)-methyl 6-(bromomethyl)-4-(2,4-dichlorophenyl)-2-(thiazol-2-yl)-1,4-dihydropyrimidine-5-carboxylate (0.72 g, 1.56 mmol), (R)-3-(morpholin-2-yl)propanoic acid hydrochloric (0.31 g, 1.56 mmol), potassium carbonate (0.22 g, 1.56 mmol) and anhydrous ethyl alcohol (15 mL) to give the title compound as a yellow solid (0.37 g, 44%). The compound was characterized by the following spectroscopic data:

MS (ESI, pos.ion) m/z: 538.8$[M+H]^+$; and $^1H$ NMR (400 MHz, DMSO-$d_6$): δ 12.03 (s, 1H), 9.70 (s, 1H), 8.01 (d, 1H), 7.94 (d, 1H), 7.59 (br, 1H), 7.37 (br, 2H), 6.04 (s, 1H), 3.89-3.86 (m, 3H), 3.63-3.57 (m, 1H), 3.52 (s, 3H), 3.49-3.47 (m, 1H), 2.76 (t, 2H), 2.39-2.24 (m, 3H), 2.04 (t, 1H), 1.63 (dd, 2H).

Example 14

3-((R)-4-(((R)-6-(2-Bromo-4-fluorophenyl)-5-(methoxycarbonyl)-2-(thiazol-2-yl)-3,6-dihydropyrimidin-4-yl)methyl)morpholin-3-yl)propanoic acid

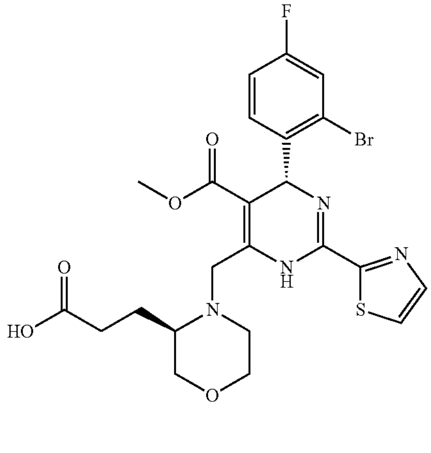 [SMILES: COC(=O)C1=C(CN2CCOC[C@H]2CCC(=O)O)NC(c2nccs2)=N[C@H]1c1ccc(F)cc1Br]

The title compound was prepared by the procedure described in step 6 of Example 2 using (R)-methyl 4-(2-bromo-4-fluorophenyl)-6-(bromomethyl)-2-(thiazol-2-yl)-1,4-dihydropyrimidine-5-carboxylate (0.98 g, 2 mmol), (R)-3-(morpholin-3-yl)propanoic acid hydrochloride (0.39 g, 2 mmol), potassium carbonate (0.14 g, 1 mmol) and anhydrous ethyl alcohol (20 mL) to give the title compound as a yellow solid (0.52 g, 46%). The compound was characterized by the following spectroscopic data:

MS (ESI, pos.ion) m/z: 567.1[M+H]$^+$; and $^1$H NMR (400 MHz, DMSO-$d_6$): δ 12.06 (s, 1H), 9.81 (s, 1H), 8.01 (d, 1H), 7.96 (d, 1H), 7.54 (dd, 1H), 7.41 (dd, 1H), 7.23 (td, 1H), 6.02 (s, 1H), 4.24 (d, 1H), 3.90 (d, 1H), 3.78-3.70 (m, 2H), 3.65-3.61 (m, 1H), 3.52 (s, 3H), 3.42 (dd, 1H), 2.89-2.83 (m, 1H), 2.58-2.53 (m, 1H), 2.48-2.43 (m, 1H), 2.37-2.17 (m, 2H), 1.81-1.72 (m, 1H), 1.65-1.55 (m, 1H).

Example 15

3-((S)-4-(((R)-6-(2-Bromo-4-fluorophenyl)-5-(ethoxycarbonyl)-2-(thiazol-2-yl)-3,6-dihydropyrimidin-4-yl)methyl)morpholin-3-yl)propanoic acid

Step 1) (R)-tert-butyl 3-formylmorpholine-4-carboxylate

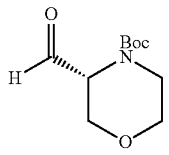 [SMILES: CC(C)(C)OC(=O)N1CCOC[C@@H]1C=O]

To a solution of (S)-tert-butyl 3-(hydroxymethyl)morpholine-4-carboxylate (2.17 g, 10 mmol) in DCM (44 mL) was added Dess-Martin periodinane (5.1 g, 12 mmol) at 0° C. After the addition, the reaction mixture was stirred at 0° C. for 1 hour, then to the mixture was added saturated aqueous $NaHCO_3$ solution (40 mL). The resulting mixture was stirred for another 30 minutes. The separated organic phase was washed with saturated aqueous $NaHCO_3$ solution (40 mL×3) and saturated brine (40 mL), dried over anhydrous $Na_2SO_4$, filtered, and concentrated in vacuo to give the title compound as light yellow oil (1.72 g, 80%).

Step 2) (S)-tert-butyl 3-(3-ethoxy-3-oxoprop-1-en-1-yl)morpholine-4-carboxylate

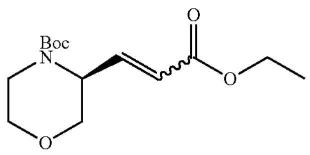

(Z) or (E)

To a solution of (R)-tert-butyl 3-formylmorpholine-4-carboxylate (1.72 g, 8 mmol) in DCM (40 mL) was added ethyl 2-(triphenylphosphoranylidene)acetate (2.78 g, 8 mmol) at 25° C. The reaction was stirred at 25° C. for 12 hours. After the reaction was finished, the reaction mixture was filtered, and the filtrate was concentrated in vacuo. The residue was purified by silica column chromatography (PE/EtOAc (v/v)=10/1) to give the title compound as colourless oil (1.78 g, 78%). The compound was characterized by the following spectroscopic data:

MS (ESI, pos.ion) m/z: 186.2[M+H−100]$^+$.

Step 3) (S)-tert-butyl 3-(3-ethoxy-3-oxopropyl)morpholine-4-carboxylate

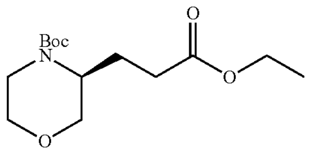 [SMILES: CCOC(=O)CC[C@H]1COCCN1C(=O)OC(C)(C)C]

A mixture of (S)-tert-butyl 3-(3-ethoxy-3-oxoprop-1-en-1-yl)morpholine-4-carboxylate (1.78 g, 6.2 mmol), anhydrous ethyl alcohol (40 mL) and Pd/C (10%, 0.2 g) was stirred at 30° C. 12 hours. After the reaction was finished, the reaction mixture was filtered, and the filtrate was concentrated in vacuo to give the title compound as colourless oil (1.66 g, 93%). The compound was characterized by the following spectroscopic data:

MS (ESI, pos.ion) m/z: 188.1[M+H−100]$^+$.

Step 4) (S)-3-(4-(tert-butoxycarbonyl)morpholin-3-yl)propanoic acid

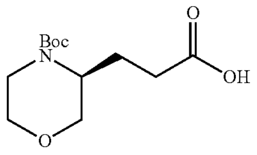 [SMILES: CC(C)(C)OC(=O)N1CCOC[C@@H]1CCC(=O)O]

A mixture of (S)-tert-butyl 3-(3-ethoxy-3-oxopropyl)morpholine-4-carboxylate (1.66 g, 5.8 mmol), anhydrous ethyl alcohol (10 mL) and aqueous $LiOH.H_2O$ solution (2.43 g, 58 mmol in 10 mL of water) was stirred at 25° C. for 30 minutes, then to the mixture was added EtOAc (150 mL) and water (50 mL). The resulting mixture was adjusted to pH 5-6 with concentrated hydrochloric acid at 0° C., then the separated organic phase was washed with saturated brine (100 mL), dried over anhydrous $Na_2SO_4$, filtered, and concentrated in vacuo to give the title compound as colourless oil (1.44 g, 96%). The compound was characterized by the following spectroscopic data:

MS (ESI, pos.ion) m/z: 160.1[M+H−100]$^+$.

Step 5) (S)-3-(morpholin-3-yl)propanoic acid hydrochloride

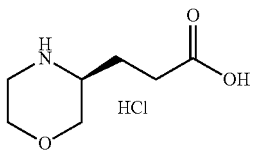 [SMILES: O=C(O)CC[C@H]1COCCN1 ; Cl]

A mixture of (S)-3-(4-(tert-butoxycarbonyl)morpholin-3-yl)propanoic acid (1.44 g, 5.55 mmol) and a solution of HCl in EtOAc (4 mol/L, 15 mL) was stirred at 25° C. for 4 hours. The reaction mixture was filtered, and the filtrate was concentrated in vacuo to give the title compound as a white solid (0.92 g, 85%). The compound was characterized by the following spectroscopic data:

MS (ESI, pos.ion) m/z: 160.3[M+H]$^+$.

Step 6) 3-((S)-4-(((R)-6-(2-bromo-4-fluorophenyl)-5-(ethoxycarbonyl)-2-(thiol-2-yl)-3,6-dihydropyrimidin-4-yl)methyl)morpholin-3-yl)propanoic acid

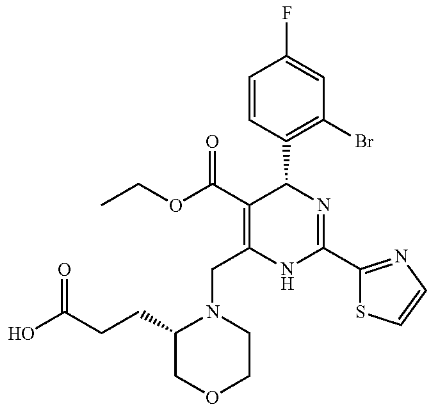 [SMILES: CCOC(=O)C1=C(CN2CCOC[C@@H]2CCC(=O)O)NC(c2nccs2)=N[C@H]1c1ccc(F)cc1Br]

The title compound was prepared by the procedure described in step 6 of Example 2 using (R)-ethyl 4-(2-bromo-4-fluorophenyl)-6-(bromomethyl)-2-(thiazol-2-yl)-1,4-dihydropyrimidine-5-carboxylate (0.5 g, 1 mmol), (S)-3-(morpholin-3-yl)propanoic acid hydrochloride (0.2 g, 1 mmol), potassium carbonate (0.28 g, 2 mmol) and anhydrous ethyl alcohol (10 mL) to give the title compound as a yellow solid (0.23 g, 39%). The compound was characterized by the following spectroscopic data:

MS (ESI, pos.ion) m/z: 580.9[M+H]$^+$; and $^1$H NMR (400 MHz, DMSO-$d_6$): δ 12.14 (br, 1H), 9.82 (s, 1H), 8.02 (d, 1H), 7.92 (d, 1H), 7.54 (dd, 1H), 7.40 (dd, 1H), 7.22 (td, 1H), 6.03 (s, 1H), 4.18 (d, 1H), 3.96 (q, 2H), 3.91 (d, 1H), 3.82-3.79 (m, 1H), 3.74-3.71 (m, 1H), 3.61-3.57 (m, 1H), 3.37-3.32 (m, 1H), 2.78-2.75 (m, 1H), 2.57-2.53 (m, 1H), 2.49-2.47 (m, 1H), 2.38-2.32 (m, 2H), 1.89-1.84 (m, 1H), 1.68-1.58 (m, 1H), 1.06 (t, 3H).

Example 16

3-((S)-4-(((R)-6-(2-Bromo-4-fluorophenyl)-5-(methoxycarbonyl)-2-(thiazol-2-yl)-3,6-dihydropyrimidin-4-yl)methyl)morpholin-3-yl)propanoic acid

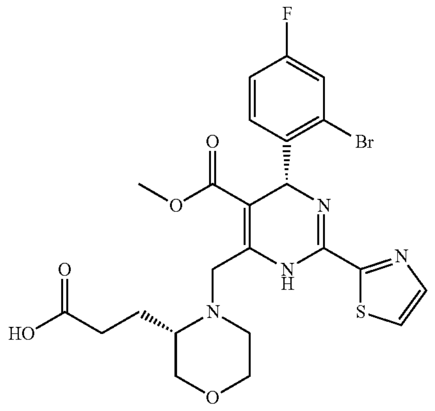 [SMILES: COC(=O)C1=C(CN2CCOC[C@@H]2CCC(=O)O)NC(c2nccs2)=N[C@H]1c1ccc(F)cc1Br]

The title compound was prepared by the procedure described in step 6 of Example 2 using (R)-methyl 4-(2-bromo-4-fluorophenyl)-6-(bromomethyl)-2-(thiazol-2-yl)-1,4-dihydropyrimidine-5-carboxylate (0.98 g, 2 mmol), (S)-3-(morpholin-3-yl)propanoic acid hydrochloride (0.4 g, 2 mmol), potassium carbonate (0.28 g, 2 mmol) and anhydrous ethyl alcohol (20 mL) to give the title compound as a yellow solid (0.42 g, 37%). The compound was characterized by the following spectroscopic data:

MS (ESI, pos.ion) m/z: 567.2[M+H]$^+$; and $^1$H NMR (400 MHz, DMSO-$d_6$): δ 9.87 (s, 1H), 8.03 (d, 1H), 7.94 (d, 1H), 7.56 (dd, 1H), 7.38 (dd, 1H), 7.23 (td, 1H), 6.01 (s, 1H), 4.18 (d, 1H), 3.91 (d, 1H), 3.83-3.79 (m, 1H), 3.75-3.70 (m, 1H), 3.61-3.56 (m, 1H), 3.53 (s, 3H), 3.47-3.40 (m, 1H), 3.04-2.86 (m, 1H), 2.77-2.75 (m, 1H), 2.58-2.54 (m, 1H), 2.37-2.22 (m, 2H), 1.88-1.84 (m, 1H), 1.65-1.58 (m, 1H).

Example 17

3-((S)-4-(((R)-6-(2-Chloro-4-fluorophenyl)-5-(ethoxycarbonyl)-2-(thiazol-2-yl)-3,6-dihydropyrimidin-4-yl)methyl)morpholin-3-yl)propanoic acid

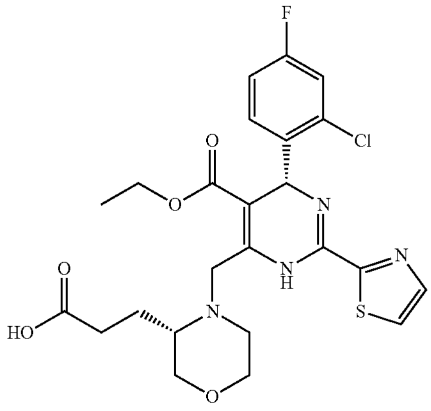 [SMILES: CCOC(=O)C1=C(CN2CCOC[C@@H]2CCC(=O)O)NC(c2nccs2)=N[C@H]1c1ccc(F)cc1Cl]

The title compound was prepared by the procedure described in step 6 of Example 2 using (R)-ethyl 6-(bromomethyl)-4-(2-chloro-4-fluorophenyl)-2-(thiazol-2-yl)-1,4-dihydropyrimidine-5-carboxylate (1.38 g, 3 mmol), (S)-3-(morpholin-3-yl)propanoic acid hydrochloride (0.6 g, 3 mmol), potassium carbonate (0.83 g, 6 mmol) and anhydrous ethyl alcohol (30 mL) to give the title compound as a yellow solid (0.56 g, 35%). The compound was characterized by the following spectroscopic data:

MS (ESI, pos.ion) m/z: 537.2[M+H]$^+$; and $^1$H NMR (400 MHz, DMSO-$d_6$): δ 12.13 (br, 1H), 9.81 (s, 1H), 8.02 (d, 1H), 7.94 (d, 1H), 7.44-7.38 (m, 2H), 7.18 (td, 1H), 6.02 (s, 1H), 4.20 (d, 1H), 3.98 (q, 2H), 3.92 (d, 1H), 3.83-3.78 (m, 1H), 3.75-3.72 (m, 1H), 3.62-3.58 (m, 1H), 3.37-3.33 (m, 1H), 2.79-2.75 (m, 1H), 2.58-2.53 (m, 1H), 2.49-2.46 (m, 1H), 2.39-2.32 (m, 2H), 1.89-1.83 (m, 1H), 1.66-1.58 (m, 1H), 1.06 (t, 3H).

Example 18

3-((S)-4-(((R)-6-(2-Chloro-4-fluorophenyl)-5-(methoxycarbonyl)-2-(thiazol-2-yl)-3,6-dihydropyrimidin-4-yl)methyl)morpholin-3-yl)propanoic acid

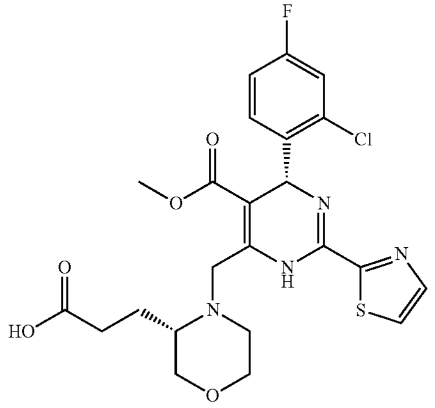 [SMILES: COC(=O)C1=C(CN2CCOC[C@@H]2CCC(=O)O)NC(c2nccs2)=N[C@H]1c1ccc(F)cc1Cl]

The title compound was prepared by the procedure described in step 6 of Example 2 using (R)-methyl 6-(bromomethyl)-4-(2-chloro-4-fluorophenyl)-2-(thiazol-2-yl)-1,4-dihydropyrimidine-5-carboxylate (0.44 g, 1 mmol), (S)-3-(morpholin-3-yl)propanoic acid hydrochloride (0.2 g, 1 mmol), potassium carbonate (0.14 g, 1 mmol) and anhydrous ethyl alcohol (10 mL) to give the title compound as a yellow solid (0.2 g, 39%). The compound was characterized by the following spectroscopic data:

MS (ESI, pos.ion) m/z: 523.1[M+H]$^+$; and $^1$H NMR (400 MHz, DMSO-$d_6$): δ 9.87 (s, 1H), 8.03 (d, 1H), 7.94 (d, 1H), 7.44-7.40 (m, 2H), 7.16 (td, 1H), 6.02 (s, 1H), 4.20 (d, 1H), 3.93 (d, 1H), 3.84-3.79 (m, 1H), 3.75-3.71 (m, 1H), 3.62-3.56 (m, 1H), 3.52 (s, 3H), 3.48-3.41 (m, 1H), 3.05-2.87 (m, 1H), 2.78-2.75 (m, 1H), 2.58-2.56 (m, 1H), 2.38-2.23 (m, 2H), 1.87-1.84 (m, 1H), 1.66-1.58 (m, 1H).

Example 19

3-((S)-4-(((R)-6-(2,4-Dichlorophenyl)-5-(ethoxycarbonyl)-2-(thiazol-2-yl)-3,6-dihydropyrimidin-4-yl)methyl)morpholin-3-yl)propanoic acid

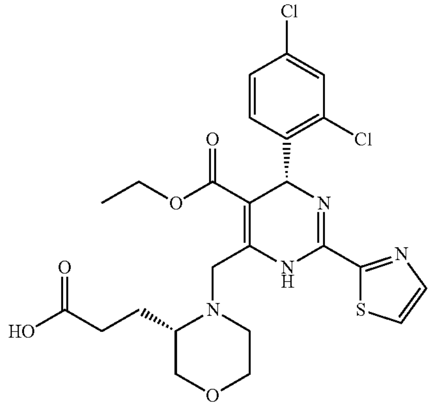 [SMILES: CCOC(=O)C1=C(CN2CCOC[C@@H]2CCC(=O)O)NC(c2nccs2)=N[C@H]1c1ccc(Cl)cc1Cl]

The title compound was prepared by the procedure described in step 6 of Example 2 using (R)-ethyl 6-(bromomethyl)-4-(2,4-dichlorophenyl)-2-(thiazol-2-yl)-1,4-dihydropyrimidine-5-carboxylate (1 g, 2.1 mmol), (S)-3-(morpholin-3-yl)propanoic acid hydrochloride (0.41 g, 2.1 mmol), potassium carbonate (0.58 g, 4.2 mmol) and anhydrous ethyl alcohol (20 mL) to give the title compound as a yellow solid (0.52 g, 45%). The compound was characterized by the following spectroscopic data:

MS (ESI, pos.ion) m/z: 552.9[M+H]$^+$; and $^1$H NMR (400 MHz, DMSO-$d_6$): δ 9.84 (s, 1H), 8.03 (d, 1H), 7.95 (d, 1H), 7.60 (br, 1H), 7.40 (br, 2H), 6.05 (s, 1H), 4.18 (d, 1H), 3.97 (q, 2H), 3.90 (d, 1H), 3.82-3.80 (m, 1H), 3.74-3.72 (m, 1H), 3.61-3.55 (m, 1H), 3.37-3.35 (m, 1H), 2.78-2.76 (m, 1H), 2.56-2.54 (m, 1H), 2.49-2.46 (m, 1H), 2.35-2.20 (m, 2H), 1.88-1.83 (m, 1H), 1.64-1.54 (m, 1H), 1.07 (t, 3H).

Example 20

3-((S)-4-(((R)-6-(2,4-Dichlorophenyl)-5-(methoxycarbonyl)-2-(thiazol-2-yl)-3,6-dihydropyrimidin-4-yl)methyl)morpholin-3-yl)propanoic acid

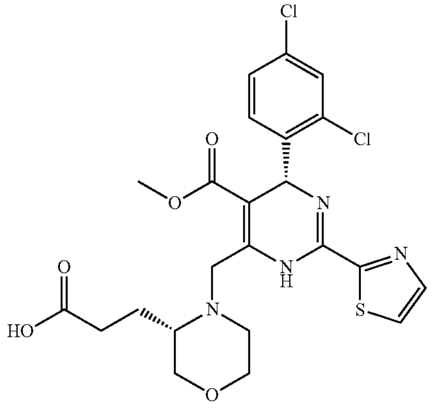 [SMILES: COC(=O)C1=C(CN2CCOC[C@@H]2CCC(=O)O)NC(c2nccs2)=N[C@H]1c1ccc(Cl)cc1Cl]

The title compound was prepared by the procedure described in step 6 of Example 2 using (R)-methyl 6-(bromomethyl)-4-(2,4-dichlorophenyl)-2-(thiazol-2-yl)-1,4-dihydropyrimidine-5-carboxylate (0.46 g, 1 mmol), (S)-3-(morpholin-3-yl)propanoic acid hydrochloride (0.2 g, 1 mmol), potassium carbonate (0.14 g, 1 mmol) and anhydrous ethyl alcohol (10 mL) to give the title compound as a yellow solid (0.22 g, 41%). The compound was characterized by the following spectroscopic data:

MS (ESI, pos.ion) m/z: 538.9[M+H]$^+$; and $^1$H NMR (400 MHz, DMSO-$d_6$): δ 12.17 (s, 1H), 9.89 (s, 1H), 8.04 (d, 1H), 7.95 (d, 1H), 7.60 (br, 1H), 7.42-7.37 (m, 2H), 6.04 (s, 1H), 4.18 (d, 1H), 3.90 (d, 1H), 3.84-3.80 (m, 1H), 3.76-3.72 (m, 1H), 3.61-3.56 (m, 1H), 3.53 (s, 3H), 3.46-3.42 (m, 1H), 3.30-3.26 (m, 1H), 2.80-2.75 (m, 1H), 2.56-2.53 (m, 1H), 2.37-2.22 (m, 2H), 1.93-1.83 (m, 1H), 1.62-1.58 (m, 1H).

Example 21

3-((S)-4-(((R)-6-(2-Bromo-4-fluorophenyl)-5-(ethoxycarbonyl)-2-(thiazol-2-yl)-3,6-dihydropyrimidin-4-yl)methyl)morpholin-2-yl)propanoic acid Step 1) (R)-tert-butyl 2-formylmorpholine-4-carboxylate

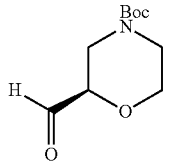 [SMILES: CC(C)(C)OC(=O)N1CCO[C@@H](C=O)C1]

The title compound was prepared by the procedure described in step 1 of Example 14 using (R)-tert-butyl 2-(hydroxymethyl)morpholine-4-carboxylate (2.17 g, 10 mmol), DCM (44 mL) and Dess-Martin periodinane (5.1 g, 12 mmol) to give the title compound as colorless oil (1.81 g, 84%). The compound was characterized by the following spectroscopic data:

MS (ESI, pos.ion) m/z: 160.2[M+H−56]$^+$.

Step 2) (S)-tert-butyl 2-(3-ethoxy-3-oxoprop-1-en-1-yl)morpholine-4-carboxylate

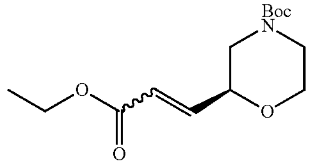

(Z) or (E)

The title compound was prepared by the procedure described in step 2 of Example 14 using (R)-tert-butyl 2-formylmorpholine-4-carboxylate (1.81 g, 8.4 mmol), DCM (40 mL) and ethyl 2-(triphenylphosphoranylidene) acetate (2.93 g, 8.4 mmol) to give the title compound as colorless oil (1.94 g, 81%). The compound was characterized by the following spectroscopic data:

MS (ESI, pos.ion) m/z: 186.1[M+H−100]$^+$.

Step 3) (S)-tert-butyl 2-(3-ethoxy-3-oxopropyl)morpholine-4-carboxylate

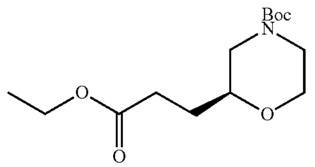 [SMILES: CCOC(=O)CC[C@H]1CN(C(=O)OC(C)(C)C)CCO1]

The title compound was prepared by the procedure described in step 3 of Example 14 using (S)-tert-butyl 2-(3-ethoxy-3-oxoprop-1-en-1-yl)morpholine-4-carboxylate (1.94 g, 6.8 mmol), Pd/C (10%, 0.2 g) and anhydrous ethanol (40 mL) to give the title compound as colorless oil (1.78 g, 91%). The compound was characterized by the following spectroscopic data:

MS (ESI, pos.ion) m/z: 232.1[M+H−56]$^+$.

Step 4) (S)-3-(4-(tert-butoxycarbonyl)morpholin-2-yl)propanoic acid

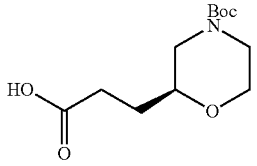 [SMILES: CC(C)(C)OC(=O)N1CCO[C@@H](CCC(=O)O)C1]

The title compound was prepared by the procedure described in step 4 of Example 14 using (S)-tert-butyl 2-(3-ethoxy-3-oxopropyl)morpholine-4-carboxylate (1.78 g, 6.2 mmol), a solution of $LiOH.H_2O$ (2.6 g, 62 mmol) in $H_2O$ (10 mL) and anhydrous ethanol (10 mL) to give the title compound as colorless oil (1.59 g, 99%). The compound was characterized by the following spectroscopic data:

MS (ESI, pos.ion) m/z: 160.2[M+H−100]$^+$.

Step 5) (S)-3-(morpholin-2-yl)propanoic acid hydrochloride

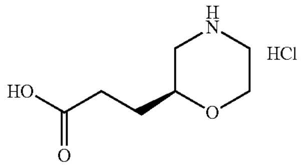 [SMILES: O=C(O)CC[C@H]1CNCCO1 ; Cl]

A mixture of (S)-3-(4-(tert-butoxycarbonyl)morpholin-2-yl)propanoic acid (1.59 g, 6.1 mmol) and a solution of HCl in EtOAc (4 mol/L, 15 mL) was stirred at 25° C. for 4 hours. Then the mixture was filtered to give the title compound as a white solid (0.94 g, 79%). The compound was characterized by the following spectroscopic data:

MS (ESI, pos.ion) m/z: 160.1 [M+H]$^+$; and $^1H$ NMR (400 MHz, $D_2O$): δ 4.10-4.02 (m, 1H), 3.80-3.74 (m, 2H), 3.32-3.25 (m, 2H), 3.10 (td, 1H), 2.89 (t, 1H), 2.47-2.43 (m, 2H), 1.88-1.70 (m, 2H).

Step 6) 3-((S)-4-(((R)-6-(2-bromo-4-fluorophenyl)-5-(ethoxycarbonyl)-2-(thiazol-2-yl)-3,6-dihydropyrimidin-4-yl)methyl)morpholin-2-yl)propanoic acid

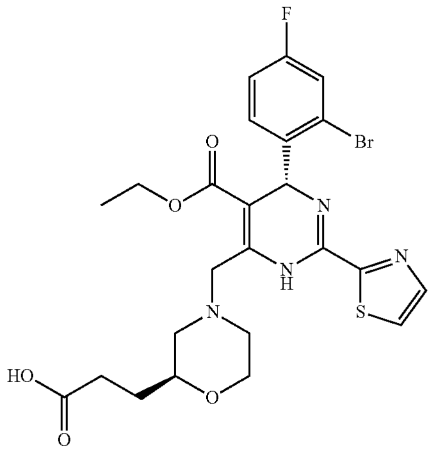 [SMILES: CCOC(=O)C1=C(CN2CCO[C@@H](CCC(=O)O)C2)NC(c2nccs2)=N[C@H]1c1ccc(F)cc1Br]

The title compound was prepared by the procedure described in step 6 of Example 2 using (R)-ethyl 4-(2-bromo-4-fluorophenyl)-6-(bromomethyl)-2-(thiazol-2-yl)-1,4-dihydropyrimidine-5-carboxylate (0.5 g, 1 mmol), (S)-3-(morpholin-2-yl)propanoic acid hydrochloride (0.2 g, 1 mmol), potassium carbonate (0.28 g, 2 mmol) and anhydrous ethyl alcohol (10 mL) to give the title compound as a yellow solid (0.33 g, 56%). The compound was characterized by the following spectroscopic data:

MS (ESI, pos.ion) m/z: 580.9[M+H]$^+$; and $^1$H NMR (400 MHz, DMSO-$d_6$): δ 12.06 (s, 1H), 9.66 (s, 1H), 8.02 (d, 1H), 7.95 (d, 1H), 7.56 (dd, 1H), 7.41 (dd, 1H), 7.20 (td, 1H), 6.03 (s, 1H), 3.97 (q, 2H), 3.93-3.83 (m, 3H), 3.57-3.46 (m, 2H), 2.88 (d, 1H), 2.63 (d, 1H), 2.37-2.22 (m, 3H), 2.13-2.08 (m, 1H), 1.75-1.65 (m, 2H), 1.06 (t, 3H).

Example 22

3-((S)-4-(((R)-6-(2-Bromo-4-fluorophenyl)-5-(methoxycarbonyl)-2-(thiazol-2-yl)-3,6-dihydropyrimidin-4-yl)methyl)morpholin-2-yl)propanoic acid

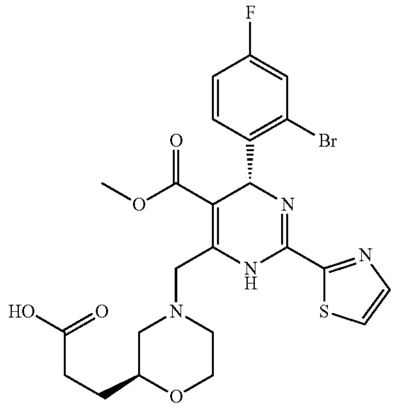 [SMILES: COC(=O)C1=C(CN2CCO[C@@H](CCC(=O)O)C2)NC(c2nccs2)=N[C@H]1c1ccc(F)cc1Br]

The title compound was prepared by the procedure described in step 6 of Example 2 using (R)-methyl 4-(2-bromo-4-fluorophenyl)-6-(bromomethyl)-2-(thiazol-2-yl)-1,4-dihydropyrimidine-5-carboxylate (1 g, 2 mmol), (S)-3-(morpholin-2-yl)propanoic acid hydrochloride (0.39 g, 2 mmol), potassium carbonate (0.28 g, 2 mmol) and anhydrous ethyl alcohol (10 mL) to give the title compound as a yellow solid (0.54 g, 48%). The compound was characterized by the following spectroscopic data:

MS (ESI, pos.ion) m/z: 567.2[M+H]$^+$; and $^1$H NMR (600 MHz, DMSO-$d_6$): δ 12.06 (s, 1H), 9.70 (s, 1H), 8.03 (d, 1H), 7.94 (d, 1H), 7.57 (dd, 1H), 7.39 (dd, 1H), 7.23 (td, 1H), 6.02 (s, 1H), 3.95 (d, 1H), 3.86-3.80 (m, 2H), 3.56-3.54 (m, 1H), 3.53 (s, 3H), 3.52-3.49 (m, 1H), 2.88 (d, 1H), 2.62 (d, 1H), 2.37-2.21 (m, 3H), 2.15-2.08 (m, 1H), 1.72-1.64 (m, 2H).

Example 23

3-((S)-4-(((R)-6-(2-Chloro-4-fluorophenyl)-5-(ethoxycarbonyl)-2-(thiazol-2-yl)-3,6-dihydropyrimidin-4-yl)methyl)morpholin-2-yl)propanoic acid

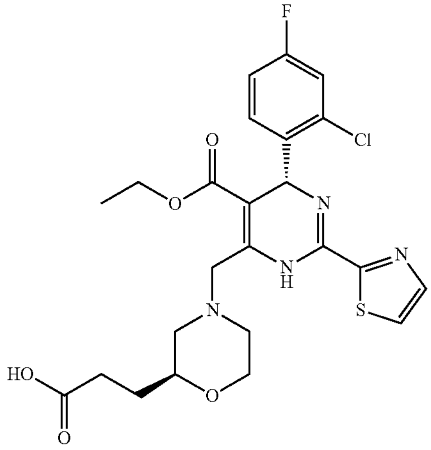 [SMILES: CCOC(=O)C1=C(CN2CCO[C@@H](CCC(=O)O)C2)NC(c2nccs2)=N[C@H]1c1ccc(F)cc1Cl]

The title compound was prepared by the procedure described in step 6 of Example 2 using (R)-ethyl 6-(bromomethyl)-4-(2-chloro-4-fluorophenyl)-2-(thiazol-2-yl)-1,4-dihydropyrimidine-5-carboxylate (0.46 g, 1 mmol), (S)-3-(morpholin-2-yl)propanoic acid hydrochloride (0.2 g, 1 mmol), potassium carbonate (0.28 g, 2 mmol) and anhydrous ethyl alcohol (10 mL) to give the title compound as a yellow solid (0.29 g, 54%). The compound was characterized by the following spectroscopic data:

MS (ESI, pos.ion) m/z: 536.9[M+H]$^+$; and $^1$H NMR (400 MHz, DMSO-$d_6$): δ 12.07 (s, 1H), 9.65 (s, 1H), 8.02 (d, 1H), 7.94 (d, 1H), 7.44-7.40 (m, 2H), 7.19 (td, 1H), 6.06 (s, 1H), 3.97 (q, 2H), 3.92-3.82 (m, 3H), 3.58-3.46 (m, 2H), 2.88 (d, 1H), 2.63 (d, 1H), 2.37-2.22 (m, 3H), 2.08-1.99 (m, 1H), 1.72-1.65 (m, 2H), 1.05 (t, 3H).

Example 24

3-((S)-4-(((R)-6-(2-Chloro-4-fluorophenyl)-5-(methoxycarbonyl)-2-(thiazol-2-yl)-3,6-dihydropyrimidin-4-yl)methyl)morpholin-2-yl)propanoic acid

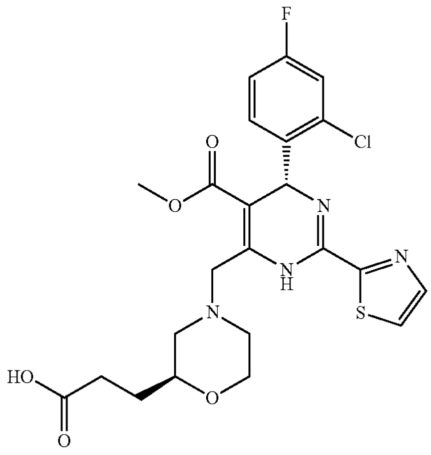 [SMILES: COC(=O)C1=C(CN2CCO[C@@H](CCC(=O)O)C2)NC(c2nccs2)=N[C@H]1c1ccc(F)cc1Cl]

The title compound was prepared by the procedure described in step 6 of Example 2 using (R)-methyl 6-(bromomethyl)-4-(2-chloro-4-fluorophenyl)-2-(thiazol-2-yl)-1,4-dihydropyrimidine-5-carboxylate (0.89 g, 2 mmol), (S)-3-(morpholin-2-yl)propanoic acid hydrochloride (0.4 g, 2 mmol), potassium carbonate (0.28 g, 2 mmol) and anhydrous ethyl alcohol (20 mL) to give the title compound as a yellow solid (0.41 g, 39%). The compound was characterized by the following spectroscopic data:

MS (ESI, pos.ion) m/z: 523.2 $[M+H]^+$; and $^1H$ NMR (400 MHz, DMSO-$d_6$): δ 12.09 (br, 1H), 9.70 (s, 1H), 8.03 (d, 1H), 7.94 (d, 1H), 7.44-7.38 (m, 2H), 7.18 (td, 1H), 6.04 (s, 1H), 3.95 (d, 1H), 3.86-3.81 (m, 2H), 3.57-3.54 (m, 1H), 3.52 (s, 3H), 3.50-3.47 (m, 1H), 2.87 (d, 1H), 2.62 (d, 1H), 2.35-2.19 (m, 3H), 2.14-2.08 (m, 1H), 1.73-1.61 (m, 2H).

Example 25

3-((S)-4-(((R)-6-(2,4-Dichlorophenyl)-5-(ethoxycarbonyl)-2-(thiazol-2-yl)-3,6-dihydropyrimidin-4-yl)methyl)morpholin-2-yl)propanoic acid

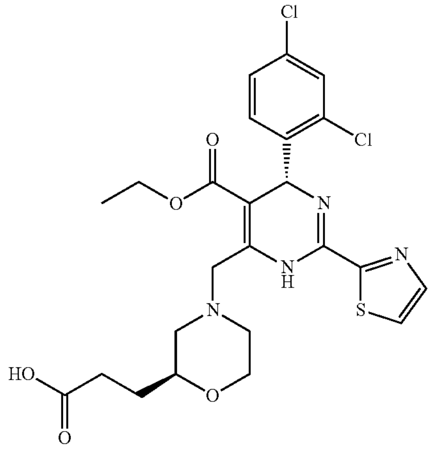

The title compound was prepared by the procedure described in step 6 of Example 2 using (R)-ethyl 6-(bromomethyl)-4-(2,4-dichlorophenyl)-2-(thiazol-2-yl)-1,4-dihydropyrimidine-5-carboxylate (0.48 g, 1 mmol), (S)-3-(morpholin-2-yl)propanoic acid hydrochloride (0.2 g, 1 mmol), potassium carbonate (0.28 g, 2 mmol) and anhydrous ethyl alcohol (10 mL) to give the title compound as a yellow solid (0.34 g, 62%). The compound was characterized by the following spectroscopic data:

MS (ESI, pos.ion) m/z: 552.9$[M+H]^+$; and $^1H$ NMR (400 MHz, DMSO-$d_6$): δ 12.08 (s, 1H), 9.66 (s, 1H), 8.03 (d, 1H), 7.95 (d, 1H), 7.61 (br, 1H), 7.40 (br, 2H), 6.06 (s, 1H), 3.98-3.93 (m, 3H), 3.86-3.82 (m, 2H), 3.58-3.48 (m, 2H), 2.87 (d, 1H), 2.63 (d, 1H), 2.36-2.23 (m, 3H), 2.10 (t, 1H), 1.72-1.63 (m, 2H), 1.06 (t, 3H).

Example 26

3-((S)-4-(((R)-6-(2,4-Dichlorophenyl)-5-(methoxycarbonyl)-2-(thiazol-2-yl)-3,6-dihydropyrimidin-4-yl)methyl)morpholin-2-yl)propanoic acid

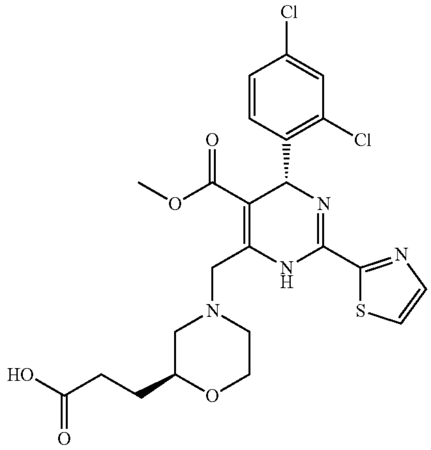 [SMILES: COC(=O)C1=C(CN2CCO[C@@H](CCC(=O)O)C2)NC(c2nccs2)=N[C@H]1c1ccc(Cl)cc1Cl]

The title compound was prepared by the procedure described in step 6 of Example 2 using (R)-methyl 6-(bromomethyl)-4-(2,4-dichlorophenyl)-2-(thiazol-2-yl)-1,4-dihydropyrimidine-5-carboxylate (0.46 g, 1 mmol), (S)-3-(morpholin-2-yl)propanoic acid hydrochloride (0.2 g, 1 mmol), potassium carbonate (0.14 g, 1 mmol) and anhydrous ethyl alcohol (10 mL) to give the title compound as a yellow solid (0.2 g, 37%). The compound was characterized by the following spectroscopic data:

MS (ESI, pos.ion) m/z: 539.1$[M+H]^+$; and $^1H$ NMR (600 MHz, DMSO-$d_6$): δ 12.06 (s, 1H), 9.70 (s, 1H), 8.03 (d, 1H), 7.94 (d, 1H), 7.59 (br, 1H), 7.40 (br, 2H), 6.03 (s, 1H), 3.96 (d, 1H), 3.85-3.80 (m, 2H), 3.57-3.55 (m, 1H), 3.52 (s, 3H), 3.51-3.48 (m, 1H), 2.88 (d, 1H), 2.61 (d, 1H), 2.38-2.21 (m, 3H), 2.16-2.09 (m, 1H), 1.72-1.65 (m, 2H).

Example 27

3-((2S,3S)-4-(((R)-6-(2-Bromo-4-fluorophenyl)-5-(ethoxycarbonyl)-2-(thiazol-2-yl)-3,6-dihydropyrimidin-4-yl)methyl)-2-methylmorpholin-3-yl)propanoic acid Step 1) (2R,3S)-2-(benzylamino)-3-hydroxybutanoic acid

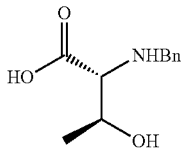

A mixture of (2R,3S)-2-amino-3-hydroxybutanoic acid (16.7 g, 140 mmol), aqueous sodium hydroxide solution (2 mol/L, 70 mL, 140 mmol) and benzaldehyde (14.56 g, 137 mmol) was stirred at 25° C. for 1 hour. Then the mixture was cooled to 0° C., and to the mixture was added sodium borohydride (3 g, 80 mmol) in portions. After the addition, the resulted mixture was stirred at 25° C. for 12 hours. After the reaction was finished, the reaction mixture was extracted with DCM (30 mL×3). The organic phases were discarded. The water phase was cooled to 5° C., adjusted to pH 1-2 with concentrated hydrochloric acid, and the resulting mixture was stirred at 5° C. for 4 hours to precipitate out solid, then the mixture was filtrated to give the title compound as a white solid (20.9 g, 73%). The compound was characterized by the following spectroscopic data:

MS (ESI, pos.ion) m/z: 210.1[M+H]$^+$.

Step 2) (2S,3R)-4-benzyl-2-methyl-5-oxomorpholine-3-carboxylic acid

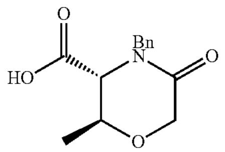 [SMILES: C[C@@H]1OCC(=O)N(Cc2ccccc2)[C@H]1C(=O)O]

To a mixture of (2R,3S)-2-(benzylamino)-3-hydroxybutanoic acid (21.4 g, 102.4 mmol), THF (110 mL) and a solution of $K_2CO_3$ (42.5 g, 307.2 mmol) in water (70 mL) was added 2-chloroacetyl chloride (17.8 g, 157.7 mmol) dropwise slowly at 0° C. After the addition, the mixture was stirred at 0° C. for 3 hours, then to the mixture was added a solution of sodium hydroxide (16.4 g, 409.6 mmol) in water (40 mL). After the addition, the mixture was stirred at 3° C. for 4 hours. Then the mixture was warmed to 25° C., and extracted with PE (50 mL×2). The separated water phase was cooled to 15° C., and to the water phase was added concentrated hydrochloric acid until a lot of solid precipitate was formed. The mixture was stirred at 10° C. for 12 hours, and filtered. The filter cake was washed with water to give the title compound as a white solid (16.1 g, 63%). The compound was characterized by the following spectroscopic data:

MS (ESI, pos.ion) m/z: 250.1[M+H]$^+$.

Step 3) (2S,3S)-4-benzyl-2-methylmorpholin-3-yl)methanol

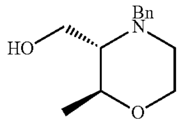 [SMILES: C[C@@H]1OCCN(Cc2ccccc2)[C@H]1CO]

To a solution of (2S,3R)-4-benzyl-2-methyl-5-oxomorpholine-3-carboxylic acid (26.5 g, 106 mmol) in toluene (237 mL) was added 70% sodium bis(2-methoxyethoxy) aluminumhydride (153 mL, 549 mmol) slowly at 0° C. under $N_2$. After the addition, the mixture was stirred at 25° C. for 12 hours, then cooled to 10° C. To the mixture was added EtOH (43 mL) dropwise. The mixture was washed with 2 mol/L aqueous NaOH solution (50 mL×3), the separated water phase was discarded, and the organic phase was extracted with 2 mol/L hydrochloric acid (100 mL×2). The separated organic phase was discarded. To the water phase was added EtOAc (300 mL), and the resulting mixture was adjusted to pH 8 with 2 mol/L aqueous NaOH solution, and the organic phase was dried over anhydrous $Na_2SO_4$, and concentrated in vacuo to give the title compound as a light yellow solid (9.5 g, 40%).

MS (ESI, pos.ion) m/z: 222.1 [M+H]$^+$.

Step 4) (2S,3S)-tert-butyl 3-(hydroxymethyl)-2-methylmorpholine-4-carboxylate

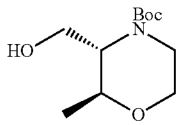 [SMILES: C[C@@H]1OCCN(C(=O)OC(C)(C)C)[C@H]1CO]

A mixture of (2S,3S)-4-benzyl-2-methylmorpholin-3-yl) methanol (9.5 g, 43 mmol), MeOH (100 mL), Pd/C (0.95 g, 10%) and $(Boc)_2O$ (10 g, 46 mmol) was stirred at 25° C. under $N_2$ for 24 hours, and filtered. The filtrate was concentrated in vacuo. The residue was purified by silica column chromatography (PE/EtOAc (v/v)=2/1) to give the title compound as light yellow oil (8.9 g, 90%). The compound was characterized by the following spectroscopic data:

MS (ESI, pos.ion) m/z: 132.2 [M+H−100]$^+$.

Step 5) (2S,3S)-tert-butyl 3-(3-ethoxy-3-oxoprop-1-en-1-yl)-2-methylmorpholine-4-carboxylate

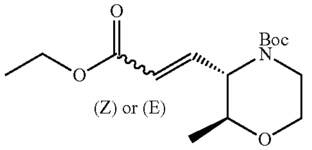 [SMILES: CCOC(=O)C=C[C@H]1[C@H](C)OCCN1C(=O)OC(C)(C)C]

To a mixture of (2S,3S)-tert-butyl 3-(hydroxymethyl)-2-methylmorpholine-4-carboxylate (8.9 g, 38 mmol) and DCM (250 mL) was added Dess-Martin periodinane (19.5 g, 46 mmol) at 0° C. After the addition, the reaction mixture was stirred at 0° C. for 3 hours. Then to the mixture was added ethyl 2-(triphenylphosphoranylidene)acetate (40 g, 115 mmol) at 0° C. The reaction mixture was stirred at 25° C. for 12 hours, then to the mixture was added saturated aqueous $NaHCO_3$ solution (250 mL). The resulting mixture was stirred for 1 hour and left to stand. The separated organic phases were washed with saturated aqueous $NaHCO_3$ solution (150 mL×2) and saturated brine (150 mL×2) in turn, dried over anhydrous $Na_2SO_4$, filtered, and concentrated in vacuo. The residue was purified by silica column chromatography (PE/EtOAc (v/v)=20/1) to give the title compound as yellow oil (9.5 g, 83%). The compound was characterized by the following spectroscopic data:

MS (ESI, pos.ion) m/z: 200.2 [M+H−100]$^+$.

Step 6) (2S,3S)-tert-butyl 3-(3-ethoxy-3-oxopropyl)-2-methylmorpholine-4-carboxylate

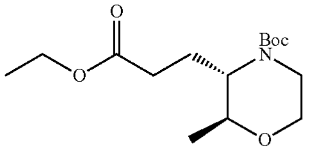 [SMILES: CCOC(=O)CC[C@H]1[C@H](C)OCCN1C(=O)OC(C)(C)C]

A mixture of (2S,3S)-tert-butyl 3-(3-ethoxy-3-oxoprop-1-en-1-yl)-2-methylmorpholine-4-carboxylate (9.5 g, 32 mmol), MeOH (200 mL mL) and Pd/C (10%, 0.95 g) was stirred at 25° C. for 12 hours under $H_2$, filtered, and the filtrate was concentrated in vacuo to give the title compound as colourless oil (8 g, 83%). The compound was characterized by the following spectroscopic data:

MS (ESI, pos.ion) m/z: 202.3 $[M+H-100]^+$.

Step 7) 3-((2S,3S)-4-(tert-butoxycarbonyl)-2-methylmorpholin-3-yl)propanoic acid

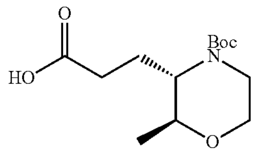 [SMILES: C[C@@H]1OCCN(C(=O)OC(C)(C)C)[C@H]1CCC(=O)O]

A mixture of (2S,3S)-tert-butyl 3-(3-ethoxy-3-oxopropyl)-2-methylmorpholine-4-carboxylate (7.9 g, 26.2 mmol), EtOH (150 mL) and a solution of $LiOH.H_2O$ (4.2 g, 100 mmol) in water (50 mL) was stirred at 25° C. for 30 minutes, then concentrated in vacuo. To the mixture was added EtOAc (300 mL) and water (100 mL). The resulting mixture was adjusted pH 4-6 with concentrated hydrochloric acid. The separated organic phases were washed with saturated brine (100 mL×2), dried over anhydrous $Na_2SO_4$, and concentrated in vacuo to give the title compound as colourless oil (6.5 g, 91%). The compound was characterized by the following spectroscopic data:

MS (ESI, pos.ion) m/z: 174.2 $[M+H-100]^+$.

Step 8) 3-((2S,3S)-2-methylmorpholin-3-yl)propanoic acid hydrochloride

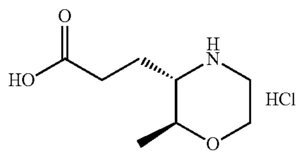

A mixture of 3-((2S,3S)-4-(tert-butoxycarbonyl)-2-methylmorpholin-3-yl)propanoic acid (1 g, 3.7 mmol) and a solution of HCl in EtOAc (4 mol/L, 10 mL) was stirred at 25° C. for 4 hours, then filtered to give the title compound as a white solid (0.6 g, 77%). The compound was characterized by the following spectroscopic data:

MS (ESI, pos.ion) m/z: 174.3 $[M+H]^+$; and $^1H$ NMR (600 MHz, $D_2O$): δ 4.05 (dd, 1H), 3.84-3.79 (m, 1H), 3.74-3.70 (m, 1H), 3.34 (d, 1H), 3.21 (td, 1H), 3.10 (td, 1H), 2.55 (t, 2H), 2.06-2.03 (m, 1H), 1.82-1.76 (m, 1H), 1.26 (d, 3H).

Step 9) 3-((2S,3S)-4-(((R)-6-(2-bromo-4-fluorophenyl)-5-(ethoxycarbonyl)-2-(thiazol-2-yl)-3,6-dihydropyrimidin-4-yl)methyl)-2-methylmorpholin-3-yl) propanoic acid

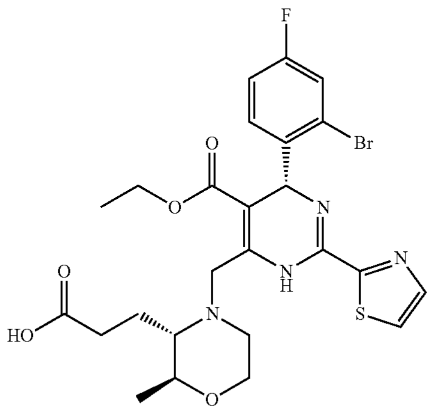 [SMILES: CCOC(=O)C1=C(CN2CCO[C@@H](C)[C@@H]2CCC(=O)O)NC(c2nccs2)=N[C@H]1c1ccc(F)cc1Br]

The title compound was prepared by the procedure described in step 6 of Example 2 using (R)-ethyl 4-(2-bromo-4-fluorophenyl)-6-(bromomethyl)-2-(thiazol-2-yl)-1,4-dihydropyrimidine-5-carboxylate (0.5 g, 1 mmol), 3-((2S,3S)-2-methylmorpholin-3-yl)propanoic acid hydrochloride (0.21 g, 1 mmol), potassium carbonate (0.28 g, 2 mmol) and anhydrous ethyl alcohol (10 mL) to give the title compound as a yellow solid (0.25 g, 42%). The compound was characterized by the following spectroscopic data:

MS (ESI, pos.ion) m/z: 594.6$[M+H]^+$; and $^1H$ NMR (400 MHz, DMSO-$d_6$): δ 12.11 (s, 1H), 9.74 (s, 1H), 8.02 (d, 1H), 7.95 (d, 1H), 7.56 (dd, 1H), 7.39 (dd, 1H), 7.19 (td, 1H), 6.04 (s, 1H), 4.16 (d, 1H), 4.00-3.93 (m, 2H), 3.86 (d, 1H), 3.77-3.72 (m, 1H), 3.59-3.53 (m, 1H), 3.51-3.45 (m, 1H), 2.66 (d, 1H), 2.46-2.40 (m, 1H), 2.37-2.30 (m, 3H), 2.03-1.91 (m, 1H), 1.80-1.73 (m, 1H), 1.20 (d, 3H), 1.06 (t, 3H).

Example 28

3-((2S,3S)-4-(((R)-6-(2-Bromo-4-fluorophenyl)-5-(methoxycarbonyl)-2-(thiazol-2-yl)-3,6-dihydropyrimidin-4-yl)methyl)-2-methylmorpholin-3-yl)propanoic acid

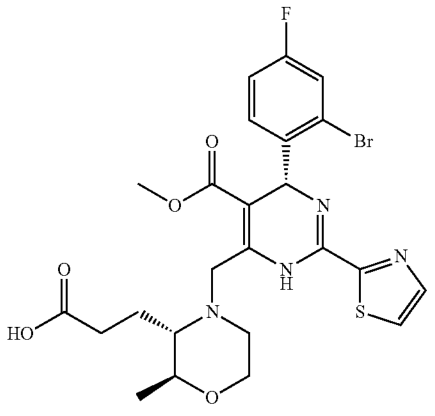 [SMILES: COC(=O)C1=C(CN2CCO[C@@H](C)[C@@H]2CCC(=O)O)NC(c2nccs2)=N[C@H]1c1ccc(F)cc1Br]

The title compound was prepared by the procedure described in step 6 of Example 2 using (R)-methyl 4-(2-bromo-4-fluorophenyl)-6-(bromomethyl)-2-(thiazol-2-yl)-1,4-dihydropyrimidine-5-carboxylate (0.8 g, 1.64 mmol), 3-((2S,3S)-2-methylmorpholin-3-yl)propanoic acid hydrochloride (0.34 g, 1.64 mmol), potassium carbonate (0.45 g, 3.3 mmol) and anhydrous ethyl alcohol (16 mL) to give the title compound as a yellow solid (0.37 g, 39%). The compound was characterized by the following spectroscopic data:

MS (ESI, pos.ion) m/z: 581.2[M+H]$^+$; and $^1$H NMR (400 MHz, DMSO-$d_6$): δ 12.10 (s, 1H), 9.75 (s, 1H), 8.01 (d, 1H), 7.96 (d, 1H), 7.54 (dd, 1H), 7.40 (dd, 1H), 7.20 (td, 1H), 6.02 (s, 1H), 4.18 (d, 1H), 3.88 (d, 1H), 3.78-3.73 (m, 1H), 3.60-3.54 (m, 1H), 3.52 (s, 3H), 3.50-3.45 (m, 1H), 2.68 (d, 1H), 2.47-2.41 (m, 1H), 2.36-2.30 (m, 3H), 2.04-1.92 (m, 1H), 1.81-1.73 (m, 1H), 1.21 (d, 3H).

Example 29

3-((2S,3S)-4-(((R)-6-(2-Chloro-4-fluorophenyl)-5-(ethoxycarbonyl)-2-(thiazol-2-yl)-3,6-dihydropyrimidin-4-yl)methyl)-2-methylmorpholin-3-yl)propanoic acid

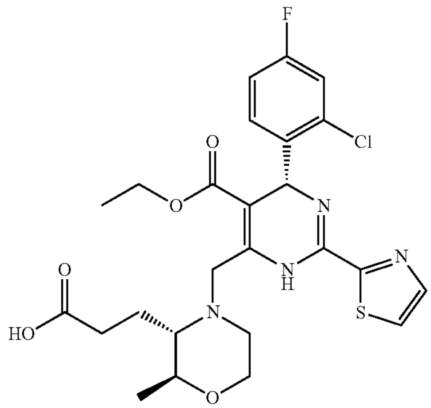 [SMILES: CCOC(=O)C1=C(CN2CCO[C@@H](C)[C@@H]2CCC(=O)O)NC(c2nccs2)=N[C@H]1c1ccc(F)cc1Cl]

The title compound was prepared by the procedure described in step 6 of Example 2 using (R)-ethyl 6-(bromomethyl)-4-(2-chloro-4-fluorophenyl)-2-(thiazol-2-yl)-1,4-dihydropyrimidine-5-carboxylate (0.46 g, 1 mmol), 3-((2S,3S)-2-methylmorpholin-3-yl) propanoic acid hydrochloride (0.21 g, 1 mmol), potassium carbonate (0.28 g, 2 mmol) and anhydrous ethyl alcohol (10 mL) to give the title compound as a yellow solid (0.26 g, 47%. The compound was characterized by the following spectroscopic data:

MS (ESI, pos.ion) m/z: 551.2[M+H]$^+$; and $^1$H NMR (400 MHz, DMSO-$d_6$): δ 12.12 (s, 1H), 9.75 (s, 1H), 8.02 (d, 1H), 7.95 (d, 1H), 7.42-7.36 (m, 2H), 7.15 (td, 1H), 6.06 (s, 1H), 4.15 (d, 1H), 4.02-3.91 (m, 2H), 3.86 (d, 1H), 3.75-3.73 (m, 1H), 3.59-3.54 (m, 1H), 3.51-3.45 (m, 1H), 2.66 (d, 1H), 2.46-2.40 (m, 1H), 2.37-2.30 (m, 3H), 2.03-1.92 (m, 1H), 1.80-1.74 (m, 1H), 1.20 (d, 3H), 1.06 (t, 3H).

Example 30

3-((2S,3S)-4-(((R)-6-(2-Chloro-4-fluorophenyl)-5-(methoxycarbonyl)-2-(thiazol-2-yl)-3,6-dihydropyrimidin-4-yl)methyl)-2-methylmorpholin-3-yl)propanoic acid

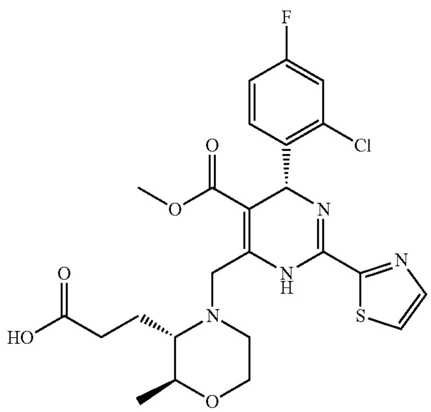 [SMILES: COC(=O)C1=C(CN2CCO[C@@H](C)[C@@H]2CCC(=O)O)NC(c2nccs2)=N[C@H]1c1ccc(F)cc1Cl]

The title compound was prepared by the procedure described in step 6 of Example 2 using (R)-methyl 6-(bromomethyl)-4-(2-chloro-4-fluorophenyl)-2-(thiazol-2-yl)-1,4-dihydropyrimidine-5-carboxylate (0.44 g, 1 mmol), 3-((2S,3S)-2-methylmorpholin-3-yl) propanoic acid hydrochloride (0.21 g, 1 mmol), potassium carbonate (0.14 g, 1 mmol) and anhydrous ethyl alcohol (10 mL) to give the title compound as a yellow solid (0.18 g, 34%). The compound was characterized by the following spectroscopic data:

MS (ESI, pos.ion) m/z: 537.1 [M+H]$^+$; and $^1$H NMR (400 MHz, DMSO-$d_6$): δ 12.11 (s, 1H), 9.76 (s, 1H), 8.02 (d, 1H), 7.96 (d, 1H), 7.44-7.40 (m, 2H), 7.16 (td, 1H), 6.01 (s, 1H), 4.16 (d, 1H), 3.88 (d, 1H), 3.78-3.74 (m, 1H), 3.60-3.55 (m, 1H), 3.53 (s, 3H), 3.50-3.46 (m, 1H), 2.68 (d, 1H), 2.48-2.42 (m, 1H), 2.36-2.31 (m, 3H), 2.04-1.93 (m, 1H), 1.82-1.73 (m, 1H), 1.21 (d, 3H).

Example 31

3-((2S,3S)-4-(((R)-6-(2,4-Dichlorophenyl)-5-(ethoxycarbonyl)-2-(thiazol-2-yl)-3,6-dihydropyrimidin-4-yl)methyl)-2-methylmorpholin-3-yl)propanoic acid

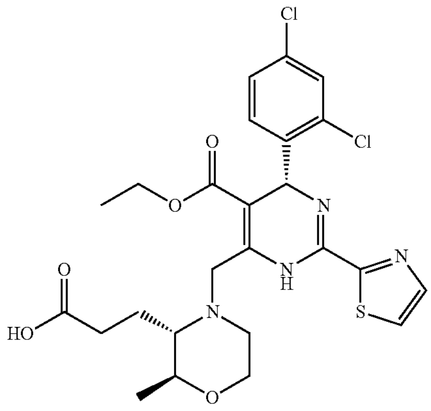 [SMILES: CCOC(=O)C1=C(CN2CCO[C@@H](C)[C@@H]2CCC(=O)O)NC(c2nccs2)=N[C@H]1c1ccc(Cl)cc1Cl]

The title compound was prepared by the procedure described in step 6 of Example 2 using (R)-ethyl 6-(bromomethyl)-4-(2,4-dichlorophenyl)-2-(thiazol-2-yl)-1,4-dihydropyrimidine-5-carboxylate (0.48 g, 1 mmol), 3-((2S, 3S)-2-methylmorpholin-3-yl) propanoic acid hydrochloride (0.21 g, 1 mmol), potassium carbonate (0.28 g, 2 mmol) and anhydrous ethyl alcohol (10 mL) to give the title compound as a yellow solid (0.28 g, 49%). The compound was characterized by the following spectroscopic data:

MS (ESI, pos.ion) m/z: 567.1[M+H]$^+$; and $^1$H NMR (400 MHz, DMSO-$d_6$): δ 12.09 (s, 1H), 9.76 (s, 1H), 8.03 (d, 1H), 7.96 (d, 1H), 7.59 (br, 1H), 7.38 (br, 2H), 6.06 (s, 1H), 4.15 (d, 1H), 4.02-3.93 (m, 2H), 3.87 (d, 1H), 3.78-3.73 (m, 1H), 3.60-3.54 (m, 1H), 3.51-3.46 (m, 1H), 2.67 (d, 1H), 2.45-2.41 (m, 1H), 2.38-2.30 (m, 3H), 2.04-1.92 (m, 1H), 1.81-1.73 (m, 1H), 1.21 (d, 3H), 1.08 (t, 3H).

Example 32

3-((2S,3S)-4-(((R)-6-(2,4-Dichlorophenyl)-5-(methoxycarbonyl)-2-(thiazol-2-yl)-3,6-dihydropyrimidin-4-yl)methyl)-2-methylmorpholin-3-yl)propanoic acid

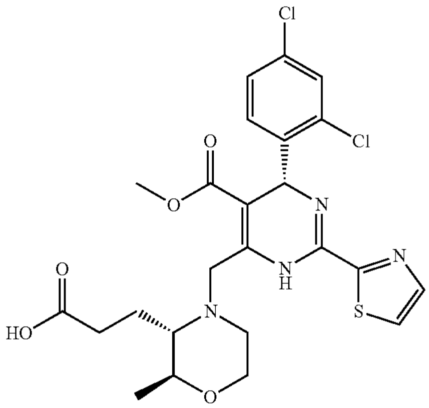 [SMILES: COC(=O)C1=C(CN2CCO[C@@H](C)[C@@H]2CCC(=O)O)NC(c2nccs2)=N[C@H]1c1ccc(Cl)cc1Cl]

The title compound was prepared by the procedure described in step 6 of Example 2 using (R)-methyl 6-(bromomethyl)-4-(2,4-dichlorophenyl)-2-(thiazol-2-yl)-1,4-dihydropyrimidine-5-carboxylate (0.46 g, 1 mmol), 3-((2S, 3S)-2-methylmorpholin-3-yl) propanoic acid hydrochloride (0.21 g, 1 mmol), potassium carbonate (0.14 g, 1 mmol) and anhydrous ethyl alcohol (10 mL) to give the title compound as a yellow solid (0.18 g, 33%). The compound was characterized by the following spectroscopic data:

MS (ESI, pos.ion) m/z: 553.1[M+H]$^+$; and $^1$H NMR (400 MHz, DMSO-$d_6$): δ 12.09 (s, 1H), 9.76 (s, 1H), 8.03 (d, 1H), 7.94 (d, 1H), 7.59 (br, 1H), 7.39 (br, 1H), 6.03 (s, 1H), 4.17 (d, 1H), 3.89 (d, 1H), 3.78-3.74 (m, 1H), 3.61-3.55 (m, 1H), 3.53 (s, 3H), 3.50-3.46 (m, 1H), 2.67 (d, 1H), 2.48-2.42 (m, 1H), 2.37-2.31 (m, 3H), 2.03-1.93 (m, 1H), 1.82-1.73 (m, 1H), 1.21 (d, 3H).

Example 33

3-((R)-4-(((R)-6-(2-Chlorophenyl)-5-(methoxycarbonyl)-2-(thiazol-2-yl)-3,6-dihydropyrimidin-4-yl)methyl)morpholin-2-yl)propanoic acid Step 1) methyl 4-(2-chlorophenyl)-6-methyl-2-(thiazol-2-yl)-1,4-dihydropyrimidine-5-carboxylate

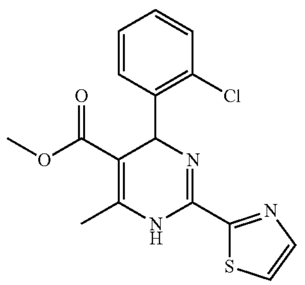 [SMILES: COC(=O)C1=C(C)NC(c2nccs2)=NC1c1ccccc1Cl]

To a flask were added thiazole-2-carboximidamide hydrochloride (10.00 g, 61.11 mmol), 2-chlorobenzaldehyde (8.59 g, 61.11 mmol), methyl 3-oxobutanoate (7.10 g, 61.11 mmol) anhydrous sodium acetate (5.01 g, 61.11 mmol) and absolute methanol (50 mL) in turn. The reaction mixture was stirred at 70° C. for 12 hours, and then was cooled to rt and stirred for another 6 hours. The resulting mixture was filtered and the filter cake was washed with methanol (10 mL) and water (100 mL) in turn. The filter cake was then dried under vacuum to give the title compound as a yellow solid (12.54 g, 59%). The compound was characterized by the following spectroscopic data:

MS (ESI. pos.ion) m/z: 348.9[M+H]$^+$.

Step 2) (R)-methyl 4-(2-chlorophenyl)-6-methyl-2-(thiazol-2-yl)-1,4-dihydropyrimidine-5-carboxylate

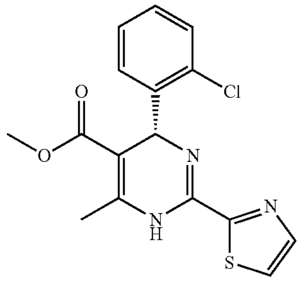 [SMILES: COC(=O)C1=C(C)NC(c2nccs2)=N[C@H]1c1ccccc1Cl]

The title compound was prepared by the procedure described in step 1 of Example 1 using methyl 4-(2-chlorophenyl)-6-methyl-2-(thiazol-2-yl)-1,4-dihydropyrimidine-5-carboxylate (5 g, 14.38 mmol), the crude product was purified by pre-HPLC to give the title compound as a yellow solid (2.33 g, 47%). The compound was characterized by the following spectroscopic data:

MS (ESI. pos.ion) m/z: 348.9[M+H]$^+$.

Step 3) (R)-methyl 6-(bromomethyl)-4-(2-chlorophenyl)-2-(thiazol-2-yl)-1,4-dihydropyrimidine-5-carboxylate

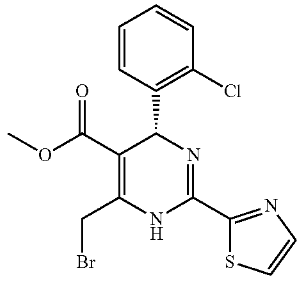 [SMILES: COC(=O)C1=C(CBr)NC(c2nccs2)=N[C@H]1c1ccccc1Cl]

To a mixture of (R)-methyl 4-(2-chlorophenyl)-6-methyl-2-(thiazol-2-yl)-1,4-dihydropyrimidine-5-carboxylate (0.332 g, 0.95 mmol) in $CCl_4$ (10 mL) was added NBS (0.19 g, 1.05 mmol) in portions. After the addition, the reaction mixture was stirred for another 10 minutes. The resulting mixture was filtered and the filtrate was concentrated in vacuum to give the title compound as a yellow dope (0.352 g, 86%) which was used directly for the next step.

Step 4) 3-((R)-4-(((R)-6-(2-chlorophenyl)-5-(methoxycarbonyl)-2-(thiazol-2-yl)-3,6-dihydropyrimidin-4-yl)methyl)morpholin-2-yl)propanoic acid

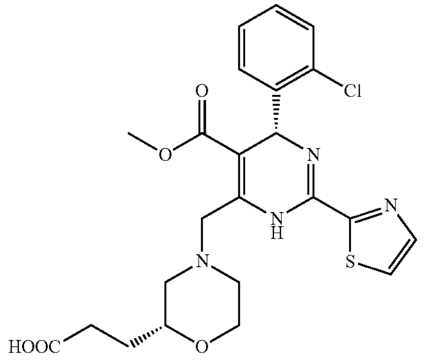 [SMILES: COC(=O)C1=C(CN2CCO[C@H](CCC(=O)O)C2)NC(c2nccs2)=N[C@H]1c1ccccc1Cl]

A mixture of (R)-methyl 6-(bromomethyl)-4-(2-chlorophenyl)-2-(thiazol-2-yl)-1,4-dihydropyrimidine-5-carboxylate (0.352 g, 0.82 mmol), potassium carbonate (0.166 g, 1.91 mmol), (R)-3-(morpholin-2-yl)propanoic acid hydrochloride (0.161 g, 0.82 mmol) and anhydrous ethyl alcohol (15 mL) was stirred at 25° C. for 12 hours. The resulting mixture was filtered and the filtrate was concentrated in vacuum. The residue was purified by silica gel column chromatography (DCM/$CH_3OH$ (v/v)=20/1) to give the title compound as a yellow solid (0.316 g, 75%). The compound was characterized by the following spectroscopic data:

MS (ESI. pos.ion) m/z: 505.1[M+H]$^+$; and $^1$H NMR (400 MHz, DMSO-$d_6$): δ 9.67 (s, 1H), 8.01-7.91 (m, 2H), 7.47-7.23 (m, 4H), 6.08 (s, 1H), 3.89 (s, 3H), 3.56-3.50 (m, 4H), 3.17 (s, 1H), 2.80-2.73 (m, 2H), 2.40-2.22 (m, 3H), 2.02 (t, 1H), 1.63 (dd, 2H).

Example 34

3-((R)-4-(((R)-6-(2-Chlorophenyl)-5-(ethoxycarbonyl)-2-(thiazol-2-yl)-3,6-dihydropyrimidin-4-yl)methyl)morpholin-2-yl)propanoic acid Step 1) ethyl 4-(2-chlorophenyl)-6-methyl-2-(thiazol-2-yl)-1,4-dihydropyrimidine-5-carboxylate

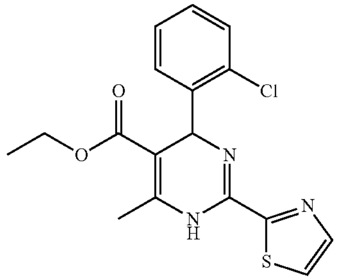 [SMILES: CCOC(=O)C1=C(C)NC(c2nccs2)=NC1c1ccccc1Cl]

To a flask were added thiazole-2-carboximidamide hydrochloride (10.00 g, 61.11 mmol), 2-chlorobenzaldehyde (8.59 g, 61.11 mmol), ethyl 3-oxobutanoate (7.95 g, 61.11 mmol), anhydrous sodium acetate (5.01 g, 61.11 mmol) and anhydrous ethyl alcohol (50 mL) in turn. The reaction mixture was stirred at 80° C. for 12 hours and then was cooled to rt and stirred for another 6 hours. The resulting mixture was filtered and the filter cake was washed with ethanol (10 mL) and water (100 mL) in turn. The filter cake was then dried under vacuum to give the title compound as a yellow solid (11.06 g, 50%). The compound was characterized by the following spectroscopic data:

MS (ESI. pos.ion) m/z: 361.6[M+H]$^+$.

Step 2) (R)-ethyl 4-(2-chlorophenyl)-6-methyl-2-(thiazol-2-yl)-1,4-dihydropyrimidine-5-carboxylate

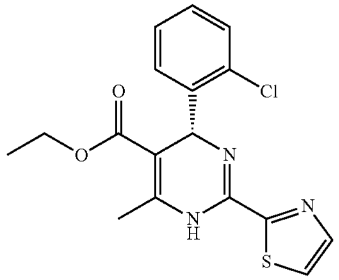 [SMILES: CCOC(=O)C1=C(C)NC(c2nccs2)=N[C@H]1c1ccccc1Cl]

The title compound was prepared by the procedure described in step 1 of Example 1 using ethyl 4-(2-chlorophenyl)-6-methyl-2-(thiazol-2-yl)-1,4-dihydropyrimidine-5-carboxylate (5 g, 13.82 mmol), the crude product was purified by pre-HPLC to give the title compound as a yellow solid (2.12 g, 42%). The compound was characterized by the following spectroscopic data:

MS (ESI. pos.ion) m/z: 361.6[M+H]$^+$.

Step 3) (R)-ethyl 6-(bromomethyl)-4-(2-chlorophenyl)-2-(thiazol-2-yl)-1,4-dihydropyrimidine-5-carboxylate

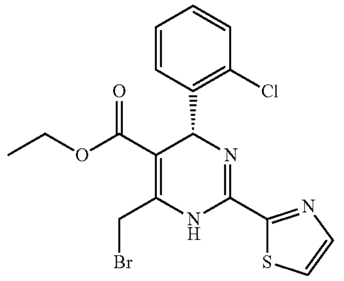 [SMILES: CCOC(=O)C1=C(CBr)NC(c2nccs2)=N[C@H]1c1ccccc1Cl]

The title compound was prepared by the procedure described in step 3 of Example 33 using (R)-ethyl 4-(2-chlorophenyl)-6-methyl-2-(thiazol-2-yl)-1,4-dihydropyrimidine-5-carboxylate (0.398 g, 1.10 mmol), $CCl_4$ (10 mL) and NBS (0.219 g, 1.21 mmol) to give the title compound as a yellow dope (0.34 g, 70%).

Step 4) 3-((R)-4-(((R)-6-(2-chlorophenyl)-5-(ethoxycarbonyl)-2-(thiazol-2-yl)-3,6-dihydropyrimidin-4-yl)methyl)morpholin-2-yl)propanoic acid

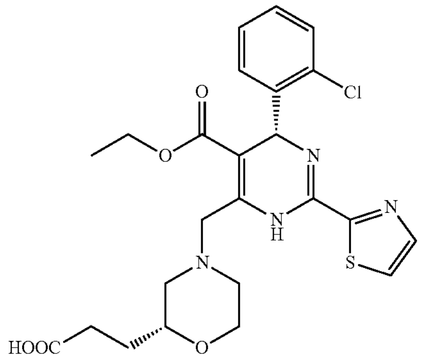 [SMILES: CCOC(=O)C1=C(CN2CCO[C@H](CCC(=O)O)C2)NC(c2nccs2)=N[C@H]1c1ccccc1Cl]

The title compound was prepared by the procedure described in step 4 of Example 33 using (R)-ethyl 6-(bromomethyl)-4-(2-chlorophenyl)-2-(thiazol-2-yl)-1,4-dihydropyrimidine-5-carboxylate (0.34 g, 0.77 mmol), potassium carbonate (0.307 g, 2.20 mmol), (R)-3-(morpholin-2-yl)propanoic acid hydrochloride (0.15 g, 0.77 mmol) and anhydrous ethyl alcohol (15 mL) to give the title compound as a yellow solid (0.155 g, 35%). The compound was characterized by the following spectroscopic data:

MS (ESI. pos.ion) m/z: 520.2$[M+H]^+$; and $^1H$ NMR (400 MHz, DMSO-$d_6$): δ 9.62 (s, 1H), 8.01-7.92 (m, 2H), 7.48-7.22 (m, 4H), 6.09 (s, 1H), 3.96-3.82 (m, 5H), 3.62-3.45 (m, 4H), 3.17 (s, 1H), 2.83-2.68 (m, 2H), 2.35-2.25 (m, 3H), 2.02 (t, 1H), 1.65-1.60 (m, 2H).

Example 35

3-((R)-4-(((S)-6-(2-Bromo-4-fluorophenyl)-5-(ethoxycarbonyl)-2-(thiazol-2-yl)-3,6-dihydropyrimidin-4-yl)methyl)morpholin-2-yl)propanoic acid Step 1) (S)-ethyl 4-(2-bromo-4-fluorophenyl)-6-methyl-2-(thiazol-2-yl)-1,4-dihydropyrimidine-5-carboxylate

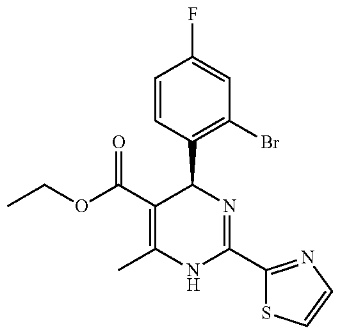 [SMILES: CCOC(=O)C1=C(C)NC(c2nccs2)=N[C@@H]1c1ccc(F)cc1Br]

The title compound was prepared by the procedure described in step 1 of Example 1 using 4-(2-bromo-4-fluorophenyl)-6-(bromomethyl)-2-(thiazol-2-yl)-1,4-dihydropyrimidine-5-carboxylate (5 g, 11.8 mmol), the crude product was purified by pre-HPLC to give the title compound as a yellow solid (1.74 g, 35%). The compound was characterized by the following spectroscopic data:

MS (ESI. pos.ion) m/z: 424.0$[M+H]^+$.

Step 2) (S)-ethyl 4-(2-bromo-4-fluorophenyl)-6-(bromomethyl)-2-(thiazol-2-yl)-1,4-dihydropyrimidine-5-carboxylate

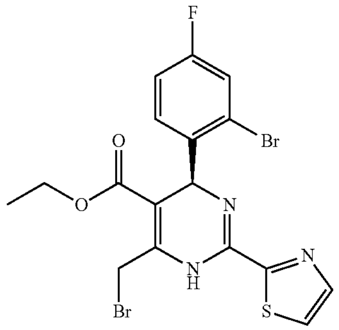 [SMILES: CCOC(=O)C1=C(CBr)NC(c2nccs2)=N[C@@H]1c1ccc(F)cc1Br]

The title compound was prepared by the procedure described in step 2 of Example 1 using (S)-ethyl 4-(2-bromo-4-fluorophenyl)-6-methyl-2-(thiazol-2-yl)-1,4-dihydropyrimidine-5-carboxylate (1 g, 2.4 mmol), $CCl_4$ (20 mL) and NBS (0.47 g, 2.64 mmol) to give the title compound as a yellow solid (0.83 g, 68%). The compound was characterized by the following spectroscopic data:

MS (ESI, pos.ion) m/z: 503.9$[M+H]^+$.

Step 3) 3-((R)-4-(((S)-6-(2-bromo-4-fluorophenyl)-5-(ethoxycarbonyl)-2-(thiazol-2-yl)-3,6-dihydropyrimidin-4-yl)methyl)morpholin-2-yl)propanoic acid

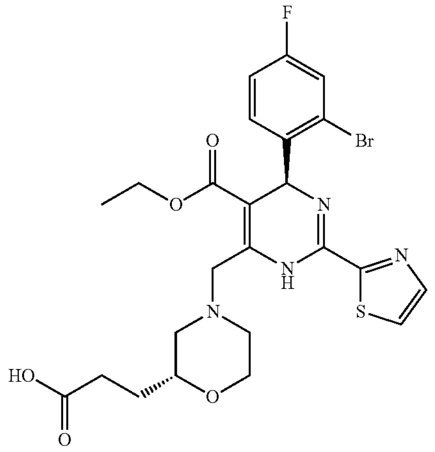 [SMILES: CCOC(=O)C1=C(CN2CCO[C@H](CCC(=O)O)C2)NC(c2nccs2)=N[C@@H]1c1ccc(F)cc1Br]

The title compound was prepared by the procedure described in step 6 of Example 2 using (S)-ethyl 4-(2-bromo-4-fluorophenyl)-6-(bromomethyl)-2-(thiazol-2-yl)-1,4-dihydropyrimidine-5-carboxylate (4.74 g, 9.42 mmol), (R)-3-(morpholin-2-yl)propanoic acid hydrochloric (1.84 g, 9.42 mmol), potassium carbonate (2.6 g, 18.84 mmol) and anhydrous ethyl alcohol (90 mL) to give the title compound as a yellow solid (2.14 g, 39%). The compound was characterized by the following spectroscopic data:

MS (ESI, pos.ion) m/z: 581.2[M+H]$^+$; and $^1$H NMR (400 MHz, DMSO-$d_6$): δ 12.12 (s, 1H), 9.65 (s, 1H), 8.03 (br, 1H), 7.94 (br, 1H), 7.58 (dd, 1H), 7.41 (br, 1H), 7.23 (br, 1H), 6.02 (s, 1H), 3.97 (q, 2H), 3.91-3.84 (m, 3H), 3.62-3.51 (m, 2H), 2.93-2.85 (m, 1H), 2.68-2.62 (m, 1H), 2.39-2.22 (m, 3H), 2.13-2.06 (m, 1H), 1.72-1.62 (m, 2H), 1.06 (t, 3H).

Example 36

3-((S)-4-(((S)-6-(2-Bromo-4-fluorophenyl)-5-(ethoxycarbonyl)-2-(thiazol-2-yl)-3,6-dihydropyrimidin-4-yl)methyl)morpholin-2-yl)propanoic acid

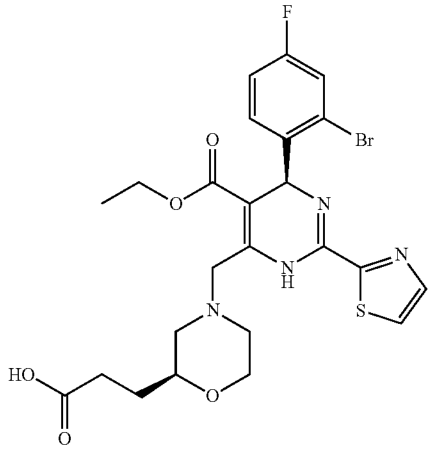 [SMILES: CCOC(=O)C1=C(CN2CCO[C@@H](CCC(=O)O)C2)NC(c2nccs2)=N[C@@H]1c1ccc(F)cc1Br]

The title compound was prepared by the procedure described in step 6 of Example 2 using (S)-ethyl 4-(2-bromo-4-fluorophenyl)-6-(bromomethyl)-2-(thiazol-2-yl)-1,4-dihydropyrimidine-5-carboxylate (0.5 g, 1 mmol), (S)-3-(morpholin-2-yl)propanoic acid (0.2 g, 1 mmol), potassium carbonate (0.28 g, 2 mmol) and anhydrous ethyl alcohol (10 mL) to give the title compound as a yellow solid (0.32 g, 54%). The compound was characterized by the following spectroscopic data:

MS (ESI, pos.ion) m/z: 580.9[M+H]$^+$; and $^1$H NMR (400 MHz, DMSO-$d_6$): δ 12.01 (br, 1H), 9.65 (s, 1H), 8.01 (d, 1H), 7.92 (d, 1H), 7.56 (dd, 1H), 7.40 (dd, 1H), 7.21 (td, 1H), 6.03 (s, 1H), 3.96 (q, 2H), 3.89-3.86 (m, 3H), 3.60-3.47 (m, 2H), 2.81-2.74 (m, 2H), 2.37-2.31 (m, 1H), 2.30-2.25 (m, 2H), 2.02 (t, 1H), 1.64 (q, 2H), 1.05 (t, 3H).

Example 37

3-((R)-4-(((S)-6-(2-Chloro-4-fluorophenyl)-5-(ethoxycarbonyl)-2-(thiazol-2-yl)-3,6-dihydropyrimidin-4-yl)methyl)morpholin-2-yl)propanoic acid Step 1) (S)-ethyl 4-(2-chloro-4-fluorophenyl)-6-methyl-2-(thiazol-2-yl)-1,4-dihydropyrimidine-5-carboxylate

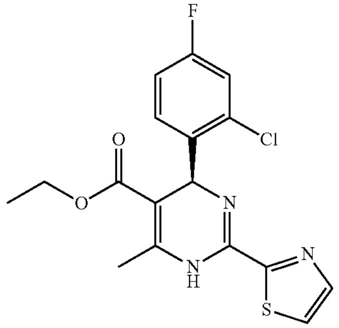 [SMILES: CCOC(=O)C1=C(C)NC(c2nccs2)=N[C@@H]1c1ccc(F)cc1Cl]

The title compound was prepared by the procedure described in step 1 of Example 1 using 4-(2-chloro-4-fluorophenyl)-6-methyl-2-(thiazol-2-yl)-1,4-dihydropyrimidine-5-carboxylate (5 g, 13.2 mmol) to give the title compound as a yellow solid (1.7 g, 34%). The compound was characterized by the following spectroscopic data:

MS (ESI, pos.ion) m/z: 380.2 [M+H]$^+$.

Step 2) (S)-ethyl 6-(bromomethyl)-4-(2-chloro-4-fluorophenyl)-2-(thiazol-2-yl)-1,4-dihydropyrimidine-5-carboxylate

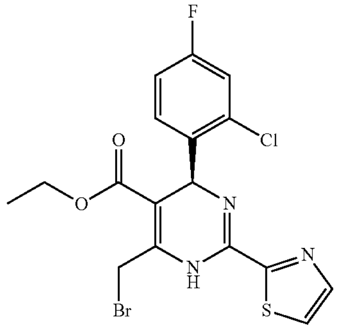 [SMILES: CCOC(=O)C1=C(CBr)NC(c2nccs2)=N[C@@H]1c1ccc(F)cc1Cl]

The title compound was prepared by the procedure described in step 2 of Example 1 using (S)-ethyl 4-(2-chloro-4-fluorophenyl)-6-methyl-2-(thiazol-2-yl)-1,4-dihydropyrimidine-5-carboxylate (0.91 g, 2.4 mmol), $CCl_4$ (20 mL) and NBS (0.47 g, 2.64 mmol) to give the title compound as a yellow solid (0.77 g, 70%). The compound was characterized by the following spectroscopic data:

MS (ESI, pos.ion) m/z: 457.9 [M+H]$^+$.

Step 3) 3-((R)-4-(((S)-6-(2-chloro-4-fluorophenyl)-5-(ethoxycarbonyl)-2-(thiazol-2-yl)-3,6-dihydropyrimidin-4-yl)methyl)morpholin-2-yl)propanoic acid

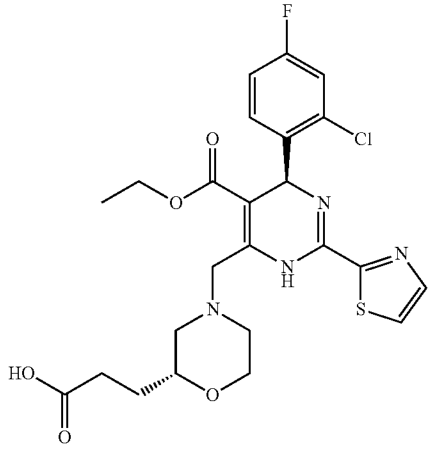 [SMILES: CCOC(=O)C1=C(CN2CCO[C@H](CCC(=O)O)C2)NC(c2nccs2)=N[C@@H]1c1ccc(F)cc1Cl]

The title compound was prepared by the procedure described in step 6 of Example 2 using (S)-ethyl 6-(bromomethyl)-4-(2-chloro-4-fluorophenyl)-2-(thiazol-2-yl)-1,4-dihydropyrimidine-5-carboxylate (0.46 g, 1 mmol), (R)-3-(morpholin-2-yl)propanoic acid hydrochloric (0.2 g, 1 mmol), potassium carbonate (0.28 g, 2 mmol) and anhydrous ethyl alcohol (10 mL) to give the title compound as a yellow solid (0.26 g, 50%). The compound was characterized by the following spectroscopic data:

MS (ESI, pos.ion) m/z: 537.3 $[M+H]^+$; and $^1H$ NMR (400 MHz, DMSO-$d_6$): δ 9.65 (s, 1H), 8.03 (d, 1H), 7.96 (d, 1H), 7.45-7.39 (m, 2H), 7.18 (td, 1H), 6.06 (s, 1H), 3.96 (q, 2H), 3.91-3.86 (m, 3H), 3.61-3.48 (m, 2H), 2.92-2.86 (m, 1H), 2.69-2.64 (m, 1H), 2.38-2.21 (m, 3H), 2.03-1.99 (m, 1H), 1.69-1.60 (m, 2H), 1.06 (t, 3H).

Example 38

3-((S)-4-(((S)-6-(2-Chloro-4-fluorophenyl)-5-(ethoxycarbonyl)-2-(thiazol-2-yl)-3,6-dihydropyrimidin-4-yl)methyl)morpholin-2-yl)propanoic acid

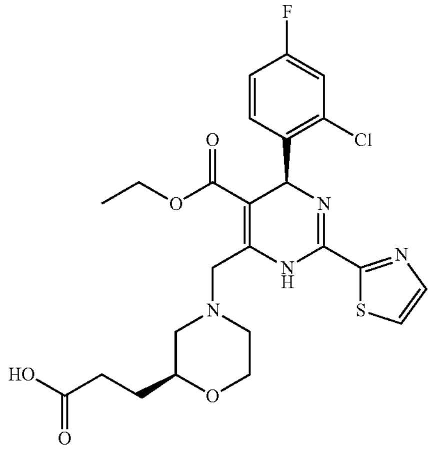 [SMILES: CCOC(=O)C1=C(CN2CCO[C@@H](CCC(=O)O)C2)NC(c2nccs2)=N[C@@H]1c1ccc(F)cc1Cl]

The title compound was prepared by the procedure described in step 6 of Example 2 using (S)-ethyl 6-(bromomethyl)-4-(2-chloro-4-fluorophenyl)-2-(thiazol-2-yl)-1,4-dihydropyrimidine-5-carboxylate (0.46 g, 1 mmol), (S)-3-(morpholin-3-yl)propanoic acid hydrochloride (0.2 g, 1 mmol), potassium carbonate (0.28 g, 2 mmol) and anhydrous ethyl alcohol (10 mL) to give the title compound as a yellow solid (0.27 g, 50%). The compound was characterized by the following spectroscopic data:

MS (ESI, pos.ion) m/z: 536.9$[M+H]^+$; and $^1H$ NMR (400 MHz, DMSO-$d_6$): δ 12.01 (br, 1H), 9.65 (s, 1H), 8.01 (d, 1H), 7.92 (d, 1H), 7.47-7.38 (m, 2H), 7.18 (td, 1H), 6.03 (s, 1H), 3.97 (q, 2H), 3.90-3.87 (m, 3H), 3.61-3.48 (m, 2H), 2.83-2.75 (m, 2H), 2.39-2.32 (m, 1H), 2.31-2.26 (m, 2H), 2.02 (t, 1H), 1.65 (q, 2H), 1.06 (t, 3H).

Example 39

3-((R)-4-(((S)-6-(2-Chloro-4-fluorophenyl)-5-(methoxycarbonyl)-2-(thiazol-2-yl)-3,6-dihydropyrimidin-4-yl)methyl)morpholin-2-yl)propanoic acid Step 1) (S)-methyl 4-(2-chloro-4-fluorophenyl)-6-methyl-2-(thiazol-2-yl)-1,4-dihydropyrimidine-5-carboxylate

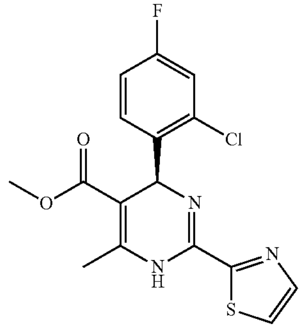 [SMILES: COC(=O)C1=C(C)NC(c2nccs2)=N[C@@H]1c1ccc(F)cc1Cl]

The title compound was prepared by the procedure described in step 1 of Example 1 using methyl 4-(2-chloro-4-fluorophenyl)-6-methyl-2-(thiazol-2-yl)-1,4-dihydropyrimidine-5-carboxylate (5 g, 13.7 mmol) to give the title compound as a yellow solid (1.8 g, 36%). The compound was characterized by the following spectroscopic data:

MS (ESI, pos.ion) m/z: 366.1 $[M+H]^+$.

Step 2) (S)-methyl 6-(bromomethyl)-4-(2-chloro-4-fluorophenyl)-2-(thiazol-2-yl)-1,4-dihydropyrimidine-5-carboxylate

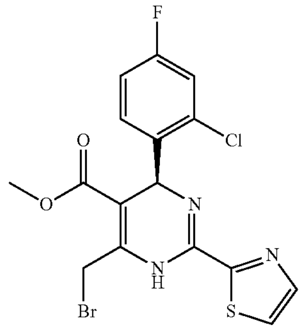 [SMILES: COC(=O)C1=C(CBr)NC(c2nccs2)=N[C@@H]1c1ccc(F)cc1Cl]

The title compound was prepared by the procedure described in step 2 of Example 1 using (S)-methyl 4-(2-chloro-4-fluorophenyl)-6-methyl-2-(thiazol-2-yl)-1,4-dihydropyrimidine-5-carboxylate (0.88 g, 2.4 mmol), $CCl_4$ (20 mL) and NBS (0.47 g, 2.64 mmol) to give the title compound as a yellow solid (0.75 g, 70%). The compound was characterized by the following spectroscopic data:

MS (ESI, pos.ion) m/z: 445.6 $[M+H]^+$.

Step 3) 3-((R)-4-(((S)-6-(2-chloro-4-fluorophenyl)-5-(methoxycarbonyl)-2-(thiazol-2-yl)-3,6-dihydropyrimidin-4-yl)methyl)morpholin-2-yl)propanoic acid

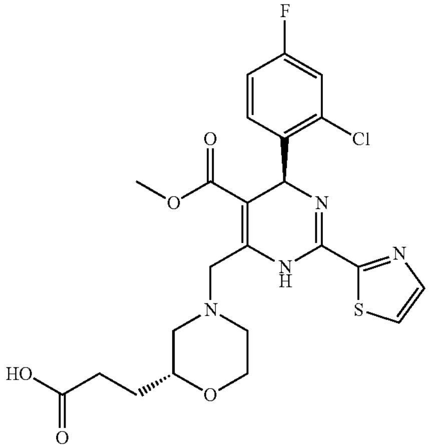 [SMILES: COC(=O)C1=C(CN2CCO[C@H](CCC(=O)O)C2)NC(c2nccs2)=N[C@@H]1c1ccc(F)cc1Cl]

The title compound was prepared by the procedure described in step 6 of Example 2 using (S)-methyl 6-(bromomethyl)-4-(2-chloro-4-fluorophenyl)-2-(thiazol-2-yl)-1,4-dihydropyrimidine-5-carboxylate (1 g, 2.25 mmol), (R)-3-(morpholin-2-yl)propanoic acid hydrochloric (0.44 g, 2.25 mmol), potassium carbonate (0.16 g, 1.1 mmol) and anhydrous ethyl alcohol (20 mL) to give the title compound as a yellow solid (0.42 g, 35%). The compound was characterized by the following spectroscopic data:

MS (ESI, pos.ion) m/z: 522.9 $[M+H]^+$; and $^1$H NMR (400 MHz, DMSO-$d_6$): δ 12.13 (br, 1H), 9.71 (s, 1H), 8.04 (d, 1H), 7.96 (d, 1H), 7.45-7.39 (m, 2H), 7.18 (td, 1H), 6.03 (s, 1H), 3.97-3.84 (m, 3H), 3.64-3.55 (m, 2H), 3.53 (s, 3H), 2.91-2.84 (m, 1H), 2.68-2.63 (m, 1H), 2.38-2.25 (m, 3H), 2.05-1.99 (m, 1H), 1.64-1.59 (m, 2H).

Example 40

3-((S)-4-(((S)-6-(2-Chloro-4-fluorophenyl)-5-(methoxycarbonyl)-2-(thiazol-2-yl)-3,6-dihydropyrimidin-4-yl)methyl)morpholin-2-yl)propanoic acid

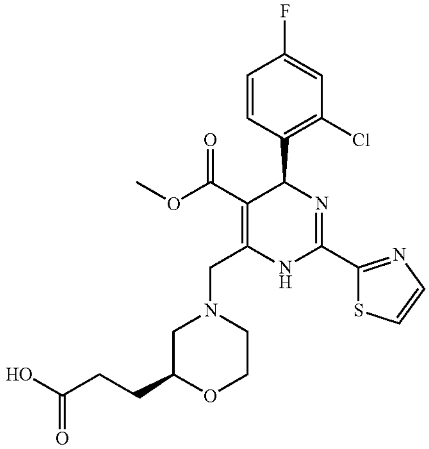 [SMILES: COC(=O)C1=C(CN2CCO[C@@H](CCC(=O)O)C2)NC(c2nccs2)=N[C@@H]1c1ccc(F)cc1Cl]

The title compound was prepared by the procedure described in step 6 of Example 2 using (S)-methyl 6-(bromomethyl)-4-(2-chloro-4-fluorophenyl)-2-(thiazol-2-yl)-1,4-dihydropyrimidine-5-carboxylate (0.89 g, 2 mmol), (S)-3-(morpholin-3-yl)propanoic acid hydrochloride (0.4 g, 2 mmol), potassium carbonate (0.28 g, 2 mmol) and anhydrous ethyl alcohol (20 mL) to give the title compound as a yellow solid (0.39 g, 37%). The compound was characterized by the following spectroscopic data:

MS (ESI, pos.ion) m/z: 523.2 $[M+H]^+$; and $^1$H NMR (400 MHz, DMSO-$d_6$): δ 12.02 (br, 1H), 9.68 (s, 1H), 8.02 (d, 1H), 7.94 (d, 1H), 7.46-7.39 (m, 2H), 7.18 (td, 1H), 6.03 (s, 1H), 3.94-3.87 (m, 3H), 3.63-3.55 (m, 2H), 3.52 (s, 3H), 2.87-2.73 (m, 2H), 2.39-2.35 (m, 1H), 2.32-2.26 (m, 2H), 2.02 (t, 1H), 1.65 (q, 2H).

Example 41

3-((R)-4-(((S)-6-(2-Bromo-4-fluorophenyl)-5-(methoxycarbonyl)-2-(thiazol-2-yl)-3,6-dihydropyrimidin-4-yl)methyl)morpholin-2-yl)propanoic acid Step 1) (S)-methyl 4-(2-bromo-4-fluorophenyl)-6-methyl-2-(thiazol-2-yl)-1,4-dihydropyrimidine-5-carboxylate

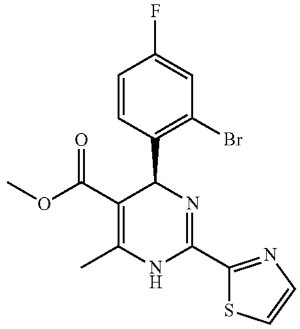 [SMILES: COC(=O)C1=C(C)NC(c2nccs2)=N[C@@H]1c1ccc(F)cc1Br]

The title compound was prepared by the procedure described in step 1 of Example 1 using methyl 4-(2-bromo-4-fluorophenyl)-6-methyl-2-(thiazol-2-yl)-1,4-dihydropyrimidine-5-carboxylate (5 g, 12.2 mmol) to give the title compound as a yellow solid (1.7 g, 34%). The compound was characterized by the following spectroscopic data:

MS (ESI, pos.ion) m/z: 410.0 $[M+H]^+$.

Step 2) (S)-methyl 4-(2-bromo-4-fluorophenyl)-6-(bromomethyl)-2-(thiazol-2-yl)-1,4-dihydropyrimidine-5-carboxylate

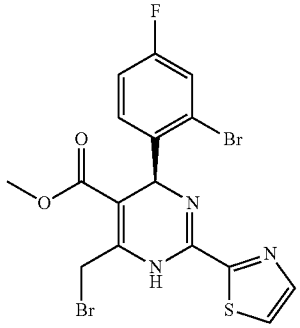 [SMILES: COC(=O)C1=C(CBr)NC(c2nccs2)=N[C@@H]1c1ccc(F)cc1Br]

The title compound was prepared by the procedure described in step 2 of Example 1 using (S)-methyl 4-(2-bromo-4-fluorophenyl)-6-methyl-2-(thiazol-2-yl)-1,4-dihydropyrimidine-5-carboxylate (0.98 g, 2.4 mmol), $CCl_4$ (20 mL) and NBS (0.47 g, 2.64 mmol) to give the title compound as a yellow solid (0.82 g, 70%). The compound was characterized by the following spectroscopic data:

MS (ESI, pos.ion) m/z: 489.9[M+H]$^+$.

Step 3) 3-((R)-4-(((S)-6-(2-bromo-4-fluorophenyl)-5-(methoxycarbonyl)-2-(thiazol-2-yl)-3,6-dihydro-pyrimidin-4-yl)methyl)morpholin-2-yl)propanoic acid

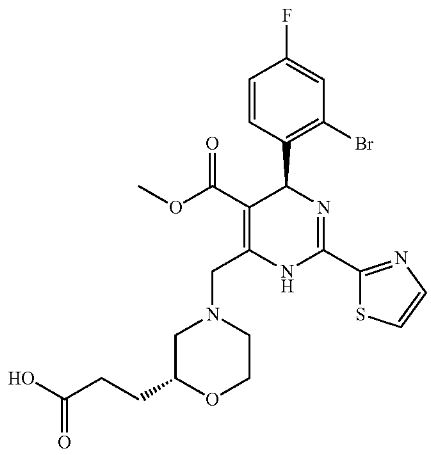 [SMILES: COC(=O)C1=C(CN2CCO[C@H](CCC(=O)O)C2)NC(c2nccs2)=N[C@@H]1c1ccc(F)cc1Br]

The title compound was prepared by the procedure described in step 6 of Example 2 using (S)-methyl 4-(2-bromo-4-fluorophenyl)-6-(bromomethyl)-2-(thiazol-2-yl)-1,4-dihydropyrimidine-5-carboxylate (0.49 g, 1 mmol), (R)-3-(morpholin-2-yl)propanoic acid hydrochloric (0.2 g, 1 mmol), potassium carbonate (0.14 g, 1 mmol) and anhydrous ethyl alcohol (10 mL) to give the title compound as a yellow solid (0.27 g, 54%). The compound was characterized by the following spectroscopic data:

MS (ESI, pos.ion) m/z: 567.2[M+H]$^+$; and $^1$H NMR (400 MHz, DMSO-$d_6$): δ12.03 (s, 1H), 9.69 (s, 1H), 8.02 (d, 1H), 7.94 (d, 1H), 7.57 (dd, 1H), 7.38 (dd, 1H), 7.23 (td, 1H), 6.03 (s, 1H), 3.94-3.84 (m, 3H), 3.62-3.54 (m, 2H), 3.52 (s, 3H), 2.88-2.84 (m, 1H), 2.67-2.62 (m, 1H), 2.39-2.26 (m, 3H), 2.06-1.99 (m, 1H), 1.64-1.59 (m, 2H).

Example 42

3-((S)-4-(((S)-6-(2-Bromo-4-fluorophenyl)-5-(methoxycarbonyl)-2-(thiazol-2-yl)-3,6-dihydropyrimidin-4-yl)methyl)morpholin-2-yl)propanoic acid

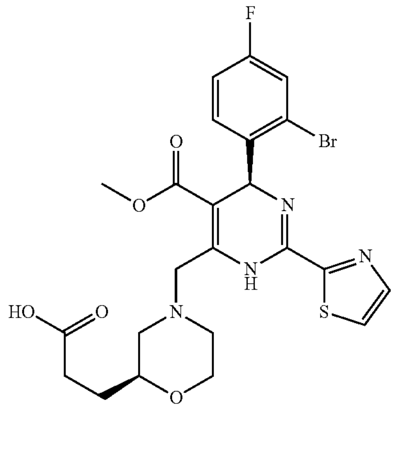 [SMILES: COC(=O)C1=C(CN2CCO[C@@H](CCC(=O)O)C2)NC(c2nccs2)=N[C@@H]1c1ccc(F)cc1Br]

The title compound was prepared by the procedure described in step 6 of Example 2 using (S)-methyl 4-(2-bromo-4-fluorophenyl)-6-(bromomethyl)-2-(thiazol-2-yl)-1,4-dihydropyrimidine-5-carboxylate (1 g, 2 mmol), (S)-3-(morpholin-3-yl)propanoic acid hydrochloride (0.39 g, 2 mmol), potassium carbonate (0.28 g, 2 mmol) and anhydrous ethyl alcohol (10 mL) to give the title compound as a yellow solid (0.52 g, 46%). The compound was characterized by the following spectroscopic data:

MS (ESI, pos.ion) m/z: 567.2[M+H]$^+$; and $^1$H NMR (600 MHz, DMSO-$d_6$): δ 12.07 (s, 1H), 9.71 (s, 1H), 8.04 (d, 1H), 7.94 (d, 1H), 7.57 (dd, 1H), 7.39 (dd, 1H), 7.23 (td, 1H), 6.04 (s, 1H), 3.96 (d, 1H), 3.87-3.81 (m, 2H), 3.57-3.54 (m, 1H), 3.53 (s, 3H), 3.53-3.49 (m, 1H), 2.88 (d, 1H), 2.62 (d, 1H), 2.38-2.20 (m, 3H), 2.16-2.09 (m, 1H), 1.73-1.65 (m, 2H).

Example 43

3-((R)-4-(((S)-6-(2,4-Dichlorophenyl)-5-(ethoxycarbonyl)-2-(thiazol-2-yl)-3,6-dihydropyrimidin-4-yl)methyl)morpholin-2-yl)propanoic acid Step 1) (S)-ethyl 4-(2,4-dichlorophenyl)-6-methyl-2-(thiazol-2-yl)-1,4-dihydropyrimidine-5-carboxylate

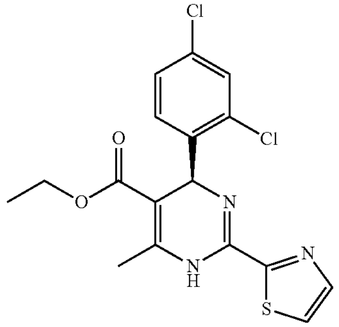 [SMILES: CCOC(=O)C1=C(C)NC(c2nccs2)=N[C@@H]1c1ccc(Cl)cc1Cl]

The title compound was prepared by the procedure described in step 1 of Example 1 using ethyl 4-(2,4-dichlorophenyl)-6-methyl-2-(thiazol-2-yl)-1,4-dihydropyrimidine-5-carboxylate (5 g, 12.6 mmol) to give the title compound as a yellow solid (1.5 g, 30%). The compound was characterized by the following spectroscopic data:

MS (ESI, pos.ion) m/z: 396.1 [M+H]$^+$.

Step 2) (S)-ethyl 6-(bromomethyl)-4-(2,4-dichlorophenyl)-2-(thiazol-2-yl)-1,4-dihydropyrimidine-5-carboxylate

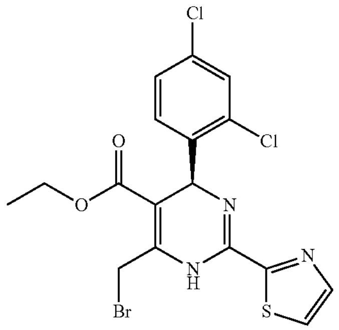

The title compound was prepared by the procedure described in step 2 of Example 1 using ((S)-ethyl 4-(2,4-dichlorophenyl)-6-methyl-2-(thiazol-2-yl)-1,4-dihydropyrimidine-5-carboxylate (0.95 g, 2.4 mmol), $CCl_4$ (20 mL)

and NBS (0.47 g, 2.64 mmol) to give the title compound as a yellow solid (0.73 g, 64%). The compound was characterized by the following spectroscopic data:

MS (ESI, pos.ion) m/z: 475.6 $[M+H]^+$.

Step 3) 3-((R)-4-(((S)-6-(2,4-dichlorophenyl)-5-(ethoxycarbonyl)-2-(thiazol-2-yl)-3,6-dihydropyrimidin-4-yl)methyl)morpholin-2-yl)propanoic acid

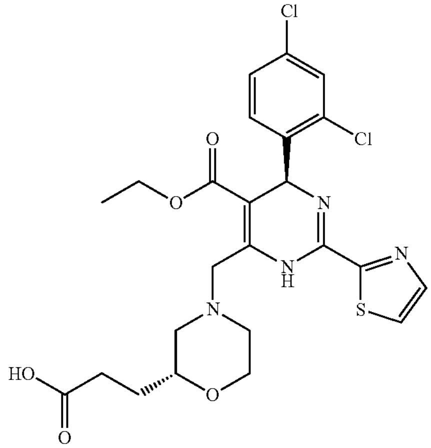

The title compound was prepared by the procedure described in step 6 of Example 2 using (S)-ethyl 6-(bromomethyl)-4-(2,4-dichlorophenyl)-2-(thiazol-2-yl)-1,4-dihydropyrimidine-5-carboxylate (0.98 g, 2.1 mmol), (R)-3-(morpholin-2-yl)propanoic acid hydrochloric (0.4 g, 2.1 mmol), potassium carbonate (0.58 g, 4.2 mmol) and anhydrous ethyl alcohol (20 mL) to give the title compound as a yellow solid (0.69 g, 59%). The compound was characterized by the following spectroscopic data:

MS (ESI, pos.ion) m/z: 553.2$[M+H]^+$; and $^1H$ NMR (400 MHz, DMSO-$d_6$): δ 12.06 (s, 1H), 9.66 (s, 1H), 8.02 (d, 1H), 7.94 (d, 1H), 7.60 (br, 1H), 7.38 (br, 2H), 6.03 (s, 1H), 3.96 (q, 2H), 3.89-3.85 (m, 3H), 3.60-3.47 (m, 2H), 2.89-2.84 (m, 1H), 2.66-2.63 (m, 1H), 2.37-2.23 (m, 3H), 2.10-2.05 (m, 1H), 1.70-1.63 (m, 2H), 1.06 (t, 3H).

Example 44

3-((S)-4-(((S)-6-(2,4-Dichlorophenyl)-5-(ethoxycarbonyl)-2-(thiazol-2-yl)-3,6-dihydropyrimidin-4-yl)methyl)morpholin-2-yl)propanoic acid

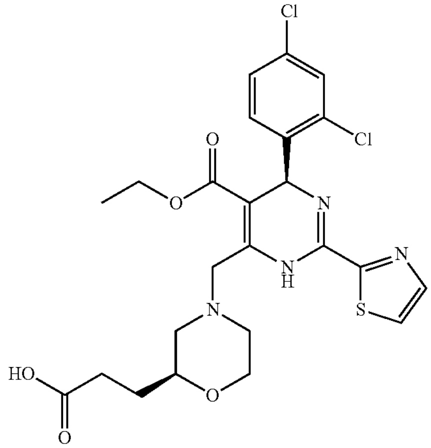

The title compound was prepared by the procedure described in step 6 of Example 2 using (S)-ethyl 6-(bromomethyl)-4-(2,4-dichlorophenyl)-2-(thiazol-2-yl)-1,4-dihydropyrimidine-5-carboxylate (0.48 g, 1 mmol), (S)-3-(morpholin-3-yl)propanoic acid hydrochloride (0.2 g, 1 mmol), potassium carbonate (0.28 g, 2 mmol) and anhydrous ethyl alcohol (10 mL) to give the title compound as a yellow solid (0.33 g, 60%). The compound was characterized by the following spectroscopic data:

MS (ESI, pos.ion) m/z: 552.9$[M+H]^+$;

$^1H$ NMR (400 MHz, DMSO-$d_6$): δ 12.04 (br, 1H), 9.65 (s, 1H), 8.01 (d, 1H), 7.92 (d, 1H), 7.58 (br, 1H), 7.38 (br, 2H), 6.04 (s, 1H), 3.98 (q, 2H), 3.91-3.87 (m, 3H), 3.61-3.48 (m, 2H), 2.86-2.65 (m, 2H), 2.36-2.33 (m, 1H), 2.31-2.24 (m, 2H), 2.01 (t, 1H), 1.66-1.63 (m, 2H), 1.05 (t, 3H).

Example 45

3-((R)-4-(((S)-6-(2,4-dichlorophenyl)-5-(methoxycarbonyl)-2-(thiazol-2-yl)-3,6-dihydropyrimidin-4-yl)methyl)morpholin-2-yl)propanoic acid Step 1) (S)-methyl 4-(2,4-dichlorophenyl)-6-methyl-2-(thiazol-2-yl)-1,4-dihydropyrimidine-5-carboxylate

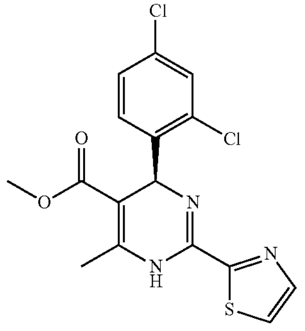 [SMILES: COC(=O)C1=C(C)NC(c2nccs2)=N[C@@H]1c1ccc(Cl)cc1Cl]

The title compound was prepared by the procedure described in step 1 of Example 1 using methyl 4-(2,4-dichlorophenyl)-6-methyl-2-(thiazol-2-yl)-1,4-dihydropyrimidine-5-carboxylate (5 g, 13.1 mmol) to give the title compound as a yellow solid (1.6 g, 32%). The compound was characterized by the following spectroscopic data:

MS (ESI, pos.ion) m/z: 382.1 $[M+H]^+$.

Step 2

(S)-methyl-6-(bromomethyl)-4-(2,4-dichlorophenyl)-2-(thiazol-2-yl)-1,4-dihydropyrimidine-5-carboxylate

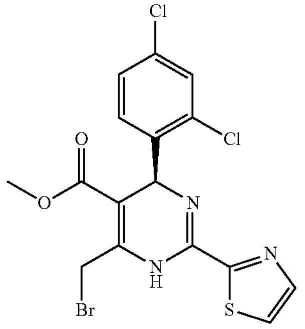

The title compound was prepared by the procedure described in step 2 of Example 1 using (S)-methyl 4-(2,4-dichlorophenyl)-6-methyl-2-(thiazol-2-yl)-1,4-dihydropyrimidine-5-carboxylate (0.92 g, 2.4 mmol), $CCl_4$ (20 mL) and NBS (0.47 g, 2.64 mmol) to give the title compound as a yellow solid (0.66 g, 60%). The compound was characterized by the following spectroscopic data:

MS (ESI, pos.ion) m/z: 459.9 $[M+H]^+$.

Step 3) 3-((R)-4-(((S)-6-(2,4-dichlorophenyl)-5-(methoxycarbonyl)-2-(thiazol-2-yl)-3,6-dihydropyrimidin-4-yl)methyl)morpholin-2-yl)propanoic acid

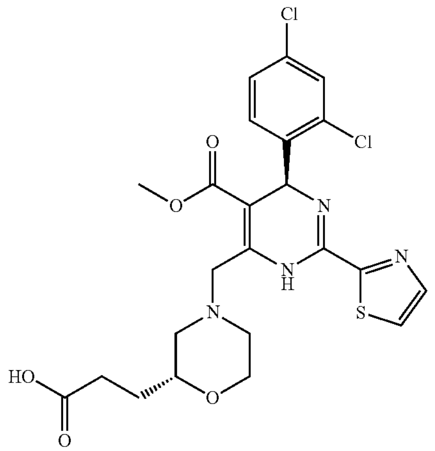 [SMILES: COC(=O)C1=C(CN2CCO[C@H](CCC(=O)O)C2)NC(c2nccs2)=N[C@@H]1c1ccc(Cl)cc1Cl]

The title compound was prepared by the procedure described in step 6 of Example 2 using (S)-methyl 6-(bromomethyl)-4-(2,4-dichlorophenyl)-2-(thiazol-2-yl)-1,4-dihydropyrimidine-5-carboxylate (0.72 g, 1.56 mmol), (R)-3-(morpholin-2-yl)propanoic acid hydrochloric (0.31 g, 1.56 mmol), potassium carbonate (0.22 g, 1.56 mmol) and anhydrous ethyl alcohol (15 mL) to give the title compound as a yellow solid (0.378 g, 45%). The compound was characterized by the following spectroscopic data:

MS (ESI, pos.ion) m/z: 538.8$[M+H]^+$; and $^1$H NMR (400 MHz, DMSO-$d_6$): δ 12.09 (br, 1H), 9.71 (s, 1H), 8.02 (d, 1H), 7.94 (d, 1H), 7.59 (s, 1H), 7.38 (s, 2H), 6.05 (s, 1H), 3.93-3.80 (m, 3H), 3.57-3.54 (m, 2H), 3.52 (s, 3H), 2.88 (d, 1H), 2.63 (d, 1H), 2.38 (q, 2H), 2.27-2.22 (m, 1H), 2.11 (t, 1H), 1.69-1.64 (m, 2H).

Example 46

3-((S)-4-(((S)-6-(2,4-Dichlorophenyl)-5-(methoxycarbonyl)-2-(thiazol-2-yl)-3,6-dihydropyrimidin-4-yl)methyl)morpholin-2-yl)propanoic acid

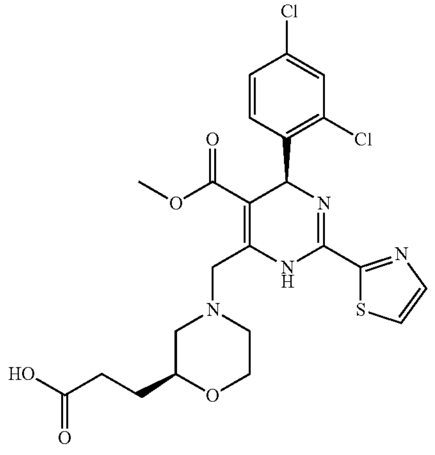

The title compound was prepared by the procedure described in step 6 of Example 2 using (S)-methyl 6-(bromomethyl)-4-(2,4-dichlorophenyl)-2-(thiazol-2-yl)-1,4-dihydropyrimidine-5-carboxylate (0.46 g, 1 mmol), (S)-3-(morpholin-3-yl)propanoic acid hydrochloride (0.2 g, 1 mmol), potassium carbonate (0.14 g, 1 mmol) and anhydrous ethyl alcohol (10 mL) to give the title compound as a yellow solid (0.19 g, 35%). The compound was characterized by the following spectroscopic data:

MS (ESI, pos.ion) m/z: 539.1$[M+H]^+$; and $^1$H NMR (600 MHz, DMSO-$d_6$): δ 12.05 (br, 1H), 9.70 (s, 1H), 8.02 (d, 1H), 7.94 (d, 1H), 7.56 (br, 1H), 7.39 (br, 2H), 6.05 (s, 1H), 3.91-3.84 (m, 3H), 3.61-3.54 (m, 2H), 3.53 (s, 3H), 2.86-2.65 (m, 2H), 2.36-2.33 (m, 1H), 2.31-2.24 (m, 2H), 2.01 (t, 1H), 1.66-1.63 (m, 2H).

Example 47

3-((R)-4-(((S)-6-(2-Bromo-4-fluorophenyl)-5-(ethoxycarbonyl)-2-(thiazol-2-yl)-3,6-dihydropyrimidin-4-yl)methyl)morpholin-3-yl)propanoic acid

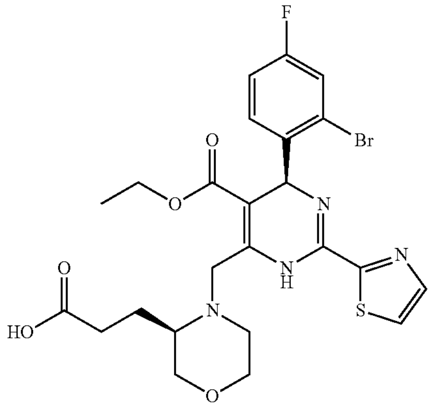 [SMILES: CCOC(=O)C1=C(CN2CCOC[C@H]2CCC(=O)O)NC(c2nccs2)=N[C@@H]1c1ccc(F)cc1Br]

The title compound was prepared by the procedure described in step 6 of Example 8 using (S)-ethyl 4-(2-bromo-4-fluorophenyl)-6-(bromomethyl)-2-(thiazol-2-yl)-1,4-dihydropyrimidine-5-carboxylate (6.5 g, 13 mmol), (R)-3-(morpholin-2-yl)propanoic acid hydrochloride (2.5 g, 13 mmol), potassium carbonate (3.4 g, 26 mmol) and anhydrous ethyl alcohol (200 mL) to give the title compound as a yellow solid (3.8 g, 50%). The compound was characterized by the following spectroscopic data:

MS (ESI, pos.ion) m/z: 581.2$[M+H]^+$; and $^1$H NMR (400 MHz, DMSO-$d_6$): δ 12.09 (s, 1H), 9.85 (s, 1H), 8.04 (d, 1H), 7.96 (d, 1H), 7.56 (dd, 1H), 7.40 (dd, 1H), 7.23 (td, 1H), 6.05 (s, 1H), 4.23 (d, 1H), 3.98 (q, 2H), 3.90 (d, 1H), 3.79-3.71 (m, 2H), 3.65-3.60 (m, 1H), 3.41 (dd, 1H), 2.89-2.84 (m, 1H), 2.58-2.52 (m, 1H), 2.49-2.44 (m, 1H), 2.38-2.19 (m, 2H), 1.82-1.74 (m, 1H), 1.65-1.54 (m, 1H), 1.06 (t, 3H).

Example 48

3-((S)-4-(((S)-6-(2-Bromo-4-fluorophenyl)-5-(ethoxycarbonyl)-2-(thiazol-2-yl)-3,6-dihydropyrimidin-4-yl)methyl)morpholin-3-yl)propanoic acid

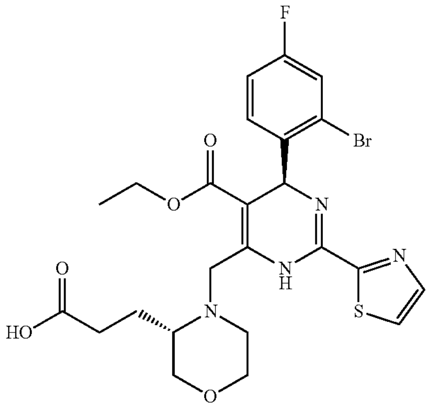 [SMILES: CCOC(=O)C1=C(CN2CCOC[C@@H]2CCC(=O)O)NC(c2nccs2)=N[C@@H]1c1ccc(F)cc1Br]

The title compound was prepared by the procedure described in step 6 of Example 2 using (S)-ethyl 4-(2-bromo-4-fluorophenyl)-6-(bromomethyl)-2-(thiazol-2-yl)-1,4-dihydropyrimidine-5-carboxylate (0.5 g, 1 mmol), (S)-3-(morpholin-2-yl)propanoic acid hydrochloride (0.2 g, 1 mmol), potassium carbonate (0.28 g, 2 mmol) and anhydrous ethyl alcohol (10 mL) to give the title compound as a yellow solid (0.21 g, 36%). The compound was characterized by the following spectroscopic data:

MS (ESI, pos.ion) m/z: 580.9[M+H]$^+$; and $^1$H NMR (400 MHz, DMSO-d$_6$): δ12.16 (br, 1H), 9.83 (s, 1H), 8.02 (d, 1H), 7.92 (d, 1H), 7.54 (dd, 1H), 7.40 (dd, 1H), 7.23 (td, 1H), 6.05 (s, 1H), 4.19 (d, 1H), 3.96 (q, 2H), 3.92 (d, 1H), 3.83-3.79 (m, 1H), 3.75-3.72 (m, 1H), 3.61-3.56 (m, 1H), 3.38-3.32 (m, 1H), 2.79-2.76 (m, 1H), 2.58-2.53 (m, 1H), 2.49-2.47 (m, 1H), 2.39-2.32 (m, 2H), 1.89-1.85 (m, 1H), 1.69-1.58 (m, 1H), 1.06 (t, 3H).

Example 49

3-((R)-4-(((S)-6-(2-Bromo-4-fluorophenyl)-5-(methoxycarbonyl)-2-(thiazol-2-yl)-3,6-dihydropyrimidin-4-yl)methyl)morpholin-3-yl)propanoic acid

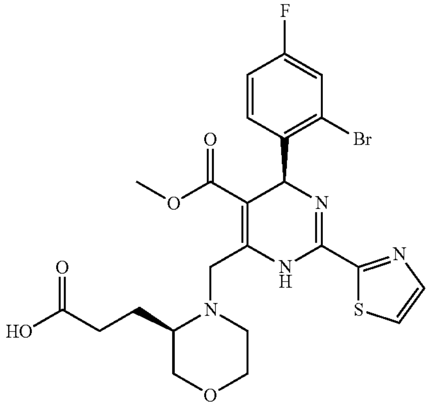 [SMILES: COC(=O)C1=C(CN2CCOC[C@H]2CCC(=O)O)NC(c2nccs2)=N[C@@H]1c1ccc(F)cc1Br]

The title compound was prepared by the procedure described in step 6 of Example 2 using (S)-methyl 4-(2-bromo-4-fluorophenyl)-6-(bromomethyl)-2-(thiazol-2-yl)-1,4-dihydropyrimidine-5-carboxylate (0.98 g, 2 mmol), (R)-3-(morpholin-3-yl)propanoic acid hydrochloride (0.39 g, 2 mmol), potassium carbonate (0.14 g, 1 mmol) and anhydrous ethyl alcohol (20 mL) to give the title compound as a yellow solid (0.5 g, 44%). The compound was characterized by the following spectroscopic data:

MS (ESI, pos.ion) m/z: 567.1[M+H]$^+$; and $^1$H NMR (400 MHz, DMSO-d$_6$): δ 12.06 (s, 1H), 9.83 (s, 1H), 8.02 (d, 1H), 7.96 (d, 1H), 7.56 (dd, 1H), 7.41 (dd, 1H), 7.23 (td, 1H), 6.05 (s, 1H), 4.24 (d, 1H), 3.92 (d, 1H), 3.79-3.71 (m, 2H), 3.66-3.61 (m, 1H), 3.52 (s, 3H), 3.43 (dd, 1H), 2.89-2.84 (m, 1H), 2.58-2.54 (m, 1H), 2.49-2.43 (m, 1H), 2.38-2.17 (m, 2H), 1.82-1.72 (m, 1H), 1.65-1.55 (m, 1H).

Example 50

3-((S)-4-(((S)-6-(2-Bromo-4-fluorophenyl)-5-(methoxycarbonyl)-2-(thiazol-2-yl)-3,6-dihydropyrimidin-4-yl)methyl)morpholin-3-yl)propanoic acid

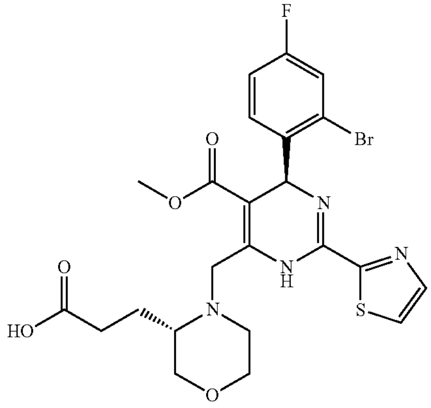 [SMILES: COC(=O)C1=C(CN2CCOC[C@@H]2CCC(=O)O)NC(c2nccs2)=N[C@@H]1c1ccc(F)cc1Br]

The title compound was prepared by the procedure described in step 6 of Example 2 using (S)-methyl 4-(2-bromo-4-fluorophenyl)-6-(bromomethyl)-2-(thiazol-2-yl)-1,4-dihydropyrimidine-5-carboxylate (0.98 g, 2 mmol), (S)-3-(morpholin-3-yl)propanoic acid hydrochloride (0.4 g, 2 mmol), potassium carbonate (0.28 g, 2 mmol) and anhydrous ethyl alcohol (20 mL) to give the title compound as a yellow solid (0.4 g, 35%). The compound was characterized by the following spectroscopic data:

MS (ESI, pos.ion) m/z: 567.2[M+H]$^+$; and $^1$H NMR (400 MHz, DMSO-d$_6$): δ 9.89 (s, 1H), 8.03 (d, 1H), 7.94 (d, 1H), 7.57 (dd, 1H), 7.38 (dd, 1H), 7.23 (td, 1H), 6.04 (s, 1H), 4.19 (d, 1H), 3.92 (d, 1H), 3.83-3.79 (m, 1H), 3.76-3.71 (m, 1H), 3.61-3.56 (m, 1H), 3.53 (s, 3H), 3.47-3.41 (m, 1H), 3.06-2.86 (m, 1H), 2.78-2.75 (m, 1H), 2.59-2.54 (m, 1H), 2.39-2.22 (m, 2H), 1.88-1.85 (m, 1H), 1.66-1.57 (m, 1H).

Example 51

In-Vitro Anti-HBV Activity of Compounds in Stable HBV-Producing Cell Line (HepG2.2.15)

1. Assay Method

HBV DNA contents in cell culture fluid were detected by the qPCR-based assay and 50% effective concentration (EC$_{50}$) values of the compounds against HBV were calculated. Specific procedures are as follows:

HepG2.2.15 cells were seeded into each well of 96-well plates, 40,000 cells per well. Cells were treated with cell culture medium containing compounds with different concentrations for 24 hours after cell seeding. The final concentration of each compound was 16.4 μM in each well and each compound was diluted to desired concentration using 3-fold gradient dilution protocol, 9 diluted points in duplicate. The culture mediums containing the compounds were refreshed on day 4 post cell seeding. Culture media were collected from the HepG2.2.15 plates on day 7 post cell seeding followed by HBV DNA extraction.

HBV DNA extraction: The HBV DNA extraction was performed using QIAamp 96 DNA Blood Kit (QIAGEN 51161).

PCR for quantification: PCR mix was prepared according to PCR system. PCR mix was dispensed to 96-well optical reaction plates (special for quantification). The standard diluted proportionally was added. Then the sample was added; The plates were sealed with optical adhesive film; PCR system was performed according to programs.

Percentage of HBV inhibition of DNA replication by compound was calculated using the following equation:

% Inh.=[1-HBV DNA quantity of sample/HBV DNA quantity of DMSO control]×100.

Calculating $EC_{50}$ value of compounds to HBV replication: the $EC_{50}$ values were calculated based on "four-parameter logistic equation" and using GraphPad Prism 5 analysis software.

2. Assay Results

Anti HBV activity of the compounds disclosed herein in HBV HepG2.2.15 cell lines were detected by the methods above. The results are shown in Table 2:

TABLE 2 anti-HBV activity of the compounds in HBV HepG2.2.15 cell line (HepG2.2.15)

| Example | $EC_{50}$ (nmol) | Example | $EC_{50}$ (nmol) |
|---|---|---|---|
| Example 2 | 35 | Example 15 | 7.94 |
| Example 3 | 135 | Example 16 | 9 |
| Example 4 | 116 | Example 17 | 12 |
| Example 5 | 306 | Example 18 | 10 |
| Example 7 | 72 | Example 19 | 6 |
| Example 8 | 25 | Example 20 | 5.5 |
| Example 9 | 48 | Example 21 | 93.6 |
| Example 10 | 45 | Example 22 | 89 |
| Example 11 | 35 | Example 23 | 110 |
| Example 12 | 26 | Example 24 | 107 |
| Example 13 | 28 | Example 25 | 86 |
| Example 14 | 140 | Example 26 | 82 |
| Example 35 | >12200 | Example 49 | >16400 |
| Example 36 | >14500 | Example 50 | >10900 |
| Example 37 | >16400 | contrast 1 | 260 |
| Example 38 | >16400 | contrast 2 | 360 |
| Example 39 | >15200 | contrast 3 | 290 |
| Example 40 | >16400 | contrast 4 | 250 |
| Example 41 | >12800 | contrast 5 | 230 |
| Example 42 | >15300 | contrast 6 | 210 |
| Example 43 | >11700 | contrast 7 | 92 |
| Example 44 | >14900 | contrast 8 | 90 |
| Example 45 | >11300 | contrast 9 | 63 |
| Example 46 | >14200 | contrast 10 | 59 |
| Example 47 | >16400 | contrast 11 | 80 |
| Example 48 | >10300 | contrast 12 | 75 |

Remark: synthetic method of contrast compounds refer to Patent CN 103626752 A, the chemical names of contrast 1-12 are as below:

contrast 1:
3-(4-((6-(2-bromo-4-fluorophenyl)-5-(ethoxycarbonyl)-2-(thiazol-2-yl)-3,6-dihydropyrimidin-4-yl)methyl)morpholin-2-yl)propanoic acid;

contrast 2:
3-(4-((6-(2-chloro-4-fluorophenyl)-5-(ethoxycarbonyl)-2-(thiazol-2-yl)-3,6-dihydropyrimidin-4-yl)methyl)morpholin-2-yl)propanoic acid contrast 3:
3-(4-((6-(2-chloro-4-fluorophenyl)-5-(methoxycarbonyl)-2-(thiazol-2-yl)-3,6-dihydropyrimidin-4-yl)methyl)morpholin-2-yl)propanoic acid contrast 4:
3-(4-((6-(2-bromo-4-fluorophenyl)-5-(methoxycarbonyl)-2-(thiazol-2-yl)-3,6-dihydropyrimidin-4-yl)methyl)morpholin-2-yl)propanoic acid contrast 5:
3-(4-((6-(2,4-dichlorophenyl)-5-(ethoxycarbonyl)-2-(thiazol-2-yl)-3,6-dihydropyrimidin-4-yl)methyl)morpholin-2-yl)propanoic acid contrast 6:
3-(4-((6-(2,4-dichlorophenyl)-5-(methoxycarbonyl)-2-(thiazol-2-yl)-3,6-dihydropyrimidin-4-yl) methyl)morpholin-2-yl)propanoic acid contrast 7:
3-(4-((6-(2-chloro-4-fluorophenyl)-5-(ethoxycarbonyl)-2-(thiazol-2-yl)-3,6-dihydropyrimidin-4-yl)methyl)morpholin-3-yl)propanoic acid contrast 8:
3-(4-((6-(2-chloro-4-fluorophenyl)-5-(methoxycarbonyl)-2-(thiazol-2-yl)-3,6-dihydropyrimidin-4-yl)methyl)morpholin-3-yl)propanoic acid contrast 9:
3-(4-((6-(2,4-dichlorophenyl)-5-(ethoxycarbonyl)-2-(thiazol-2-yl)-3,6-dihydropyrimidin-4-yl)methyl)morpholin-3-yl)propanoic acid contrast 10:
3-(4-((6-(2,4-dichlorophenyl)-5-(methoxycarbonyl)-2-(thiazol-2-yl)-3,6-dihydropyrimidin-4-yl) methyl)morpholin-3-yl)propanoic acid contrast 11:
3-(4-((6-(2-bromo-4-fluorophenyl)-5-(ethoxycarbonyl)-2-(thiazol-2-yl)-3,6-dihydropyrimidin-4-yl)methyl)morpholin-3-yl)propanoic acid contrast 12:
3-(4-((6-(2-bromo-4-fluorophenyl)-5-(methoxycarbonyl)-2-(thiazol-2-yl)-3,6-dihydropyrimidin-4-yl)methyl)morpholin-3-yl)propanoic acid 3. Conclusions:

The data of table 2 indicate that the isomer compounds disclosed herein showed potent inhibitory effect on HBV when the steric configuration at the 4 position is R configuration, the activities of such compounds are much better than those of relevant racemate compounds and isomer compounds of which the steric configuration at the 4 position is S configuration. After a large number of experiment researches, the inventor of the application found that the isomer compounds disclosed herein have a surprising antiviral activity when the steric configuration at the 4 position is R configuration and can be applied in the treatment of various kinds of disorders caused by HBV infection.

Example 52

PK of Test Compounds Assay in Beagle

I. Assay Method

The test compounds were administrated to beagle dog by gavage in dose of 2.5 mg/kg or 5 mg/kg, or by intravenous injection in dose of 1 mg/kg or 2 mg/kg. Blood sample was collected at 0.083, 0.25, 0.5, 1, 2, 4, 6, 8 and 24 hours from vein after administration into anticoagulation tubes with EDTA-$K_2$. The test compounds were extracted from plasma samples and chromatographed on a tandem mass spectrometer. Quantitation was performed using multiple reaction monitoring (MRM). Pharmacokinetic parameters were calculated using WinNonlin 6.3 software with non compartment model.

II. Assay Results

PK of test compounds were detected with the methods above. The results are shown in Table 3:

TABLE 3

| E. | A. R | Dose mg/kg | $T_{max}$ h | $C_{max}$ ng/mL | $t_{1/2}$ h | $AUC_{last}$ hr*ng/mL | $AUC_{INF}$ hr*ng/mL | F % | CL mL/min/Kg | Vss L/Kg |
|---|---|---|---|---|---|---|---|---|---|---|
| Example | iv | 1 | 0.083 | 2050 | 5.71 | 8270 | 8700 | N/A | 1.93 | 0.756 |
| 2 | po | 5 | 1.33 | 6330 | 5.1 | 47900 | 49600 | 114.1 | N/A | N/A |
| Example | iv | 1 | 0.083 | 2570 | 6.59 | 10600 | 11300 | N/A | 1.51 | 0.63 |
| 9 | po | 2.5 | 0.5 | 4360 | 4.62 | 24300 | 24800 | 87.91 | N/A | N/A |
| Example | iv | 1 | 0.083 | 2430 | 5.16 | 9400 | 9710 | N/A | 1.74 | 0.62 |
| 10 | po | 2.5 | 0.833 | 4560 | 4.57 | 27400 | 28000 | 115 | N/A | N/A |
| Example | iv | 1 | 0.139 | 3400 | 4.99 | 10500 | 10900 | N/A | 1.59 | 0.545 |
| 11 | po | 2.5 | 0.75 | 4310 | 4.92 | 23700 | 24400 | 89.66 | N/A | N/A |
| Example | iv | 1 | 0.083 | 2230 | 6.2 | 7570 | 7970 | N/A | 2.12 | 0.832 |
| 12 | po | 2.5 | 0.5 | 2660 | 9.07 | 15000 | 16800 | 84.48 | N/A | N/A |
| Example | iv | 1 | 0.083 | 2920 | 5.08 | 11200 | 11600 | N/A | 1.49 | 0.526 |
| 13 | po | 2.5 | 0.667 | 6410 | 5.29 | 32200 | 33300 | 105.6 | N/A | N/A |

N/A—There is no detection;

$AUC_{last}$—AUC in 0-24 hours;

$AUC_{INF}$—AUC in 0 hour to infinite time.

III. Conclusions

After intragastric administration of drugs in beagle, the compounds of Example 2, Example 9, Example 10, Example 11, Example 12 and the compounds of Example 13 were rapidly absorbed and the times of peak plasma concentration were 1.33 hour, 0.5 hour, 0.833 hour, 0.75 hour 0.5 hour and 0.667 hour respectively. The AUClast of the compound of Example 2 was 47900 hr*ng/mL, the $AUC_{last}$ of the compound of Example 9 was 24300×2=48600 hr*ng/mL (calculated by dosage), the $AUC_{last}$ of the compound of Example 10 was 27400×2=54000 hr*ng/mL (calculated by dosage), and the $AUC_{last}$ of the compound of Example 11 was 23700×2=47400 hr*ng/mL (calculated by dosage), the $AUC_{last}$ of the compound of Example 12 was 15000×2=30000 hr*ng/mL (calculated by dosage), the $AUC_{last}$ of the compound of Example 13 was 32200×2=64400 hr*ng/mL (calculated by dosage). The compounds have better exposure and area under the curve is larger, which showed that compounds were absorbed well and stable in beagle. The F values of the compound of Example 2, Example 9, Example 10, Example 11, Example 12 and the compound of Example 13 were 114.1%, 87.91%, 115%, 89.66%, 84.48% and 105.6% respectively.

Activity data showed that the activity of most compounds disclosed herein showed a good prospect in anti-HBV.

Example 57

Stability of Test Compound in Liver Microsome of Different Species

1. Assay Method

30 μL of a mixture of blank solution and liver microsome was added to a 96-well plates, and 15 μL of buffer solution of the text compound was added to each well. Then two parallel samples were prepared. After a 10 minutes preincubation at 37° C., 15 μL of NADPH solution (8 mM) was added according to the point-in-time. The final concentration of the text compound was 1 μM, the concentration of liver microsome was 0.1 mg/mL, the final concentration of NADPH was 2 mM. The incubations were last for 0, 15, 30, 60 min respectively, and then 150 μL of acetonitrile (include interior label) was added to the mixture system. After dilution with acetonitrile, the samples were centrifuged for 5 minutes in 4000 rpm. The supernatant liquid was collected for LC-MS/MS analysis.

2. The Results are Shown in Table 4

TABLE 4

| | species | | | | | | | |
|---|---|---|---|---|---|---|---|---|
| | human | | dog | | mouse | | monkey | |
| compound | $t_{1/2}$ (min) | CL (mL/min/kg) | $t_{1/2}$ (min) | CL (mL/min/kg) | $t_{1/2}$ (min) | CL (mL/min/kg) | $t_{1/2}$ (min) | CL (mL/min/kg) |
| verapamil | 7.78 | 223.55 | 7.12 | 485.05 | 4.23 | 1291.69 | 1.96 | 1032.09 |
| Example 2 | 99.4 | 17.49 | 241.20 | 14.32 | 14.17 | 385.14 | 18.86 | 107.48 |
| Example 9 | 151.80 | 11.45 | 177.8 | 19.43 | 19.44 | 280.73 | 26.82 | 75.58 |
| Example 10 | 466.9 | 3.72 | 563.6 | 6.13 | 94.52 | 57.74 | 131.5 | 15.41 |
| Example 11 | 250.9 | 6.93 | 343.4 | 10.06 | 63.22 | 86.32 | 140.5 | 14.43 |
| Example 12 | 93.54 | 18.58 | 197 | 17.54 | 9.03 | 604.43 | 16.64 | 121.82 |
| Example 13 | 100.8 | 17.25 | 627.10 | 5.51 | 40.4 | 135.08 | 56.38 | 35.95 |

3. Conclusion

The results of table 4 showed that the $t_{1/2}$ of Example 2, Example 9, Example 10, Example 11, Example 12 and Example 13 in liver microsome of human, dog, mouse and monkey were long, the CL were less, which showed a good stability of the compound disclosed herein.

Although the present invention has been described by a way of a detailed description in which general description, examples and assays have been described, it will be obvious to one skilled in the art that certain changes and modifications may be made without departing from the invention, and therefore, all such changes and modifications are within the scope of the invention.

What is claimed is:

1. A compound of Formula (I) or (Ia), or an enantiomer, a diastereoisomer, a tautomer, a hydrate, a solvate, a prodrug, a stereoisomer, an N-oxide, or a pharmaceutically acceptable salt thereof, (I)

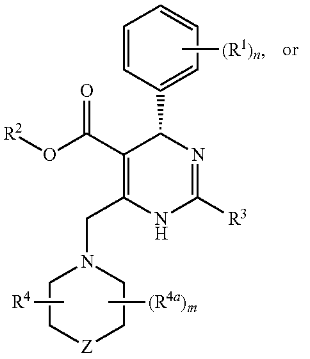

or (Ia)

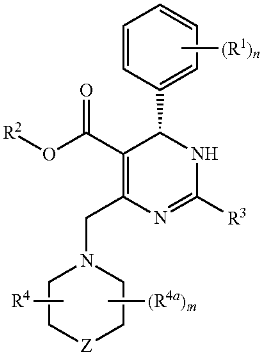

wherein each $R^1$ is independently H, F, Cl, Br, I, nitro, trifluoromethyl or cyano;

each $R^2$ is independently methyl or ethyl;

each $R^3$ is independently thiazolyl, oxazolyl or imidazolyl; wherein optionally each of thiazolyl, oxazolyl and imidazolyl is independently unsubstituted or substituted with methyl or cyclopropyl;

each Z is independently O or S;

each $R^4$ is independently —$(CR^5R^{5a})_t$—C(═O)—OH;

each $R^{4a}$ is independently H, methyl or isopropyl;

each $R^5$ and $R^{5a}$ is independently H, F or methyl, or $R^5$ and $R^{5a}$, together with the carbon atom to which they are attached, form cyclopropyl or —C(═O);

wherein each n is independently 1, 2 or 3;

each m is independently 0, 1 or 2; and t is 1, 2, 3 or 4.

2. The compound according to claim 1, wherein $R^3$ is

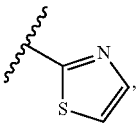

,

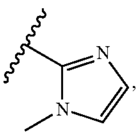

,

-continued

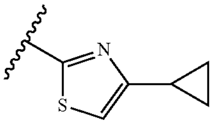

or

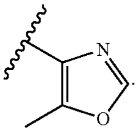

.

3. The compound according to claim 1 having one of the following structures:

(1)

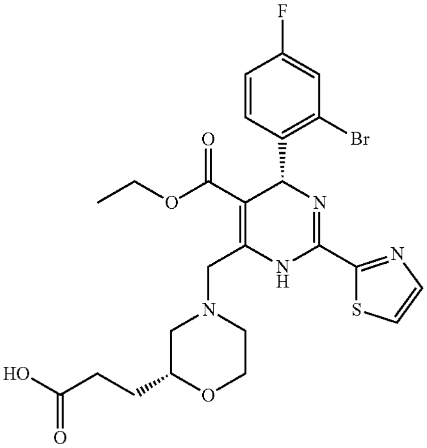

, (2)

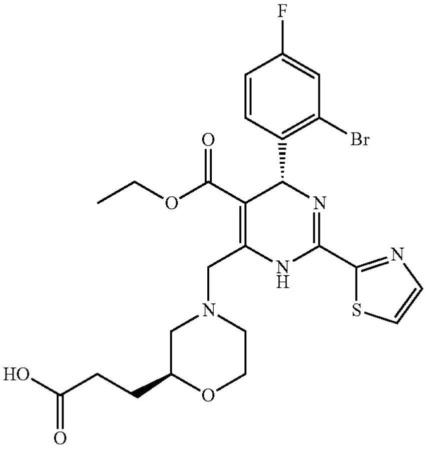

, (3)

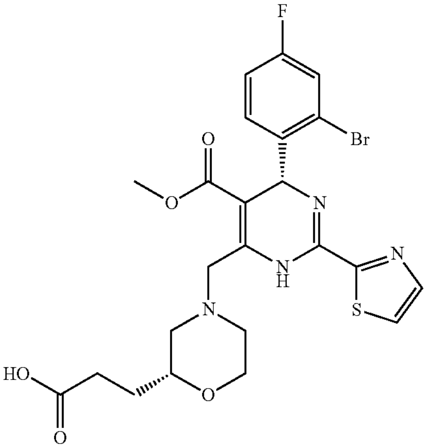

,

-continued
(4)
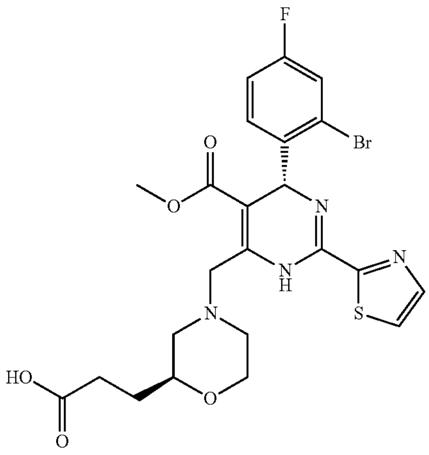
,
(5)
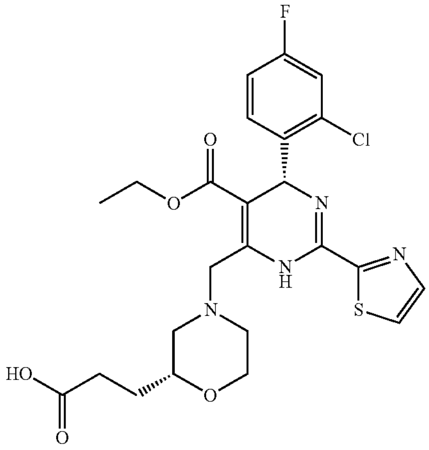
,
(6)
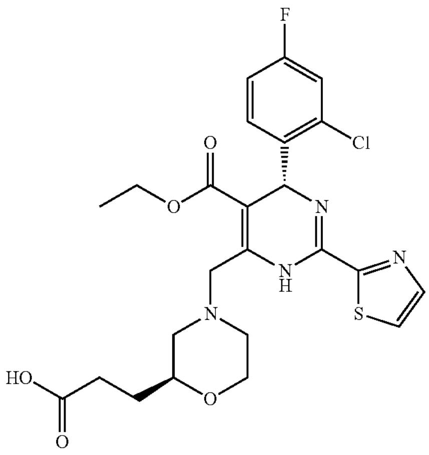
,
-continued
(7)
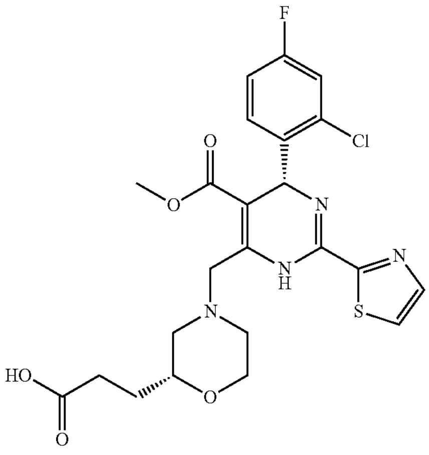
,
(8)
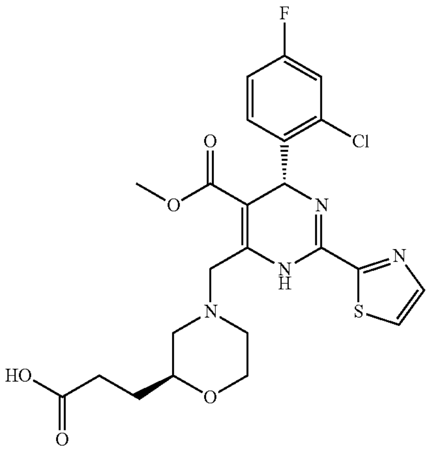
,
(9)
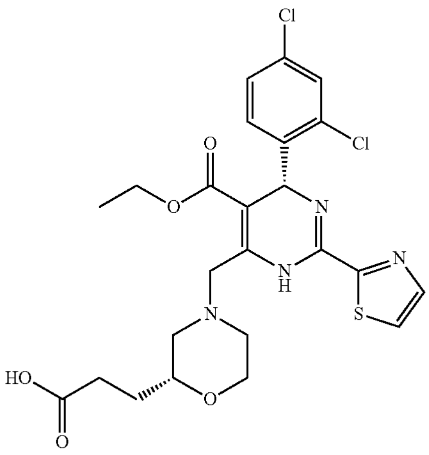
, -continued
(10)
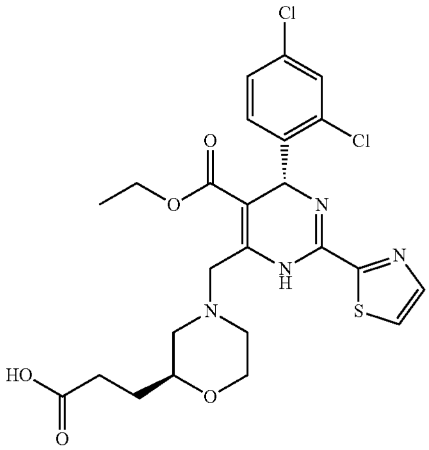
,
(11)
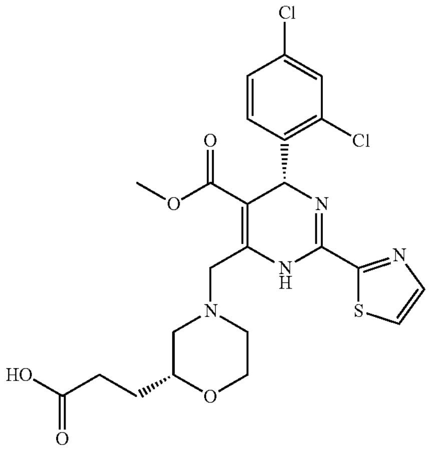
,
(12)
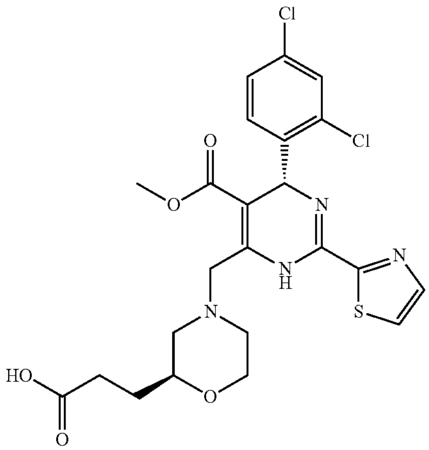
,
-continued
(13)
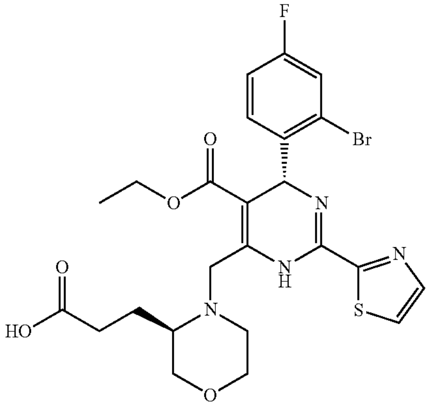
,
(14)
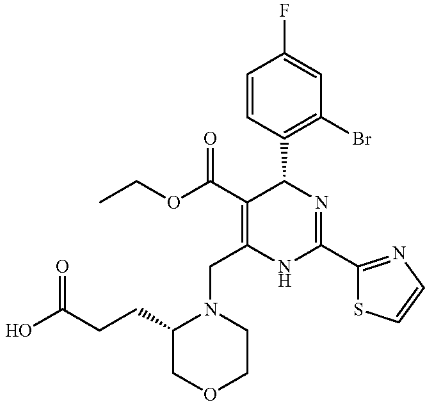
,
(15)
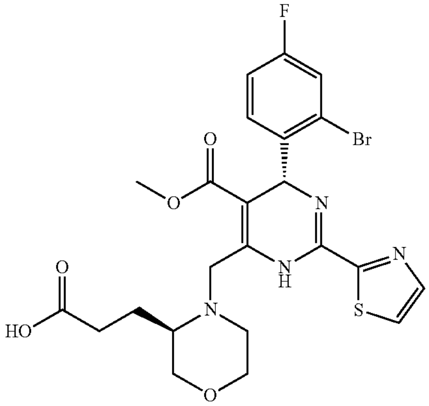
,
(16)
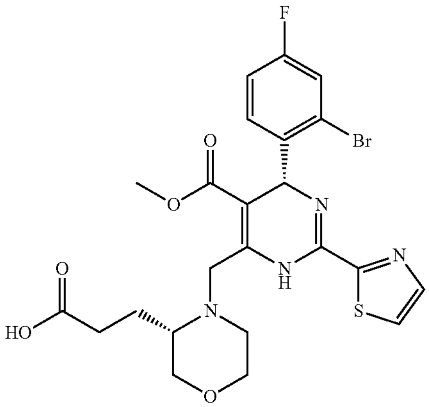
, -continued
(17)
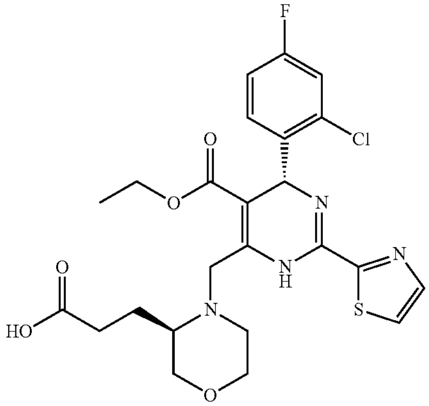
,
(18)
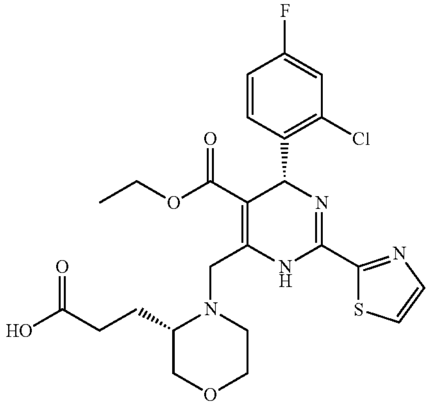
,
(19)
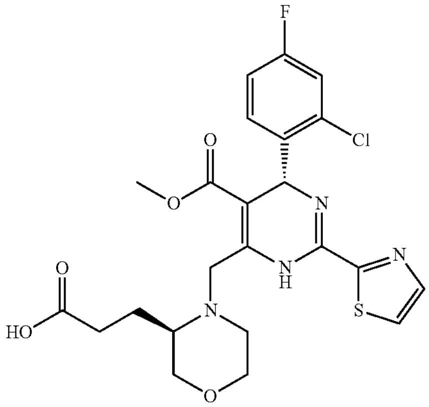
,
(20)
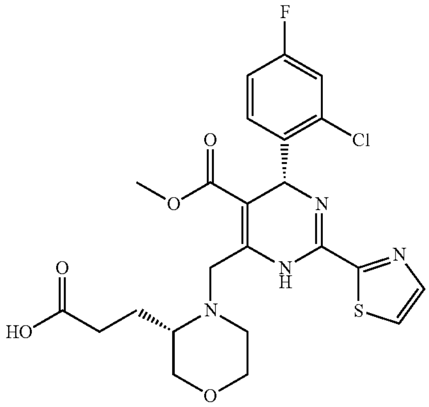
,
-continued
(21)
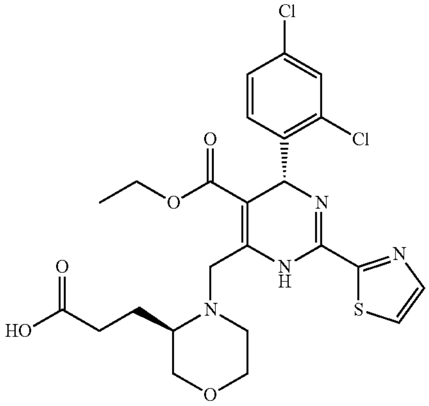
,
(22)
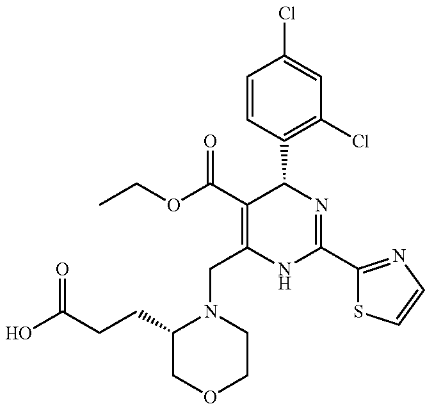
,
(23)
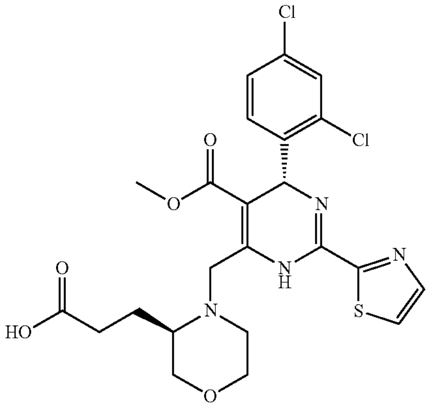
,
(24)
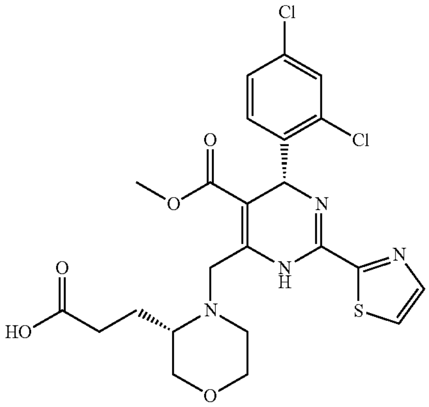
,

(25)
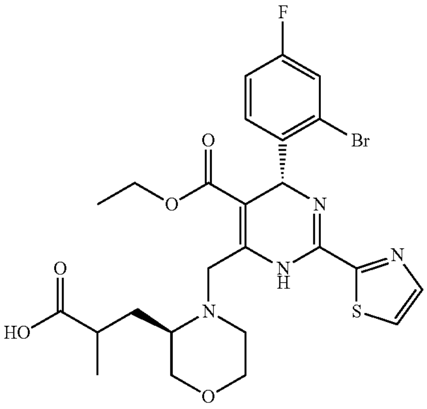
,
(26)
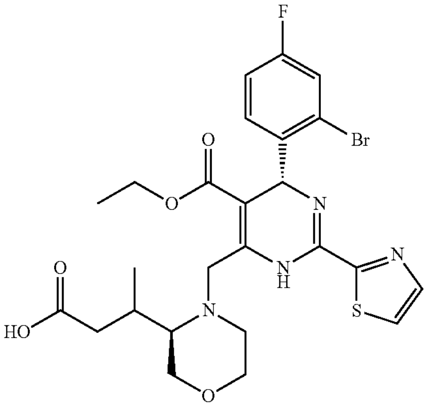
,
(27)
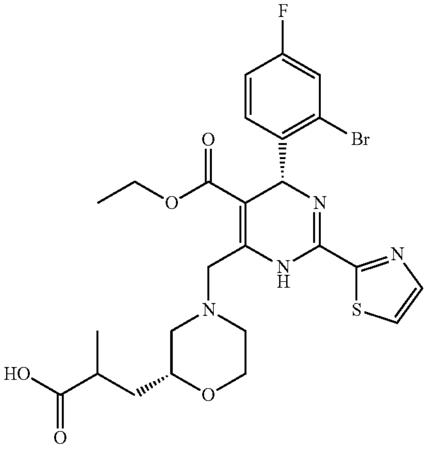
,
(28)
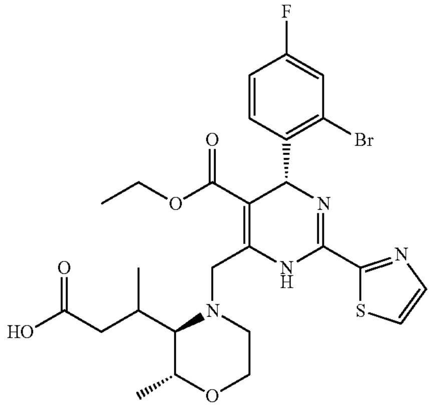
,
(29)
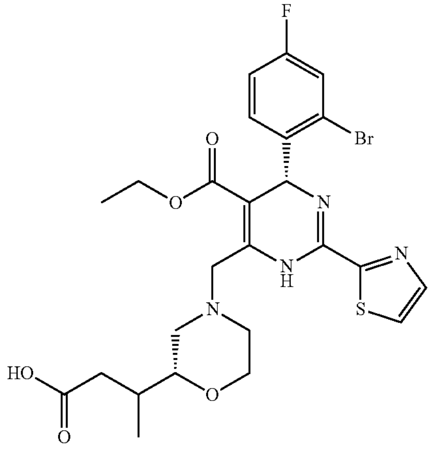
,
(30)
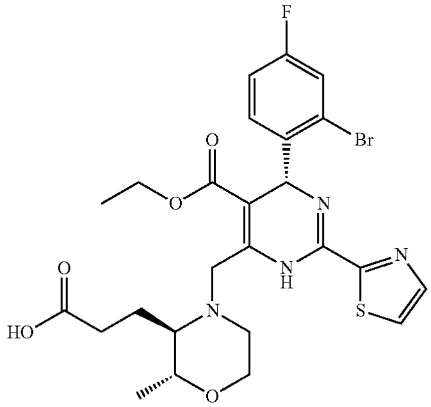
, -continued
(31)
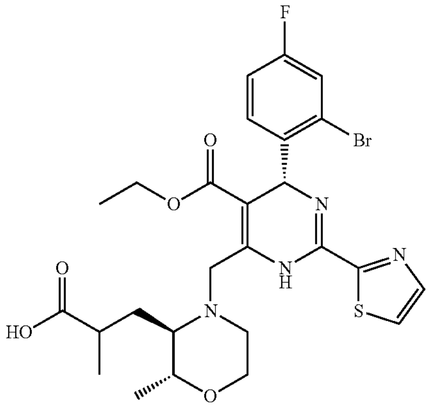
,
(32)
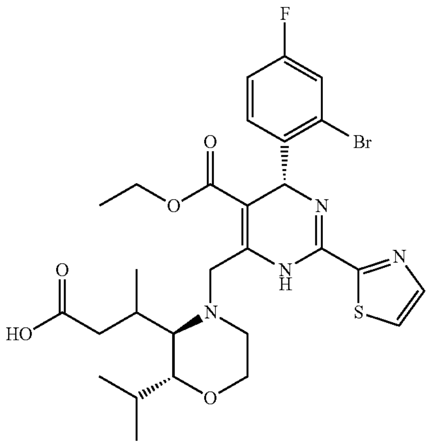
,
(33)
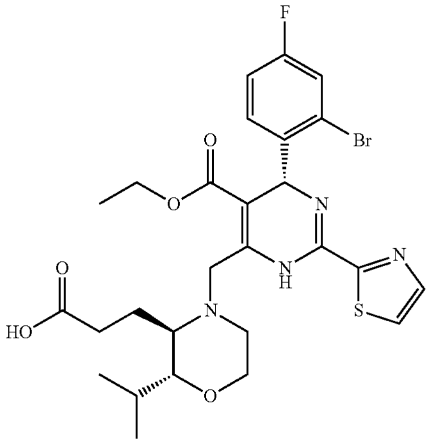
,
-continued
(34)
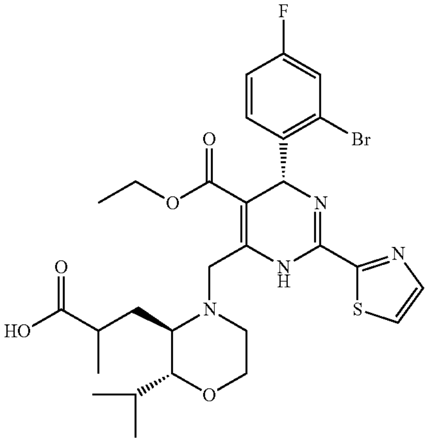
,
(35)
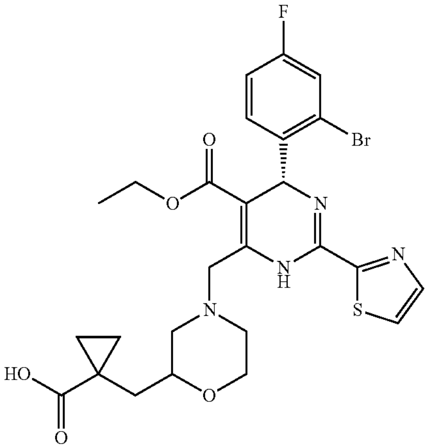
,
(36)
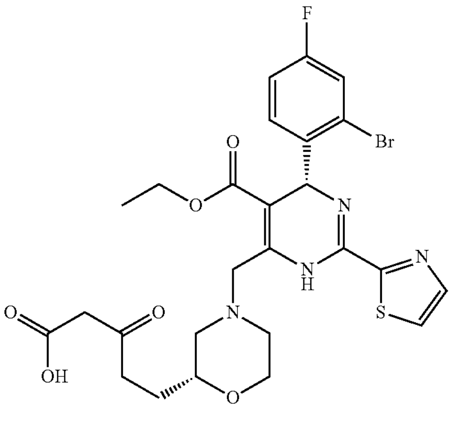
, -continued
(37)
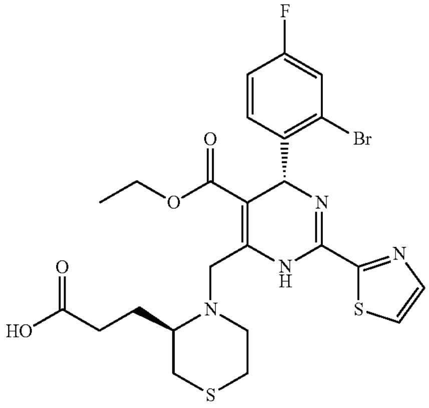
,
(38)
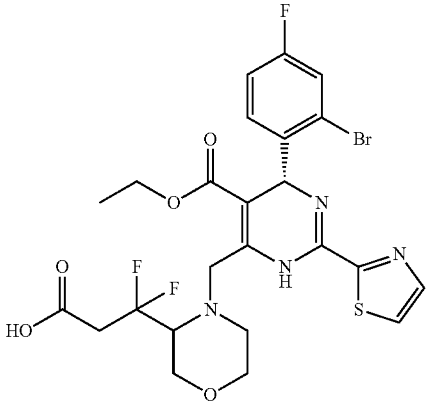
,
(39)
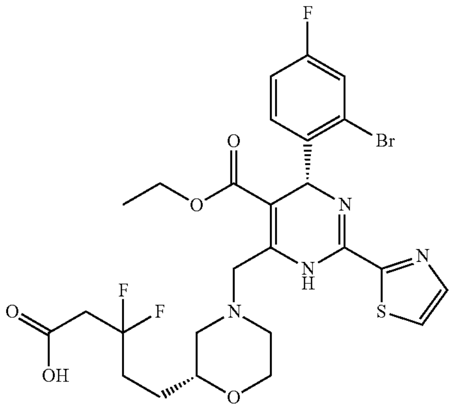
,
(40)
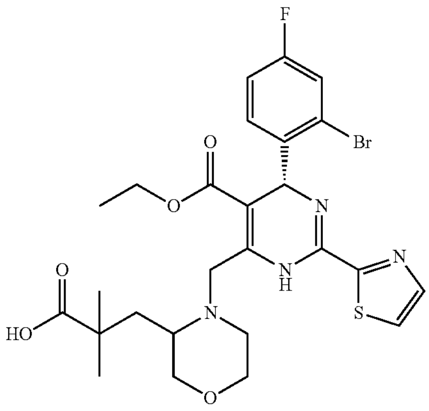
,
(41)
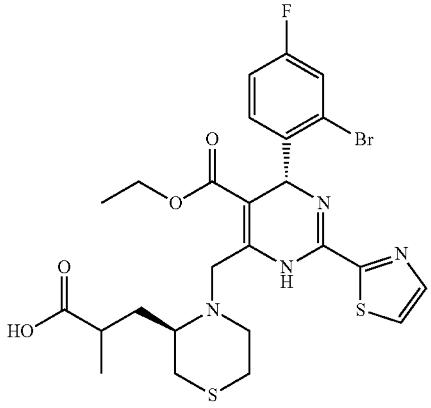
,
(42)
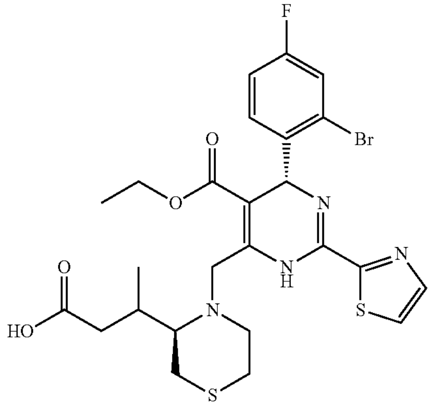
,
(43)
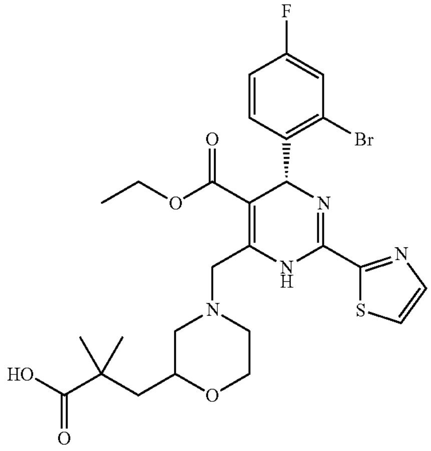
, -continued
(44)
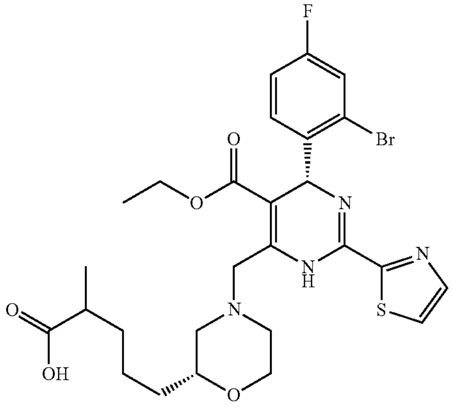
,
(45)
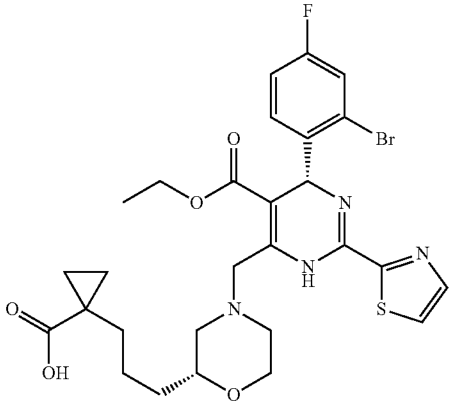
,
(46)
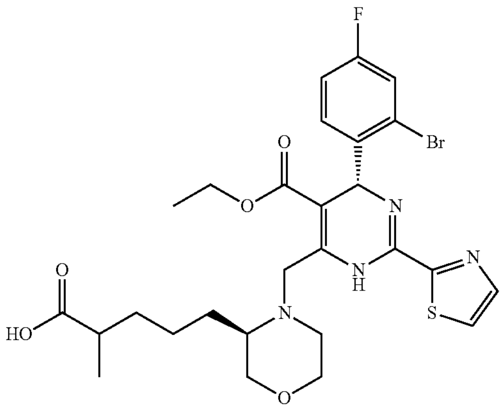
,
-continued
(47)
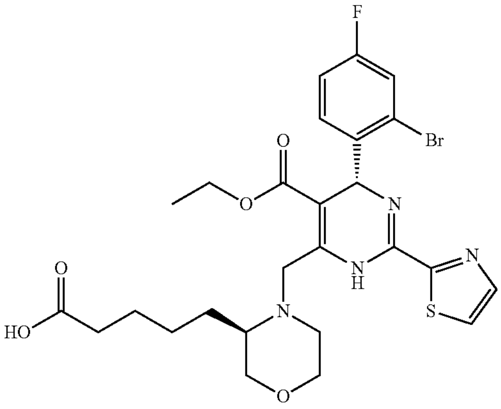
,
(48)
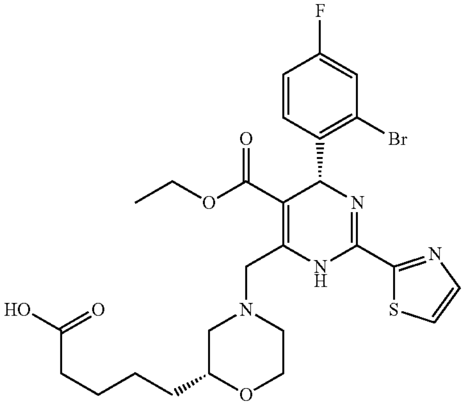
,
(49)
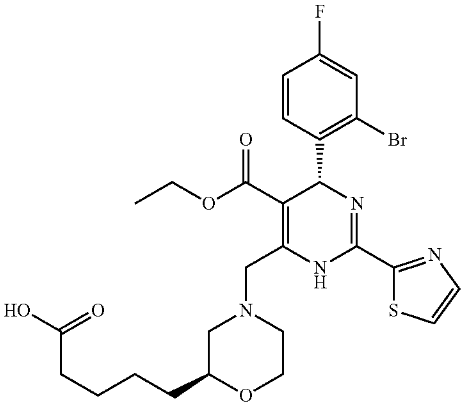
,
(50)
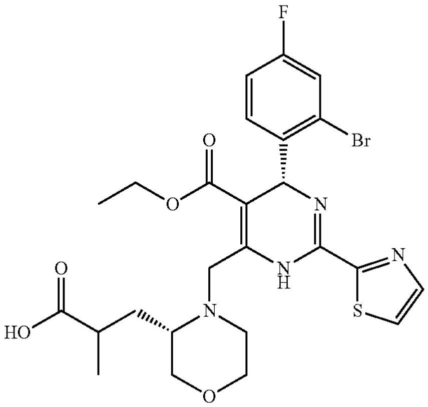
, -continued
(51)
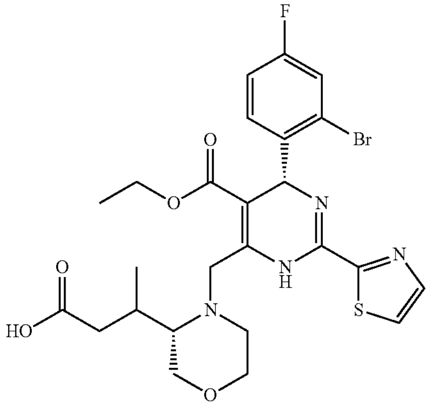
,
(52)
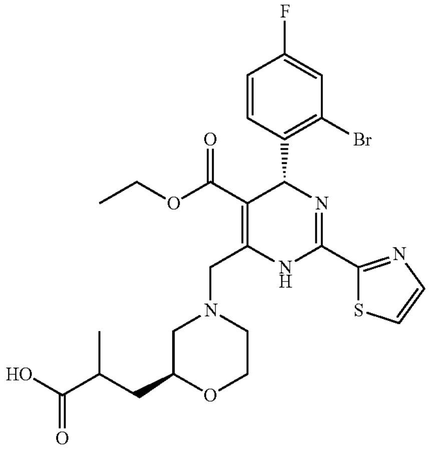
,
(53)
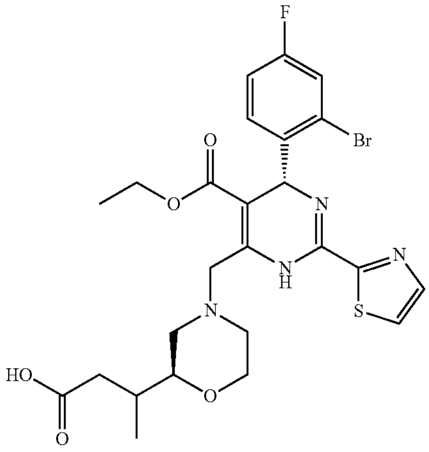
,
-continued
(54)
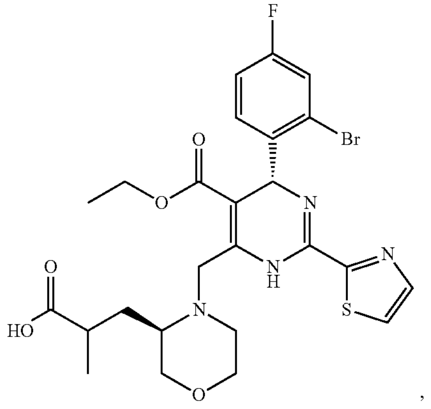
,
(55)
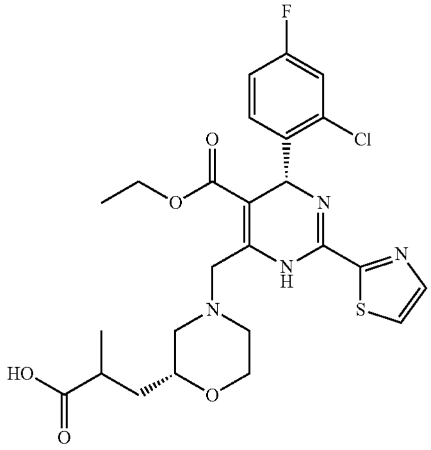
,
(56)
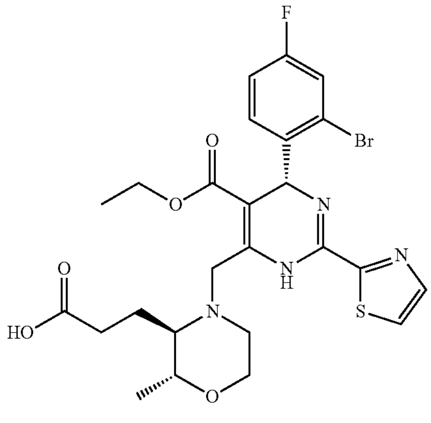
, -continued
(57)
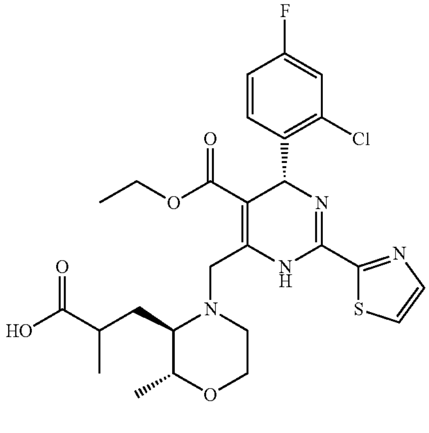
,
(58)
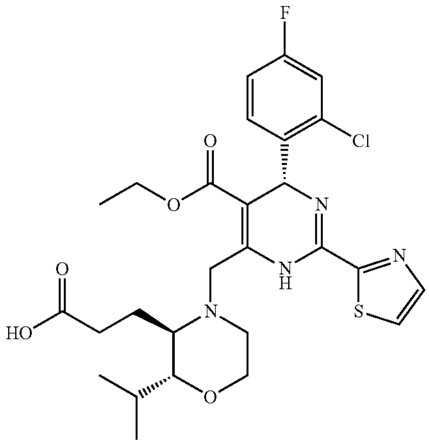
,
(59)
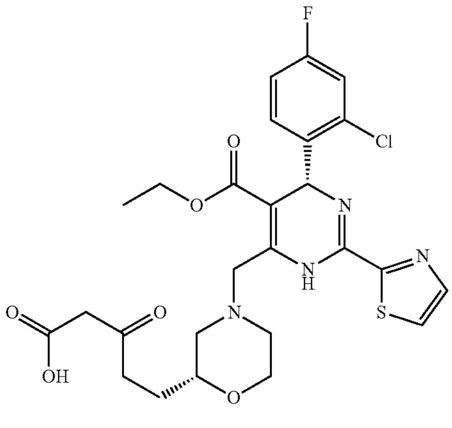
,
-continued
(60)
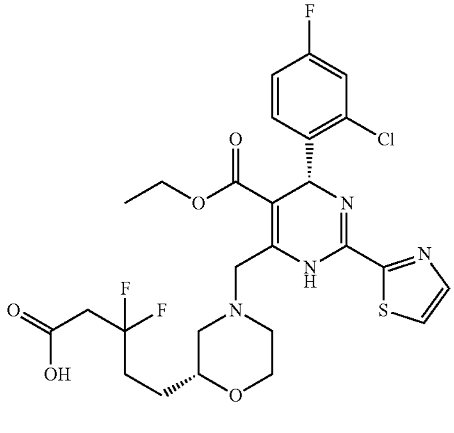
,
(61)
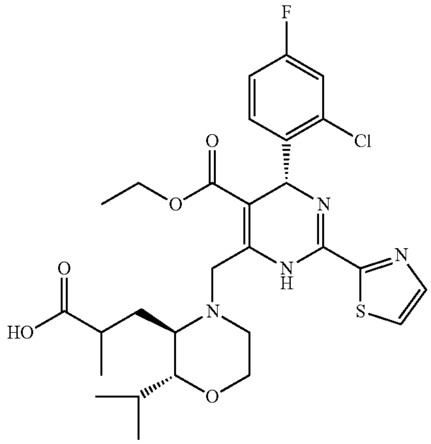
,
(62)
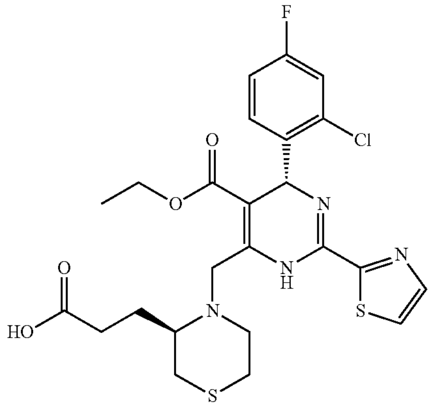
, -continued
(63)
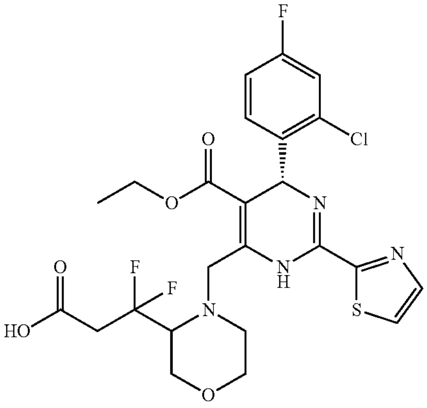
,
(64)
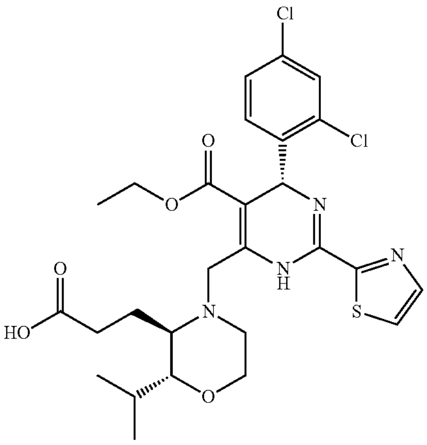
,
(65)
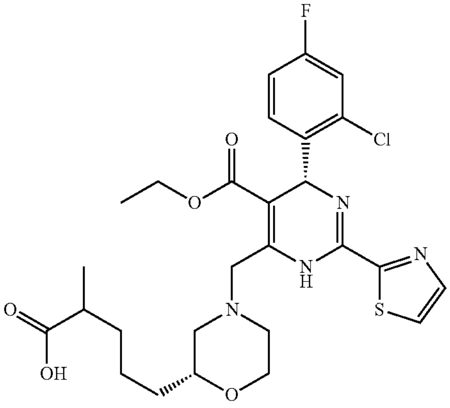
,
-continued
(66)
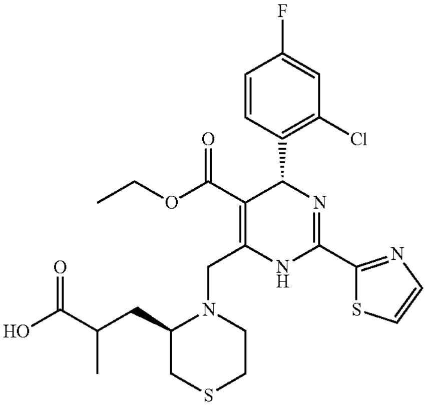
,
(67)
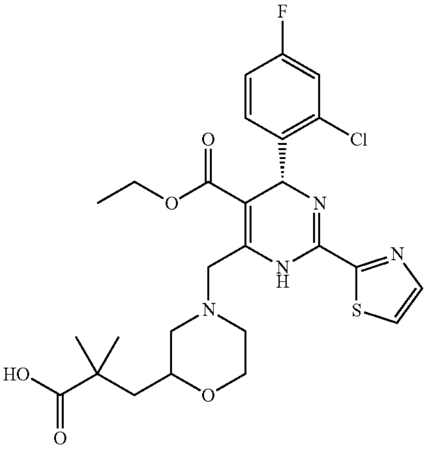
,
(68)
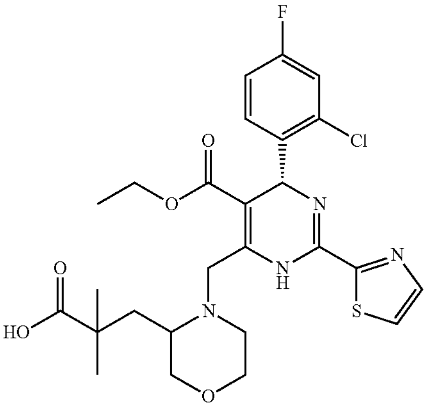
, -continued
(69)
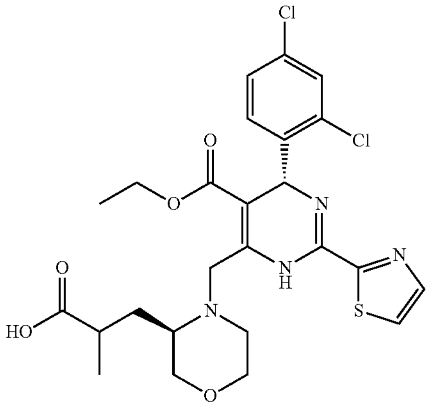
,
(70)
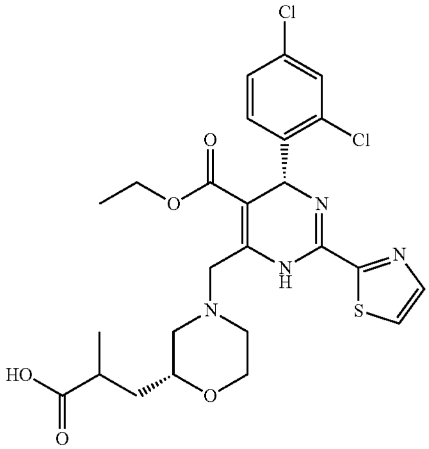
,
(71)
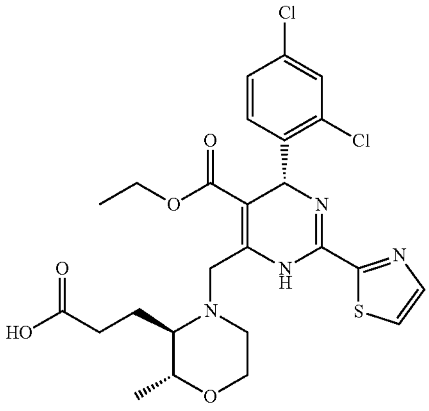
,
-continued
(72)
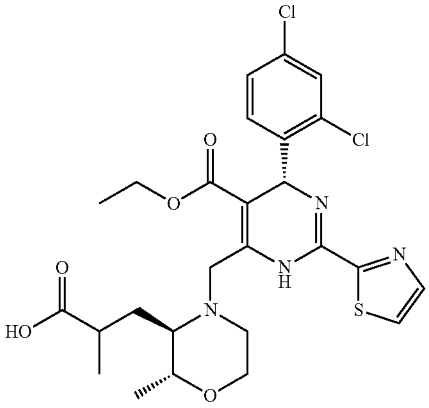
,
(73)
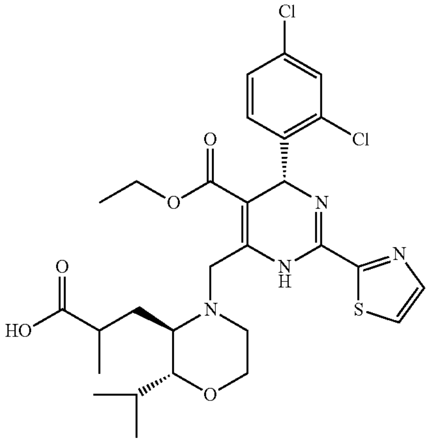
,
(74)
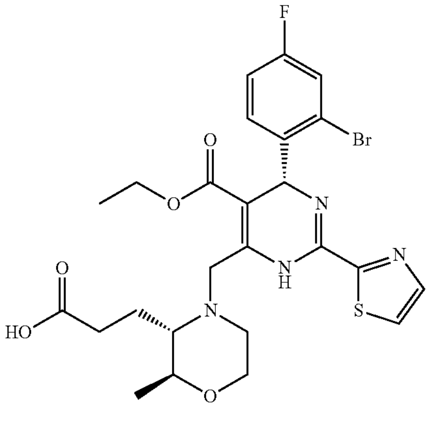
, -continued
(75)
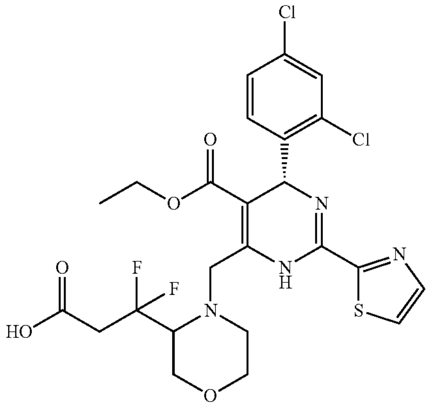
,
(76)
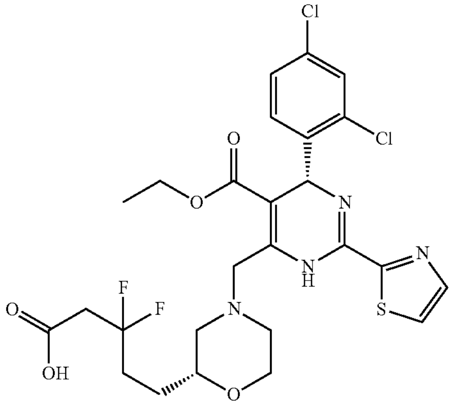
,
(77)
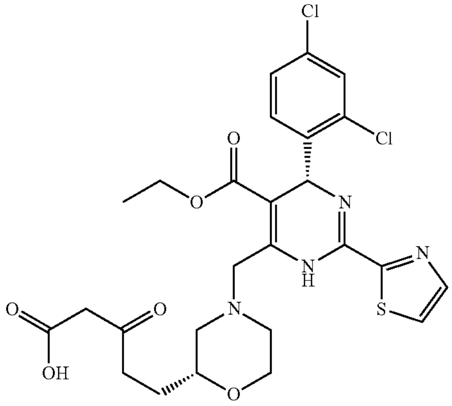
,
(78)
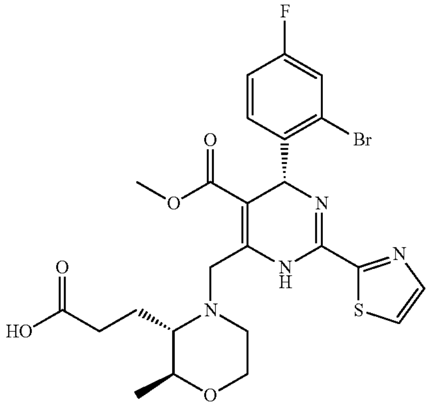
,
-continued
(79)
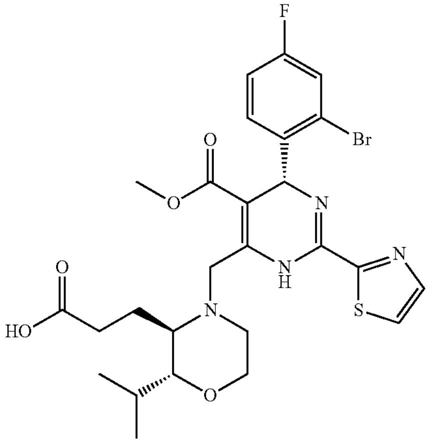
,
(80)
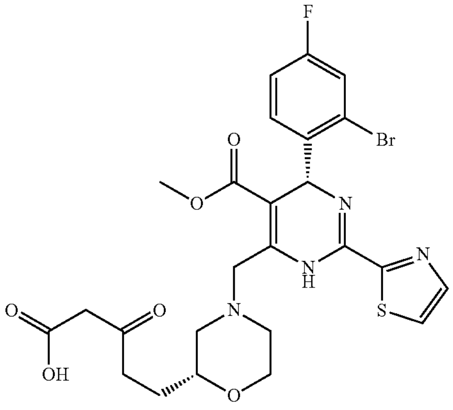
,
(81)
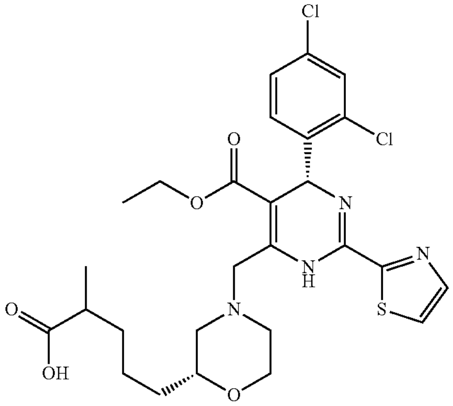
, -continued
(82)
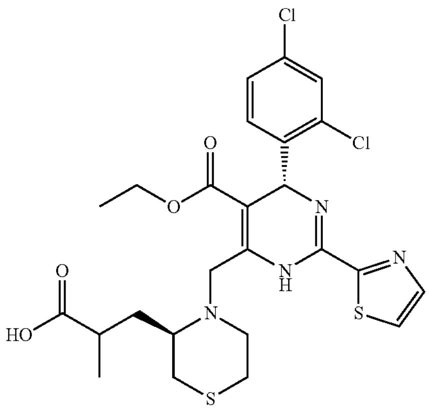
,
(83)
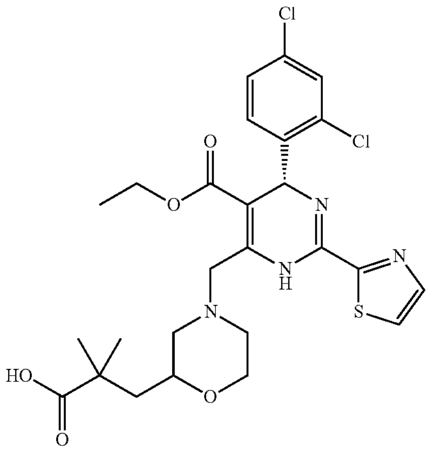
,
(84)
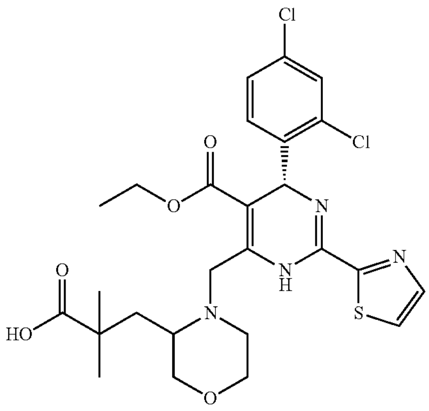
,
-continued
(85)
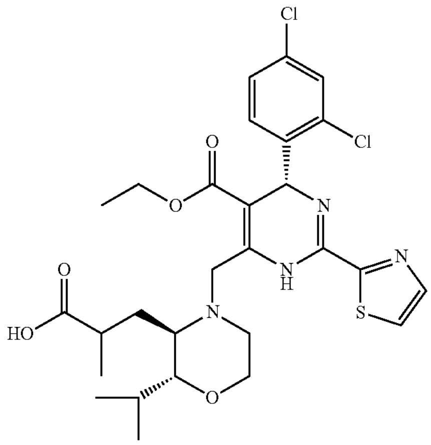
,
(86)
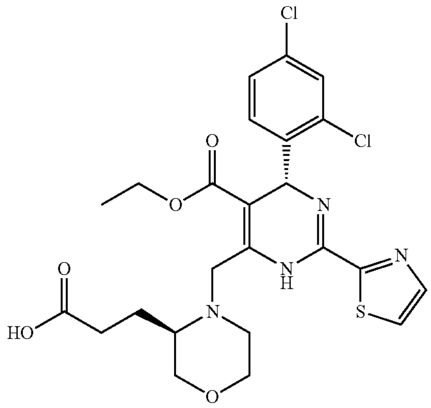
,
(87)
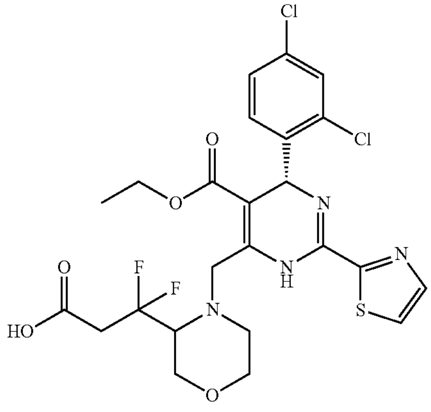
, -continued
(88)
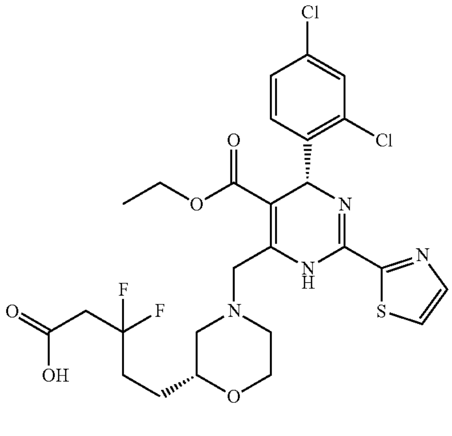
,
(89)
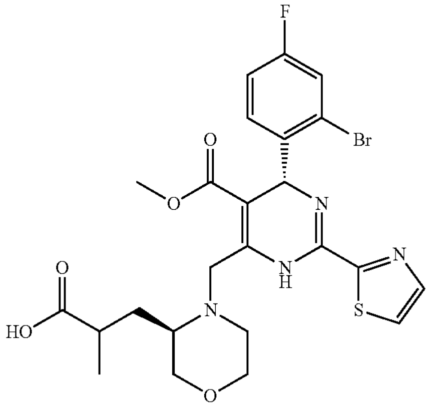
,
(90)
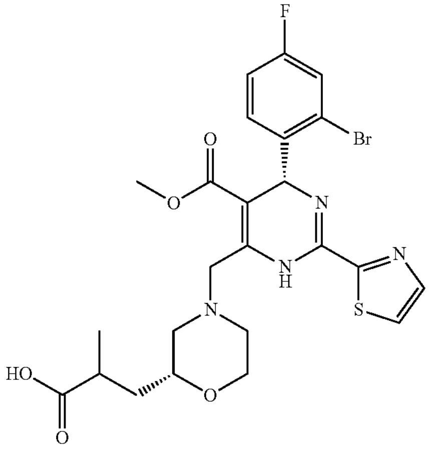
,
-continued
(91)
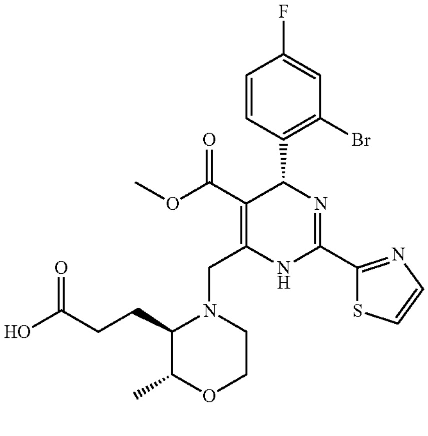
,
(92)
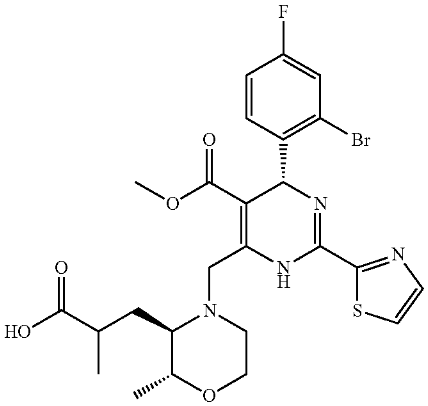
,
(93)
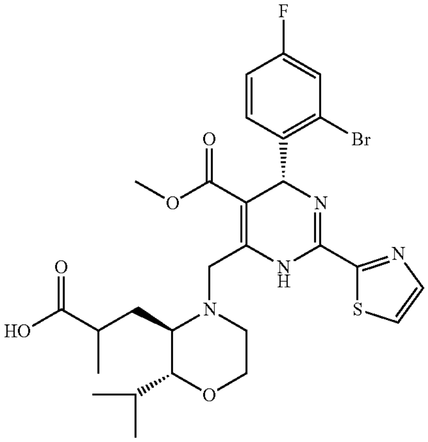
, -continued
(94)
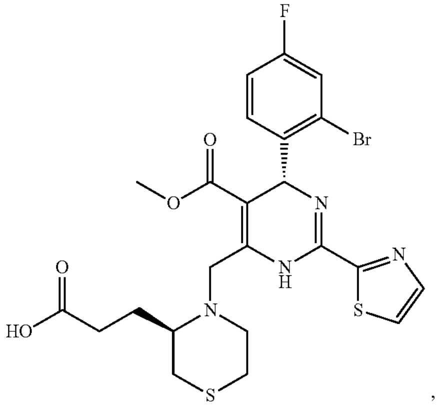
,
(95)
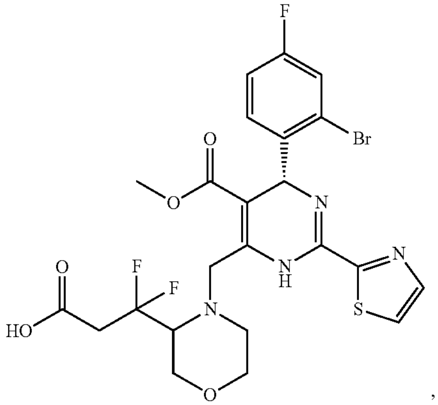
,
(96)
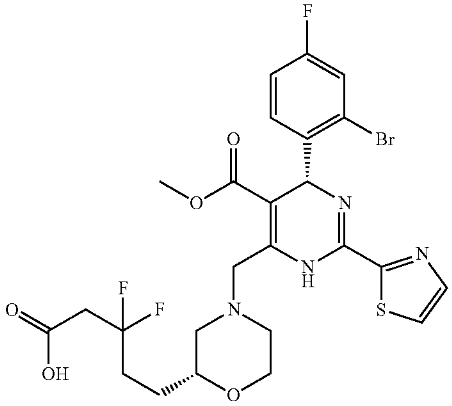
,
(97)
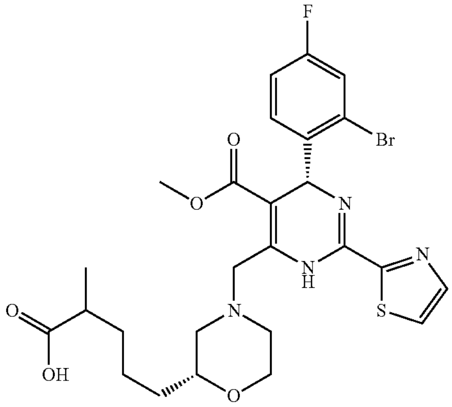
,
-continued
(98)
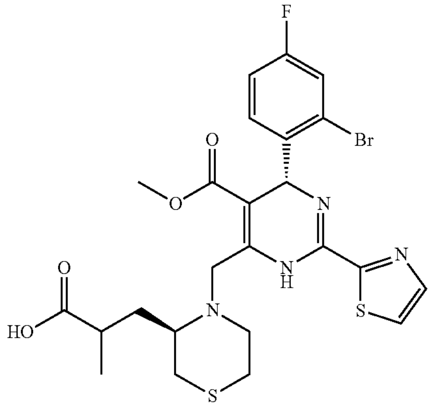
,
(99)
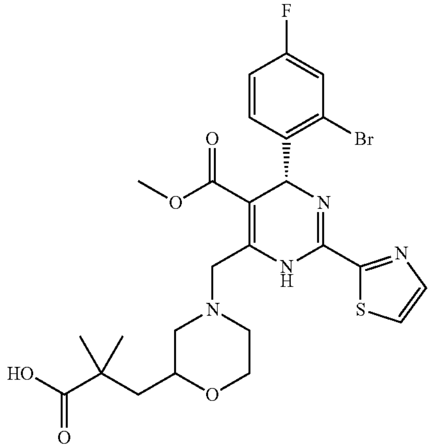
,
(100)
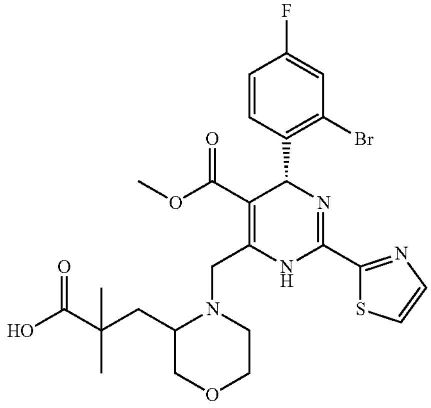
, -continued
(101)'
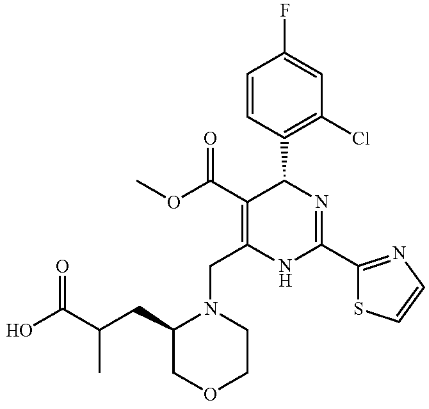
,
(102)
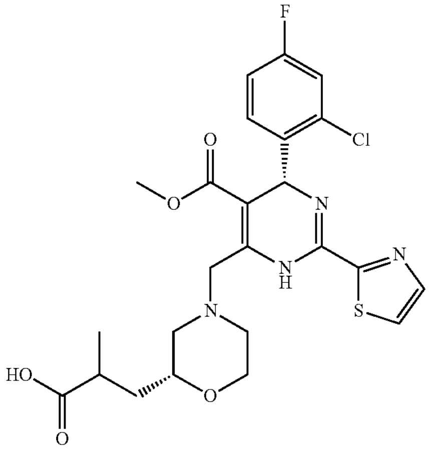
,
(103)
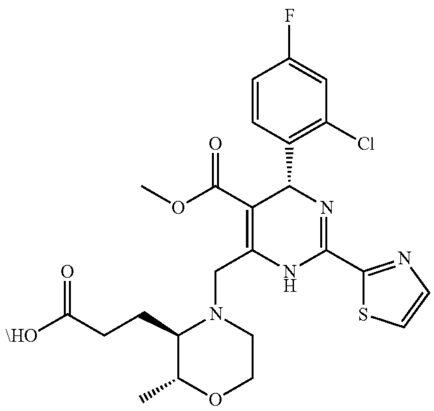
,
-continued
(104)
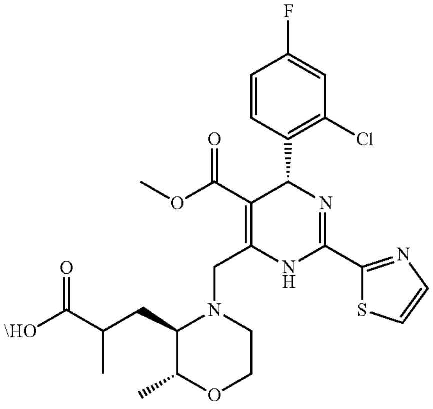
,
(105)
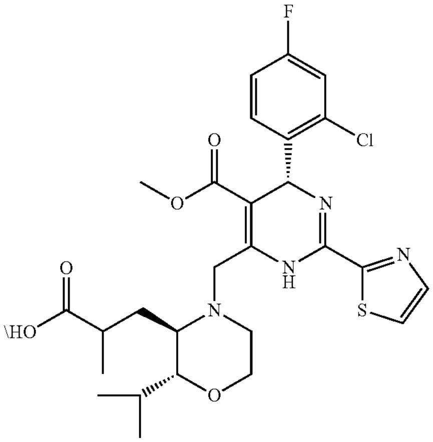
,
(106)
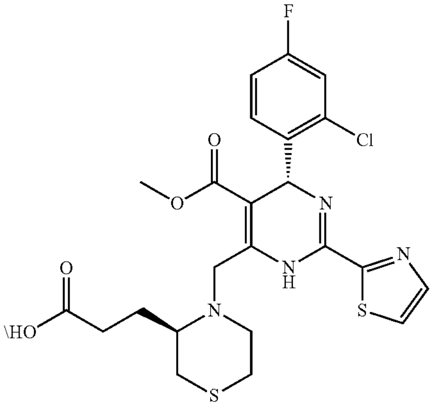
, -continued
(107)
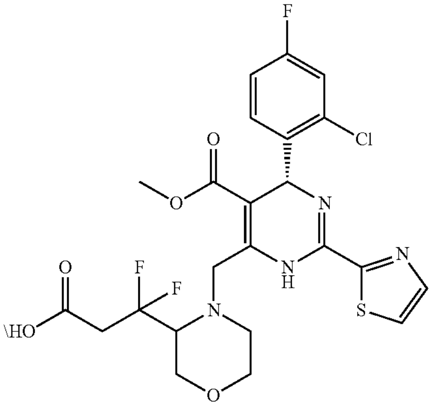
,
(108)
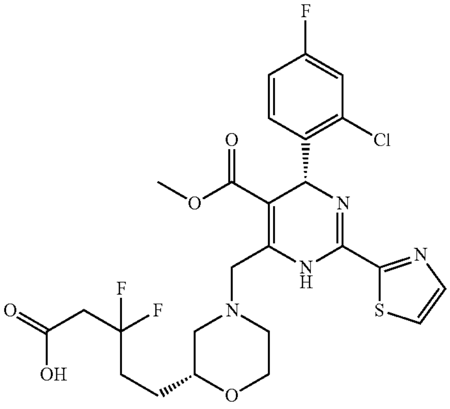
,
(109)
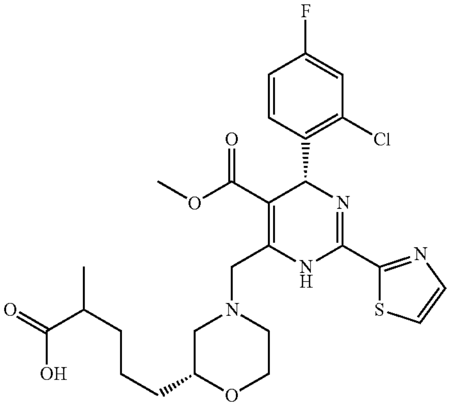
,
(110)
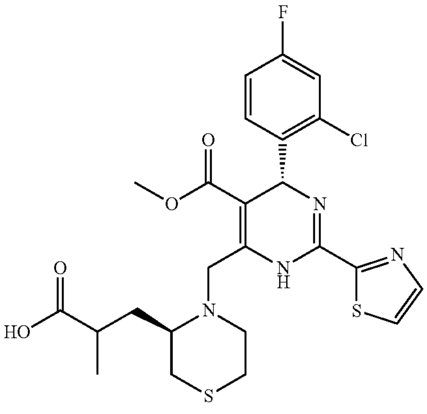
,
-continued
(111)
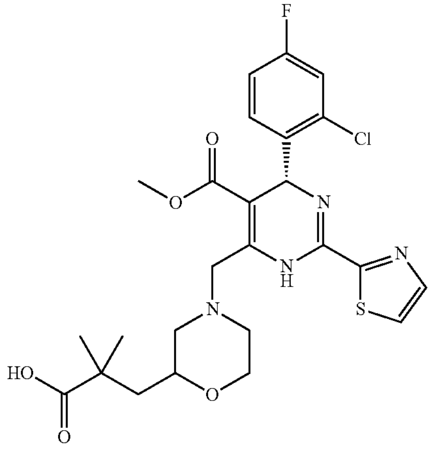
,
(112)
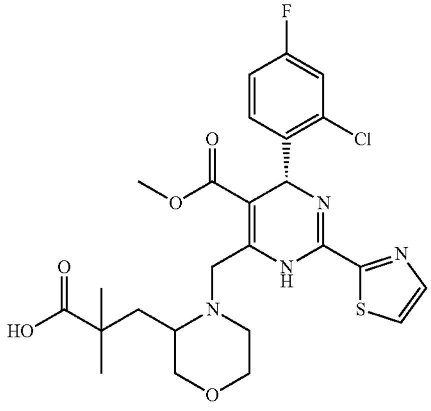
,
(113)
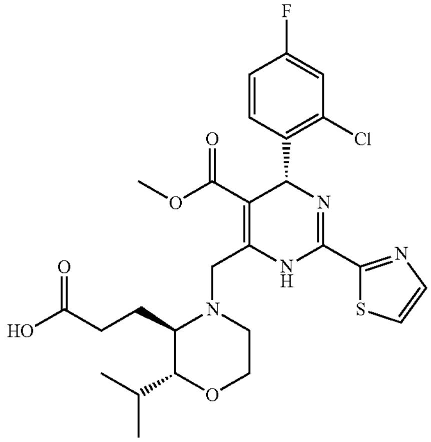
, -continued
(114)
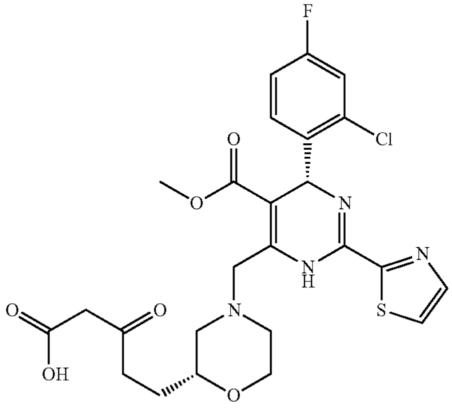
,
(115)
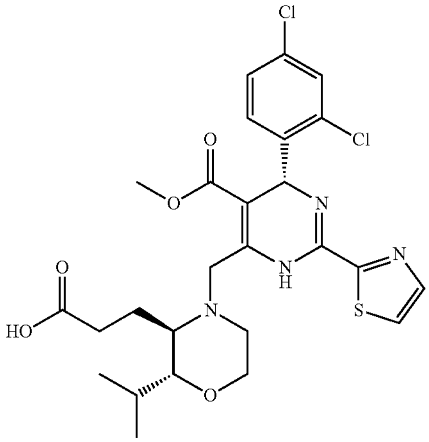
,
(116)
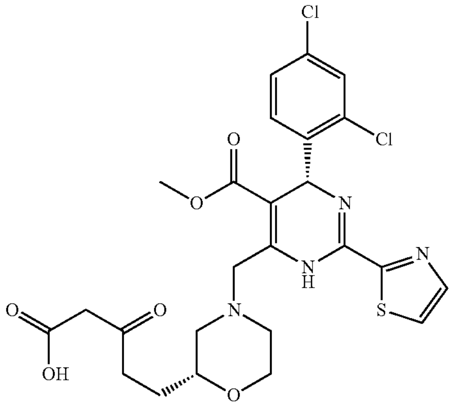
,
-continued
(117)
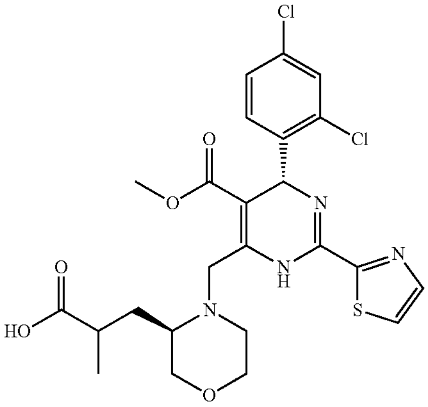
,
(118)
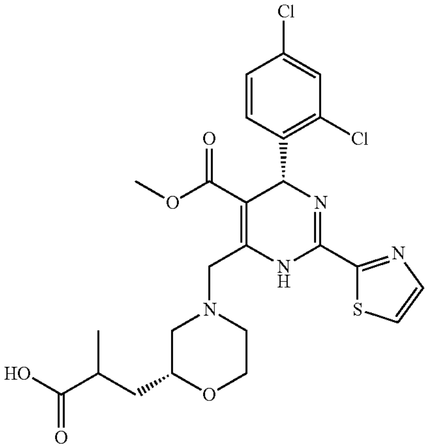
,
(119)
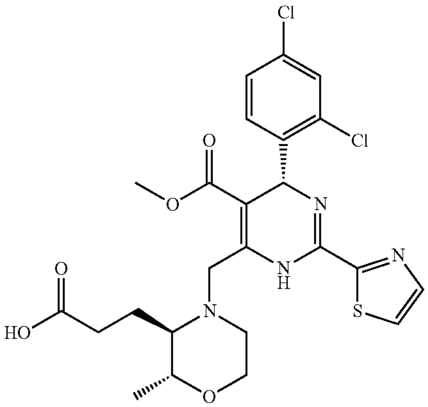
, -continued
(120)
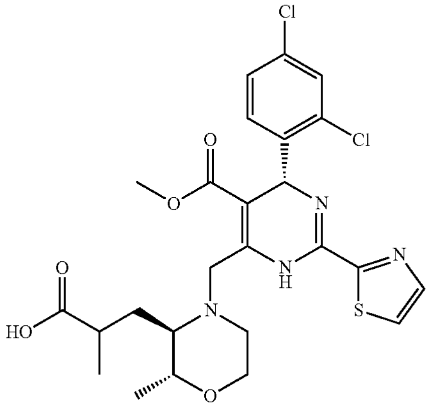
,
(121)
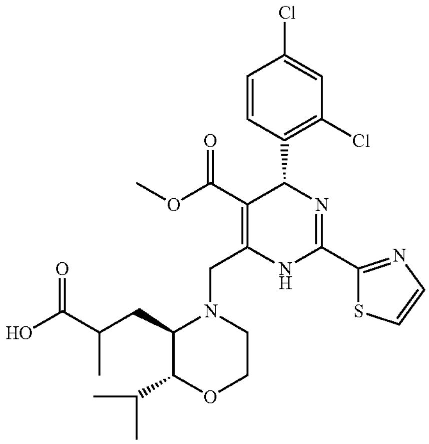
,
(122)
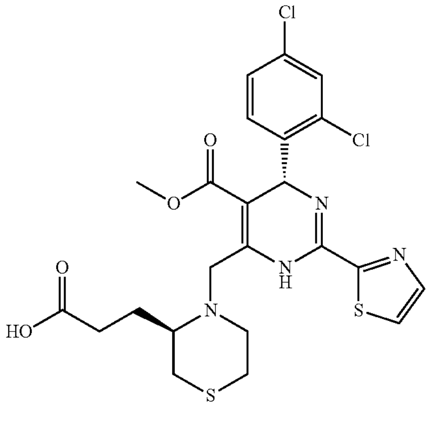
,
-continued
(123)
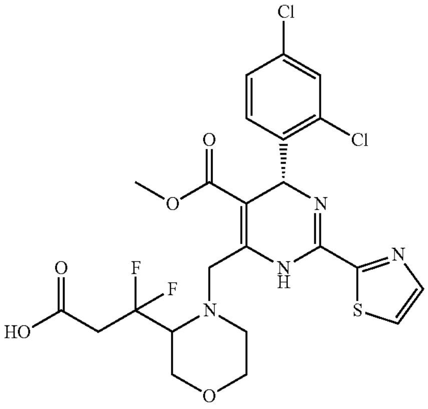
,
(124)
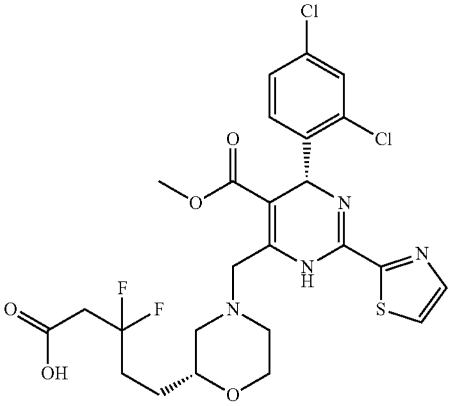
,
(125)
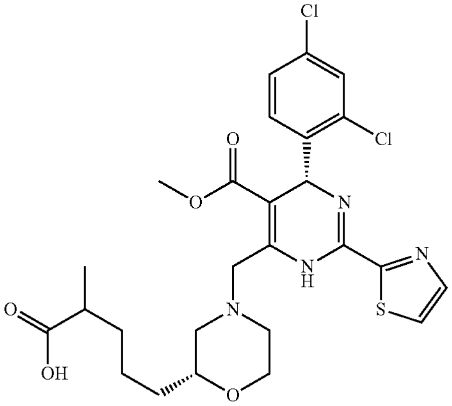
,
(126)
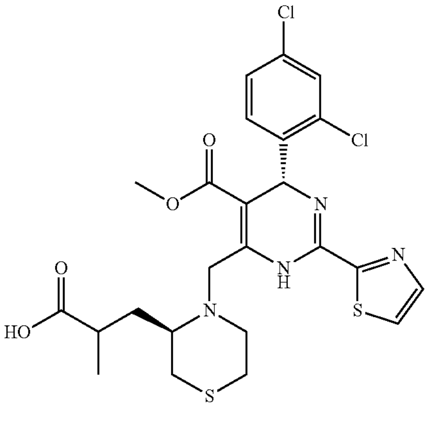
, -continued
(127)
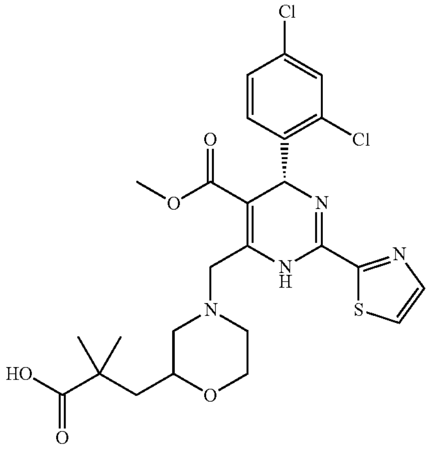
,
(128)
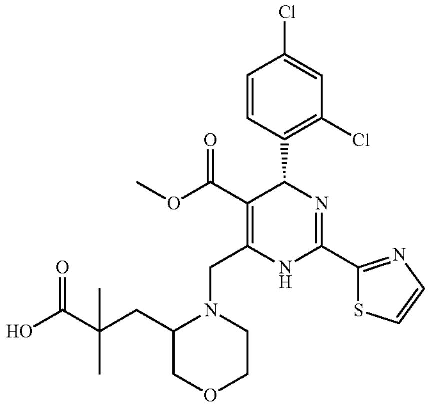
,
(129)
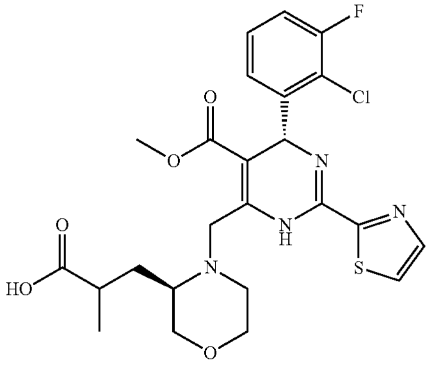
,
(130)
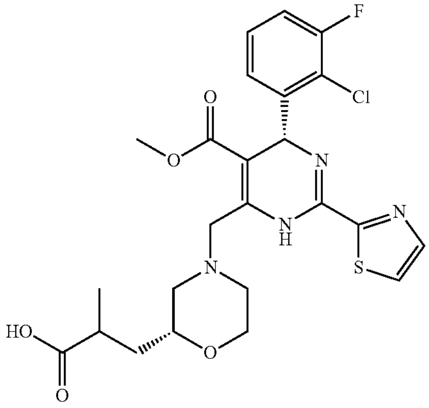
,
-continued
(131)
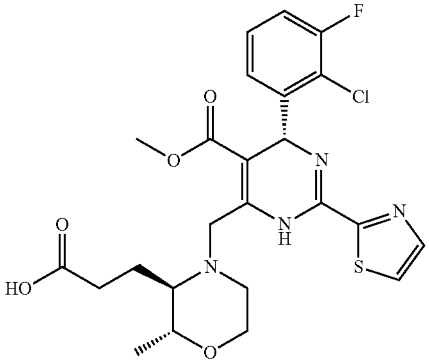
,
(132)
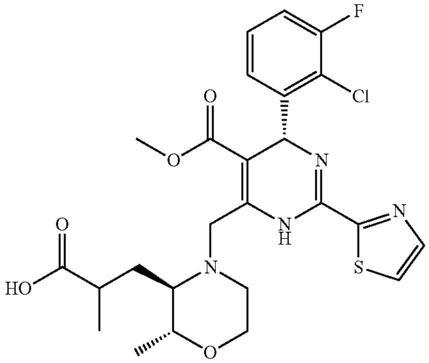
,
(133)
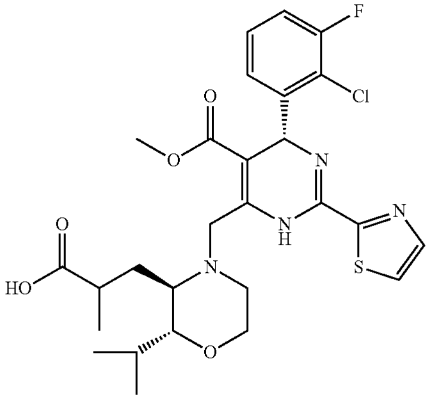
,
(134)
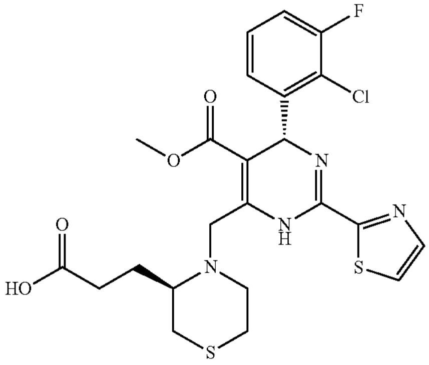
, -continued
(135)
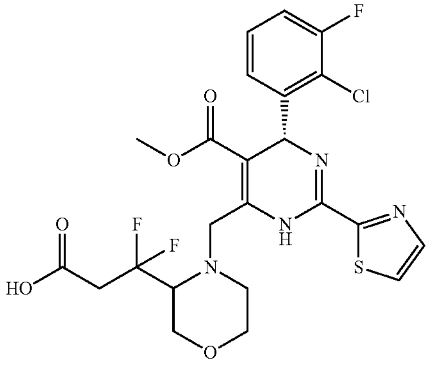
,
(136)
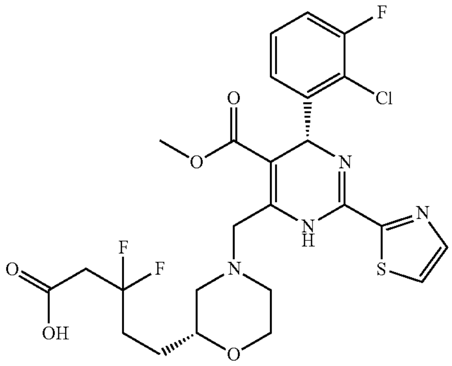
,
(137)
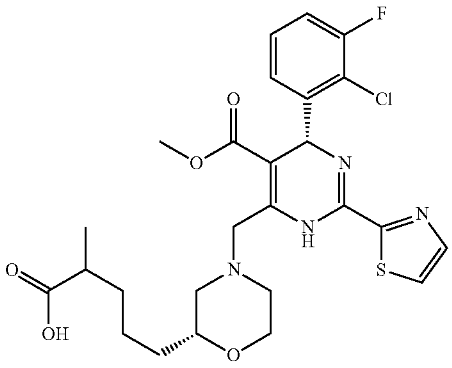
,
(138)
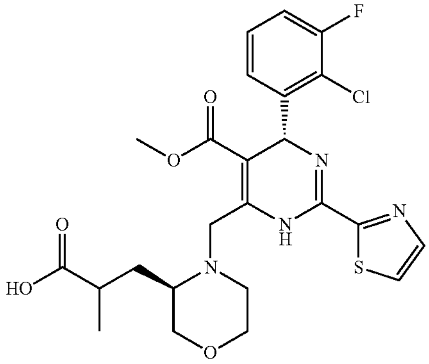
,
-continued
(139)
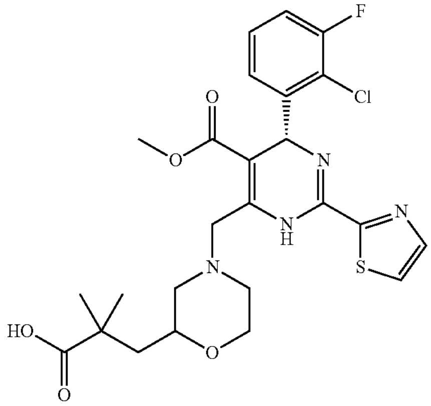
,
(140)
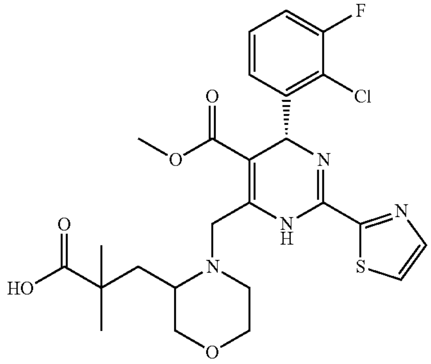
,
(141)
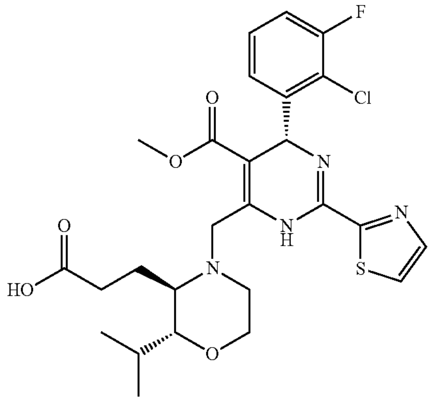
,
(142)
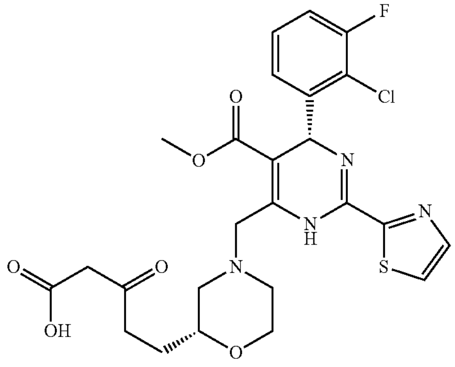
, -continued
(143)
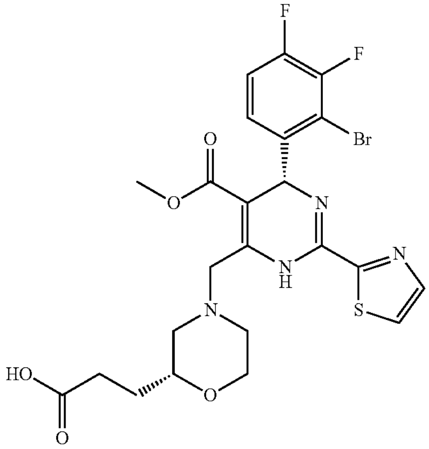
,
(144)
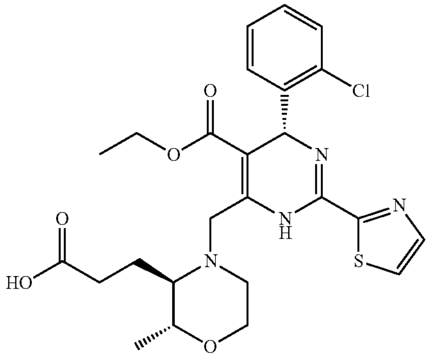
,
(145)
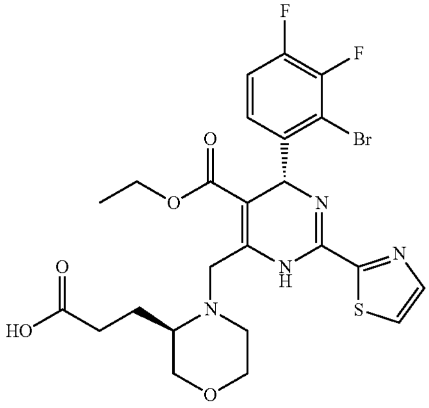
,
(146)
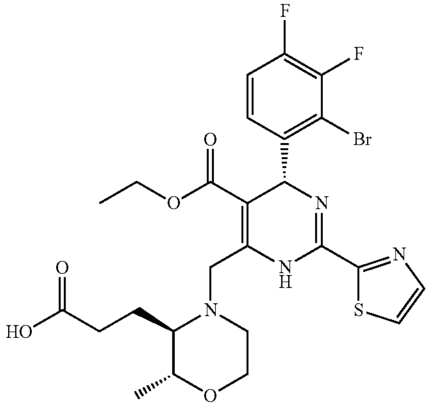
,
-continued
(147)
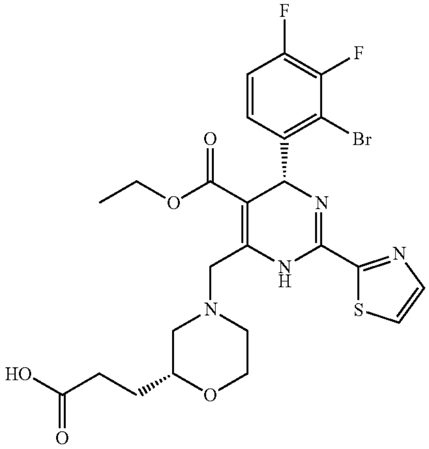
,
(148)
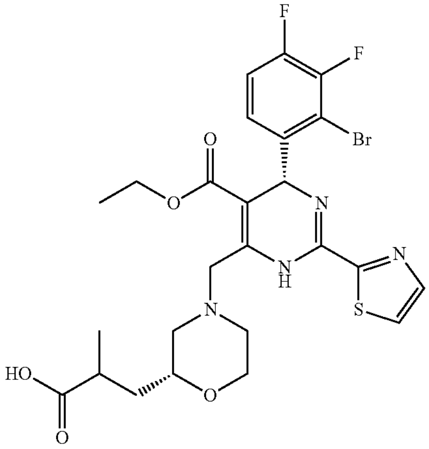
,
(149)
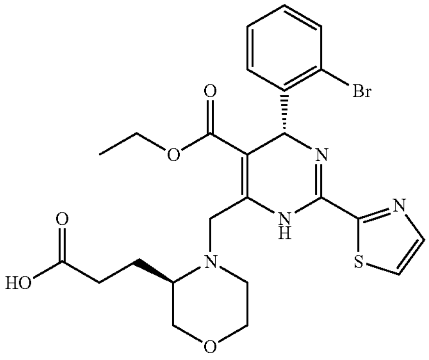
,
(150)
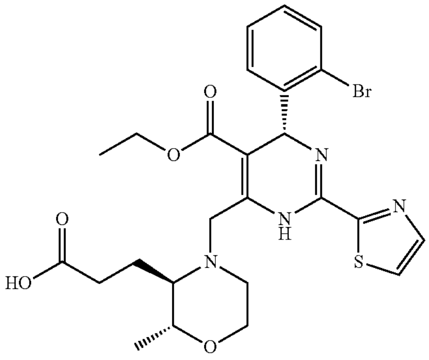
, -continued
(151)
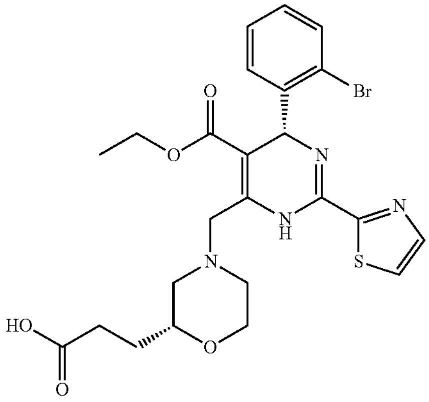
,
(152)
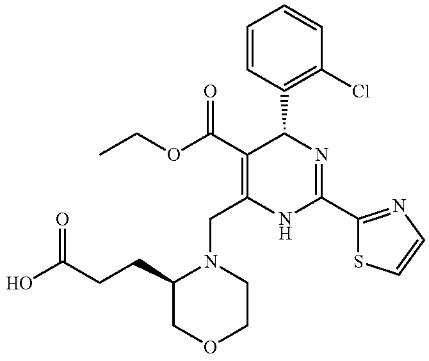
,
(153)
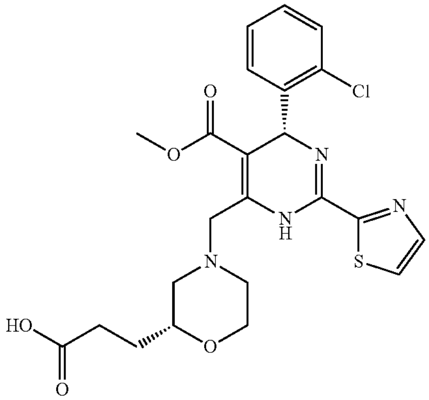
,
(154)
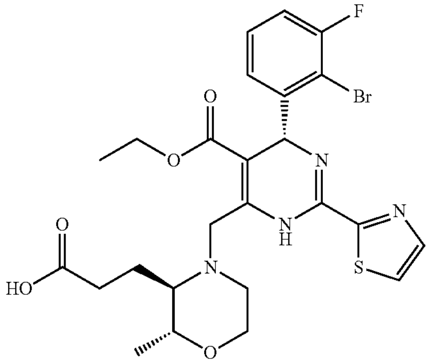
,
-continued
(155)
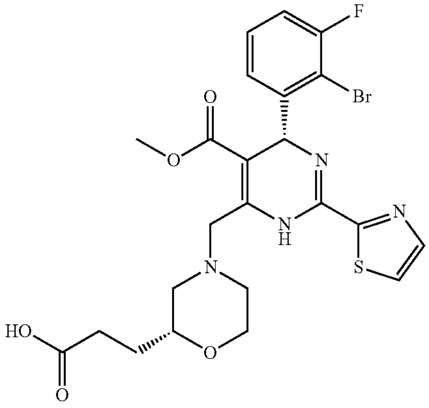
,
(156)
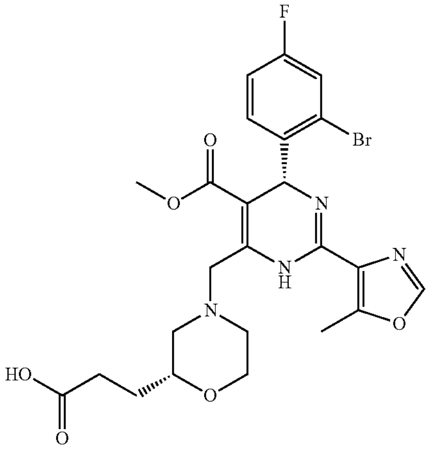
,
(157)
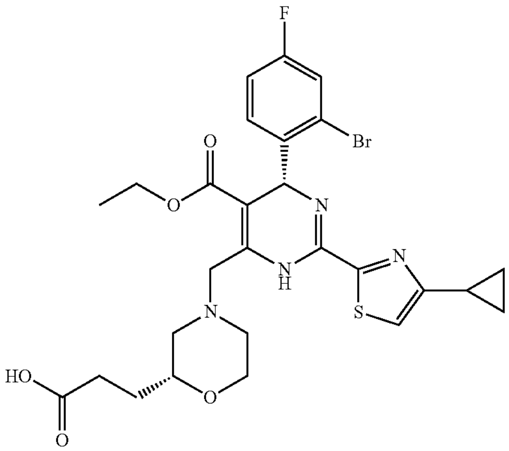
, -continued
(158)
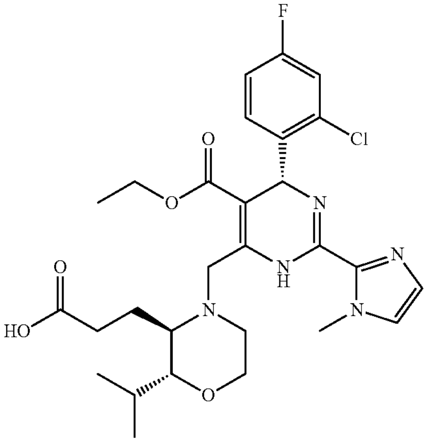
,
(159)
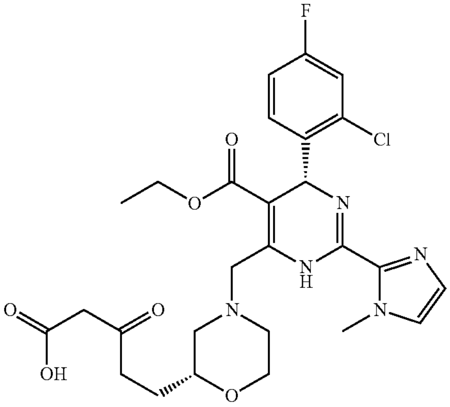
,
(160)
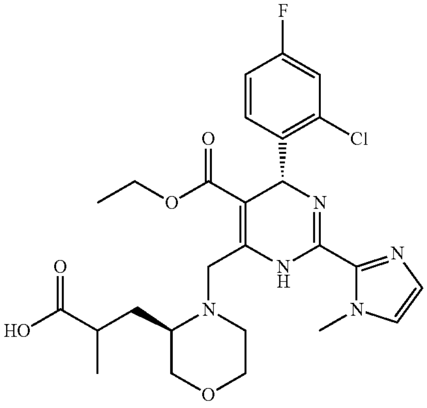
,
-continued
(161)
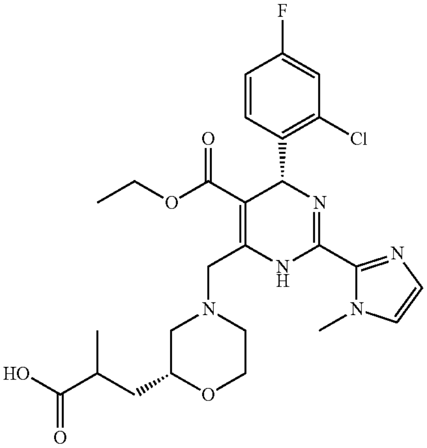
,
(162)
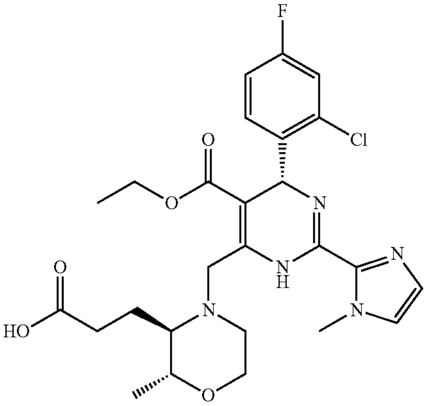
,
(163)
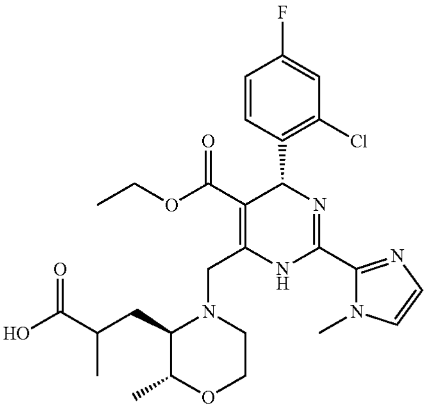
, -continued
(164)
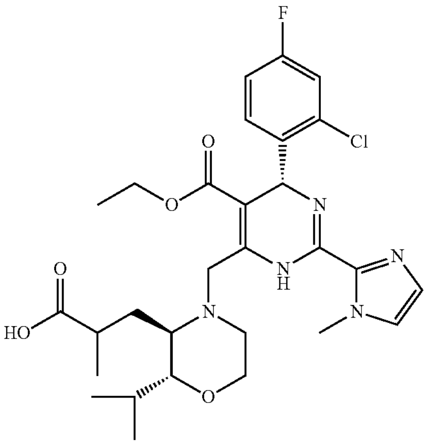
,
(165)
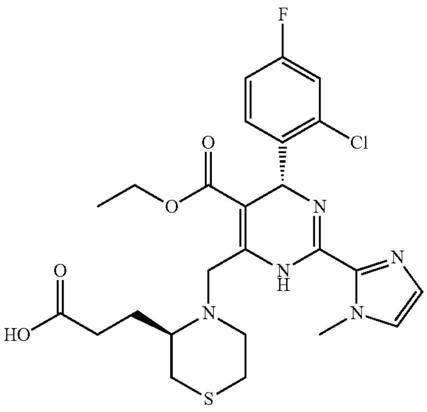
,
(166)
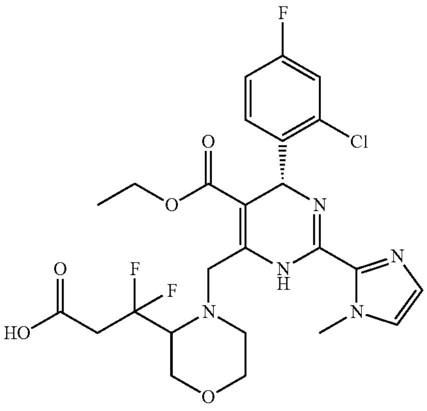
,
-continued
(167)
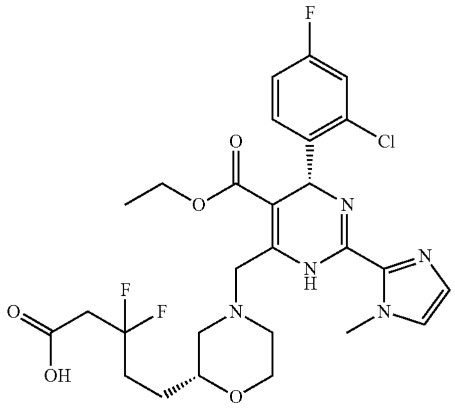
,
(168)
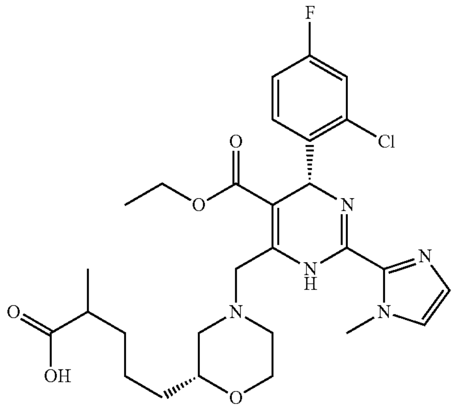
,
(169)
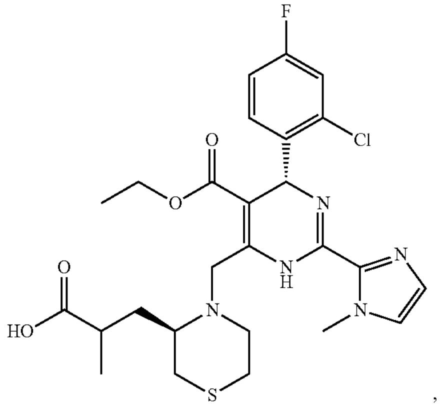
, -continued
(170)
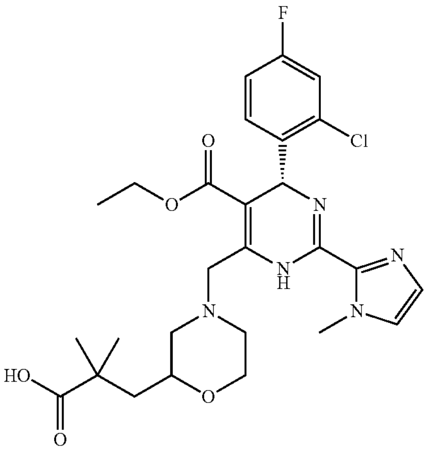
,
(171)
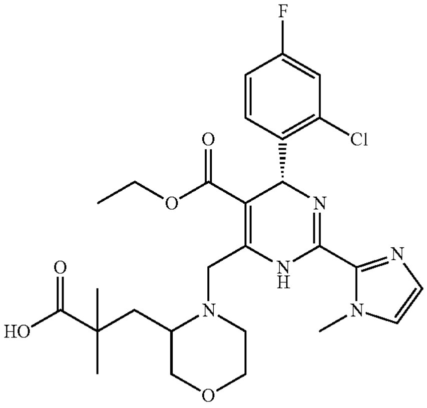
,
(172)
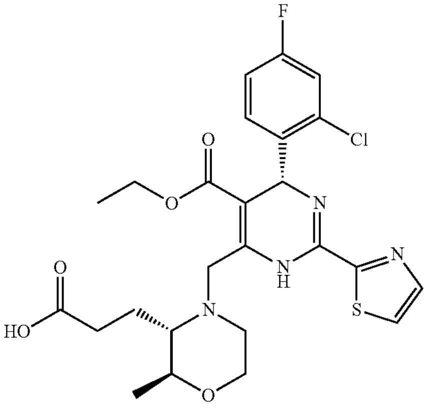
,
-continued
(173)
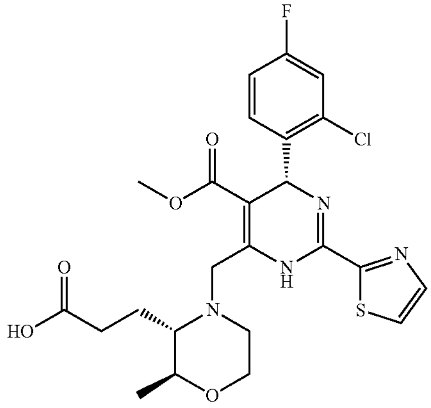
,
(174)
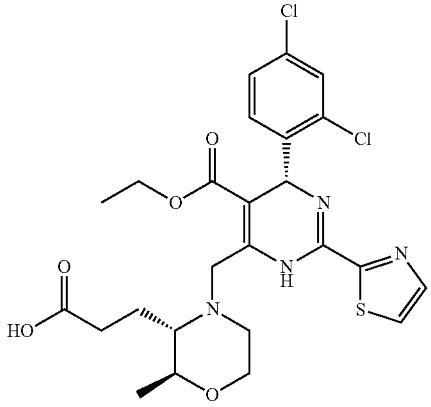
,
(175)
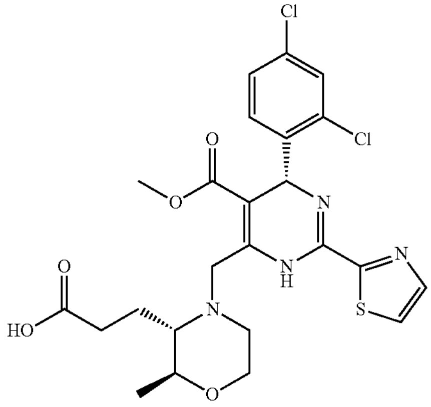
,
(176)
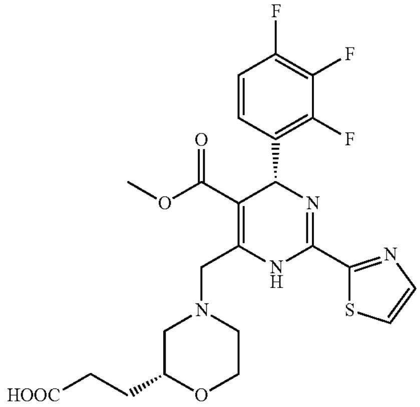
, -continued
(177)
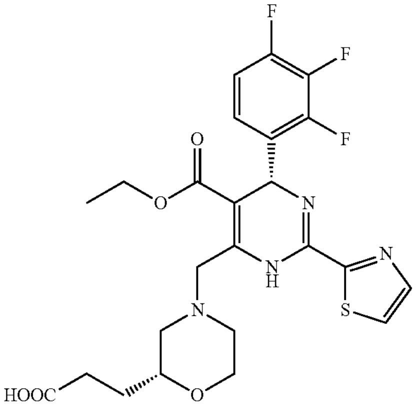
,
(178)
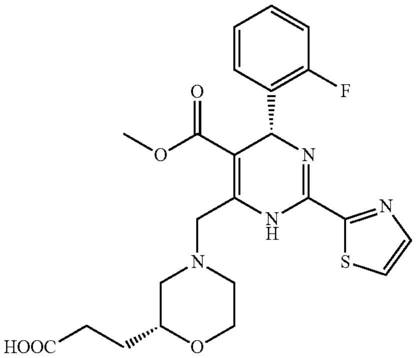
,
(179)
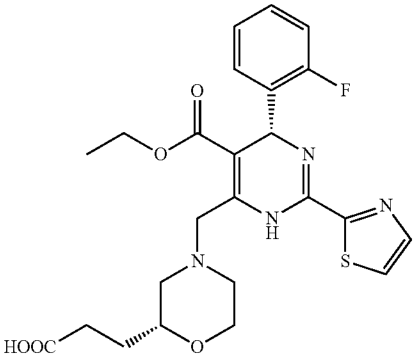
,
(180)
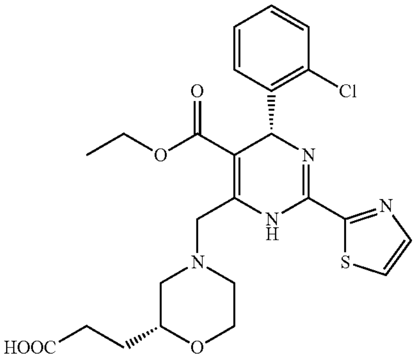
,
-continued
(181)
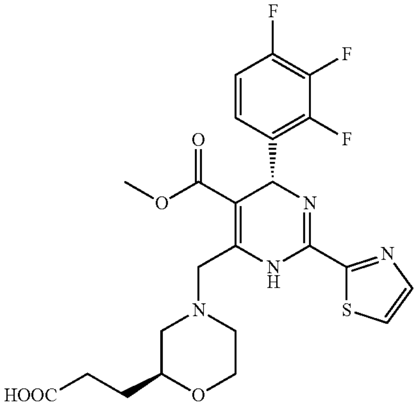
,
(182)
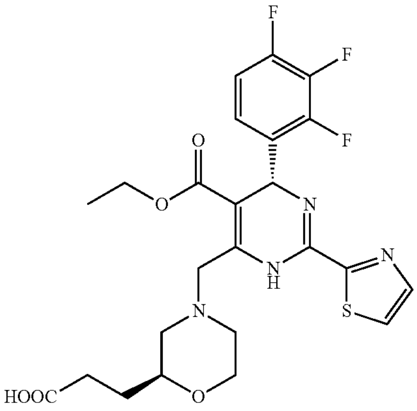
,
(183)
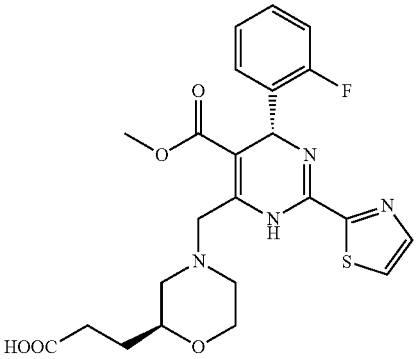
,
(184)
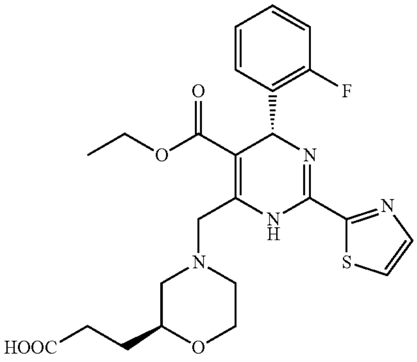
, or -continued (185)

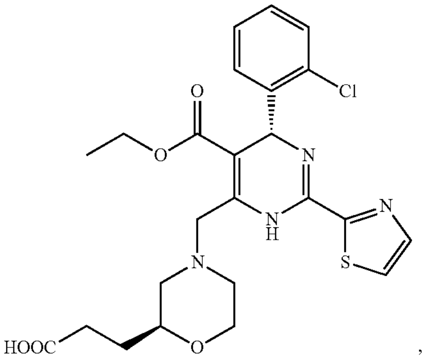

, or an enantiomer, a diastereoisomer, a tautomer, a hydrate, a solvate, a prodrug, a stereoisomer, an N-oxide, or a pharmaceutically acceptable salt thereof.

4. A pharmaceutical composition comprising the compound according to claim 1.

5. The pharmaceutical composition according to claim 4 further comprises a pharmaceutically acceptable carrier, excipient, diluent, adjuvant, vehicle or a combination thereof.

6. The pharmaceutical composition according to claim 4 further comprises an anti-HBV agent.

7. The pharmaceutical composition according to claim 6, wherein the anti-HBV agent is an HBV polymerase inhibitor, immunomodulator or interferon.

8. The pharmaceutical composition according to claim 6, wherein the anti-HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole, or propagermanium.

9. A method for managing, treating or lessening an HBV disease comprising administrating to a patient a therapeutically effective amount of the compound according to claim 1.

10. The method according to claim 9, wherein the HBV disease is hepatitis B infection or a disease caused by hepatitis B infection.

11. The method according to claim 10, wherein the disease caused by hepatitis B infection is cirrhosis or hepatocellular carcinoma.

12. A method for managing, treating or lessening an HBV disease comprising administrating to a patient a therapeutically effective amount of the pharmaceutical composition according to claim 4.

13. The method according to claim 12, wherein the HBV disease is hepatitis B infection or a disease caused by hepatitis B infection.

14. The method according to claim 13, wherein the disease caused by hepatitis B infection is cirrhosis or hepatocellular carcinoma.

15. The compound according to claim 1 having one of the following structures:

(1)

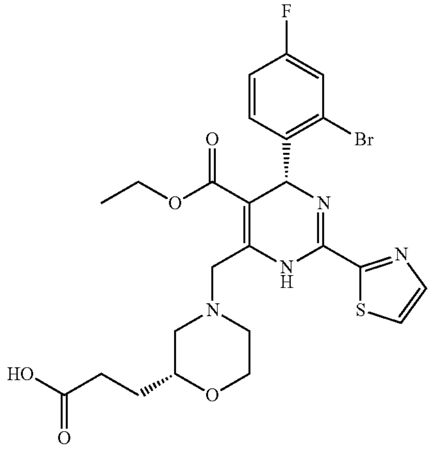

, or (2)

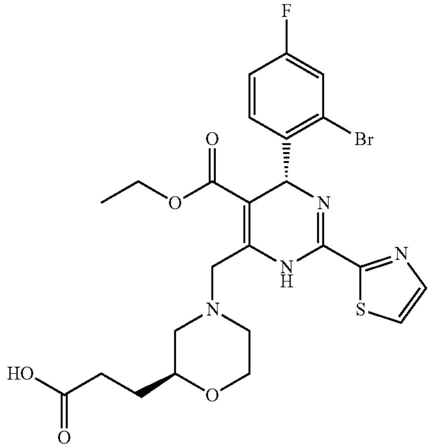

, or an enantiomer, a diastereoisomer, a tautomer, a hydrate, a solvate, a prodrug, a stereoisomer, an N-oxide, or a pharmaceutically acceptable salt thereof.

16. The compound according to claim 15, wherein the compound is a pharmaceutically acceptable salt.

17. The compound according to claim 16, wherein the pharmaceutically acceptable salt is an organic or inorganic salt.

18. The compound according to claim 16, wherein the pharmaceutically acceptable salt is hydrochloride, hydrobromide, phosphate, sulfate, perchlorate, acetate, oxalate, maleate, tartarate, citrate, succinate, malonate, adipate, 2-hydracrylic acid salt, alginate, ascorbate, aspartate, benzenesulfonate, benzoate, bisulfate, borate, butyrate, camphanic acid salt, camphorsulfonate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, or valerate salts.

* * * * *